United States Patent
Lee et al.

(10) Patent No.: US 10,392,400 B2
(45) Date of Patent: Aug. 27, 2019

(54) PALLADIUM-MEDIATED KETOLIZATION

(71) Applicant: President and Fellows of Harvard College, Cambridge, MA (US)

(72) Inventors: Jung Hwa Lee, Andover, MA (US); Yoshito Kishi, Cambridge, MA (US); Ayumi Osawa, Hyogo (JP); Zhanjie Li, Midland, MI (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 15/809,845

(22) Filed: Nov. 10, 2017

(65) Prior Publication Data

US 2018/0155361 A1   Jun. 7, 2018

Related U.S. Application Data

(60) Provisional application No. 62/420,785, filed on Nov. 11, 2016.

(51) Int. Cl.
| | |
|---|---|
| *C07D 493/22* | (2006.01) |
| *C07D 493/04* | (2006.01) |
| *C07D 519/00* | (2006.01) |
| *A61P 35/04* | (2006.01) |
| *C07D 407/06* | (2006.01) |
| *C07D 407/14* | (2006.01) |
| *A61P 35/00* | (2006.01) |
| *C07D 307/20* | (2006.01) |

(52) U.S. Cl.
CPC .......... *C07D 493/22* (2013.01); *A61P 35/00* (2018.01); *A61P 35/04* (2018.01); *C07D 307/20* (2013.01); *C07D 407/06* (2013.01); *C07D 407/14* (2013.01); *C07D 493/04* (2013.01); *C07D 519/00* (2013.01); *Y02P 20/582* (2015.11)

(58) Field of Classification Search
CPC .................................................. C07D 493/22
USPC ....................................................... 514/456
See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 5,786,492 A | 7/1998 | Gravalos et al. | |
| 6,214,865 B1 | 4/2001 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,097,648 B2 | 1/2012 | Littlefield et al. | |
| 8,203,010 B2 | 6/2012 | Endo et al. | |
| 8,350,067 B2 | 1/2013 | Endo et al. | |
| 8,445,701 B2 | 5/2013 | Austad et al. | |
| 8,598,373 B2 | 12/2013 | Hu | |
| 8,618,313 B2 | 12/2013 | Benayoud et al. | |
| 8,884,031 B2 | 11/2014 | Chase et al. | |
| RE45,324 E | 1/2015 | Austad et al. | |
| 8,927,597 B2 | 1/2015 | Endo et al. | |
| 8,975,422 B2 | 3/2015 | Fang et al. | |
| 8,987,479 B2 | 3/2015 | Chase et al. | |
| 9,206,194 B2 | 12/2015 | Hu | |
| 9,278,979 B2 | 3/2016 | Souza et al. | |
| 9,303,039 B2 | 4/2016 | Zhang et al. | |
| 9,303,050 B2 | 4/2016 | Benayoud et al. | |
| 9,382,262 B2 | 7/2016 | Endo et al. | |
| 9,469,651 B2 | 10/2016 | Hu | |
| 9,938,288 B1 | 4/2018 | Kishi et al. | |
| 2004/0198806 A1 | 10/2004 | Eisai et al. | |
| 2006/0104984 A1 | 5/2006 | Littlefield et al. | |
| 2006/0154312 A1 | 7/2006 | Agoulnik et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2010/0254996 A1 | 10/2010 | Brantley-Sieders et al. | |
| 2011/0054194 A1 | 3/2011 | Hu et al. | |
| 2011/0184190 A1 | 7/2011 | Endo et al. | |

(Continued)

FOREIGN PATENT DOCUMENTS

| | | |
|---|---|---|
| JP | 6-122687 | 5/1994 |
| JP | 6-279450 | 10/1994 |

(Continued)

OTHER PUBLICATIONS

US 9,029,573 B2, 05/2015, Hu (withdrawn)
U.S. Appl. No. 15/322,756, filed Dec. 29, 2016, Kishi et al.
U.S. Appl. No. 15/570,593, filed Oct. 30, 2017, Kishi et al.
U.S. Appl. No. 15/814,105, filed Nov. 15, 2017, Kishi et al.
PCT/US2015/038439, Sep. 29, 2015, International Search Report and Written Opinion.
PCT/US2015/038439, Jan. 12, 2017, International Preliminary Report on Patentability.

(Continued)

*Primary Examiner* — Kahsay Habte

(74) *Attorney, Agent, or Firm* — Wolf, Greenfield & Sacks, P.C.

(57) ABSTRACT

Provided herein are palladium-mediated coupling reactions useful in the preparation of ketone-containing organic molecules. The provided methods can be used for the preparation of natural products and pharmaceutical agents, including Eribulin, halichondrins, and analogs thereof. The present invention also provides novel halichondrin analogs which can be prepared via the palladium-mediated coupling reactions. The novel halichondrin analogs can be used in the prevention and/or treatment of diseases or conditions (e.g., proliferative diseases such as cancer).

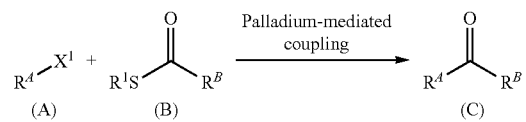

37 Claims, 17 Drawing Sheets

(56) References Cited

U.S. PATENT DOCUMENTS

| | | |
|---|---|---|
| 2013/0336974 A1 | 12/2013 | Collier et al. |
| 2014/0198806 A1 | 7/2014 | Pani et al. |
| 2017/0137437 A1 | 5/2017 | Kishi et al. |
| 2018/0230164 A1 | 8/2018 | Kishi et al. |

FOREIGN PATENT DOCUMENTS

| | | |
|---|---|---|
| JP | 6-279451 A | 10/1994 |
| JP | 2003-261447 A | 9/2003 |
| WO | WO 1993/017690 A1 | 9/1993 |
| WO | WO 1999/065894 A1 | 12/1999 |
| WO | WO 2005/118565 A1 | 12/2005 |
| WO | WO 2006/076100 A2 | 7/2006 |
| WO | WO 2007/139149 A1 | 12/2007 |
| WO | WO 2009/046308 A1 | 4/2009 |
| WO | WO 2009/064029 A1 | 5/2009 |
| WO | WO 2009/124237 A1 | 10/2009 |
| WO | WO 2011/094339 A1 | 8/2011 |
| WO | WO 2012/147900 A1 | 11/2012 |
| WO | WO 2013/097042 A1 | 4/2013 |
| WO | WO 2013/086634 A1 | 6/2013 |
| WO | WO 2013/142999 A1 | 10/2013 |
| WO | WO 2015/000070 A1 | 1/2015 |
| WO | WO 2015/066729 A1 | 5/2015 |
| WO | WO 2015/085193 A1 | 6/2015 |
| WO | WO 2016/003975 A1 | 1/2016 |
| WO | WO 2016/038624 A1 | 3/2016 |
| WO | WO 2016/176560 A1 | 11/2016 |
| WO | WO 2016/179607 A1 | 11/2016 |

OTHER PUBLICATIONS

EP 15814059.0, Nov. 24, 2017, Extended European Search Report.
PCT/US2016/030064, Nov. 9, 2017, International Preliminary Report on Patentability.
PCT/US2016/030064, Aug. 8, 2016 International Search Report and Written Opinion.
International Search Report and Written Opinion for PCT/US2018/025887, dated Jun. 21, 2018.
International Search Report and Written Opinion for PCT/US2018/031765, dated Jul. 2, 2018.
Invitation to Pay Additional Fees for PCT/US2018/041005, dated Sep. 14, 2018.
[No Author Listed] American Chemical Society. STN Database. Apr. 11, 2014. RN # 1583253-64-8.
Hickford et al., Antitumour polyether macrolides: four new halichondrins from the New Zealand deep-water marine sponge Lissodendoryx sp. Bioorg Med Chem. Mar. 15, 2009;17(6):2199-203. doi: 10.1016/j.bmc.2008.10.093. Epub Nov. 19, 2008.
Jackson et al., A total synthesis of norhalichondrin B. Angew Chem Int Ed Engl. 2009;48(13):2346-50. doi: 10.1002/anie.200806111.
Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.
Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.
Narayan et al., Novel second generation analogs of eribulin. Part II: Orally available and active against resistant tumors in vivo. Bioorg Med Chem Lett, Mar. 15, 2011;21(6):1634-8.
Narayan et al., Novel second generation analogs of eribulin. Part III: Blood-brain barrier permeability and in vivo activity in a brain tumor model. Bioorg Med Chem Lett, Mar. 15, 2011;21(6):1639-43.
Seletsky et al., Structurally simplified macrolactone analogues of halichondrin B. Bioorg Med Chem Lett, Nov. 15, 2004;14(22):5547-50.
Stamos et al., Synthetic studies on halichondrins: A practical synthesis of the C.1☐C.13 segment. Tetrahedron Letters Nov. 25, 1996;37(48):8643-8646.
Wang et al., Structure-activity relationships of Halichondrin B analogues: modifications at C.30-C.38. Bioorg Med Chem Lett, May 15, 2000;10(10):1029-32.
Xie et al., Synthesis of the C20-C26 Building Block of Halichondrins via a Regiospecific and Stereoselective SN2' Reaction. Org. Lett., 2002;4(25):4427-4429.DOI: 10.1021/o1026982p.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
[No Author Listed] Application for Product Designation Under the SAKIGAKE Designation System. Generic name E7130. Eisai Co., Ltd. Nov. 22, 2017.
[No Author Listed] Evidentiary Document for Applicability of E7130 to Designation Requirements. Eisai Co., Ltd. Nov. 22, 2017.
[No Author Listed] Overview Relating to the Suitability for Designation Requirements Under the SAKIGAKE Designation System. Generic name E7130. Eisai Co., Ltd.
Aicher et al., Synthetic studies towards halichondrins. Tetrahedron Lett. 1987;28(30):3463-66.
Aicher et al., Synthetic Studies towards Halichondrins: Synthesis of the C.27-C.38 Segment. Tetrahedron Lett. 1992;33(12):1549-52.
Aicher et al., Total synthesis of halichondrin B and norhalichondrin B. J. Am. Chem. Soc., 1992, 114 (8), pp. 3162-3164.
Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.
Berge et al., Pharmaceutical Salts. J. Pharmaceutical Sciences 1977;66(1):1-19.
Bringans, Studies on natural product derivatives : HIV therapies incorporating marine natural products. Dissertation. University of Canterbury, 2001.
Buszek et al., Synthetic Studies Towards Halichondrins: Synthesis of the Left Half of Halichondrins. Tetrahedron Lett. 1992;33:1553.
Chen et al., Ni(II)/Cr(II)-mediated coupling reaction: an asymmetric process. J. Org. Chem., 1995, 60 (17), pp. 5386-5387.
Cherney et al., Catalytic Asymmetric Reductive Acyl Cross-Coupling: Synthesis of Enantioenriched Acyclic α,α-Disubstituted Ketones. J. Am. Chem. Soc., 2013, 135 (20), pp. 7442-7445. doi: 10.1021/ja402922w.
Cherney et al., Pd-catalyzed Fukuyama cross-coupling of secondary organozinc reagents for the direct synthesis of unsymmetrical ketones. Tetrahedron 2014;70(20):3259-65.
Choi et al., Asymmetric Ni(II)/Cr(II)-Mediated Coupling Reaction: Catalytic Process. Org. Lett., 2002, 4 (25), pp. 4435-4438. doi: 10.1021/ol026981x.
Choi et al., Synthetic studies on the marine natural product halichondrins. Pure Appl. Chem., 2003, vol. 75, No. 1, pp. 1-17.
Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.
Fang et al., Synthetic Studies Towards Halichondrins: Synthesis of the Left Halves of Norhalichondrins and Homohalichondrins. Tetrahedron Lett. 1992;33(12):1557-60.
Fukuyama et al., Application of a Rotor—Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.
Fukuyama et al., Application of Continuous Flow for DIBAL-H Reduction and n-BuLi Mediated Coupling Reaction in the Synthesis

(56) References Cited

OTHER PUBLICATIONS of Eribulin Mesylate. Org. Process Res. Dev., 2016, 20 (2), pp. 503-509. doi: 10.1021/acs.oprd.5b00353.

Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.

Hirata et al., Halichondrins—antitumor polyether macrolides from a marine sponge. Pure Appl. Chem., 1986, vol. 58, No. 5, pp. 701-710.

Kaburagi et al., Effective procedure for selective ammonolysis of monosubstituted oxiranes: application to E7389 synthesis. Tetrahedron Lett. 2007;48(51):8967-71.

Kim et al., New syntheses of E7389 C14-C35 and halichondrin C14-C38 building blocks: double-inversion approach. J Am Chem Soc. Nov. 4, 2009;131(43):15636-41. doi: 10.1021/j a9058475.

Kress et al., Investigations of the intramolecular Ni(II)/Cr(II)-mediated coupling reaction: Application to the taxane ring system. Tetrahedron Letters 1993;34(38);6003-6.

Lee et al., One-Pot Ketone Synthesis with Alkylzinc Halides Prepared from Alkyl Halides via a Single Electron Transfer (SET) Process: New Extension of Fukuyama Ketone Synthesis. J. Am. Chem. Soc., 2016, 138 (22), pp. 7178-7186. doi: 10.1021/jacs.6b03897.

Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.

Lill, Studies on New Zealand marine natural products. Dissertation. University of Canterbury, 1999.

Liu et al., Catalytic enantioselective Cr-mediated propargylation: application to halichondrin synthesis. Org Lett. Oct. 15, 2009;11(20):4520-3. doi: 10.1021/ol9016595.

Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.

Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/ol300672q.

Mori et al., A Practical Synthesis of Multifunctional Ketones through the Fukuyama Coupling Reaction. Adv. Synth. Catal. 2007;349(11-12);2027.

Namba et al., New catalytic cycle for couplings of aldehydes with organochromium reagents. Org Lett. Dec. 23, 2004;6(26):5031-3.

Shan et al., Concise and Highly Stereoselective Synthesis of the C20-C26 Building Block of Halichondrins and Eribulin. Org. Lett., 2012, 14 (2), pp. 660-663. doi: 10.1021/ol203373d.

Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.

Tokuyama et al., A novel ketone synthesis by a palladium-catalyzed reaction of thiol esters and organozinc reagents. Tetrahedron Lett. 1998;39(20):3189-92.

Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.

Uemura et al., Norhalichondrin A: an antitumor polyether macrolide from a marine sponge. J. Am. Chem. Soc., 1985, 107 (16), pp. 4796-4798. doi: 10.1021/ja00302a042.

Uemura, Exploratory research on bioactive natural products with a focus on biological phenomena. Proc Jpn Acad Ser B Phys Biol Sci. 2010;86(3):190-201.

Wan et al., Asymmetric Ni(II)/Cr(II)-mediated coupling reaction: stoichiometric process. Org Lett. Dec. 12, 2002;4(25):4431-4.

Wotal et al., Stoichiometric Reactions of Acylnickel(II) Complexes with Electrophiles and the Catalytic Synthesis of Ketones. Organometallics, 2014, 33 (20), pp. 5874-5881. doi: 10.1021/om5004682.

Wotal et al., Synthesis of Functionalized Dialkyl Ketones from Carboxylic Acid Derivatives and Alkyl Halides. Org. Lett., 2012, 14 (6), pp. 1476-1479. doi: 10.1021/ol300217x.

Yamamoto et al., Total synthesis of halichondrin C. J Am Chem Soc. Jan. 18, 2012;134(2):893-6. doi: 10.1021/ja2108307. Epub Dec. 23, 2011.

Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.

Zheng et al., Macrocyclic ketone analogues of halichondrin B. Bioorg Med Chem Lett. Nov. 15, 2004;14(22):5551-4.

Halichondrin-B Series
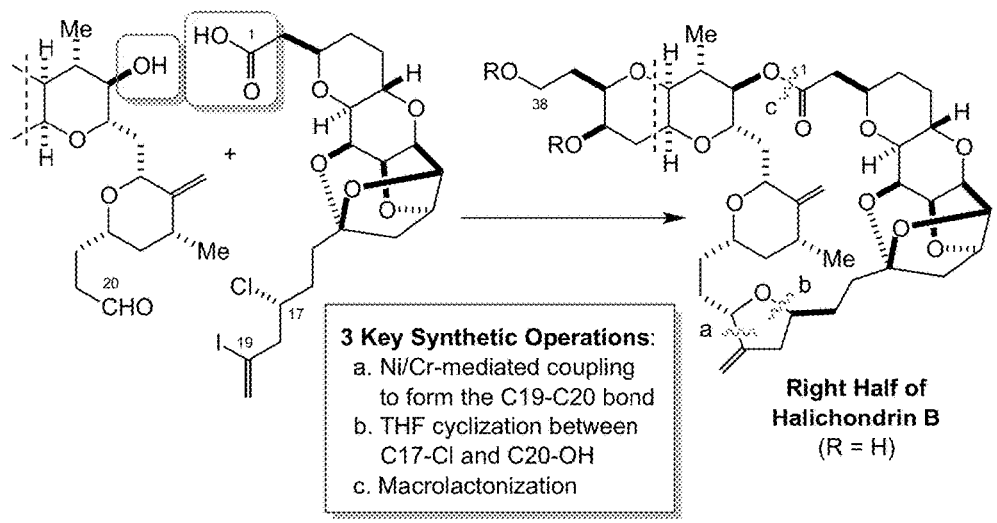
Eribulin Series
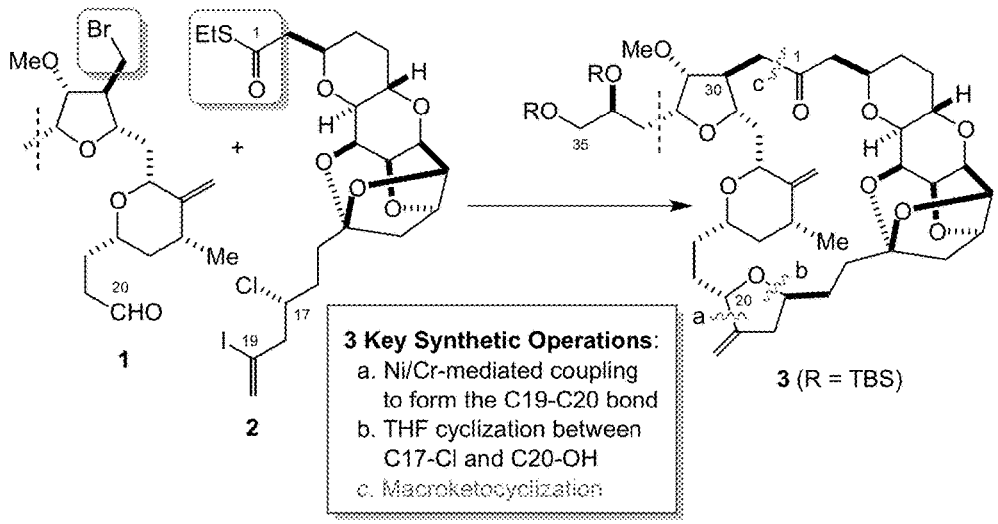
Figure 2

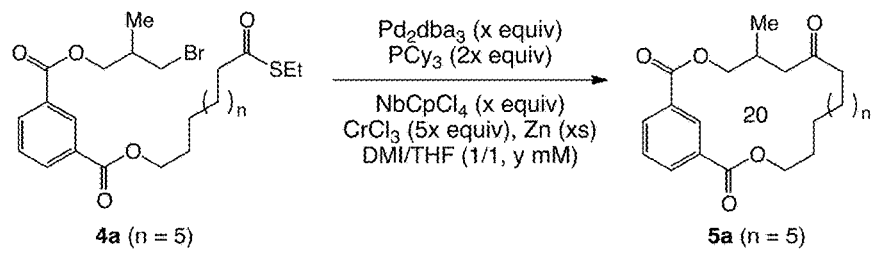

| entry | conditions (equiv) | Yield (%)[b] |
|---|---|---|
| 1[c] | LiI (1), CrCl$_2$ (0.5), NbCpCl$_4$ (0.1), TESCl (1.5), 50 mM | <10[d] |
| 2 | LiI (10), CrCl$_2$ (5), NbCpCl$_4$ (1), TESCl (1.5), 10 mM | 40 |
| 3[e] | CrCl$_2$ (5), NbCpCl$_4$ (1), 10 mM | 45[f] |
| 4 | LiI (10), CrCl$_2$ (5), TESCl (1.5), 10 mM | <5[d] |
| 5 | LiI (10), NbCpCl$_4$ (1), TESCl (1.5), 10 mM | <5[d] |
| 6 | CrCl$_2$ (5), NbCpCl$_4$ (0.7), TESCl (1.5), 10 mM | 25 |
| 7 | CrCl$_2$ (5), NbCpCl$_4$ (1), 15 mM | 35[g] |
| 8 | CrCl$_2$ (5), NbCpCl$_4$ (1), 7 mM | 25[h] |
| 9 | CrCl$_3$ (5), NbCpCl$_4$ (1), 10 mM | 50[f] |
| 10 | CrCl$_3$ (5), NbCpCl$_4$ (1), 5 mM | 50[f] |
| 11 | CrCl$_3$ (5), NbCpCl$_4$ (1), 2.5 mM | 40[h] |

Figure 3

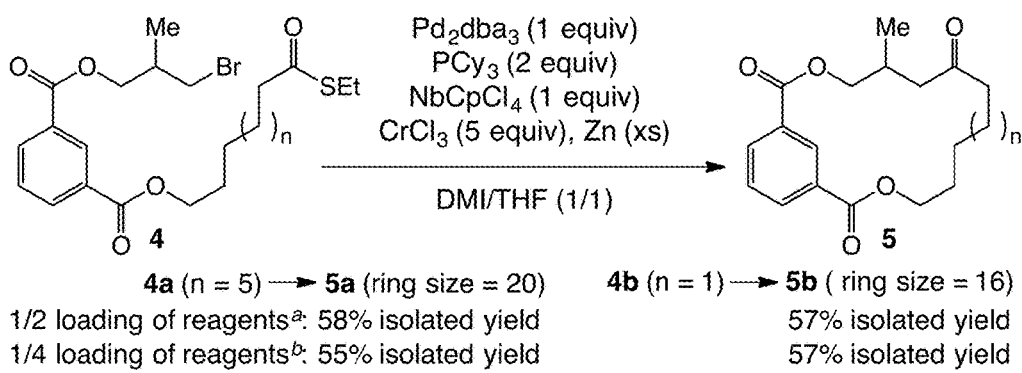

4a (n = 5) → 5a (ring size = 20)          4b (n = 1) → 5b (ring size = 16)
1/2 loading of reagents[a]: 58% isolated yield          57% isolated yield
1/4 loading of reagents[b]: 55% isolated yield          57% isolated yield
1/8 loading of reagents[b]: 55% isolated yield          57% isolated yield

Figure 4

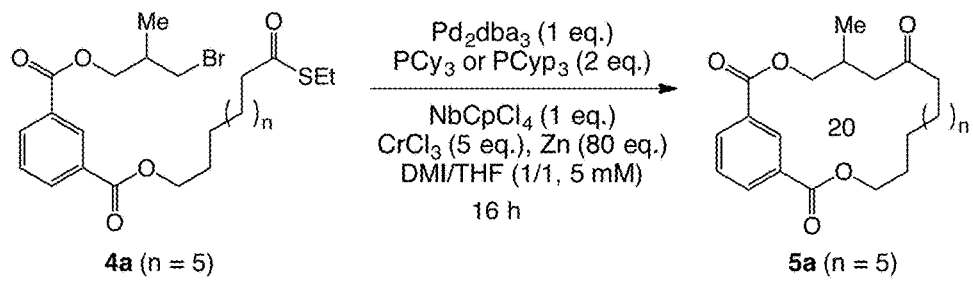

| Entry | conditions (eq.) | Yield (%)[b] |
|---|---|---|
| 1[c] | LiI (1), CrCl₂ (0.5), NbCpCl₄ (0.1), Zn (20), TESCl (1.5), 50 mM | <10 |
| 2 | LiI (1), CrCl₃ (0.5), NbCpCl₄ (0.1), Zn (20), TESCl (1.5), 50 mM | 15 |
| 3 | LiI (10), CrCl₂ (5), NbCpCl₄ (1), Zn (80), TESCl (1.5), 10 mM | 40 |
| 4 | LiI (10), CrCl₂ (5), Zn (80), TESCl (1.5), 10 mM | <5[d] |
| 5 | LiI (10), NbCpCl₄ (1), Zn (80), TESCl (1.5), 10 mM | <5[d] |
| 6[e] | CrCl₂ (5), NbCpCl₄ (0.5), Zn (80), TESCl (1.5), 10 mM | 25 |
| 7 | CrCl₂ (5), CoPc (1), Zn (80), 10 mM | 40 |
| 8 | CrCl₂ (5), NbCpCl₄ (1), Zn (80), 10 mM | 45[f] |
| 9 | CrCl₂ (5), NbCpCl₄ (0.7), Zn (80), TESCl (1.5), 10 mM | 25 |
| 10 | CrCl₂ (5), NbCpCl₄ (1.2), Zn (80), 10 mM | 40 |
| 11 | CrCl₂ (5), NbCpCl₄ (1), Zn (40), 10 mM | 40 |
| 12 | CrCl₂ (5), NbCpCl₄ (1), Zn (20), 10 mM | 40 |
| 13 | CrCl₂ (5), NbCpCl₄ (1), Zn (80), 15 mM | 35[g] |
| 14 | CrCl₂ (5), NbCpCl₄ (1), Zn (80), 7 mM | 25[h] |
| 15 | CrBr₃ (5), NbCpCl₄ (1), Zn (80), 10 mM | 45[f] |
| 16 | CrCl₃ (5), NbCpCl₄ (1), Zn (80), 10 mM | 50[f] |
| 17 | CrCl₃ (5), NbCpCl₄ (1), Zn (80), 7 mM | 50[f] |
| 18 | CrCl₃ (5), NbCpCl₄ (1), Zn (80), 5 mM | 55[f] |
| 19 | CrCl₃ (5), NbCpCl₄ (1), Zn (80), 2.5 mM | 40[h] |
| 20 | CrCl₃ (5), NbCpCl₄ (1), Zn (80), 1.4 mM | <10[h] |

Figure 7

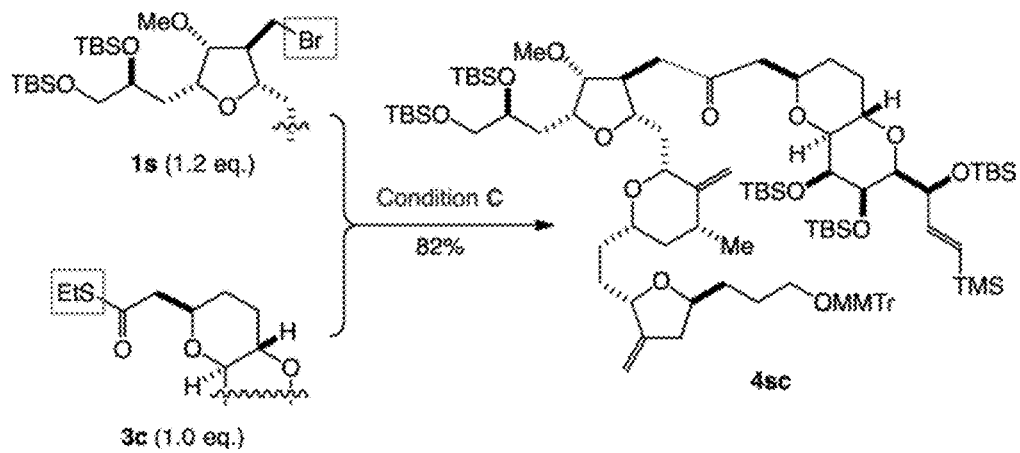
Figure 8
Weinreb Ketone Synthesis
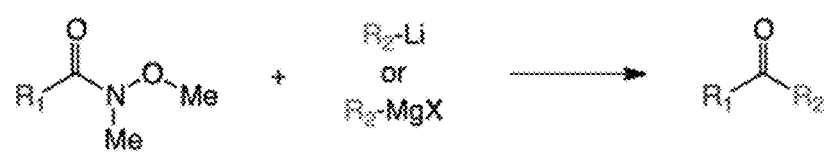
Fukuyama Ketone Synthesis
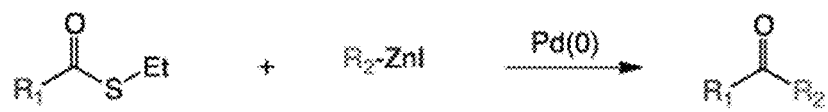
Figure 9

| entry | R¹ | R² | X | solvent | additive (equiv) | RH/RBr/RI[b] |
|---|---|---|---|---|---|---|
| 1 | H | H | Br | THF | LiI (1.0) | 3/1/0 |
| 2 | H | H | Br | DMI[c] | LiI (1.0) | 1/0/0 |
| 3 | H | H | Br | DMI | LiBr (1.0) | 1/9/0 |
| 4 | H | H | Br | DMI | LiCl (1.0) | 0/1/0 |
| 5 | H | Me | Br | DMI[d] | LiI (1.0) | 1/0/0 |
| 6 | H | Me | Br | DMI | LiI (0.5) | 1/60/10 |
| 7 | H | Me | I | DMI | none | 1/0/18 |
| 8 | H | Me | Cl | DMI | LiI (1.0) | NR |
| 9 | H | Me | Br | DMI | LiI (0.5)/ TESCl (1.5) | 6/1/0 |
| 10 | H | Me | Br | DMI | CoPc (0.1) | 1/0/0 |
| 11 | H | Me | Br | DMI | NbCpCl₄ (0.1) | 8/1/0 |
| 12 | Me | H | Br | DMI | LiI (1.0) | 1/1/0 |
| 13 | Me | H | I | DMI | LiI (0.5) | 1/0/0 |
| 14 | Me | H | Br | DMI | CoPc (0.1) | 1/0/0 |
| 15 | Me | H | Br | DMI | NbCpCl₄ (0.1) | 1/0/0 |

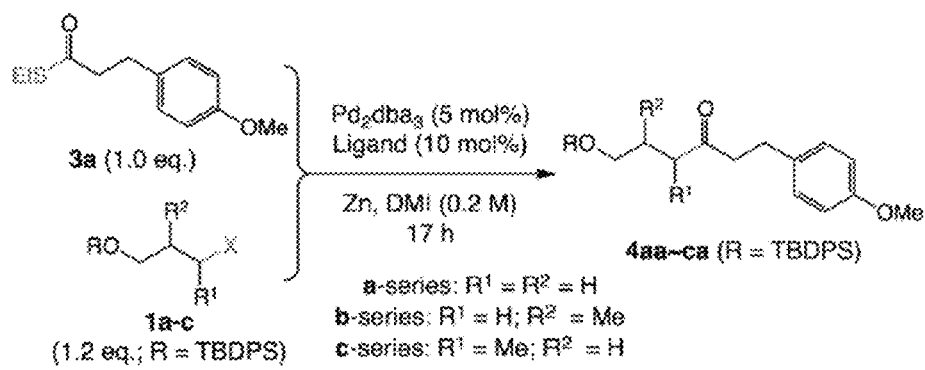

| entry | R¹ | R² | X | ligand | additives (equiv) | 4/3[b] |
|---|---|---|---|---|---|---|
| 1 | H | H | Br | PPh₃ | LiI (1.0) | 1/2.5 |
| 2 | H | H | Br | PPh₃ | LiI (1.0)/TESCl (1.5) | 1.5/1 |
| 3 | H | H | Br | PCy₃ | LiI (1.0)/TESCl (1.5) | 4.3/1 |
| 4 | H | Me | Br | PCy₃ | LiI (1.0)/TESCl (1.5) | 1.1/1 |
| 5[c] | H | Me | Br | PCy₃ | LiI (1.0)/TESCl (1.5)/ CrCl₂ (0.25) | 3/1 |
| 6 | H | Me | Br | PCy₃ | CoPc (0.05)/TESCl (1.5) | 0/1[d] |
| 7 | H | Me | Br | PCy₃ | CoPc (0.05)/TESCl (1.5)/ CrCl₂ (0.25) | 1/15[e] |
| 8 | H | Me | Br | PCy₃ | NbCpCl₄ (0.05)/ TESCl (1.5) | 0/1[d] |
| 9 | H | Me | Br | PCy₃ | NbCpCl₄ (0.05)/ TESCl (1.5)/CrCl₂ (0.25) | 5/1 |
| 10 | H | Me | I | PCy₃ | LiI (0.6)/TESCl (1.5) | 2.6/1 |
| 11 | H | Me | I | PCy₃ | LiI (0.6)/TESCl (1.5)/ CrCl₂ (0.25) | 10/1 |
| 12 | Me | H | I | PCy₃ | LiI (1.0)/TESCl (1.5) | 1.8/1[f] |
| 13 | Me | H | I | PCy₃ | LiI (1.0)/TESCl (1.5)/ CrCl₂ (0.25) | 1/1.3 |
| 14 | Me | H | I | PCy₃ | NbCpCl₄ (0.02)/ TESCl (1.5) | 1/1 |
| 15 | Me | H | I | PCy₃ | NbCpCl₄ (0.02)/ TESCl (1.5)/CrCl₂ (0.25) | 1/3.4 |

Figure 13

Alkylzinc halides prepared via direct zinc insertion: 1b + 3a → 4ba one-step (one-pot) procedure[b]:  95% isolated yield two-step procedure
   1st step: LiI, Zn followed by
   2nd step: CrCl$_2$, Pd$_2$dba$_3$, PCy$_3$  91% isolated yield

Alkylzinc halides prepared via a SET process: 1b + 3a → 4ba one-step (one-pot) procedure[c]:  96% isolated yield two-step procedure with CoPc: test #1
   1st step: CoPc, Zn followed by
   2nd step: CrCl$_3$, Pd$_2$dba$_3$, PCy$_3$, 3a  0% isolated yield
two-step procedure with CoPc: test #2
   1st step: CoPc, Zn, CrCl$_3$, followed by
   2nd step: Pd$_2$dba$_3$, PCy$_3$, 3a  85% isolated yield one-step (one-pot) procedure[d]:  95% isolated yield two-step procedure with NbCpCl$_4$: test #1
   1st step: NbCpCl$_4$, Zn followed by
   2nd step: CrCl$_2$, Pd$_2$dba$_3$, PCy$_3$, 3a  0% isolated yield
two-step procedure with NbCpCl$_4$: test #2
   1st step: NbCpCl$_4$, Zn, CrCl$_2$, followed by
   2nd step: Pd$_2$dba$_3$, PCy$_3$, 3a  95% isolated yield

Figure 15

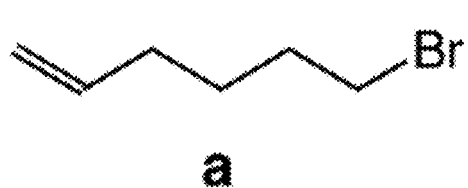
a

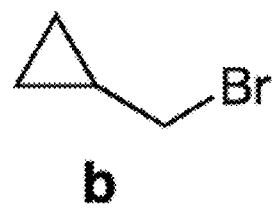
b

Figure 16

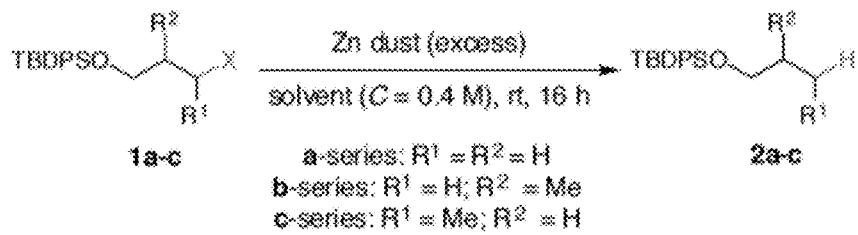

| Entry | R¹ | R² | X | solvent | additive (eq.) | RH/RBr/RI |
|---|---|---|---|---|---|---|
| 1 | H | H | Br | THF | LiI (1.0) | 3/1/0 |
| 2 | H | H | Br | DMI | LiI (1.0) | 1/0/0 |
| 3 | H | H | Br | DMA | LiI (1.0) | 1/0/0 |
| 4 | H | H | Br | NMP | LiI (1.0) | 1/0/0 |
| 5 | H | H | Br | DMI | LiBr (1.0) | 1/9/0 |
| 6 | H | H | Br | DMI | LiCl (1.0) | 0/1/0 |
| 7 | H | Me | Br | DMI | LiI (1.0) | 1/0/0 |
| 8 | H | Me | Br | DMA | LiI (1.0) | 0/5/1 |
| 9 | H | Me | Br | NMP | LiI (1.0) | 0/10/1 |
| 10 | H | Me | Br | DMI | LiI (0.5) | 1/60/10 |
| 11 | H | Me | Br | DMI | I₂ (0.05) | NR |
| 12 | H | Me | I | DMI | none | 1/0/18 |
| 13 | H | Me | Cl | DMI | LiI (1.0) | NR |
| 14 | H | Me | Br | DMI | LiI (0.5)/TESCl (1.5) | 6/1/0 |
| 15 | H | Me | Br | DMI | CoPc (0.1) | 1/0/0 |
| 16 | H | Me | Br | DMI | NbCpCl₄ (0.1) | 8/1/0 |
| 17 | Me | H | Br | DMI | LiI (1.0) | 1/1/0 |
| 18 | Me | H | I | DMI | LiI (0.5) | 1/0/0 |
| 19 | Me | H | Br | DMI | CoPc (0.1) | 1/0/0 |
| 20 | Me | H | Br | DMI | NbCpCl₄ (0.1) | 1/0/0 |

Figure 19

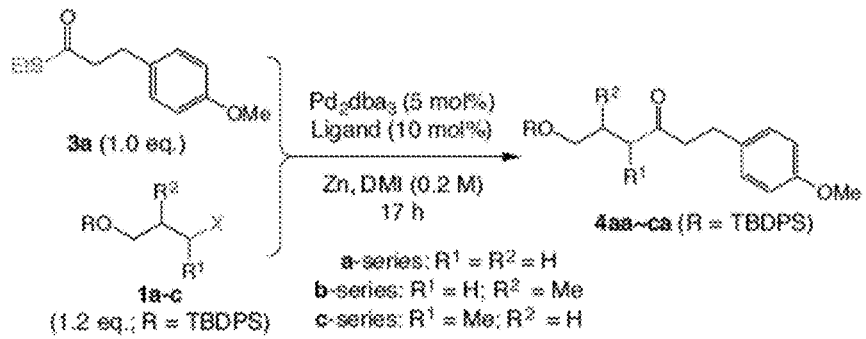

| Entry | R¹ | R² | X | Ligand (mol%) | additives (eq.) | 4/3[b] |
|---|---|---|---|---|---|---|
| 1 | H | H | Br | PPh₃ (10) | LiI (1.0) | 1/2.5 |
| 2 | H | H | Br | PPh₃ (10) | LiI (1.0)/TESCl (1.5) | 1.5/1 |
| 3 | H | H | Br | PCyp₃ (10) | LiI (1.0)/TESCl (1.5) | 2.8/1 |
| 4 | H | H | Br | PCy₃ (10) | LiI (1.0)/TESCl (1.5) | 4.3/1 |
| 5 | H | Me | Br | PCy₃ (10) | LiI (1.0)/TESCl (1.5) | 1.1/1 |
| 6 | H | Me | Br | PCy₃ (10) | LiI (1.5)/TESCl (1.5) | 1.2/1 |
| 7 | H | Me | Br | PCy₃ (10) | LiI (0.5)/TESCl (1.5) | 1.1/1 |
| 8 | H | Me | Br | PCy₃ (10) | LiI (0.25)/TESCl (1.5) | 1/3 |
| 9[c] | H | Me | Br | PCy₃ (20) | LiI (1.0)/TESCl (1.5) | 1/2 |
| 10[d] | H | Me | Br | PCy₃ (10) | LiI (1.0)/CrCl₂ (0.25)/TESCl (1.5) | 3/1 |
| 11 | H | Me | Br | PCy₃ (10) | CoPc (0.05)/TESCl (1.5) | 0/1[e] |
| 12 | H | Me | Br | PCy₃ (10) | CoPc (0.05)/CrCl₂ (0.25)/TESCl (1.5) | 1/15[f] |
| 13 | H | Me | Br | PCy₃ (10) | NbCpCl₄ (0.05)/TESCl (1.5) | 0/1[e] |
| 14 | H | Me | Br | PCy₃ (10) | NbCpCl₄ (0.05)/CrCl₂ (0.25)/TESCl (1.5) | 5/1 |
| 15 | H | Me | I | PCy₃ (10) | LiI (0.6)/TESCl (1.5) | 2.6/1 |
| 16 | H | Me | I | PCy₃ (10) | LiI (0.6)/CrCl₂ (0.25)/TESCl (1.5) | 10/1 |
| 17 | Me | H | Br | PCy₃ (10) | LiI (1.0)/TESCl (1.5) | 1/5 |
| 18 | Me | H | Br | PCy₃ (10) | NbCpCl₄ (0.05)/CrCl₂ (0.25)/TESCl (1.5) | 1/4 |
| 19 | Me | H | I | PCy₃ (10) | LiI (1.0)/TESCl (1.5) | 1.8/1 |
| 20 | Me | H | I | PCy₃ (10) | LiI (1.0)/CrCl₂ (0.25)/TESCl (1.5) | 1/1.3 |
| 21 | Me | H | I | PCy₃ (10) | NbCpCl₄ (0.02)/CrCl₂ (0.25)/TESCl (1.5) | 1/3.4 |
| 22 | Me | H | I | PCy₃ (10) | NbCpCl₄ (0.02)/TESCl (1.5) | 1/1 |
| 23 | Me | H | I | PCy₃ (10) | CoPc (0.02)/CrCl₂ (0.25)/TESCl (1.5) | 1/5 |
| 24 | Me | H | I | PCy₃ (10) | CoPc (0.02)/TESCl (1.5) | 1/1.2 |
| 25 | Me | H | I | PCy₃ (10) | LiI (1.0)/TESCl (1.5) | 2.3/1[g] |
| 26 | Me | H | I | PCy₃ (10) | LiI (1.0)/TESCl (1.5) | 1/0[h] |

Figure 20

PALLADIUM-MEDIATED KETOLIZATION

RELATED APPLICATIONS

This application claims priority under 35 U.S.C. § 119(e) to U.S. Provisional Patent Application, U.S. Ser. No. 62/420,785, filed Nov. 11, 2016, and claims priority under 35 U.S.C. § 119(a) to Japanese Patent Application No. 2016-221064, filed Nov. 11, 2016; the entire contents of each of which is incorporated herein by reference.

BACKGROUND OF THE INVENTION

The ketone is one of the most important functional groups in organic chemistry, as it not only is widely found in natural/man-made products, but also is a versatile synthetic intermediate to other functionalities. Over the past several decades, progress has been made to achieve a ketone synthesis with high selectivity and efficiency. The Weinreb amide is recognized as the method of choice for monoaddition of an organometallic reagent, i.e., organolithium or Grignard reagent, and the reliability and effectiveness of Weinreb ketone synthesis have been demonstrated for a wide range of substrates (FIG. 9) (see, e.g., Nahm et al., *Tetrahedron Lett.* 1981, 22, 3815). However, there are limitations in functional group tolerance with an organolithium or Grignard reagent. In that respect, work has been done to prepare Grignard reagents under mild conditions (see, e.g., Krasovskiy et al., *Angew. Chem., Int. Ed.* 2004, 43, 3333). In contrast, a transition-metal-catalyzed ketone synthesis, represented by Fukuyama ketone synthesis, has advantages, because it does not require a strongly basic and nucleophilic reagent (FIG. 9) (see, e.g., Dieter, *Tetrahedron* 1999, 55, 4177, Fiandanese et al., *Tetrahedron Lett.* 1983, 24, 3677, Cardellicchio et al., *Tetrahedron Lett.* 1985, 26, 3595, Bagheri et al., *Tetrahedron Lett.* 1983, 24, 5181, Wittenberg et al., *Org. Lett.* 2003, 5, 3033, Liebeskind et al., *J. Am. Chem. Soc.* 2000, 122, 11260, Li et al., *Org. Lett.* 2011, 13, 3682, Zhang et al., *J. Am. Chem. Soc.* 2004, 126, 15964, Tokuyama et al., *Tetrahedron Lett.* 1998, 39, 3189, Miyazaki et al., *Synlett* 2004, 2004, 477, Fukuyama et al., *Aldrichimica Acta* 2004, 37, 87, and Cherney et al., *Tetrahedron* 2014, 70, 3259). The effectiveness of Fukuyama ketone synthesis has been demonstrated for a variety of substrates, even in an industrial scale (see, e.g., Shimizu et al., *Tetrahedron Lett.* 2001, 42, 429 and Mori et al., *Adv. Synth. Catal.* 2007, 349, 2027). However, this method has been used for relatively small nucleophiles (often excess equivalents), thereby hinting at a potential issue in its use at a late stage in a multistep synthesis of complex molecules. In addition, preparation of an organometallic reagent is often cumbersome for complex substrates and their stability might become problematic during preparation.

Halichondrins are polyether macrolides, originally isolated from the marine sponge *Halichondria okadai* (see, e.g., Uemura et al., *J. Am. Chem. Soc.* 1985, 107, 4796 and Hirata et al., *Pure Appl. Chem.* 1986, 58, 701). This class of natural products displays interesting structure diversities on the oxidation state at C12 and C13, cf., halichondrin A-C in FIG. 1. Halichondrin B was chosen as a synthetic target and experimental work began, leading to the first total synthesis of halichondrin B in 1992. On completion of the synthesis (see, e.g., Aicher et al., *J. Am. Chem. Soc.* 1992, 114, 3162 and Ueda et al., *J. Am. Chem. Soc.* 2014, 136, 5171), the antitumor activities of the totally synthetic halichondrins were tested, along with several synthetic intermediates. The experiments clearly demonstrated that the antitumor activities of halichondrin B resided in the right portion of the molecule, which served as the foundation for successful development of the antitumor drug Halaven (Eribulin) (see, e.g., Zheng et al., *J. Bioorg. Med. Chem. Lett.* 2004, 14, 5551, Yu et al., *Anticancer Agents from Natural Products*; CRC Press: 2005, p 241, Yu et al., *Annu. Rep. Med. Chem.*; John, E. M., Ed.; Academic Press: 2011, Vol. 46, p 227, and Austad et al., *Synlett* 2013, 24, 333). The structure of Eribulin is shown below.

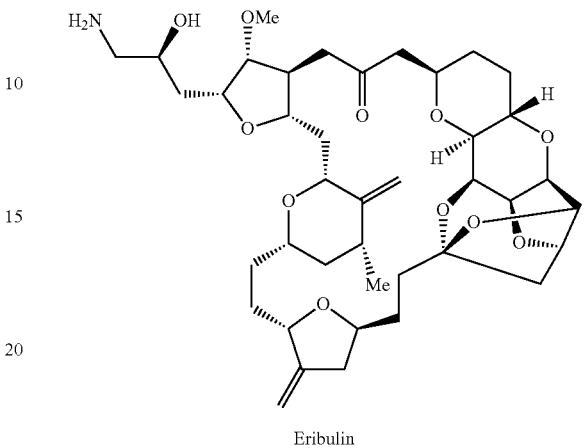

Eribulin

SUMMARY OF THE INVENTION

Provided herein are methods for the preparation of ketone-containing organic molecules based on a palladium-mediated coupling reaction (also referred to herein as "palladium-mediated ketolization"). As represented in Scheme 1, the palladium-mediated ketolization involves the coupling a compound of Formula (A) to a thioester of Formula (B), to yield a ketone of Formula (C).

Scheme 1

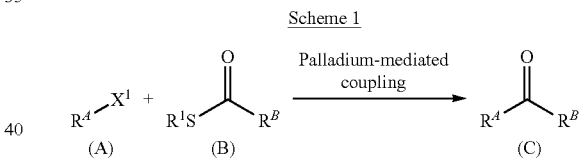

Both inter- and intra-molecular palladium-mediated ketolization reactions are provided herein. Intramolecular variants are useful for the preparation of cyclic ketones, including macrocyclic ketones (Scheme 3).

Scheme 3

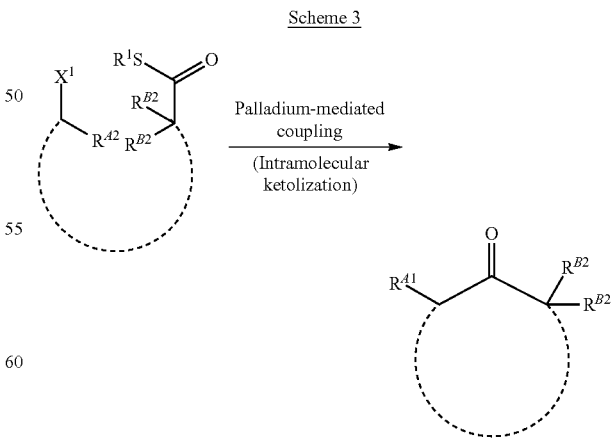

The palladium-mediated ketolization reactions provided herein are useful in the synthesis of complex molecules, including natural products, pharmaceutical agents, and intermediates in the synthesis thereof. In particular, provided herein are methods for the preparation of compounds useful as intermediates in the synthesis of Eribulin and analogs thereof. Scheme 4, Scheme 5, and Scheme 6 show intermolecular palladium-mediated ketolization reactions that furnish useful intermediates (e.g., compounds of Formulae (E-C-1), (E-C-2), (E-C-3)) en route to Eribulin and analogs thereof.

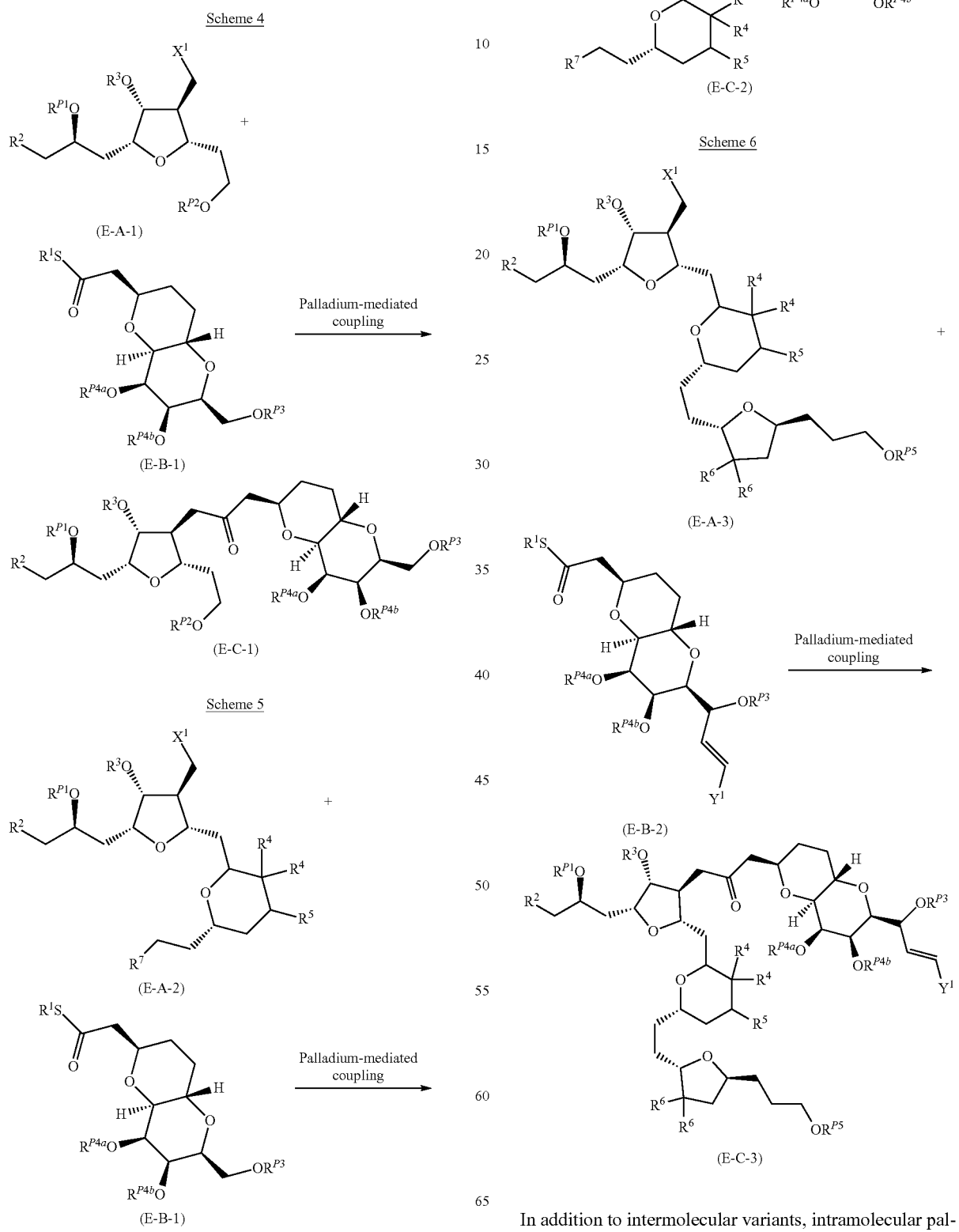

In addition to intermolecular variants, intramolecular palladium-mediated ketolization reactions provided herein are also useful in the preparation of Eribulin, and analogs thereof, and intermediates in the synthesis thereto. For example, Scheme 7 shows an intramolecular palladium-mediated ketolization reaction to form a compound of Formula (E-1). Compounds of Formula (E-1) are useful intermediates in the preparation of Eribulin and analogs thereof. All substituent groups are as defined herein.

The methods provided herein are also useful in the preparation of keto analogs of halichondrins (e.g., halichondrin A, B, C; homohalichondrin A, C, B, norhalichondrin A, B, C), including compounds of Formulae (H-1), (HH-1), and (NH-1). These keto analogs include a ketone where the halichondrins typically include a lactone ester (denoted by* in the formulae below).

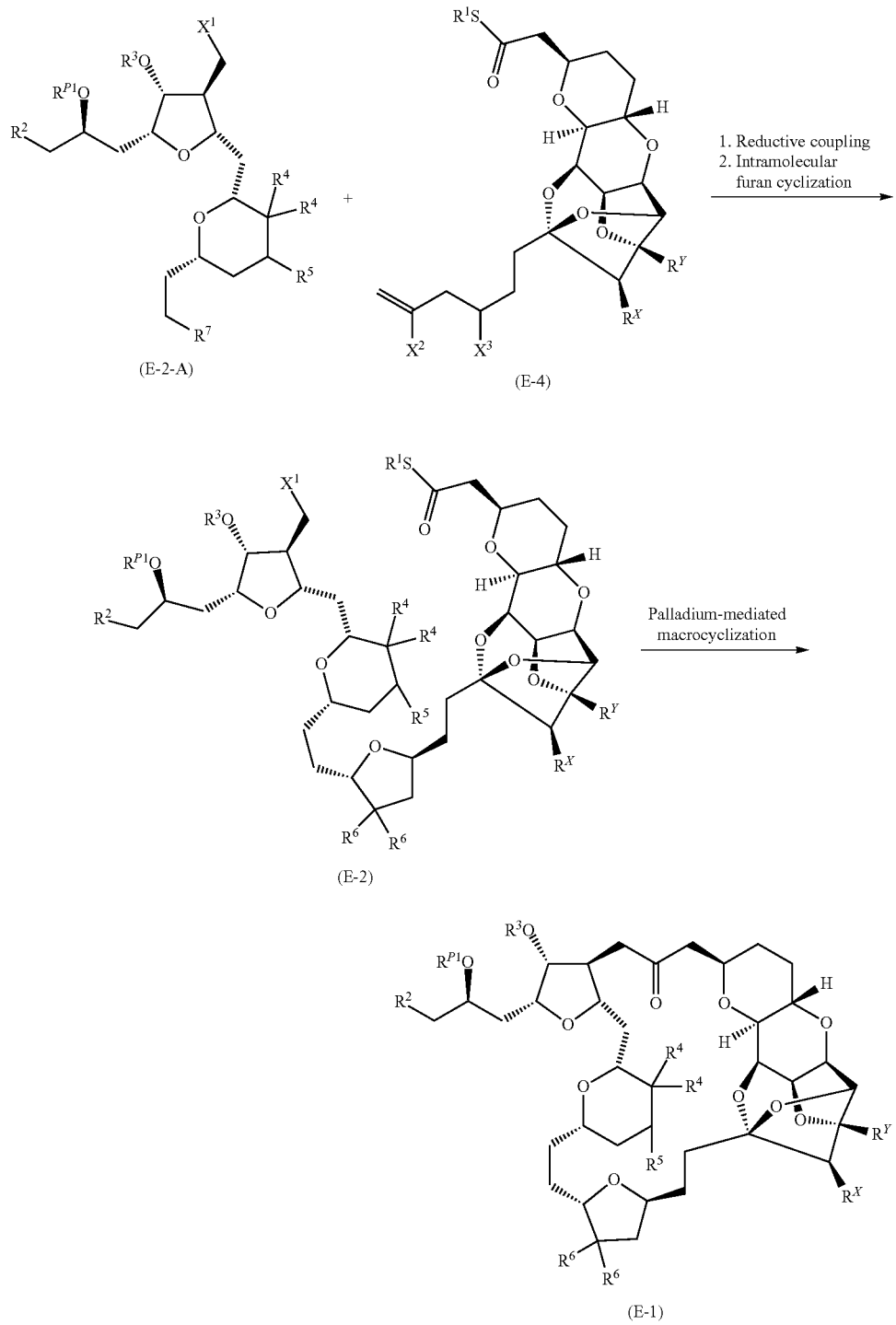

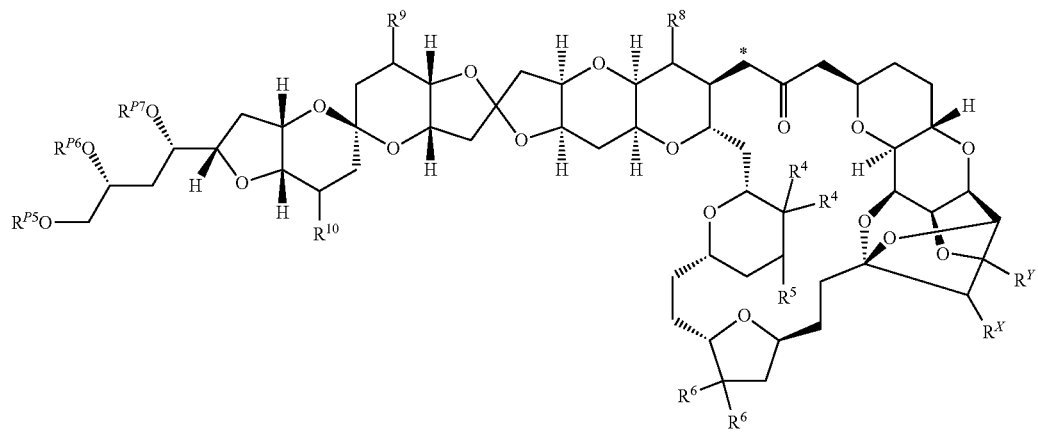

Keto analogs of halichondrin A, B, C

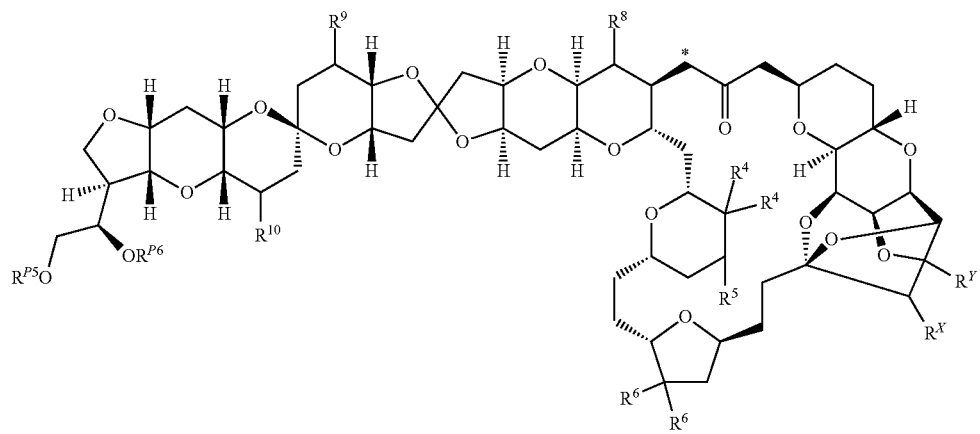

Keto analogs of homohalichondrin A, B, C

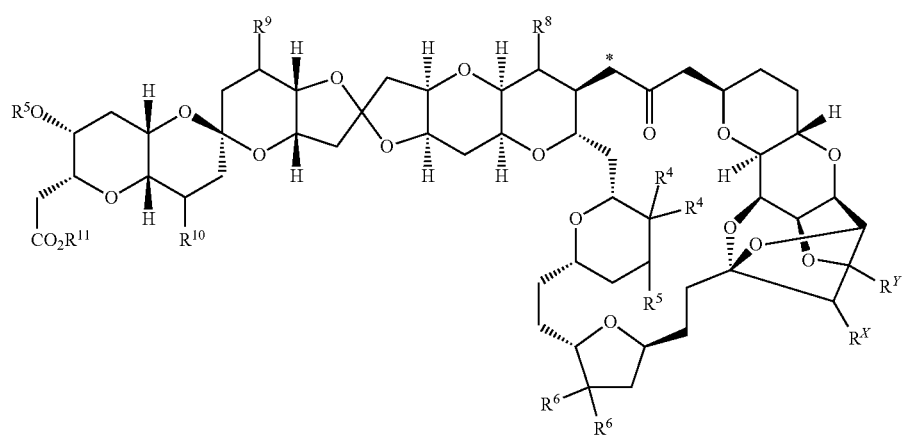

Keto analogs of norhalichondrin A, B, C

Compounds of Formula (H-2) are key intermediates in the synthesis of compounds of Formulae (H-1), (HH-1), and (NH-1), and can be prepared as shown in Scheme 8. A palladium-mediated ketolization provided herein can be used to convert a compound of Formula (H-3) to a compound of Formula (H-2).

Scheme 8

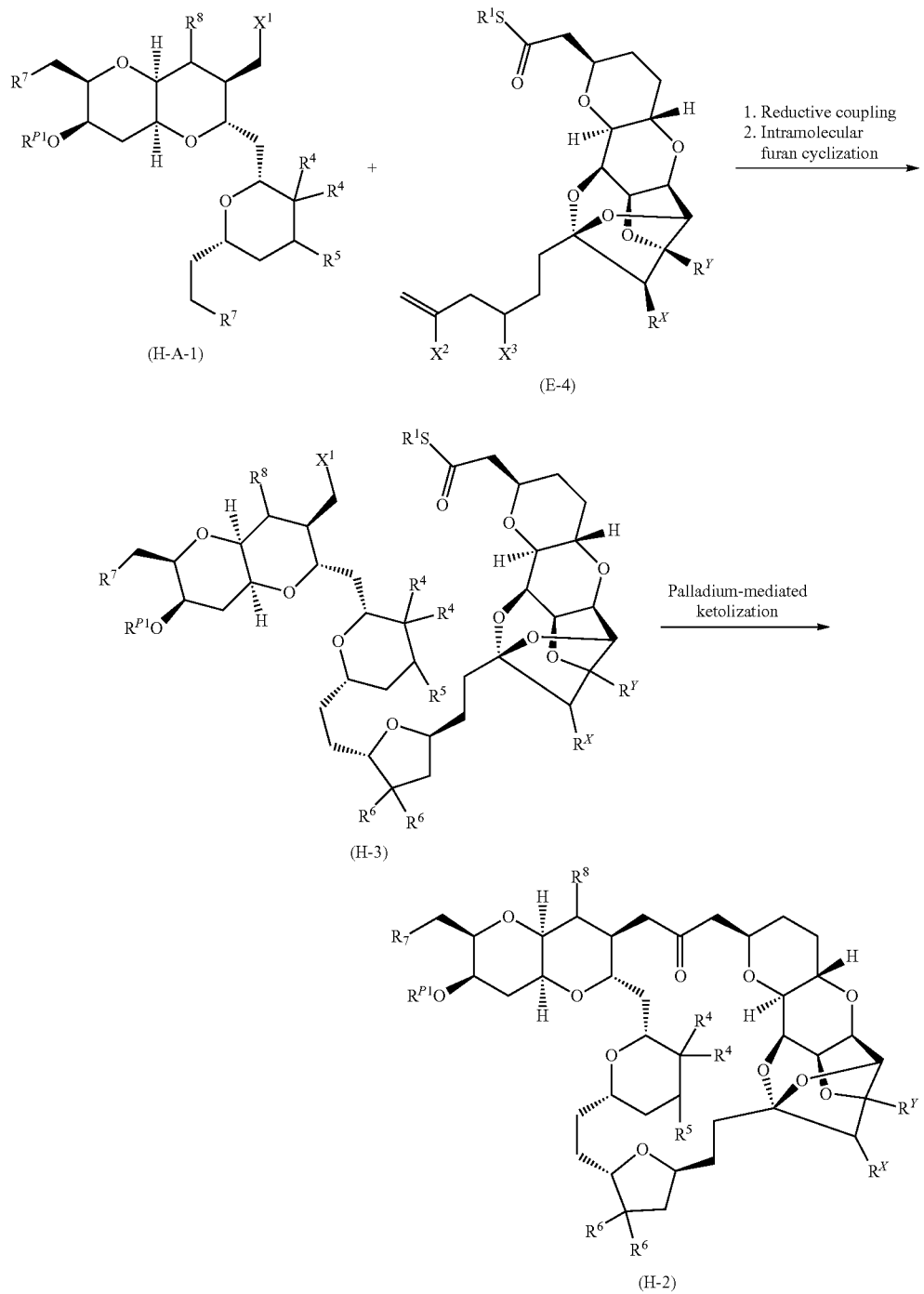

The present invention also provides pharmaceutical compositions comprising a compound of Formula (H-1), (HH-1), or (NH-1), or a pharmaceutically acceptable salt thereof. Also provided herein are uses of compounds of Formula (H-1), (HH-1), and (NH-1), or pharmaceutically acceptable salts thereof, or pharmaceutical compositions thereof, for the treatment of diseases and conditions (e.g., proliferative diseases). Additionally, provided herein are kits comprising a compound of Formula (H-1), (HH-1), or (NH-1), or a pharmaceutically acceptable salt thereof, or a pharmaceutical composition thereof.

Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as radiopharmaceuticals.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$, ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

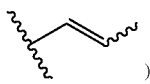
)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b] pyranyl, 5,7-dihydro-4H-thieno[2,3-c]pyranyl, 2,3-dihydro-1H-pyrrolo[2,3-b]pyridinyl, 2,3-dihydrofuro[2,3-b] pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 □ electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 □ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^{30}$ X$^-$, —P(R$^{cc}$)$_4$, —P(OR$^{cc}$)$_4$, —OP(R$^{cc}$)$_2$, —OP(R$^{cc}$)$_3$$^{30}$ X$^-$, —OP(OR$^{cc}$)$_2$, —OP(OR$^{cc}$)$_3$$^{30}$ X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$ X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3$$^+$X$^-$, —NH(C$_{1-6}$ alkyl)$_2$$^+$X$^-$, —NH$_2$(C$_{1-6}$ alkyl) $^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO2 (C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl), —C(=NH)NH(C$_{1-6}$ alkyl), —C(=NH)NH$_2$, —OC(=NH)N(C$_{1-6}$ alkyl), —OC(NH)NH(C$_{1-6}$ alkyl), —OC(NH)NH$_2$, —NHC(NH)N(C$_{1-6}$ alkyl), —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si (C$_{1-6}$ alkyl)$_3$, —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl), —P(=O)(C$_{1-6}$ alkyl), —OP(=O)(C$_{1-6}$ alkyl), —OP(=O)(OC$_{1-6}$ alkyl), C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, substituents include: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl), —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl), —C(=NH)NH(C$_{1-6}$ alkyl), —C(=NH)NH$_2$, —OC(=NH)N(C$_{1-6}$ alkyl), —OC(=NH)NH(C$_{1-6}$ alkyl), —OC(=NH)NH$_2$, —NHC(=NH)N(C$_{1-6}$ alkyl), —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$(C$_{1-6}$ alkyl), —SO$_2$O(C$_{1-6}$ alkyl), —SO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl), —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal hydrogens can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OS i(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N($R^{bb}$)$_2$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N($R^{bb}$)$_2$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

The term "sulfonyl" refers to a group selected from —SO$_2$N($R^{bb}$)$_2$, —SO$_2R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$), —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$_{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4$^1$,4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$, $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, $OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "salt" refers to ionic compounds that result from the neutralization reaction of an acid and a base. A salt is composed of one or more cations (positively charged ions) and one or more anions (negative ions) so that the salt is electrically neutral (without a net charge). The term "salt"

refers to any and all salts, and encompasses pharmaceutically acceptable salts. Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, acetate, sulfate, phosphate, nitrate, lower alkyl sulfonate, succinimide, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms. In certain embodiments, a catalyst in present in a reaction mixture at an amount less than 100 mol %. In certain embodiments, a catalyst in present in a reaction mixture at an amount between 0.1-1 mol %, 1-5 mol %, 5-10 mol %, 10-15 mol %, 15-20 mol %, 20-25 mol %, 25-30 mol %, 30-35 mol %, 35-40 mol %, 40-45 mol %, 45-50 mol %, 50-55 mol %, 55-60 mol %, 60-65 mol %, 65-70 mol %, 75-80 mol %, 80-85 mol %, 85-90 mol %, 90-95 mol %, or 95-99 mol %. In certain embodiments, the catalyst is present in approximately 1, 2, 3, 4, 5, 10, 15, 20, 25, 30, 35, 40, 45, 50, 55, 60, 65, 70, 75, 80, 85, 90, or 95 mol %.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, p-xylene.

These and other exemplary substituents are described in more detail in the Detailed Description, Examples, and Claims. The invention is not intended to be limited in any manner by the above exemplary listing of substituents.

BRIEF DESCRIPTION OF THE DRAWINGS

The accompanying drawings, which constitute a part of this specification, illustrate several embodiments of the invention and together with the description, serve to explain the principles of the invention.

FIG. 2 shows three key transformations employed in the unified convergent synthesis of halichondrins.

FIG. 3 shows various conditions for the macroketocyclization reaction. The conditions of this experiment were as follows: to $Pd_2dba_3$ (0.04 mmol) and $PCy_3$ (0.08 mmol) in DMI (2 mL) were added Zn (0) (xs), $CrCl_3$ (0.2 mmol), and $NbCpCl_4$ (0.04 mmol) at room temperature in a glove box. Then, if needed, LiI (0.4 mmol) and TESCl (0.06 mmol) were added to the reaction mixture followed by S.M. in THF (2 mL). [b]Roughly estimated yield based on a ratio of 5a to side products (debrominated RH and dimer) in a crude $^1H$ NMR. Also see FIG. 7 and Examples. [c]$Pd_2dba_3$ (0.1 equiv), $PCy_3$ (0.2 equiv) used. [d]RH was a major product. [e]Reduction of Zn (20-40 equiv) provided slightly lower yield. [f]Trace amount of RH. [g]Lower yield mainly due to dimer. [h]Lower yield mainly due to debromination, yet dimer-formation was not noticeably reduced. Abbreviations: DMI=1,3-dimethyl-2-imidazolinone; $NbCpCl_4$=tetrachloro(cyclopeantadienyl)niobium; $Pd_2dba_3$=tris(dibenzyli-deneacetone)dipalladium(0); $PCy_3$=tricyclohexylphosphine.

FIG. 4 shows the macroketocyclization reaction on a larger scale. The conditions of this experiment were as follows: to $Pd_2dba_3$ (0.1 mmol) and $PCy_3$ (0.2 mmol) in DMI/THF (10 mL/5 mL) were added $CrCl_3$ (0.5 mmol), Zn (xs), and $NbCpCl_4$ (0.5 mmol) at room temperature in a glove box. Then, substrate (0.1 mmol) in THF (2.5 mL) was added to the reaction mixture and stirred at room temperature. After 7 h, S.M (0.1 mmol) in THF (2.5 mL) was added and stirred overnight. [b]See Examples

FIG. 6A shows the comparison of conditions A, B, and C at 25 mM. FIG. 6B shows reactivity versus concentration under condition C.

FIG. 7 shows various conditions for macroketocyclization. The conditions for this experiment were as follows: to $Pd_2dba_3$ (0.04 mmol) and $PCy_3$ (0.08 mmol) in DMI (2 mL) were added Zn (0) (x equiv), $CrCl_3$ (0.2 mmol), and $NbCpCl_4$ (0.04 mmol) at room temperature in a glove box. Then, if needed, LiI (0.04 mmol) and TESCl (0.06 mmol) were added to the reaction mixture followed by S.M. in THF (2 mL). [b]Roughly estimated yield based on a ratio of 5a to side products (debrominated product and dimer) in a crude $^1H$ NMR. [c]$Pd_2dba_3$ (0.1 equiv), $PCy_3$ (0.2 equiv) used. Under catalytic conditions (C=50 mM and 25 mM), debrominated compound was a major product. [d]RH was major. [e]$Pd_2dba_3$ (0.5 equiv), $PCy_3$ (1.0 equiv) used. [f]Trace amount of RH. [g]Mainly, due to dimer. [h]Mainly, lower yield was obtained due to RH, yet dimer-formation was not noticeably reduced. Abbreviation: $NbCpCl_4$=tetrachloro(cyclopentadienyl)niobium(V); CoPc=Cobalt(II) phthalocyanine; $Pd_2dba_3$=tris(dibenzylideneacetone)dipalladium(0); $PCy_3$=tricyclohexylphosphine; DMI=1,3-dimethyl-2-imidazolidinone.

FIG. 8 shows one-pot ketone synthesis developed with in situ activation of alkyl halides to alkylzinc halides in the presence of thioesters and a Pd-catalyst.

FIG. 9 shows Weinreb and Fukuyama ketone syntheses.

FIG. 13 shows one-pot ketone synthesis via in situ activation of alkyl halides. The conditions for this experiment were as follows: to 1 (0.048 mmol), 3a (0.04 mmol), and Zn (0) (>5 equiv) was added premixture II-A [0.1 mL, LiI (0.4 M) in DMI] or premixture II-B [0.1 mL, $CrCl_2$ (0.1 M), LiI (0.4 M) in DMI]. Then, premixture I [0.1 mL, $Pd_2dba_3$ (0.02 M), Ligand (0.04 M) in DMI], TESCl (1.5 equiv), and additional additive(s) were added to the reaction mixture at rt in a glovebox. [b]Ratio was estimated from $^1H$ NMR of crude products. [c]In 0.2 mmol scale in DMI (C=0.4 M) after 1d, 4ba was isolated in 95% yield. [d]Only 2b and 3a were detected. [e]Full conversion was achieved after 2 days. [f]Full conversion was obtained when 1c (2.0 equiv) was used. Abbreviations: $Pd_2dba_3$=tris(dibenzylideneacetone)dipalladium(0); $PPh_3$=triphenyl-phosphine; $PCy_3$=tricyclohexylphosphine.

FIG. 15 shows a comparison of one-versus two-step procedure. The conditions for this procedure were as follows: one-pot coupling was carried out under the conditions specified in FIG. 13 (entries 5,b 7,c and 9d).

FIG. 16 is a schematic showing that alkyl bromides do not survive in the one-pot ketone synthesis.

FIG. 19 shows the activation of alkyl halides. Unless indicated, the reactions were run with 1 (0.04 mmol), Zn (0) (>5 eq.) and an additive(s) in solvent (0.4 M) at room temperature in a glove box. [b]Product distribution was estimated from $^1$H NMR of crude products. Abbreviation: DMI=1,3-dimethyl-2-imidazolidinone; DMA=N,N-dimethylacetamide; NMP=N-methyl-2-pyrrolidone; CoPc=Cobalt(II) phthalocyanine; NbCpCl4=cyclopentadienylniobium(V) tetrachloride; NR=no reaction.

FIG. 20 shows one-pot ketone synthesis. The conditions for this experiment were as follows: to 1 (0.048 mmol), 3a (0.04 mol), and Zn (0) (>5 eq.) was added pre-mixture II-A [0.1 mL, LiI (0.4 M) in DMI] or pre-mixture II-B [0.1 mL, CrCl2 (0.1 M), LiI (0.4 M) in DMI]. Then, pre-mixture I [0.1 mL, Pd2dba3 (0.02 M), Ligand (0.04 M) in DMI], TESCl (1.5 eq.) and additional additive(s) were added to the reaction mixture at room temperature in a glove box. [b]Ratio was estimated from $^1$H NMR of crude products. [c]Pd2dba3/Ligand=1/4. [d]In a 0.2 mmol scale in DMI (C=0.4 M) after 1 d, the product 4ba was isolated in 95% yield. [e]Only 2b and 3a were detected. [f]Full conversion was achieved after 2 days. [g]1c (1.5 eq.) used. [h]1c (2.0 eq.) used. Abbreviations: Pd2dba3=tris(dibenzylideneacetone)dipalladium(0); PPh3=triphenylphosphine; PCy3=tricyclohexylphosphine; PCyp3=tricyclopentylphosphine.

DETAILED DESCRIPTION OF CERTAIN EMBODIMENTS

Ketolization Reactions

Figure 1:
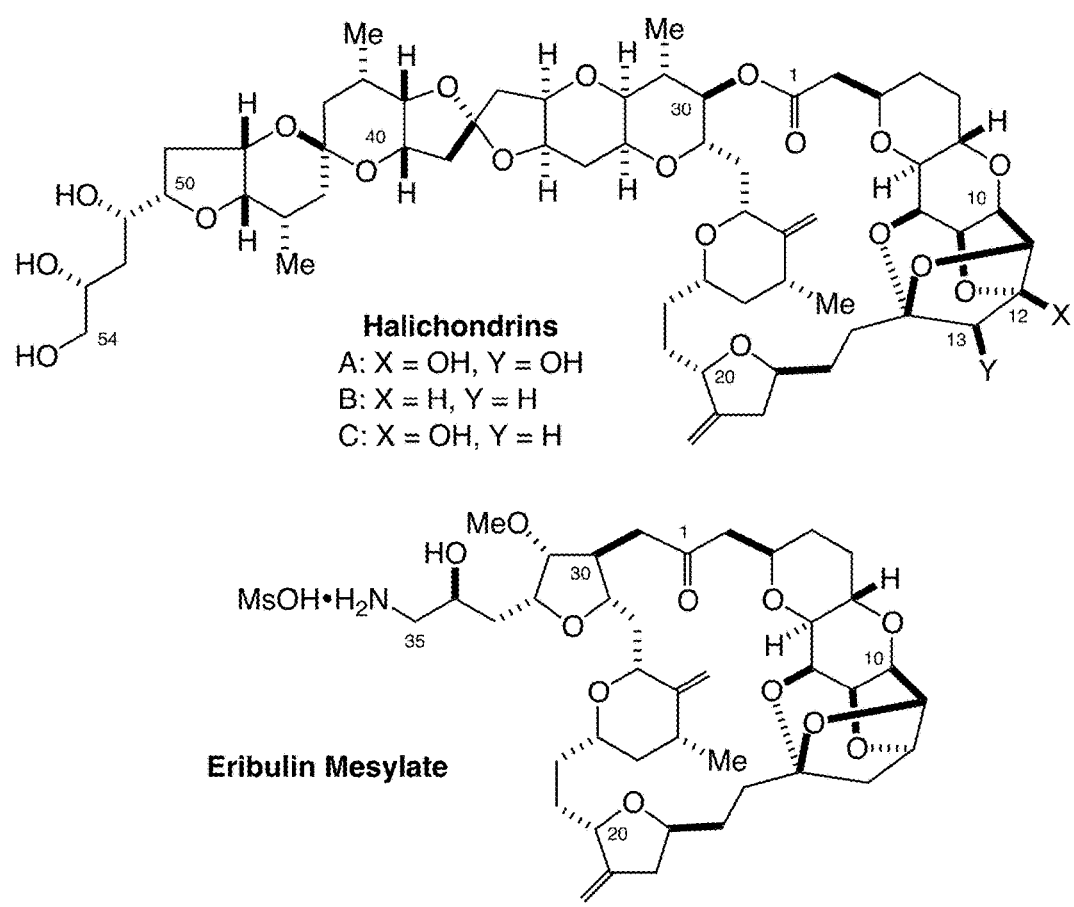
FIG. 1 shows the structure of halichondrins A-C and Eribulin mesylate.

Provided herein are palladium-mediated ketolization reactions involving a coupling of a thioester and an alkyl halide or alkyl leaving group (see Scheme 1). The ketolization reactions may be intermolecular or intramolecular (i.e., in Scheme 1, $R^A$ and $R^B$ are joined by a linker). In certain embodiments, the compound of Formula (A) is a primary or secondary alkyl halide ($X^1$=halogen) and the compound of Formula (B) is an alkyl thioester ($R^B$=optionally substituted alkyl) as shown in Scheme 2.

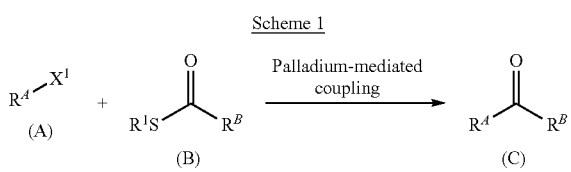

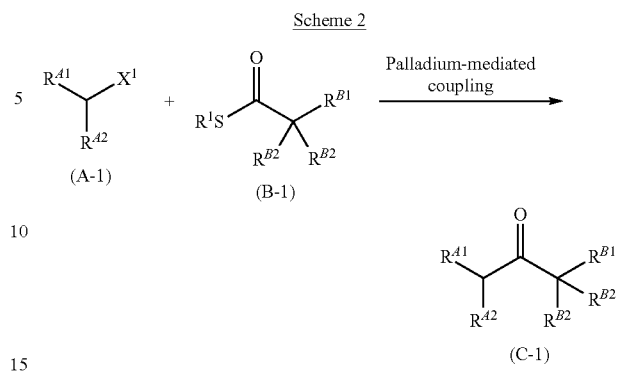

As represented in Scheme 1, provided herein is a method for preparing a compound of Formula (C):

or a salt thereof, the method comprising reacting a compound of Formula (A):

or a salt thereof, with a compound of Formula (B):

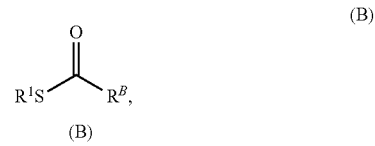

or a salt thereof, in the presence of palladium, zinc, and a single electron transfer initiator;
wherein:
$R^A$ is optionally substituted alkyl;
$R^B$ is optionally substituted alkyl, optionally substituted alkenyl, optionally substituted alkynyl, optionally substituted aryl, optionally substituted carbocyclyl, optionally substituted heteroaryl, or optionally substituted heterocyclyl; optionally wherein $R^A$ and $R^B$ are joined together via a linker, wherein the linker is selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocylylene, optionally substituted heterocyclylene, optionally substituted acylene, and combinations thereof;
$X^1$ is halogen or a leaving group; and
$R^1$ is optionally substituted alkyl.
In certain embodiments, $R^A$ is a small molecule. In certain embodiments, $R^B$ is a small molecule. Small molecules encompass complex small molecules, such as natural products, pharmaceutical agents, or fragments thereof.

As generally defined herein, a "linker" is a group comprising optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, or any combination thereof.

In certain embodiments, the compound of Formula (A) is of Formula (A-1):

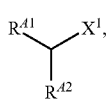
(A-1)

or a salt thereof; the compound of Formula (B) is of Formula (B-1):

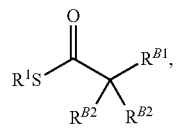
(B-1)

or a salt thereof; and the compound of Formula (C) is of Formula (C-1):

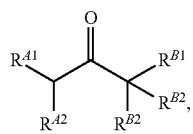
(C-1)

or a salt thereof, wherein:

$X^1$ is halogen or a leaving group;

$R^1$ is optionally substituted alkyl; each instance of $R^{A1}$, $R^{A2}$, $R^{B1}$, and $R^{B2}$ is independently optionally hydrogen, substituted alkyl, optionally substituted alkenyl, optionally substituted alkynyl, optionally substituted aryl, optionally substituted carbocyclyl, optionally substituted heteroaryl, or optionally substituted heterocyclyl; optionally wherein $R^{A1}$ and $R^{B1}$ are joined together via a linker.

In certain embodiments, $R^{A1}$ is a small molecule. In certain embodiments, $R^{B2}$ is independently a small molecule. Small molecules encompass complex small molecules, such as natural products, pharmaceutical agents, or fragments thereof.

Ketolization reactions described herein can be used for the preparation of intermediates in the synthesis of Eribulin, and analogs thereof. In certain embodiments, provided herein is a coupling reaction as shown in Scheme 4. Compounds of Formula (E-C-1) are intermediates in the preparation of Eribulin, and analogs thereof.

Scheme 4

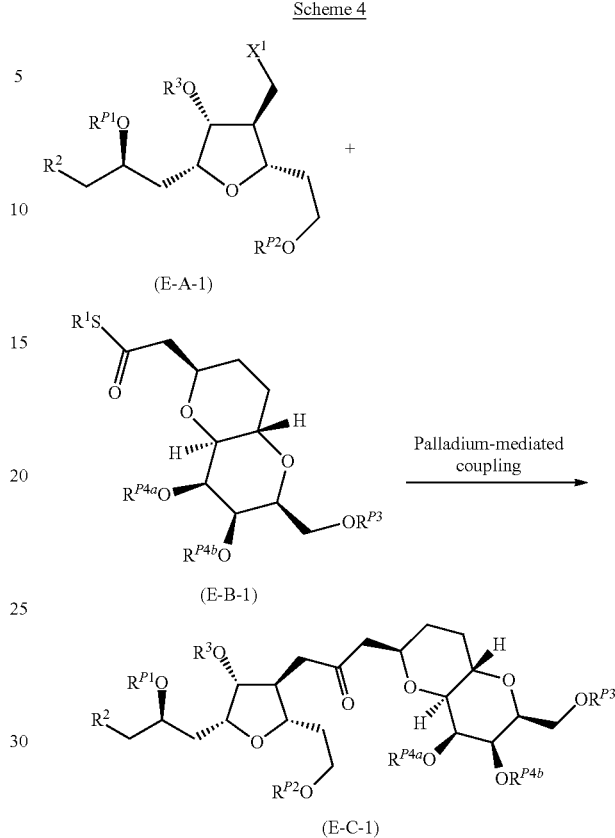

As shown in Scheme 4, provided herein is a method for preparing a compound of Formula (E-C-1):

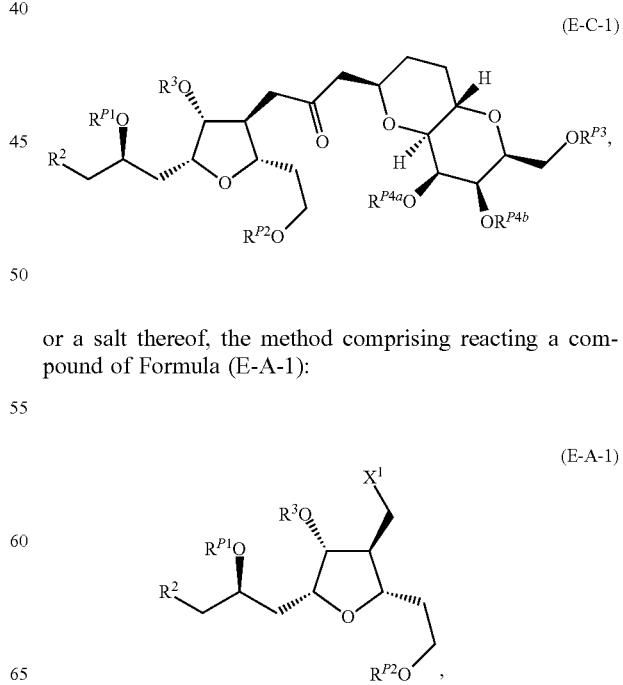

or a salt thereof, the method comprising reacting a compound of Formula (E-A-1):

or a salt thereof, with a compound of Formula (E-B-1):

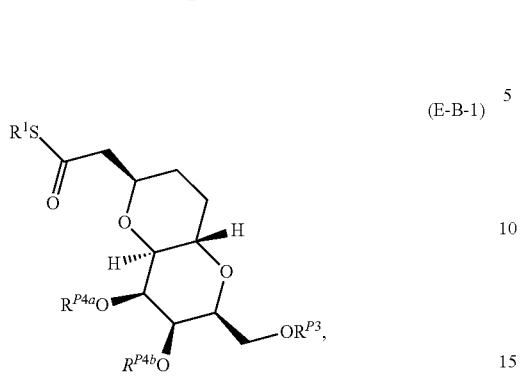

(E-B-1)

or a salt thereof, in the presence of palladium, zinc, and a single electron transfer initiator; wherein:

$X^1$ is halogen or a leaving group;

$R^1$ is optionally substituted alkyl;

$R^2$ is —$OR^{P1a}$ or —$N(R^N)_2$;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R_{P1}$, $R^{P1a}$, $R^{P2}$, $R^{P3}$, $R^{P4a}$, and $R^{P4b}$ are independently hydrogen, optionally substituted alkyl, or an oxygen protecting group; and $R^3$ is hydrogen, optionally substituted alkyl, or an oxygen protecting group;

optionally, wherein $R^{P1}$ and $R^{P1a}$ are taken together with the intervening atoms to form optionally substituted heterocyclyl; and optionally, wherein $R^{P4a}$ and $R^{P4b}$ are joined together with the intervening atoms to form optionally substituted heterocyclyl.

In certain embodiments, provided herein is are ketolization reactions as shown in Scheme 5. Ketolization products of Formula (E-C-2) are intermediates in the preparation of Eribulin, and analogs thereof.

Scheme 5

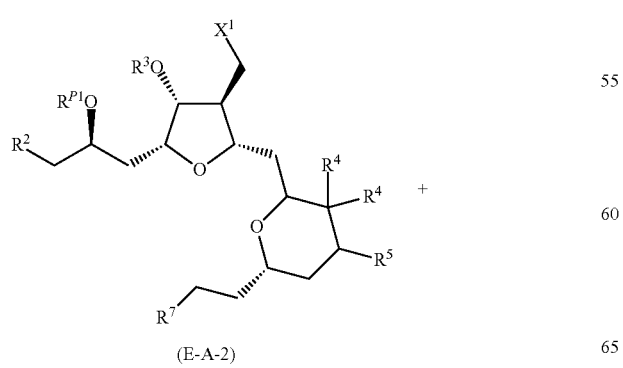

(E-A-2)

+

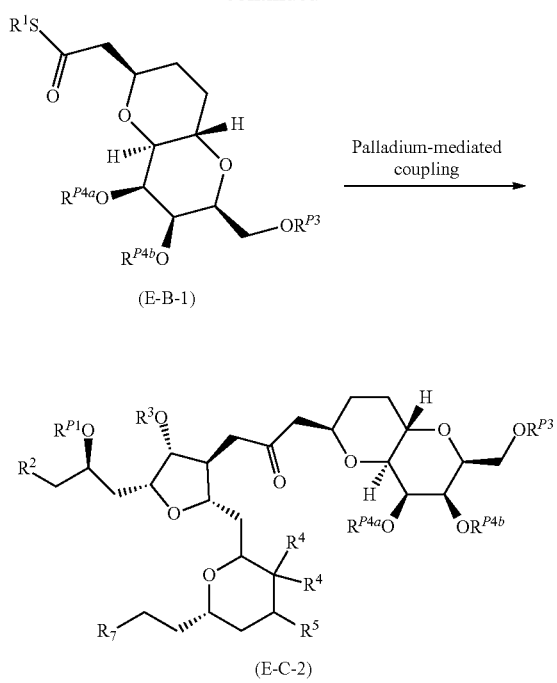

(E-B-1)

As shown in Scheme 5, provided herein is a method for preparing a compound of Formula (E-C-2):

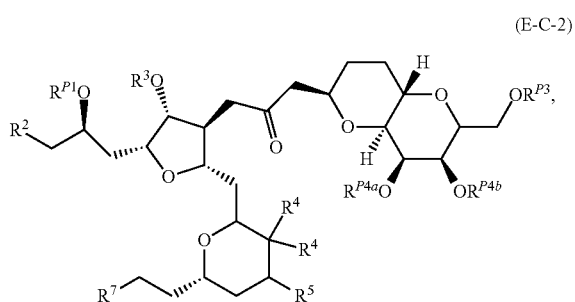

(E-C-2)

or a salt thereof, the method comprising reacting a compound of Formula (E-A-2):

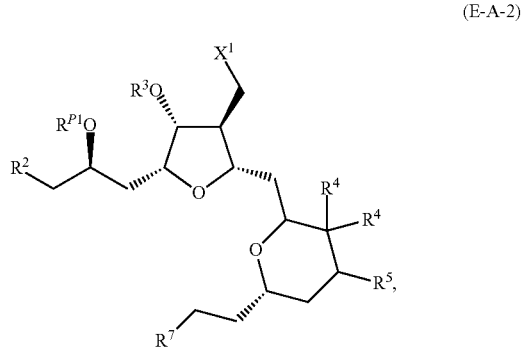

(E-A-2)

or a salt thereof, with a compound of Formula (E-B-1):

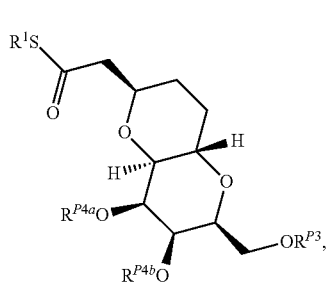

(E-B-1)

or a salt thereof, in the presence of palladium, zinc, and a single electron transfer initiator; wherein:

$X^1$ is halogen or a leaving group;

$R^1$ is optionally substituted alkyl;

$R^2$ is —$OR^{P1a}$ or —$N(R^N)_2$;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$, $R^{P1a}$, $R^{P3}$, $R^{P4a}$, $R^{P4b}$ and $R^{7a}$ are independently hydrogen, optionally substituted alkyl, or an oxygen protecting group; and $R^3$ is hydrogen, optionally substituted alkyl, or an oxygen protecting group;

$R^7$ is —$CH_2OR^{7a}$, —$CO_2R^{7a}$, or —$C(O)H$;

each instance of $R^4$ is independently hydrogen, halogen, optionally substituted alkyl, or two $R^4$ groups are taken together to form:

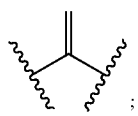

and $R^5$ is hydrogen, halogen, or optionally substituted alkyl;

optionally wherein $R^{P1}$ and $R^{P1a}$ are taken together with the intervening atoms to form optionally substituted heterocyclyl; and optionally wherein $R^{P4a}$ and $R^{P4b}$ are joined together with the intervening atoms to form optionally substituted heterocyclyl.

In certain embodiments, provided herein are ketolization reactions as shown in Scheme 6. Ketolization products of Formula (E-C-3) are intermediates in the preparation of Eribulin, and analogs thereof. Notably, compounds of Formula (E-C-3) contain all the carbons of the Eribulin scaffold.

Scheme 6

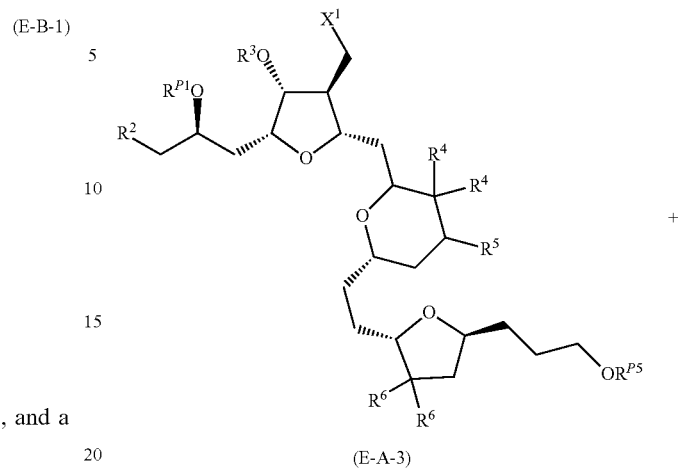

(E-A-3)

+

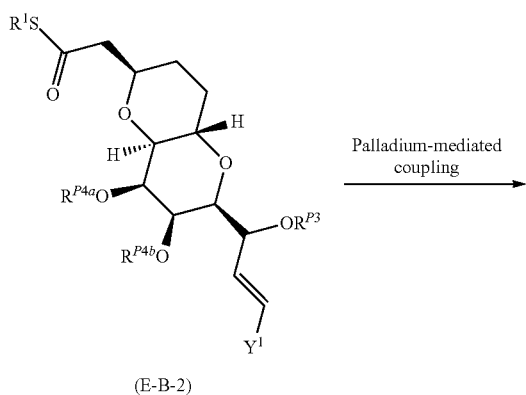

(E-B-2)

Palladium-mediated coupling →

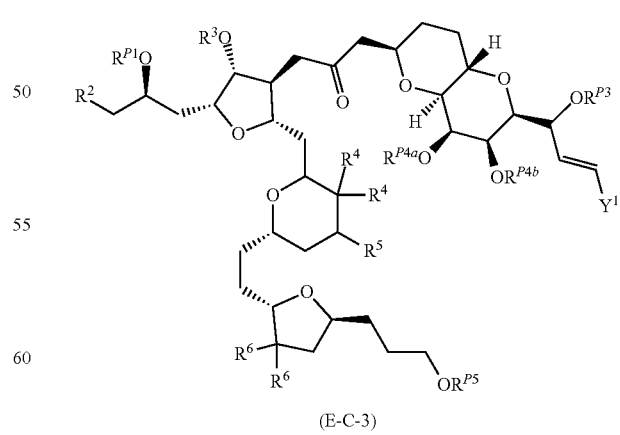

(E-C-3)

As shown in Scheme 6, provided herein is a method for preparing a compound of Formula (E-C-3):

(E-C-3)

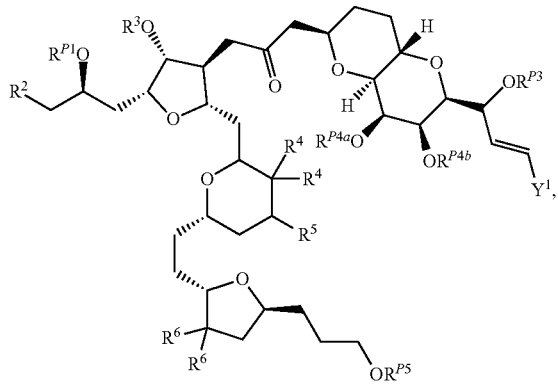

or a salt thereof, the method comprising reacting a compound of Formula (E-A-3):

(E-A-3)

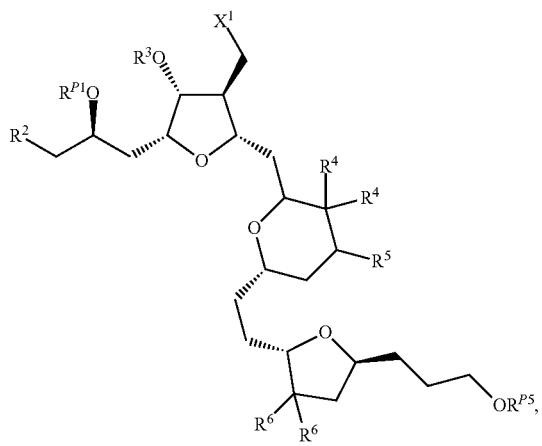

or a salt thereof, with a compound of Formula (E-B-2):

(E-B-2)

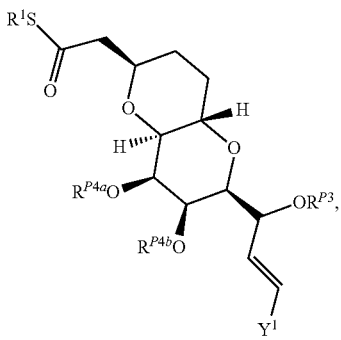

or a salt thereof, in the presence of palladium, zinc, and a single electron transfer initiator; wherein:

X$^1$ is halogen or a leaving group;

R$^1$ is optionally substituted alkyl;

R$^2$ is —OR$^{P1a}$ or —N(R$^N$)$_2$;

each instance of R$^N$ is hydrogen, optionally substituted alkyl, or a nitrogen protecting group, or optionally two R$^N$ are joined together with the intervening atoms to form optionally substituted heterocyclyl or optionally substituted heteroaryl;

R$^{P1}$, R$^{P1a}$, R$^{P3}$, R$^{P4a}$, R$^{P4b}$, R$^{P5}$, and R$^{7a}$ are independently hydrogen, optionally substituted alkyl, or an oxygen protecting group; and R$^3$ is hydrogen, optionally substituted alkyl, or an oxygen protecting group;

each instance of R$^4$ is independently hydrogen, halogen, optionally substituted alkyl, or two R$^4$ groups are taken together to form:

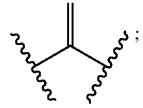 [SMILES: *C(*)=C];

each instance of R$^6$ is independently hydrogen, halogen, optionally substituted alkyl, or two R$^6$ groups are taken together to form:

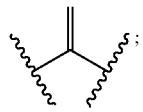;

R$^5$ is hydrogen, halogen, or optionally substituted alkyl; and

Y$^1$ is halogen, a leaving group, or silyl;

optionally wherein R$^{P1}$ and R$^{P1a}$ are taken together with the intervening atoms to form optionally substituted heterocyclyl; and optionally wherein R$^{P4a}$ and R$^{P4b}$ are joined together with the intervening atoms to form optionally substituted heterocyclyl.

The ketolization reactions provided herein may be performed in an intramolecular fashion to yield cyclic ketones as shown in Scheme 3 (also described herein as a "ketocyclization").

Scheme 3

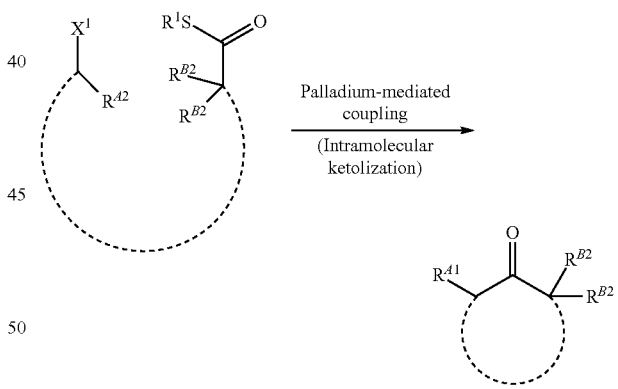

As shown in Scheme 3, provided herein is method for preparing a compound of Formula (C-2):

(C-2)

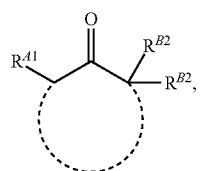

or salt thereof, comprising reacting a compound of Formula (A-B):

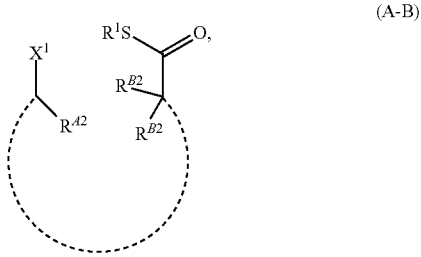

(A-B)

or a salt thereof, in the presence of palladium, zinc, and a single electron transfer initiator; wherein:

$R^{A2}$ and $R^{B2}$ are optionally substituted alkyl, optionally substituted alkenyl, optionally substituted alkynyl, optionally substituted aryl, optionally substituted carbocyclyl, optionally substituted heteroaryl, or optionally substituted heterocyclyl;

$X^1$ is halogen or a leaving group;

$R^1$ is optionally substituted alkyl; and

represents a linker selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, and combinations thereof.

For example, in certain embodiments, an intramolecular, palladium-mediated ketolization reaction provided herein can be used to prepare compounds of Formula (E-1), which are intermediates in the synthesis of Eribulin, and analogs thereof (Scheme 7). Compounds of Formula (E-2) can be prepared via reductive coupling of a compound of Formula (E-2-A) and a compound of Formula (E-4), followed by an intramolecular furan cyclization of the resulting compound. Reagents and conditions for this reductive coupling reaction (e.g., Cr/Ni-mediated reductive coupling) and the intramolecular furan cyclization can be found in, e.g., published international PCT application, WO 2016/176560, published Nov. 3, 2016, which is incorporated herein by reference.

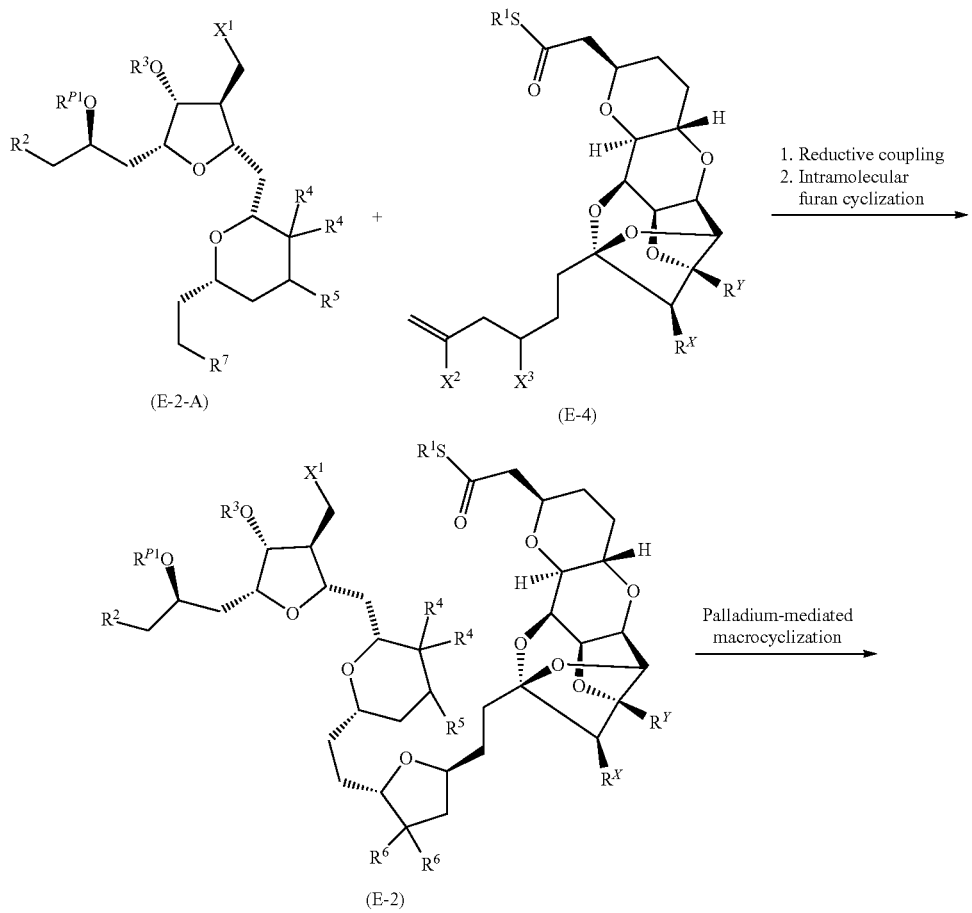

Scheme 7

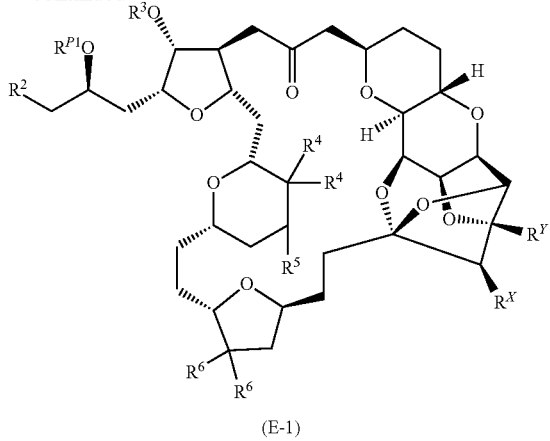

(E-1)

As shown in Scheme 7, provided herein is a method of preparing a compound of Formula (E1):

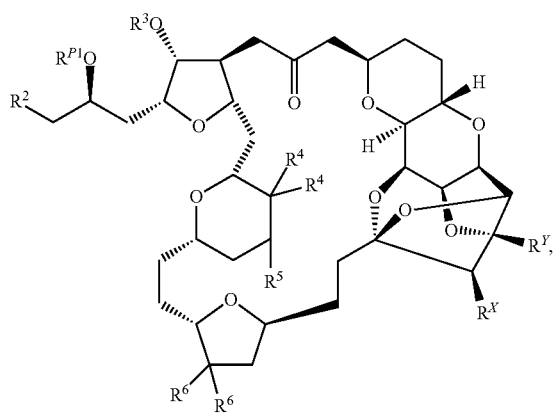

(E-1)

or salt thereof, comprising reacting a compound of Formula (E-2):

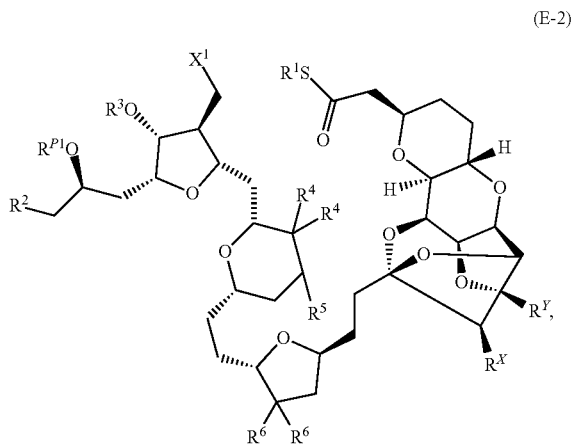

(E-2)

or a salt thereof, in the presence of palladium, zinc, and a single electron transfer initiator; wherein:

$X^1$ is halogen or a leaving group;
$R^1$ is optionally substituted alkyl;
$R^2$ is —$OR^{P1a}$ or —$N(R^N)_2$;
each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
$R^{P1}$ and $R^{P1a}$ are independently hydrogen, optionally substituted alkyl, or an oxygen protecting group;
$R^3$ is hydrogen, optionally substituted alkyl, or an oxygen protecting group;
each instance of $R^4$ is independently hydrogen, halogen, optionally substituted alkyl, or two $R^4$ groups are taken together to form:

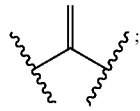

each instance of $R^6$ is independently hydrogen, halogen, optionally substituted alkyl, or two $R^6$ groups are taken together to form:

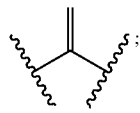

$R^5$ is hydrogen, halogen, or optionally substituted alkyl;
$R^X$ is hydrogen or —$OR^{Xa}$, wherein $R^{Xa}$ is hydrogen, optionally substituted alkyl, or an oxygen protecting group; and
$R^Y$ is hydrogen or —$OR^{Ya}$, wherein $R^{Ya}$ is hydrogen, optionally substituted alkyl, or an oxygen protecting group;
optionally wherein $R^{Xa}$ and $R^{Ya}$ are joined together with their intervening atoms to form optionally substituted heterocyclyl; and
optionally wherein $R^{P1}$ and $R^{P1a}$ are taken together with the intervening atoms to form optionally substituted heterocyclyl.

As represented in Scheme 7, the method of preparing a compound of Formula (E-1) may further comprise the steps of:

(a) reacting a compound of Formula (E-2-A):

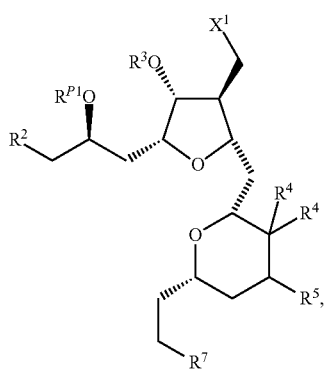
(E-2-A)

or a salt thereof, with a compound of Formula (E-4):

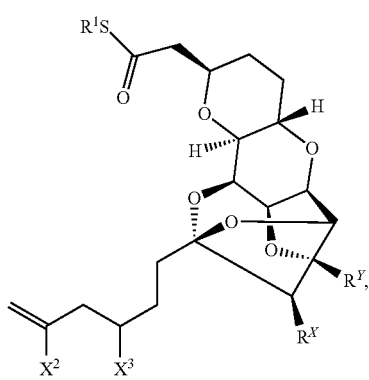
(E-4)

or a salt thereof, in the presence of nickel and chromium, to yield a compound of Formula (E-5):

(E-5)

or a salt thereof, and (b) reacting the compound of Formula (E-5) formed in step (a) in the presence of an acid to yield a compound of Formula (E-2):

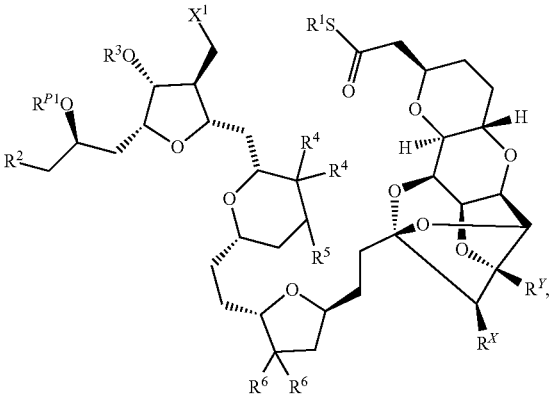
(E-2)

or a salt thereof, wherein:

$X^1$, $X^2$, and $X^3$ are independently halogen or a leaving group;

$R^1$ is optionally substituted alkyl;

$R^2$ is $-OR^{P1a}$ or $-N(R^N)_2$;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$ and $R^{P1a}$ are independently hydrogen, optionally substituted alkyl, or an oxygen protecting group;

$R^3$ is hydrogen, optionally substituted alkyl, or an oxygen protecting group;

each instance of $R^4$ is independently hydrogen, halogen, optionally substituted alkyl, or two $R^4$ groups are taken together to form:

each instance of $R^6$ is independently hydrogen, halogen, optionally substituted alkyl, or two $R^6$ groups are taken together to form:

$R^5$ is hydrogen, halogen, or optionally substituted alkyl;

$R^7$ is $-CO_2R^{7a}$ or $-C(O)H$ $R^X$ is hydrogen or $-OR^{Xa}$, wherein $R^{Xa}$ is hydrogen, optionally substituted alkyl, or an oxygen protecting group; and $R^Y$ is hydrogen or $-OR^{Ya}$ wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl; and optionally wherein $R^{P1}$ and $R^{P1a}$ are taken together with the intervening atoms to form optionally substituted heterocyclyl.

Step (a) above is a Ni/Cr-mediated reductive coupling reaction and step (b) is an acid-promoted intramolecular furan cyclization. Reagents and conditions for steps (a) and (b) above can be found in, e.g., published international PCT application, WO 2016/176560, published Nov. 3, 2016, the entire contents of which is incorporated herein by reference. In certain embodiments, step (b) above is carried out in the presence of a Lewis acid. In certain embodiments, the Lewis acid is AgOTf. In certain embodiments, the Lewis acid is $Ag_2O$. In certain embodiments, the Lewis acid is $SrCO_3$. The Lewis acid may be present in a catalytic, stoichiometric, or excess amount.

This intramolecular furan cyclization is also useful in the synthesis of halichondrins, and analogs thereof, as shown in the following scheme:

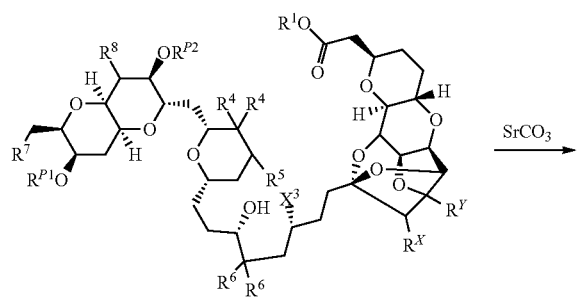

In addition to methods useful in the preparation of Eribulin, and analogs thereof, the present invention also provides methods useful in the preparation of halichondrin analogs (e.g., halichondrin A, B, C analogs; homohalichondrin A, B, C analogs; and norhalichondrin A, B, and C analogs). In particular, the palladium-mediated ketolization reactions provided herein can be used in the preparation of keto analogs of the halichondrins. Keto analogs of the halichondrins comprise a ketone where the naturally occurring halichondrins include a lactone ester (denoted by * on compounds of Formulae (H-1), (HH-1), and (NH-1)).

(H-1)

Keto analogs of halichondrin A, B, C (HH-1)

Keto analogs of homohalichondrin A, B, C

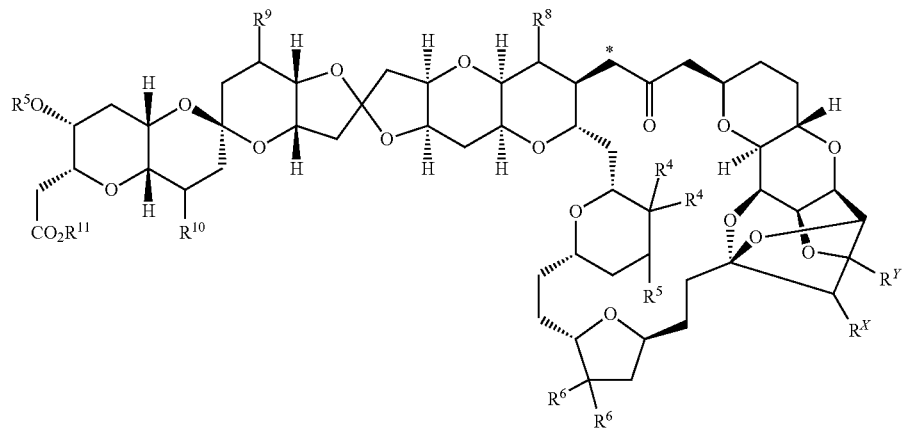

Keto analogs of norhalichondrin A, B, C

Provided herein are methods for the preparation of compounds of Formula (H-2), which are key intermediates in the synthesis of halichondrins and analogs thereof. Compounds of Formula (H-2) are can be used in the synthesis of halichondrin analogs (i.e., halichondrin A, B, C analogs; homohalichondrin A, B, C analogs; and norhalichondrin A, B, and C analogs) according to methods described in, e.g., published international PCT application, WO 2016/003975, published Jan. 7, 2016; and published international PCT application, WO 2016/176560, published Nov. 3, 2016; the entire contents of both of which are incorporated herein by reference. As shown in Scheme 8, key intermediates of Formula (H-2) can be prepared via a palladium mediated ketolization described herein. Ketolization precursors of Formula (H-3) can be prepared via a reductive coupling of a compound of Formula (H-A-1) and a compound of Formula (E-4), followed by intramolecular furan cyclization of the resulting compound. Methods for this reductive coupling and intramolecular furan cyclization can be found in, e.g., published international PCT application, WO 2016/003975, published Jan. 7, 2016; and published international PCT application, WO 2016/176560, published Nov. 3, 2016.

Scheme 8

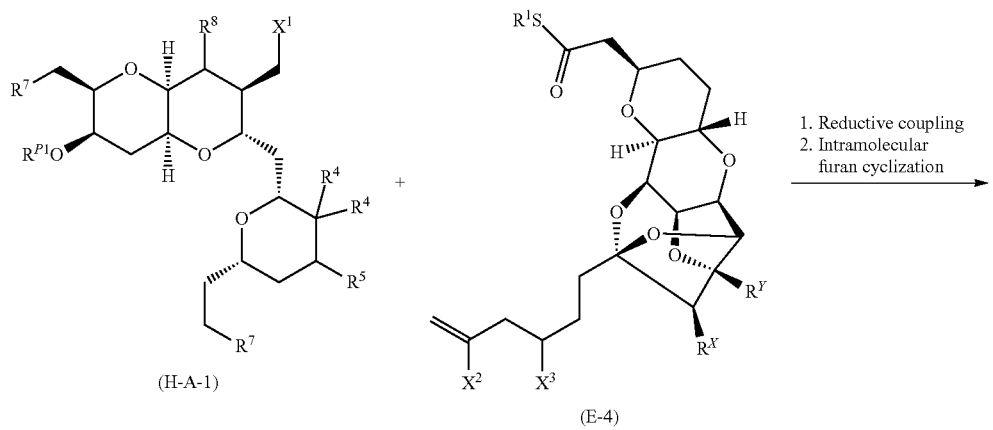

-continued

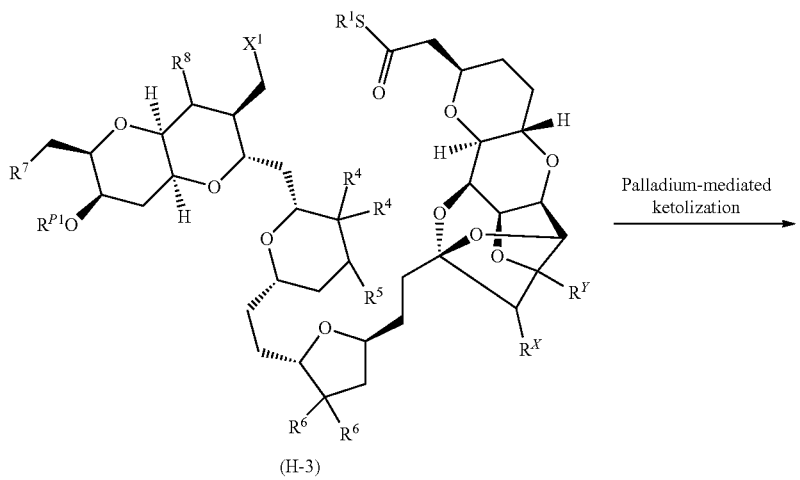

(H-3)

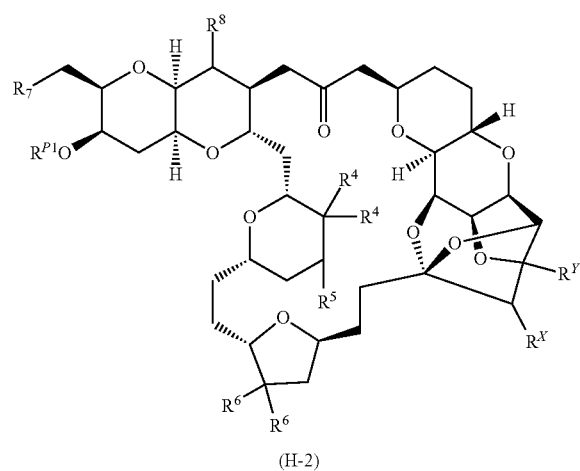

(H-2)

As shown in Scheme 8, provided herein is a method of preparing a compound of method for preparing a compound Formula (H-2):

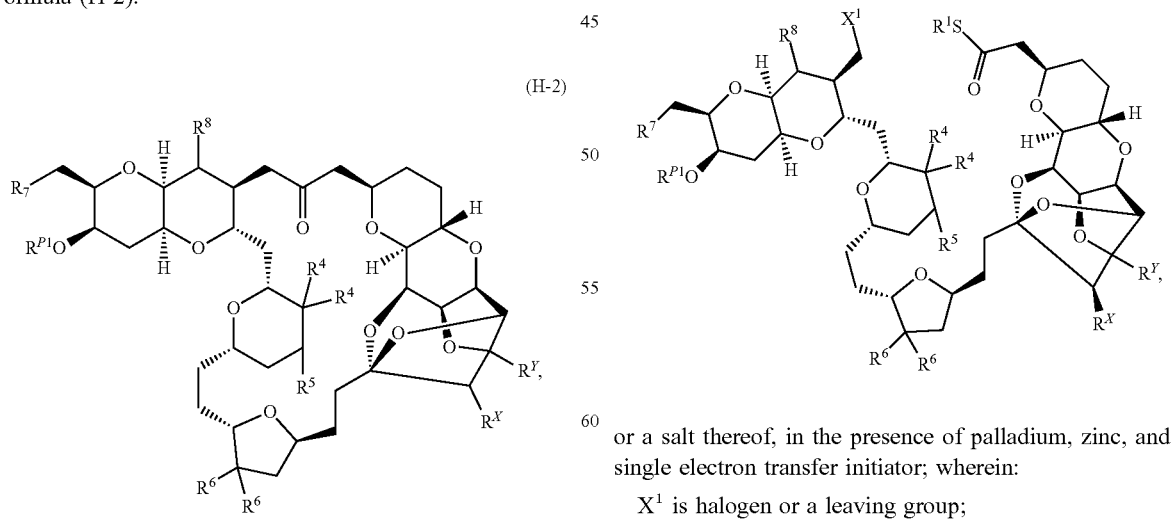

or salt thereof, comprising reacting a compound of Formula (H-3):

or a salt thereof, in the presence of palladium, zinc, and a single electron transfer initiator; wherein:

$X^1$ is halogen or a leaving group;

$R^1$ is optionally substituted alkyl;

$R^{P1}$ is hydrogen, optionally substituted alkyl, or an oxygen protecting group;

each instance of $R^4$ is independently hydrogen, halogen, optionally substituted alkyl, or two $R^4$ groups are taken together to form:

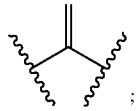 [SMILES: *C(*)=C]

each instance of $R^6$ is independently hydrogen, halogen, optionally substituted alkyl, or two $R^6$ groups are taken together to form:

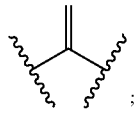 [SMILES: *C(*)=C]

$R^5$ is hydrogen, halogen, or optionally substituted alkyl;

$R^7$ is —$CH_2OR^{7a}$, —$CO_2R^{7a}$, or —$C(O)H$;

$R^8$ is hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl; and optionally wherein $R^{P1}$ and $R^{7a}$ are taken together with the intervening atoms to form optionally substituted heterocyclyl.

As represented in Scheme 8, the method of preparing a compound of Formula (H-2) may further comprise the steps of:

(a) reacting a compound of Formula (H-A-1):

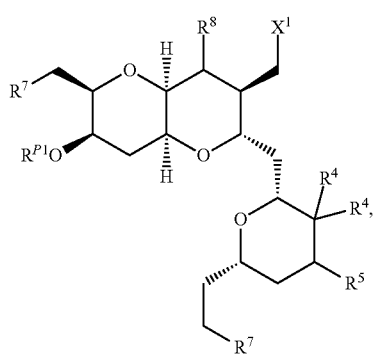

(H-A-1)

or a salt thereof, with a compound of Formula (E-4):

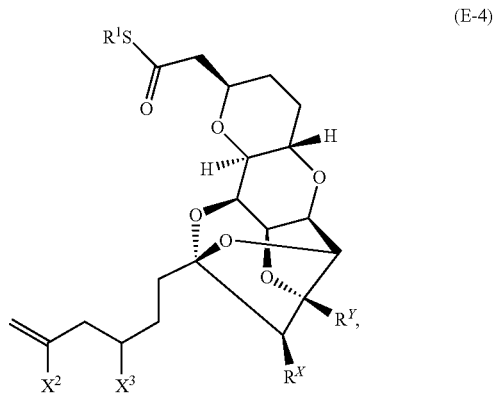

(E-4)

or a salt thereof, in the presence of nickel and chromium, to yield a compound of Formula (H-4):

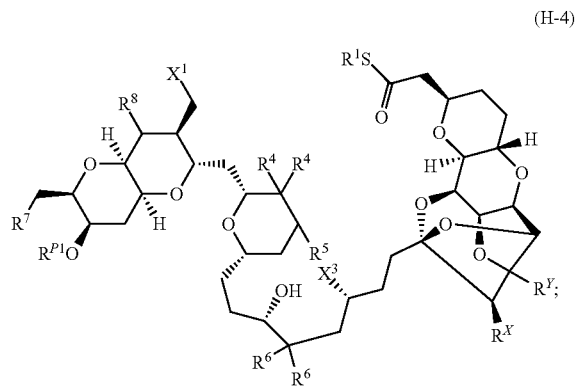

(H-4)

or a salt thereof, and (b) reacting the compound of Formula (H-4) formed in step (a) in the presence of an acid to yield a compound of Formula (H-3):

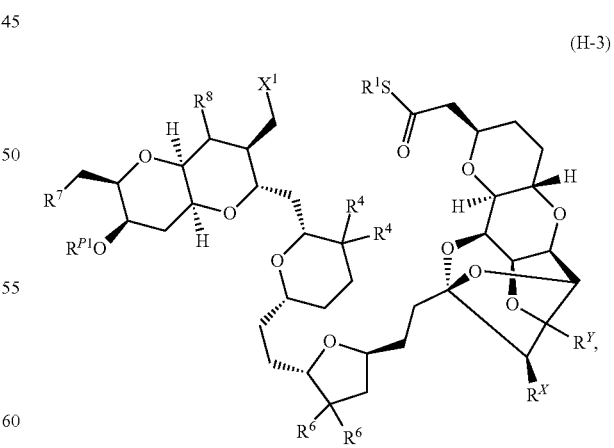

(H-3)

or a salt thereof, wherein:

$X^1$, $X^2$, and $X^3$ are independently halogen or a leaving group;

$R^1$ is optionally substituted alkyl;

$R^2$ is —$OR^{P1a}$ or —$N(R^N)_2$;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$ is hydrogen, optionally substituted alkyl, or an oxygen protecting group;

$R^3$ is hydrogen, optionally substituted alkyl, or an oxygen protecting group; each instance of $R^4$ is independently hydrogen, halogen, optionally substituted alkyl, or two $R^4$ groups are taken together to form:

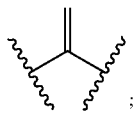 [SMILES: *C(*)=C]

each instance of $R^6$ is independently hydrogen, halogen, optionally substituted alkyl, or two $R^6$ groups are taken together to form:

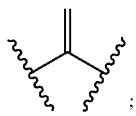 [SMILES: *C(*)=C]

$R^5$ is hydrogen, halogen, or optionally substituted alkyl;
$R^7$ is —CH$_2$OR$^{7a}$, —CO$_2$R$^{7a}$, or —C(O)H;
$R^X$ is hydrogen or —OR$^{Xa}$, wherein R$^{Xa}$ is hydrogen, optionally substituted alkyl, or an oxygen protecting group; and
$R^Y$ is hydrogen or —OR$^{Ya}$, wherein R$^{Ya}$ is hydrogen, optionally substituted alkyl, or an oxygen protecting group;
optionally wherein R$^{Xa}$ and R$^{Ya}$ are joined together with their intervening atoms to form optionally substituted heterocyclyl; and
optionally wherein R$^{P1}$ and R$^{7a}$ are taken together with the intervening atoms to form optionally substituted heterocyclyl.

Step (a) above is a Ni/Cr-mediated reductive coupling reaction and step (b) is an acid-promoted intramolecular furan cyclization. Reagents and conditions for steps (a) and (b) above can be found in, e.g., WO 2016/176560, published Nov. 3, 2016, the entire contents of which is incorporated herein by reference. In certain embodiments, step (b) above is carried out in the presence of a Lewis acid. In certain embodiments, the Lewis acid is AgOTf. In certain embodiments, the Lewis acid is Ag$_2$O. In certain embodiments, the Lewis acid is SrCO$_3$. The Lewis acid may be present in catalytic, stoichiometric, or excess amounts.

Ketolization reactions provided herein are palladium-mediated and are carried out in the presence of palladium. In certain embodiment, the reaction is carried out in the presence of a palladium complex. In certain embodiments, the reaction is carried out in the presence of palladium(0). Examples of palladium(0) reagents include, but are not limited to, bis[1,2-bis(diphenylphosphino)ethane]palladium(0), bis(dibenzylideneacetone)palladium(0), 1,3-bis(2,6-diisopropylphenyl)imidazol-2-ylidene(1,4-naphthoquinone)palladium(0) dimer, bis(3,5,3',5'-dimethoxydibenzylideneacetone)palladium(0), bis(tri-tert-butylphosphine)palladium(0), bis(tricyclohexylphosphine) palladium(0), 1,3-bis(2,4,6-trimethylphenyl)imidazol-2-ylidene (1,4-naphthoquinone)palladium(0) dimer, bis[tris(2-methylphenyl)phosphine]palladium, tetrakis(triphenylphosphine)palladium(0), and tris(3,3',3"-phosphinidynetris(benzenesulfonato) palladium(0) nonasodium salt nonahydrate. In certain embodiments, the ketolization reaction is carried out in the presence of tris(dibenzylideneacetone)dipalladium(0) (Pd$_2$dba$_3$) or bis(dibenzylideneacetone)palladium(0) (Pd(dba)$_2$). In certain embodiments, the palladium complex is Pd$_2$dba$_3$. In certain embodiments, the palladium is present in a catalytic amount. In certain embodiments, the palladium is present in between 1-5 mol %, 5-10 mol %, 5-20 mol %, 10-20 mol %, 20-30 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the palladium is present in from 5-20 mol %. In certain embodiments, the palladium is present in approximately 10 mol %. In certain embodiments, the palladium is present in a stoichiometric or excess amount relative to a compound of Formula (A) or (B) in the reaction mixture. In certain embodiments, approximately 1 equivalent of palladium is present (i.e., stoichiometric). In other embodiments, greater than 1 equivalent of palladium is present (i.e., excess).

As described above, the ketolization reaction provided herein is performed in the presence of zinc. In certain embodiments, zinc metal is used (i.e., zinc(0)). In certain embodiments, the reaction is carried out in the presence of zinc powder, zinc foil, zinc beads, or any other form of zinc metal. In certain embodiments, a zinc salt is employed such as zinc acetate, zinc sulfate, zinc chloride, zinc bromide, zinc iodide, zinc fluoride, zinc sulfide, zinc phosphate. The zinc may be present in a catalytic, stoichiometric, or excess amount. In certain embodiments, the zinc is present in excess (i.e., greater than 1 equivalent) relative to a compound of Formula (A) or Formula (B).

As described above, the ketolization reaction is carried out in the presence of a single electron transfer (SET) initiator. Any SET initiator known in the art may be used in the methods provided herein. Examples of SET initiators include, but are not limited to, Vitamin B$_{12}$, cobalt(II) pthalocyanine, iron(II) phthalocyanine, copper(II) phthalocyanine, nickel(II) phthalocyanine, zinc(II) phthalocyanine. In certain embodiments, the SET initiator is a transition metal complex. In certain embodiments, the SET initiator is an iron complex (e.g., iron(III) complex such as tris(acetylacetonato) iron(III) (Fe(acac)$_3$). In certain embodiments, the SET initiator is a cobalt complex (e.g., a cobalt(II) complex). In certain embodiments, the SET initiator is cobalt(II) phthalocyanide. In certain embodiments, the SET initiator is a niobium complex (e.g., niobium(V) complex). In certain embodiments, the SET initiator is (cyclopentadienyl)niobium(V) tetrachloride (NbCpCl$_4$). In certain embodiments, the SET initiator is present in a catalytic amount. In certain embodiments, the SET initiator is present in between 1-5 mol %, 5-10 mol %, 5-20 mol %, 10-20 mol %, 20-30 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the SET initiator is present in from 5-20 mol %. In certain embodiments, the SET initiator is present in approximately 10 mol %. In certain embodiments, the SET initiator is present in a stoichiometric or excess amount relative to a compound of Formula (A) or (B) in the reaction mixture. In certain embodiments, approximately 1 equivalent of SET initiator is present (i.e., stoichiometric).

In other embodiments, greater than 1 equivalent of SET initiator is present (i.e., excess).

In certain embodiments, the ketolization is carried out in the presence of one or more additional reagents (i.e., in addition to palladium, zinc, and an SET inhibitor).

In certain embodiments, the ketolization reaction is carried out in the presence of a phosphine reagent. In certain embodiments, the phosphine reagent is of the formula $PR_3$, wherein each $R_3$ is independently alkyl, heteroalkyl, alkoxy, carbocyclyl, aryl, heterocyclyl, heteroaryl. Examples of phosphine reagents include, but are not limited to, benzyldiphenylphosphine, 1,1'-bis(dicyclohexylphosphino)ferrocene, tert-butyldiphenylphosphine, cyclohexyldiphenylphosphine, di-tert-butylmethylphosphine, dicyclohexyl(2-methylphenyl)phosphine, dicyclohexyl(2,4,6-trimethylphenyl)phosphine, (R)-(−)-N,N-dimethyl-1-[(S)-2-(diphenylphosphino)ferrocenyl]ethylamine, P,P'-(9,9-dimethyl-9H-xanthene-4,5-diyl)bis[N,N,N',N'-tetraethylphosphonous diamide], diphenyl(2-methoxyphenyl)phosphine, (R)-(+)-1-(2-diphenylphosphino-1-naphthyl)isoquinoline, (RS)-1-(2-diphenylphosphino-1-naphthyl)isoquinoline, diphenyl(o-tolyl)phosphine, 4,4'-(phenylphosphinidene)bis(benzenesulfonic acid) dipotassium salt hydrate, tri-tert-butylphosphine, tricyclohexylphosphine, tricyclopentylphosphine, triisopropylphosphine, triphenylphosphine, tris(4-chlorophenyl)phosphine, tris(2,6-dimethoxyphenyl)phosphine, tris(4-methoxyphenyl)phosphine, tris(2,4,6-trimethylphenyl)phosphine, tri(o-tolyl)phosphine, tri(p-tolyl)phosphine, [1-(diphenylphosphino)ethyl]ferrocene. In certain embodiments, the phosphine reagent is triphenylphosphine ($PPh_3$). In certain embodiments, the phosphine reagent is tricyclohexylphosphine ($PCy_3$). In certain embodiments, the phosphine reagent is tricyclopentylphosphine ($PCyp_3$). In certain embodiments, the phosphine reagent is present in a catalytic amount. In certain embodiments, the phosphine reagent is present in between 1-5 mol %, 5-10 mol %, 5-20 mol %, 10-20 mol %, 10-30 mol %, 20-30 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the phosphine reagent is present in from 10-30 mol %. In certain embodiments, the phosphine reagent is present in approximately 20 mol %. In certain embodiments, the phosphine reagent is present in a stoichiometric or excess amount relative to a compound of Formula (A) or (B) in the reaction mixture. In certain embodiments, approximately 1 equivalent of phosphine reagent is present (i.e., stoichiometric). In certain embodiments, approximately 1.1 equivalent of phosphine reagent is present (i.e., stoichiometric). In other embodiments, greater than 1 equivalent of phosphine reagent is present (i.e., excess). In certain embodiments, approximately 2 equivalents of phosphine reagent is present.

In certain embodiments, the ketolization reaction is carried out in the presence of a chromium salt. In certain embodiments, the chromium salt is a chromium(II), chromium(III), or chromium(IV) salt. Examples of chromium salts include, but are not limited to, chromium(II) chloride ($CrCl_2$), chromium(III) chloride ($CrCl_3$), chromium(III) fluoride ($CrCl_3$), chromium(II) bromide ($CrBr_2$), chromium(III) bromide ($CrBr_3$), chromium(III) nitrate ($Cr(NO_3)_3$), chromium(III) sulfate ($Cr(SO_4)_3$) In certain embodiments, the chromium salt is chromium(II) chloride ($CrCl_2$). In certain embodiments, the chromium salt is chromium(III) chloride ($CrCl_3$). In certain embodiments, the phosphine reagent is present in a catalytic amount. In certain embodiments, the chromium salt is present in between 1-5 mol %, 5-10 mol %, 5-20 mol %, 10-20 mol %, 10-30 mol %, 20-30 mol %, 30-40 mol %, 40-50 mol %, 40-50 mol %, 50-60 mol %, 60-70 mol %, 70-80 mol %, or 80-90 mol % relative to a compound of Formula (A) or (B) in the reaction mixture. In certain embodiments, the chromium salt is present in from 40-60 mol %. In certain embodiments, the chromium salt is present in approximately 50 mol %. In certain embodiments, the chromium salt is present in a stoichiometric or excess amount relative to a compound of Formula (A) or (B) in the reaction mixture. In certain embodiments, approximately 1 equivalent of chromium salt is present (i.e., stoichiometric). In certain embodiments, approximately 1.1 equivalent of chromium salt is present (i.e., stoichiometric). In other embodiments, greater than 1 equivalent of chromium salt is present (i.e., excess). In certain embodiments, approximately 1.5, 2, 2.5, 3, 3.5, 4, 4.5, 5, 5.5, 6, 7, 8, 9, or 10 equivalents of chromium salt is present. In certain embodiments, approximately 5 equivalents of the chromium salt is present.

In certain embodiments, the ketolization reaction is carried out in the presence of a lithium halide salt (e.g., LiBr, LiI, LiCl). In certain embodiments, the reaction is carried out in the presence of lithium iodide (LiI). The lithium halide salt may be present in a catalytic, stoichiometric, or excess amount. In certain embodiments, the lithium halide salt is present in a stoichiometric or excess amount relative to a compound of Formula (A) or (B) in the reaction mixture. In certain embodiments, approximately 1 equivalent of lithium halide salt is present (i.e., stoichiometric). In certain embodiments, approximately 1.1 equivalent of lithium halide salt is present (i.e., stoichiometric). In other embodiments, greater than 1 equivalent of lithium halide salt is present (i.e., excess).

In certain embodiments, the ketolization reaction is carried out in the presence of one or more reagents which help activate zinc metal in the reaction by clearing the surface of zinc oxide. In certain embodiments, the reaction is carried out in the presence of a trialkylsilyl halide (e.g., triethylsilyl chloride (TESCl)). This reagent may be present in a catalytic, stoichiometric, or excess amount. In certain embodiments, approximately 1.5, 2, 2.5, 3, 3.5, 4, 4.5, 5, 5.5, 6, 7, 8, 9, or 10 equivalents of this reagent is present. In certain embodiments, approximately 1.5 equivalents of this reagent is present.

In certain embodiments, a reaction described herein is carried out in a solvent. Any solvent may be used, and the scope of the method is not limited to any particular solvent. The solvent may be polar or non-polar, protic or aprotic, or a combination of solvents (e.g., co-solvents). Examples of useful organic solvents are provided herein. In certain embodiments, the ketolization reaction is carried out in 1,3-dimethyl-2-imidazolidinone (DMI). In certain embodiments, the ketolization reaction is carried out in a 1,3-dimethyl-2-imidazolidinone (DMI)/tetrahydrofuran (THF) mixture.

The reactions described herein may be carried out at any concentration in solvent. Concentration refers to the molar concentration (mol/L) of a coupling partners (compounds of Formula (A) or (B)) in a solvent. In certain embodiments, the concentration is approximately 1 M. In certain embodiments, the concentration is greater an 1 M. In certain embodiments, the concentration is approximately 0.1, 0.2, 0.3, 0.4, 0.5, 0.6, 0.7, 0.8, or 0.9 M. In certain embodiments, the concentration is less than 0.1 M. In certain embodiments, the concentration is less than 0.05 M. In certain embodiments, the concentration is less than 0.001 M. In certain embodiments, the concentration is between 0.01 and 0.1 M.

In certain embodiments, the concentration is approximately 0.01, 0.02, 0.03, 0.04, 0.05, 0.06, 0.07, 0.08, or 0.09 M. In certain embodiments, the concentration is approximately 0.03 M, or 0.3 mM (e.g., 0.027 M, or 27 mM).

The reactions described herein can be carried out at any temperature. In certain embodiments, the reaction is carried out at around room temperature (i.e., between 18 and 24° C.). In certain embodiments, the reaction is carried out below room temperature (e.g., between 0° C. and room temperature). In certain embodiments, the reaction is carried out at above room temperature (e.g., between room temperature and 100° C.).

Compounds

The present invention also provides compounds useful in the ketolization reactions described herein. In certain embodiments, the compounds are useful in the synthesis of Eribulin or Eribulin analogs. For example, provided herein are compounds of Formula (E-A-1):

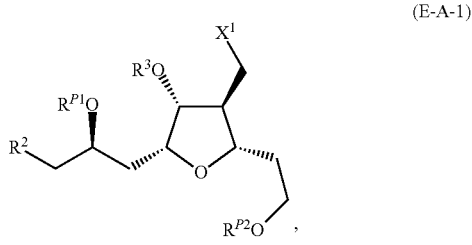

(E-A-1)

and salts thereof, wherein:
  $X^1$ is halogen or a leaving group;
  $R^2$ is —$OR^{P1a}$ or —$N(R^N)_2$;
  each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
  $R^{P1}$, $R^{P1a}$, and $R^{P2}$ are independently hydrogen, optionally substituted alkyl, or an oxygen protecting group; and
  $R^3$ is hydrogen, optionally substituted alkyl, or an oxygen protecting group;
  optionally wherein $R^{P1}$ and $R^{P1a}$ are taken together with the intervening atoms to form optionally substituted heterocyclyl.

Provided herein are compounds of Formula (E-B-1):

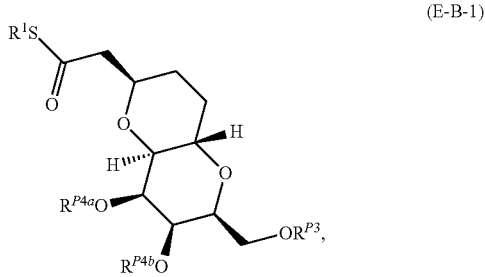

(E-B-1)

and salts thereof, wherein:
  $R^1$ is optionally substituted alkyl; and
  $R^{P3}$, $R^{P4a}$, and $R^{P4b}$ are independently hydrogen, optionally substituted alkyl, or an oxygen protecting group;
  optionally wherein $R^{P4a}$ and $R^{P4b}$ are joined together with the intervening atoms to form optionally substituted heterocyclyl.

Provided herein are compounds of Formula (E-C-1):

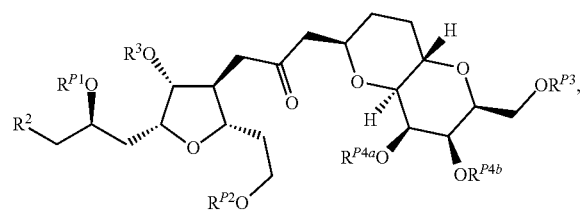

(E-C-1)

and salts thereof, wherein:
  $R^2$ is —$OR^{P1a}$ or —$N(R^N)_2$;
  each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
  $R^{P1}$, $R^{P1a}$, $R^{P2}$, $R^{P3}$, $R^{P4a}$, and $R^{P4b}$ are independently hydrogen, optionally substituted alkyl, or an oxygen protecting group; and
  $R^3$ is hydrogen, optionally substituted alkyl, or an oxygen protecting group;
  optionally wherein $R^{P1}$ and $R^{P1a}$ are taken together with the intervening atoms to form optionally substituted heterocyclyl; and
  optionally wherein $R^{P4a}$ and $R^{P4b}$ are joined together with the intervening atoms to form optionally substituted heterocyclyl.

Provided herein are compounds of Formula (E-A-2):

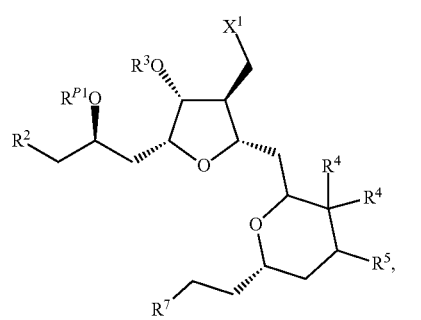

(E-A-2)

and salts thereof, wherein:
  $X^1$ is halogen or a leaving group;
  $R^2$ is —$OR^{P1a}$ or —$N(R^N)_2$;
  each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
  $R^{P1}$, $R^{P1a}$, and $R^{7a}$ are independently hydrogen, optionally substituted alkyl, or an oxygen protecting group; and
  $R^3$ is hydrogen, optionally substituted alkyl, or an oxygen protecting group;
  $R^7$ is —$CH_2OR^{7a}$, —$CO_2R^{7a}$, or —$C(O)H$;
  each instance of $R^4$ is independently hydrogen, halogen, optionally substituted alkyl, or two $R^4$ groups are taken together to form:

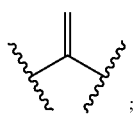 [SMILES: *C(*)=C]

and

R⁵ is hydrogen, halogen, or optionally substituted alkyl;

optionally wherein $R^{P1}$ and $R^{1a}$ are taken together with the intervening atoms to form optionally substituted heterocyclyl; and optionally wherein $R^{P4a}$ and $R^{P4b}$ are joined together with the intervening atoms to form optionally substituted heterocyclyl.

Provided herein are compounds of Formula (E-C-2):

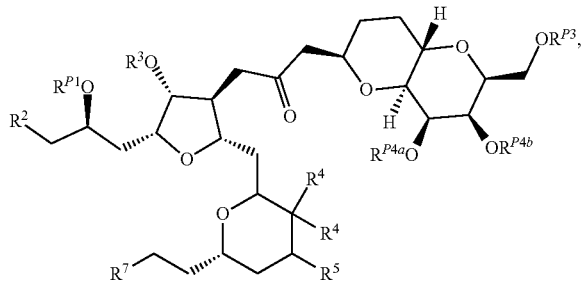

(E-C-2)

and salts thereof, wherein:

R² is —$OR^{P1a}$ or —$N(R^N)_2$;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$, $R^{P1a}$, $R^{P3}$, $R^{P4a}$, $R^{P4b}$, and $R^{7a}$ are independently hydrogen, optionally substituted alkyl, or an oxygen protecting group;

R³ is hydrogen, optionally substituted alkyl, or an oxygen protecting group;

R⁷ is —$CH_2OR^{7a}$, —$CO_2R^{7a}$, or —C(O)H;

each instance of R⁴ is independently hydrogen, halogen, optionally substituted alkyl, or two R⁴ groups are taken together to form:

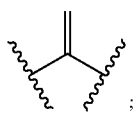

and

R⁵ is hydrogen, halogen, or optionally substituted alkyl;

optionally wherein $R^{P1}$ and $R^{P1a}$ are taken together with the intervening atoms to form optionally substituted heterocyclyl; and optionally wherein $R^{P4a}$ and $R^{P4b}$ are joined together with the intervening atoms to form optionally substituted heterocyclyl.

Provided herein are compounds of Formula (E-A-3):

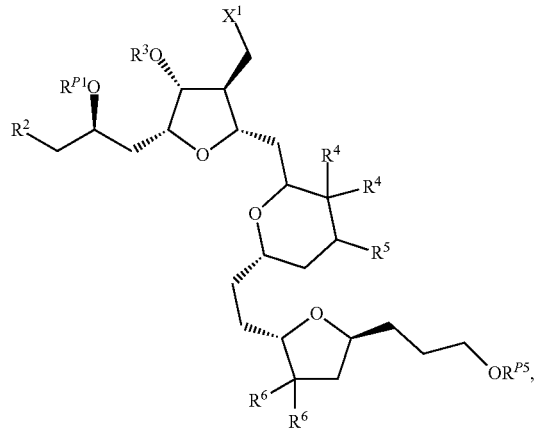

(E-A-3)

and salts thereof, wherein:

X¹ is halogen or a leaving group;

R² is —$OR^{P1a}$ or —$N(R^N)_2$; each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$, $R^{P1a}$, and $R^{P5}$ are independently hydrogen, optionally substituted alkyl, or an oxygen protecting group; and R³ is hydrogen, optionally substituted alkyl, or an oxygen protecting group;

each instance of R⁴ is independently hydrogen, halogen, optionally substituted alkyl, or two R⁴ groups are taken together to form:

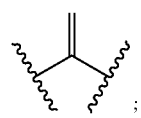

each instance of R⁶ is independently hydrogen, halogen, optionally substituted alkyl, or two R⁶ groups are taken together to form:

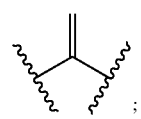

and

R⁵ is hydrogen, halogen, or optionally substituted alkyl;

optionally wherein $R^{P1}$ and $R^{P1a}$ are taken together with the intervening atoms to form optionally substituted heterocyclyl.

Provided herein are compounds of Formula (E-B-2):

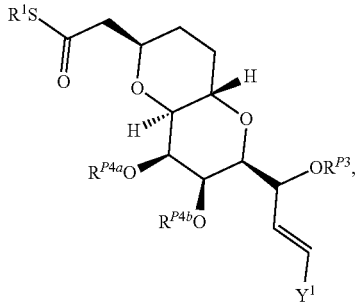

and salts thereof, wherein:

R$^1$ is optionally substituted alkyl;

R$^{P3}$, R$^{P4a}$, and R$^{P4b}$ are independently hydrogen, optionally substituted alkyl, or an oxygen protecting group; and Y$^1$ is halogen, a leaving group, or silyl;

optionally wherein R$^{P4a}$ and R$^{P4b}$ are joined together with the intervening atoms to form optionally substituted heterocyclyl.

Provided herein are compounds of Formula (E-C-3):

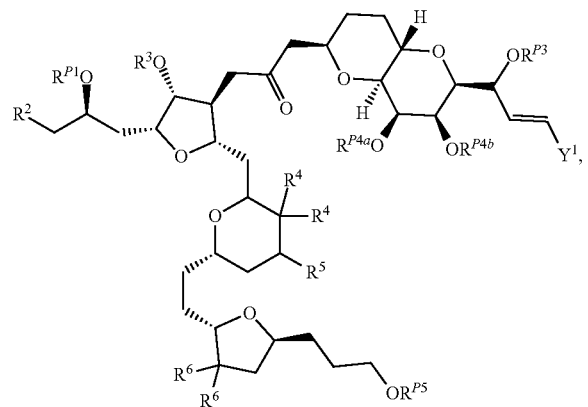

and salts thereof, wherein:

R$^2$ is —OR$^{P1a}$ or —N(R$^N$)$_2$;

each instance of R$^N$ is hydrogen, optionally substituted alkyl, or a nitrogen protecting group, or optionally two R$^N$ are joined together with the intervening atoms to form optionally substituted heterocyclyl or optionally substituted heteroaryl;

R$^{P1}$, R$^{P1a}$, R$^{P3}$, R$^{P4a}$, R$^{P4b}$, and R$^{P5}$ are independently hydrogen, optionally substituted alkyl, or an oxygen protecting group; and R$^3$ is hydrogen, optionally substituted alkyl, or an oxygen protecting group;

each instance of R$^4$ is independently hydrogen, halogen, optionally substituted alkyl, or two R$^4$ groups are taken together to form:

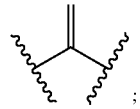 [SMILES: *C(*)=C]

each instance of R$^6$ is independently hydrogen, halogen, optionally substituted alkyl, or two R$^6$ groups are taken together to form:

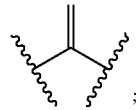 [SMILES: *C(*)=C]

R$^5$ is hydrogen, halogen, or optionally substituted alkyl; and

Y$^1$ is halogen, a leaving group, or trialkylailyl;

optionally wherein R$^{P1}$ and R$^{P1a}$ are taken together with the intervening atoms to form optionally substituted heterocyclyl; and optionally wherein R$^{P4a}$ and R$^{P4b}$ are joined together with the intervening atoms to form optionally substituted heterocyclyl.

Provided herein are compounds of Formula (E-5):

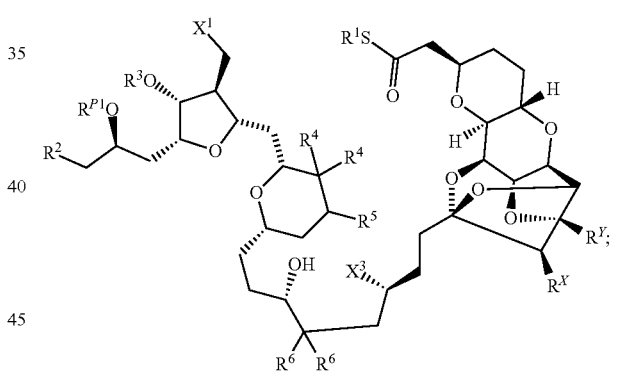

and salts thereof, wherein:

X$^1$ and X$^3$ are independently halogen or a leaving group;

R$^1$ is optionally substituted alkyl;

R$^2$ is —OR$^{P1a}$ or —N(R$^N$)$_2$;

each instance of R$^N$ is hydrogen, optionally substituted alkyl, or a nitrogen protecting group, or optionally two R$^N$ are joined together with the intervening atoms to form optionally substituted heterocyclyl or optionally substituted heteroaryl;

R$^{P1}$ and R$^{P1a}$ are independently hydrogen, optionally substituted alkyl, or an oxygen protecting group;

R$^3$ is hydrogen, optionally substituted alkyl, or an oxygen protecting group;

each instance of R$^4$ is independently hydrogen, halogen, optionally substituted alkyl, or two R$^4$ groups are taken together to form:

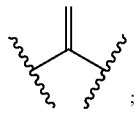 [SMILES: *C(*)=C]

each instance of $R^6$ is independently hydrogen, halogen, optionally substituted alkyl, or two $R^6$ groups are taken together to form:

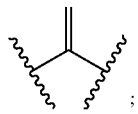 [SMILES: *C(*)=C]

$R^5$ is hydrogen, halogen, or optionally substituted alkyl;
$R^7$ is —$CO_2R^{7a}$, or —C(O)H
$R^X$ is hydrogen or —$OR^{Xa}$, wherein $R^{Xa}$ is hydrogen, optionally substituted alkyl, or an oxygen protecting group; and
$R^Y$ is hydrogen or —$OR^{Ya}$, wherein $R^{Ya}$ is hydrogen, optionally substituted alkyl, or an oxygen protecting group;
optionally wherein $R^{Xa}$ and $R^{Ya}$ are joined together with their intervening atoms to form optionally substituted heterocyclyl; and
optionally wherein $R^{P1}$ and $R^{P1a}$ are taken together with the intervening atoms to form optionally substituted heterocyclyl.

Provided herein are compounds of Formula (E-2):

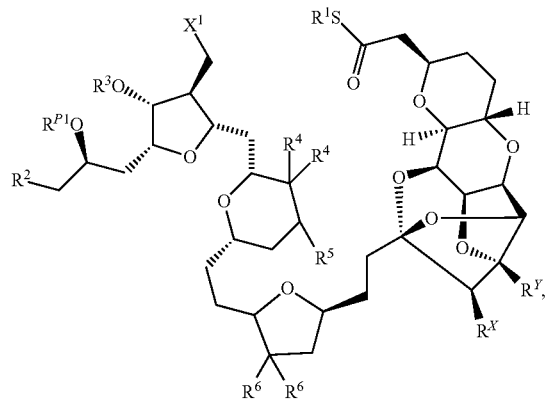

(E-2)

and salts thereof, wherein:
$X^1$ is halogen or a leaving group;
$R^1$ is optionally substituted alkyl;
$R^2$ is —$OR^{P1a}$ or —$N(R^N)_2$;
each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
$R^{P1}$ and $R^{P1a}$ are independently hydrogen, optionally substituted alkyl, or an oxygen protecting group;
$R^3$ is hydrogen, optionally substituted alkyl, or an oxygen protecting group;
each instance of $R^4$ is independently hydrogen, halogen, optionally substituted alkyl, or two $R^4$ groups are taken together to form:

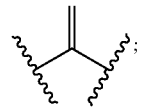 [SMILES: *C(*)=C]

each instance of $R^6$ is independently hydrogen, halogen, optionally substituted alkyl, or two $R^6$ groups are taken together to form:

$R^5$ is hydrogen, halogen, or optionally substituted alkyl;
$R^X$ is hydrogen or —$OR^{Xa}$, wherein $R^{Xa}$ is hydrogen, optionally substituted alkyl, or an oxygen protecting group; and
$R^Y$ is hydrogen or —$OR^{Ya}$, wherein $R^{Ya}$ is hydrogen, optionally substituted alkyl, or an oxygen protecting group;
optionally wherein $R^{Xa}$ and $R^{Ya}$ are joined together with their intervening atoms to form optionally substituted heterocyclyl; and
optionally wherein $R^{P1}$ and $R^{P1a}$ are taken together with the intervening atoms to form optionally substituted heterocyclyl.

Provided herein are compounds of Formula (E-2-A):

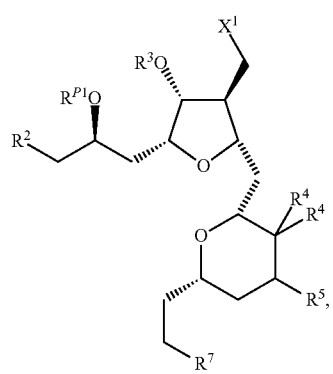

(E-2-A)

and salts thereof, wherein:
$X^1$ is halogen or a leaving group;
$R^2$ is —$OR^{P1a}$ or —$N(R^N)_2$;
each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
$R^{P1}$ and $R^{P1a}$ are independently hydrogen, optionally substituted alkyl, or an oxygen protecting group;
$R^3$ is hydrogen, optionally substituted alkyl, or an oxygen protecting group;

each instance of $R^4$ is independently hydrogen, halogen, optionally substituted alkyl, or two $R^4$ groups are taken together to form:

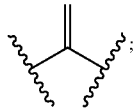

$R^5$ is hydrogen, halogen, or optionally substituted alkyl; and $R^7$ is —CH$_2$OR$^{7a}$; —CO$_2$R$^{7a}$, or —C(O)H;

optionally wherein $R^{P1}$ and $R^{P1a}$ are taken together with the intervening atoms to form optionally substituted heterocyclyl.

Provided herein are compounds of Formula (E-4):

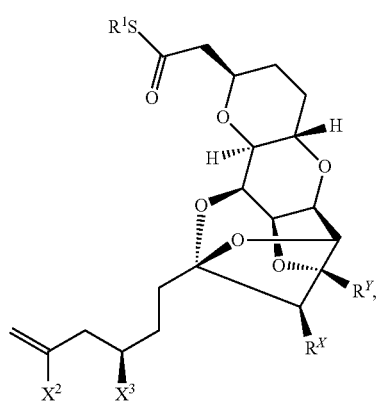

(E-4)

and salts thereof, wherein:

$X^2$ and $X^3$ are independently halogen or a leaving group;

$R^1$ is optionally substituted alkyl;

each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;

$R^{P1}$ and $R^{P1a}$ are independently hydrogen, optionally substituted alkyl, or an oxygen protecting group;

$R^X$ is hydrogen or —OR$^{Xa}$, wherein $R^{Xa}$ is hydrogen, optionally substituted alkyl, or an oxygen protecting group;

$R^Y$ is hydrogen or —OR$^{Ya}$, wherein $R^{Ya}$ is hydrogen, optionally substituted alkyl, or an oxygen protecting group; and optionally wherein $R^{Xa}$ and $R^{Ya}$ are joined together with their intervening atoms to form optionally substituted heterocyclyl; and optionally wherein $R^{P1}$ and $R^{P1a}$ are taken together with the intervening atoms to form optionally substituted heterocyclyl.

Provided herein are compounds of Formula (E-1):

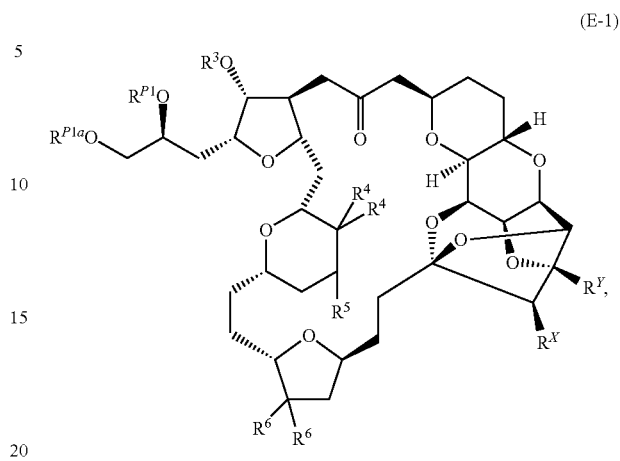

(E-1)

and salts thereof, wherein:

$R^{P1}$ and $R^{P1a}$ are independently hydrogen, optionally substituted alkyl, or an oxygen protecting group, optionally wherein $R^{P1}$ and $R^{P1a}$ are taken together with the intervening atoms to form optionally substituted heterocyclyl;

$R^3$ is hydrogen, optionally substituted alkyl, or an oxygen protecting group;

each instance of $R^4$ is independently hydrogen, halogen, optionally substituted alkyl, or two $R^4$ groups are taken together to form:

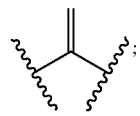 [SMILES: *C(*)=C]

each instance of $R^6$ is independently hydrogen, halogen, optionally substituted alkyl, or two $R^6$ groups are taken together to form:

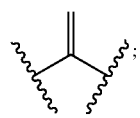 [SMILES: *C(*)=C]

$R^5$ is hydrogen, halogen, or optionally substituted alkyl;

$R^X$ is hydrogen or —OR$^{Xa}$, wherein $R^{Xa}$ is hydrogen, optionally substituted alkyl, or an oxygen protecting group; and $R^Y$ is hydrogen or —OR$^{Ya}$, wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl.

Also provided herein are keto analogs of halichondrins (e.g., halichondrin A, B, C; homohalichondrin A, B, C; norhalichondrin A, B, C) as well as compounds useful in their preparation. For example, in certain embodiments, provided herein are compounds of Formula (H-1):

(H-1)

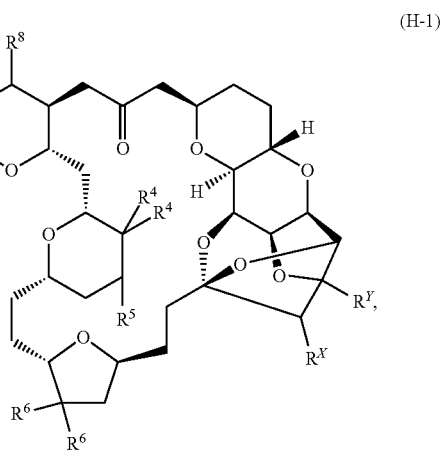

and pharmaceutically acceptable salts thereof, wherein:

$R^{P5}$, $R^{P6}$, and $R^{P7}$ are independently hydrogen, optionally substituted alkyl, or an oxygen protecting group;

each instance of $R^4$ is independently hydrogen, halogen, optionally substituted alkyl, or two $R^4$ groups are taken together to form:

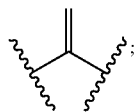

each instance of $R^6$ is independently hydrogen, halogen, optionally substituted alkyl, or two $R^6$ groups are taken together to form:

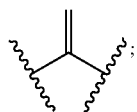 [SMILES: *C(*)=C]

$R^5$, $R^8$, $R^9$, and $R^{10}$ are independently hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with the intervening atoms to form optionally substituted heterocyclyl;

optionally wherein $R^{P5}$ and $R^{P6}$ are joined together with the intervening atoms to form optionally substituted heterocyclyl; or optionally wherein $R^{P6}$ and $R^{P7}$ are joined together with the intervening atoms to form optionally substituted heterocyclyl.

In certain embodiments, a compound of Formula (H-1) is selected from the group consisting of:

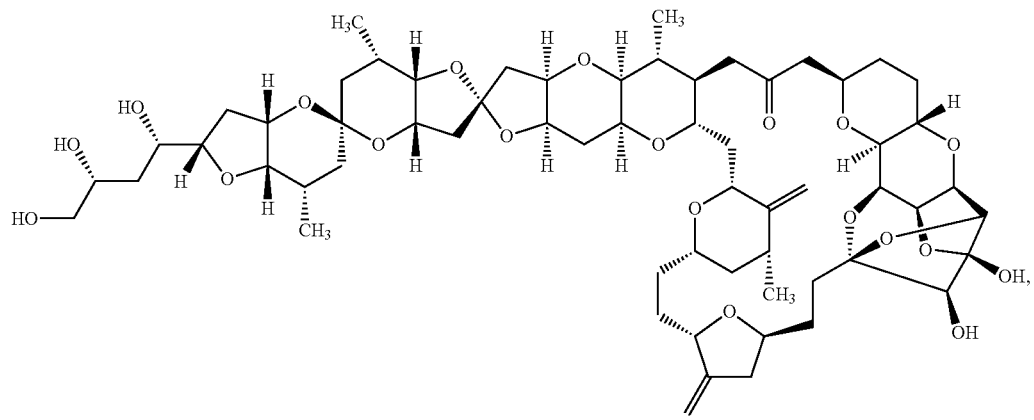

(keto-halichondrin A)

-continued

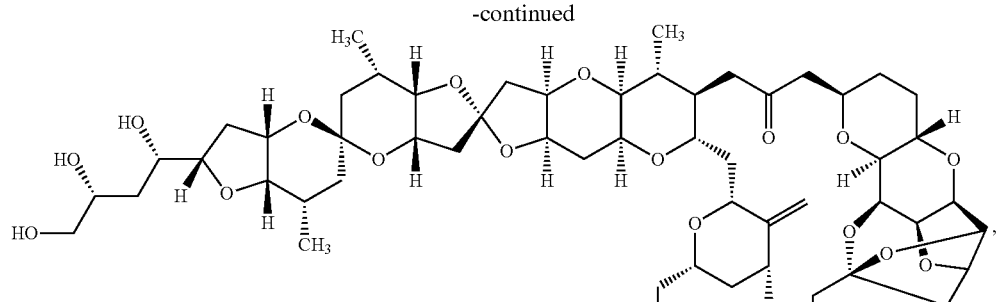
(keto-halichondrin B)

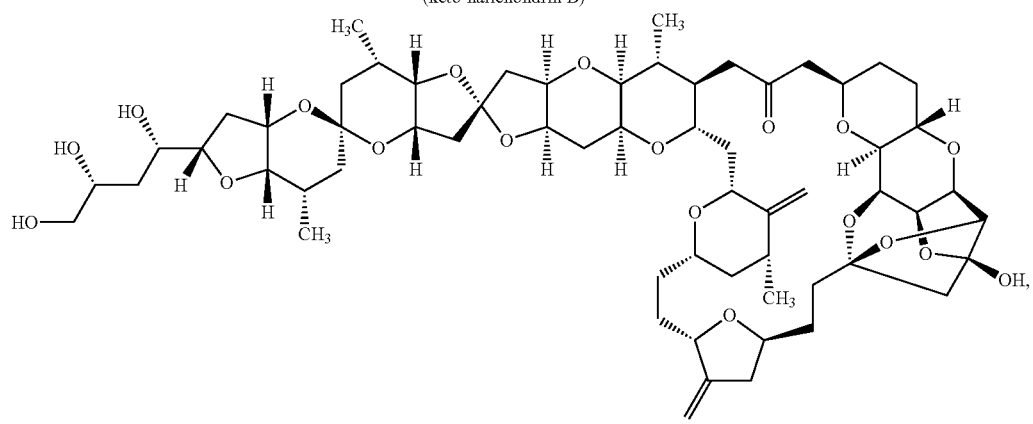
(keto-halichondrin C)

and pharmaceutically acceptable salts thereof.

Provided herein are compounds of Formula (HH-1):

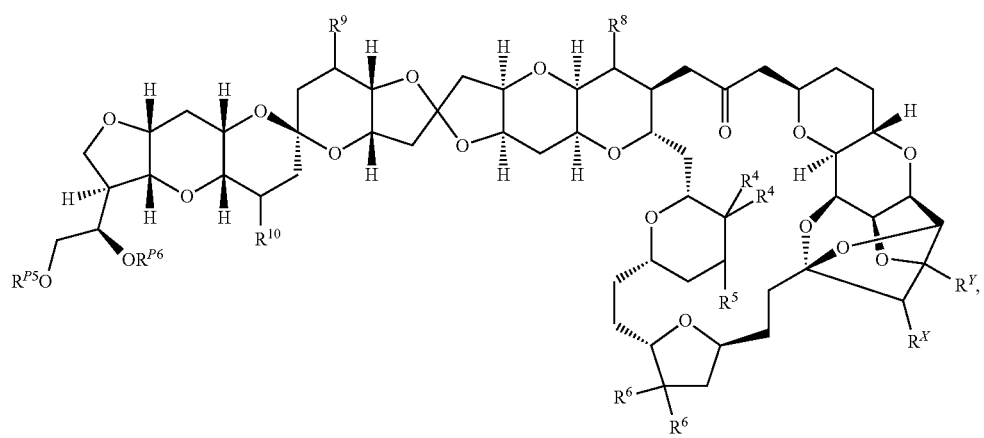

and salts thereof, wherein:

$R^{P5}$ and $R^{P6}$ are independently hydrogen, optionally substituted alkyl, or an oxygen protecting group;

each instance of $R^4$ is independently hydrogen, halogen, optionally substituted alkyl, or two $R^4$ groups are taken together to form:

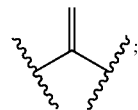 [SMILES: *C(*)=C]

each instance of $R^6$ is independently hydrogen, halogen, optionally substituted alkyl, or two $R^6$ groups are taken together to form:

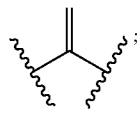

$R^5$, $R^8$, $R^9$, and $R^{10}$ are hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally, wherein $R^{Xa}$ and $R^{Ya}$ are joined together with their intervening atoms to form optionally substituted heterocyclyl; or optionally, wherein $R^{P5}$ and $R^{P6}$ are joined together with the intervening atoms to form optionally substituted heterocyclyl.

In certain embodiments, a compound of Formula (HH-1) is selected from the group consisting of:

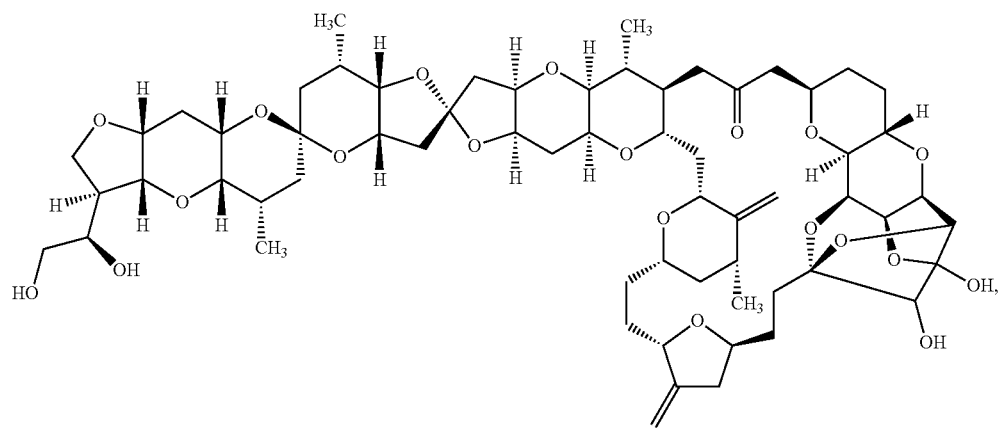

(keto-homohalichondrin A)

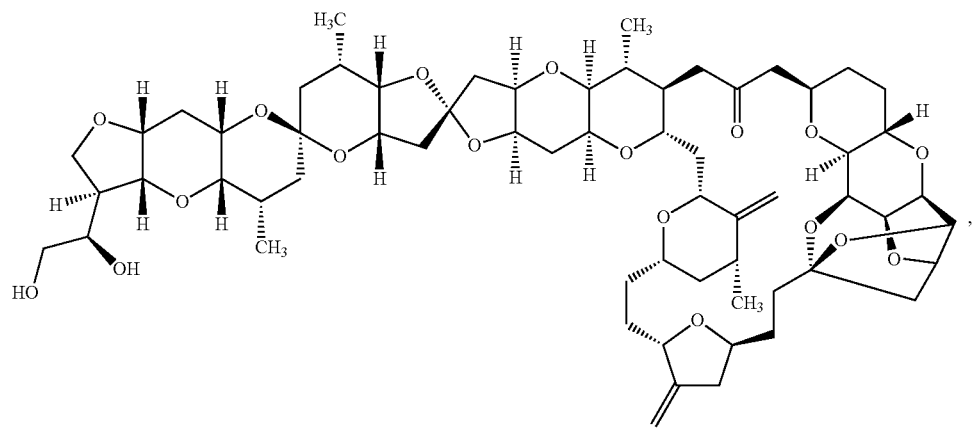

(keto-homohalichondrin B)

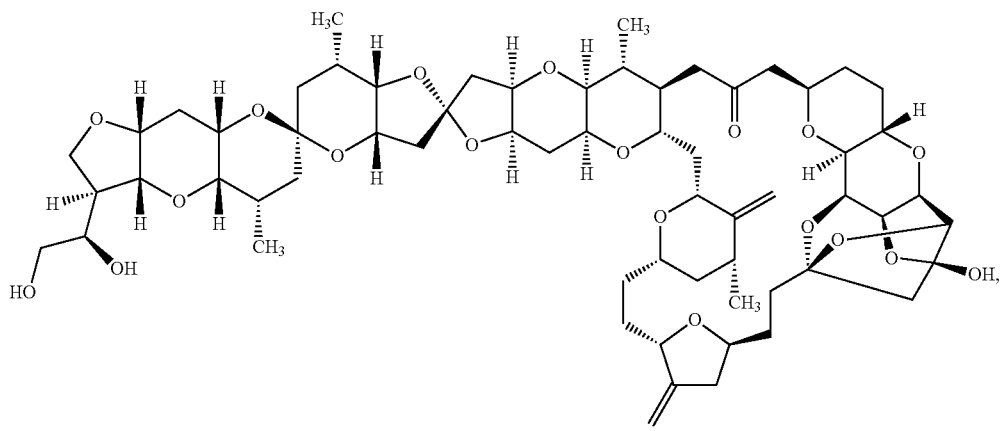

(keto-homohalichondrin C)

and pharmaceutically acceptable salts thereof.

Provided herein are compounds of Formula (NH-1):

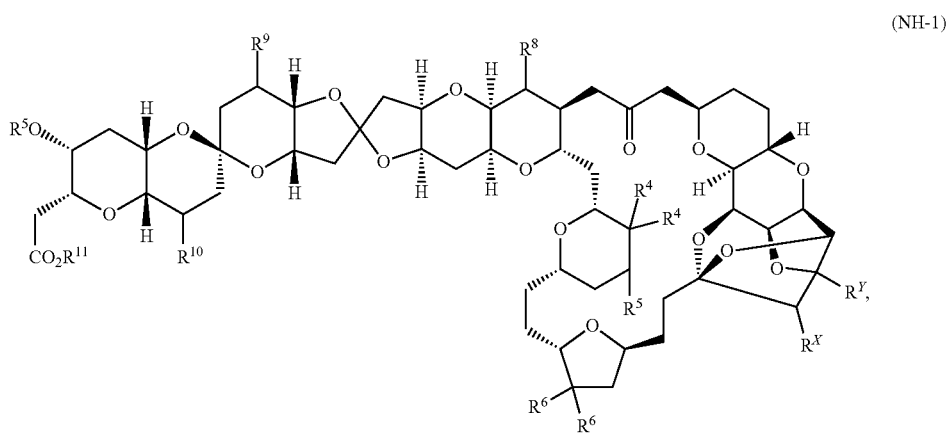

(NH-1)

and salts thereof, wherein:

$R^5$ and $R^{11}$ are independently hydrogen, optionally substituted alkyl, or an oxygen protecting group;

each instance of $R^4$ is independently hydrogen, halogen, optionally substituted alkyl, or two $R^4$ groups are taken together to form:

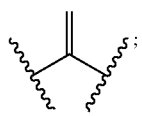 [SMILES: *C(*)=C]

each instance of $R^6$ is independently hydrogen, halogen, optionally substituted alkyl, or two $R^6$ groups are taken together to form:

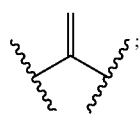 [SMILES: *C(*)=C]

$R^8$ and $R^9$ are independently hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl.

In certain embodiments, a compound of Formula (NH-1) is selected from the group consisting of:

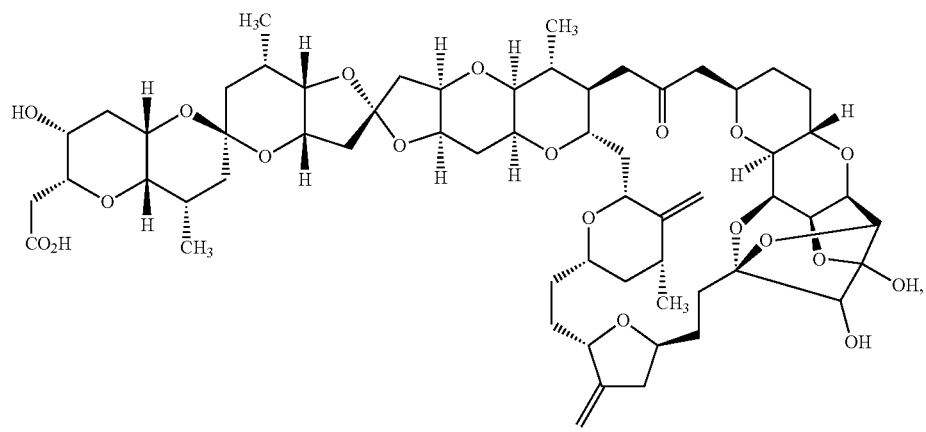
(keto-norhalichondrin A)
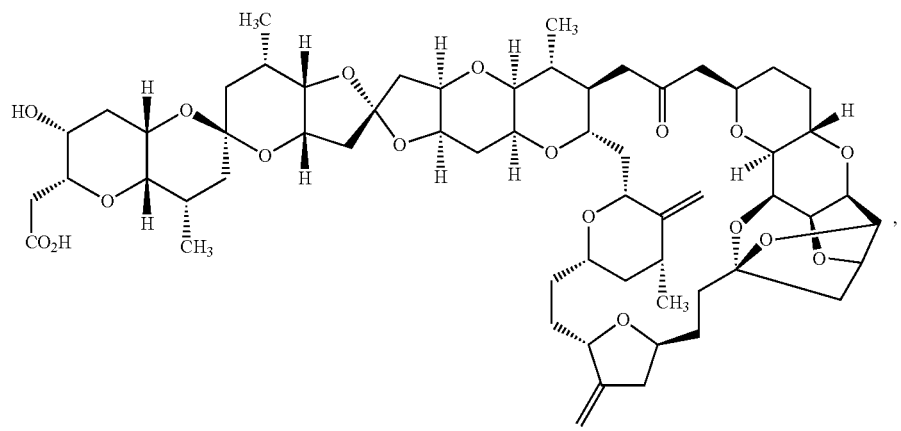
(keto-norhalichondrin B)
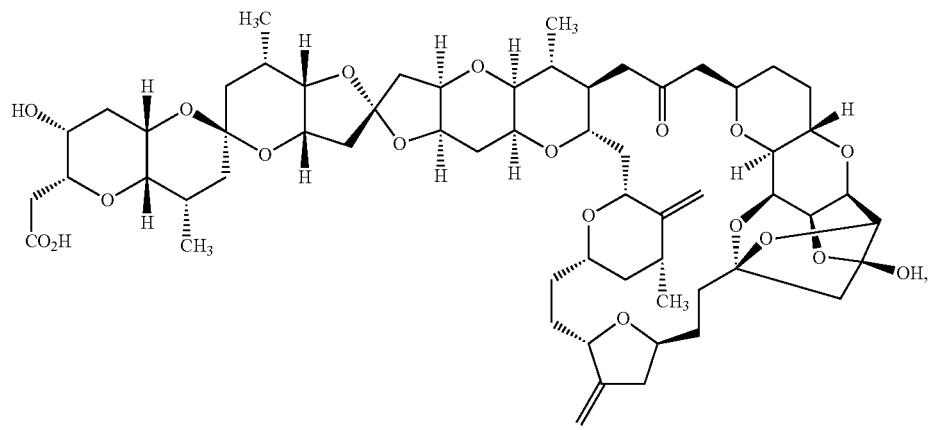
(keto-norhalichondrin C)
and pharmaceutically acceptable salts thereof.

Provided herein are compounds of Formula (H-2):

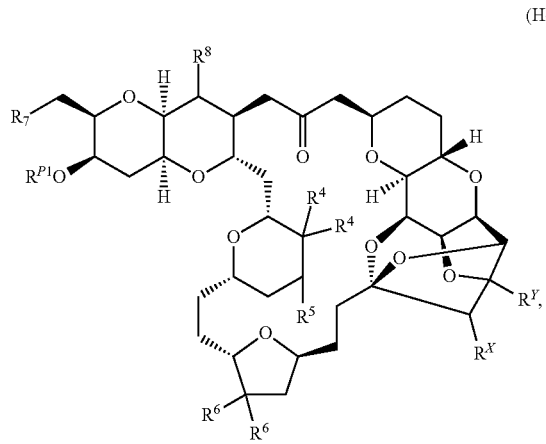

(H-2)

and salts thereof, wherein:

$R^{P1}$ is hydrogen, optionally substituted alkyl, or an oxygen protecting group;

each instance of $R^4$ is independently hydrogen, halogen, optionally substituted alkyl, or two $R^4$ groups are taken together to form:

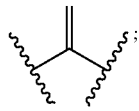

each instance of $R^6$ is independently hydrogen, halogen, optionally substituted alkyl, or two $R^6$ groups are taken together to form:

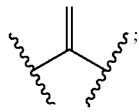 [SMILES: *C(*)=C]

$R^5$ is hydrogen, halogen, or optionally substituted alkyl;

$R^7$ is —$CH_2OR^{7a}$, —$CO_2R^{7a}$, or —$C(O)H$;

$R^8$ is hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl;

optionally wherein $R^{7a}$ and $R^{P1}$ are joined together with the intervening atoms to form optionally substituted heterocyclyl.

Provided herein are compounds of Formula (H-3):

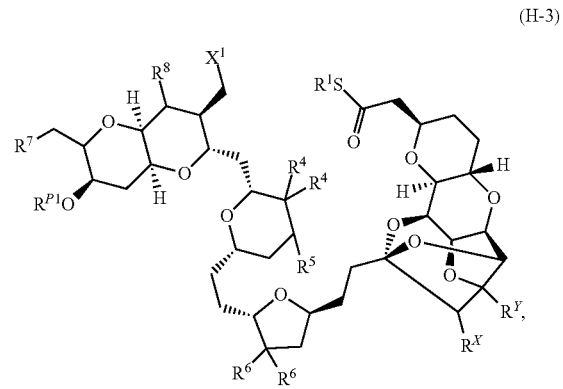

(H-3)

and salts thereof, wherein:

$X^1$ is halogen or a leaving group;

$R^1$ is optionally substituted alkyl;

$R^{P1}$ is hydrogen, optionally substituted alkyl, or an oxygen protecting group;

each instance of $R^4$ is independently hydrogen, halogen, optionally substituted alkyl, or two $R^4$ groups are taken together to form:

each instance of $R^6$ is independently hydrogen, halogen, optionally substituted alkyl, or two $R^6$ groups are taken together to form:

$R^5$ is hydrogen, halogen, or optionally substituted alkyl;

$R^7$ is —$CH_2OR^{7a}$, —$CO_2R^{7a}$, or —$C(O)H$;

$R^8$ is hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with their intervening atoms to form optionally substituted heterocyclyl;

optionally wherein $R^{7a}$ and $R^{P1}$ are joined together with the intervening atoms to form optionally substituted heterocyclyl.

Provided herein are compounds of Formula (H-A-1):

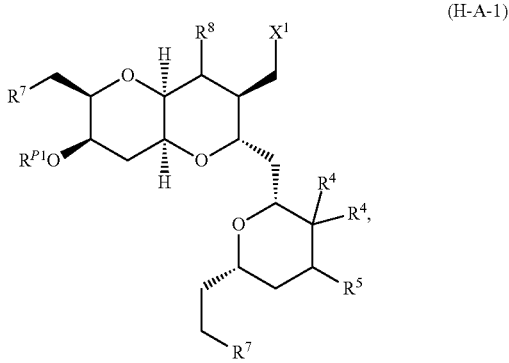

(H-A-1)

and salts thereof, wherein:
$X^1$ is halogen or a leaving group;
$R^{P1}$ is hydrogen, optionally substituted alkyl, or an oxygen protecting group;
each instance of $R^4$ is independently hydrogen, halogen, optionally substituted alkyl, or two $R^4$ groups are taken together to form:

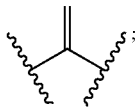 [SMILES: *C(*)=C]

$R^5$ is hydrogen, halogen, or optionally substituted alkyl;
$R^7$ is —CH$_2$OR$^{7a}$, —CO$_2$R$^{7a}$, or —C(O)H;
$R^X$ is hydrogen or —OR$^{Xa}$, wherein $R^{Xa}$ is hydrogen, optionally substituted alkyl, or an oxygen protecting group; and
$R^Y$ is hydrogen or —OR$^{Ya}$, wherein $R^{Ya}$ is hydrogen, optionally substituted alkyl, or an oxygen protecting group;
optionally wherein $R^{Xa}$ and $R^{Ya}$ are joined together with their intervening atoms to form optionally substituted heterocyclyl;
optionally wherein $R^{7a}$ and $R^{P1}$ are joined together with the intervening atoms to form optionally substituted heterocyclyl.

Provided herein are compounds of Formula (H-4):

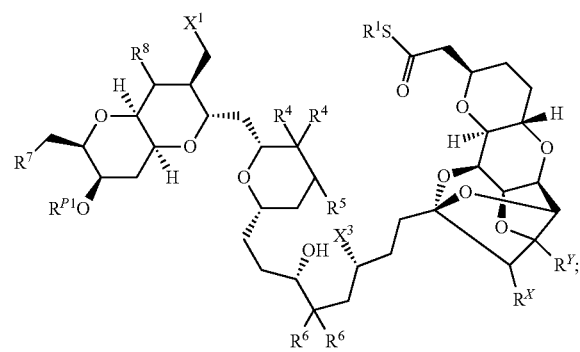

(H-4)

and salts thereof, wherein:
$X^1$, $X^2$, and $X^3$ are independently halogen or a leaving group;
$R^1$ is optionally substituted alkyl;
$R^2$ is —OR$^{P1a}$ or —N(R$^N$)$_2$;
each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl;
$R^{P1}$ is hydrogen, optionally substituted alkyl, or an oxygen protecting group;
$R^3$ is hydrogen, optionally substituted alkyl, or an oxygen protecting group;
each instance of $R^4$ is independently hydrogen, halogen, optionally substituted alkyl, or two $R^4$ groups are taken together to form:

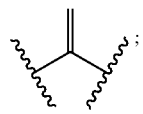

each instance of $R^6$ is independently hydrogen, halogen, optionally substituted alkyl, or two $R^6$ groups are taken together to form:

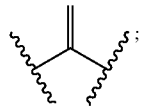

$R^5$ is hydrogen, halogen, or optionally substituted alkyl;
$R^7$ is —CH$_2$OR$^{7a}$, —CO$_2$R$^{7a}$, or —C(O)H;
$R^X$ is hydrogen or —OR$^{Xa}$, wherein $R^{Xa}$ is hydrogen, optionally substituted alkyl, or an oxygen protecting group; and
$R^Y$ is hydrogen or —OR$^{Ya}$, wherein $R^{Ya}$ is hydrogen, optionally substituted alkyl, or an oxygen protecting group;
optionally wherein $R^{Xa}$ and $R^{Ya}$ are joined together with their intervening atoms to form optionally substituted heterocyclyl; and
optionally wherein $R^{7a}$ and $R^{P1}$ are joined together with the intervening atoms to form optionally substituted heterocyclyl.

Group Definitions

The following definitions apply to all compounds and methods provided herein.

Groups $R^A$, $R^{A1}$, $R^{A2}$, $R^B$, $R^{B1}$, $R^{B2}$

As generally defined herein, $R^A$ is optionally substituted alkyl. $R^A$ may be complex group, such as a natural product, therapeutic agent, or fragment thereof. In certain embodiments, $R^A$ is a small molecule.

As generally defined herein, $R^B$ is optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, $R^B$ is optionally substituted alkyl. $R^B$ may be complex group, such as a natural product, therapeutic agent, or fragment thereof. In certain embodiments, $R^B$ is a small molecule.

In certain embodiments, $R^A$ and $R^B$ are joined together via a linker to form a compound of Formula (A-B).

As generally defined herein, each instance of $R^{A1}$, $R^{A2}$, $R^{B1}$, and $R^{B2}$ is independently hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, each instance of $R^{A1}$, $R^{A2}$, $R^{B1}$, and $R^{B2}$ is independently a small molecule.

In certain embodiments, $R^{A1}$ is hydrogen. In certain embodiments, $R^{A1}$ is optionally substituted alkyl. In certain embodiments, $R^{A1}$ is optionally substituted alkenyl. In certain embodiments, $R^{A1}$ is optionally substituted alkynyl. In certain embodiments, $R^{A1}$ is optionally substituted aryl. In certain embodiments, $R^{A1}$ is optionally substituted carbocyclyl. In certain embodiments, $R^{A1}$ is optionally substituted heteroaryl. In certain embodiments, $R^{A1}$ is optionally substituted heterocyclyl. In certain embodiments, $R^{A1}$ is a small molecule.

In certain embodiments, $R^{A2}$ is hydrogen. In certain embodiments, $R^{A2}$ is optionally substituted alkyl. In certain embodiments, $R^{A2}$ is optionally substituted alkenyl. In certain embodiments, $R^{A2}$ is optionally substituted alkynyl. In certain embodiments, $R^{A2}$ is optionally substituted aryl. In certain embodiments, $R^{A2}$ is optionally substituted carbocyclyl. In certain embodiments, $R^{A2}$ is optionally substituted heteroaryl. In certain embodiments, $R^{A2}$ is optionally substituted heterocyclyl. In certain embodiments, $R^{A2}$ is a small molecule.

In certain embodiments, $R^{B1}$ is hydrogen. In certain embodiments, $R^{B1}$ is optionally substituted alkyl. In certain embodiments, $R^{B1}$ is optionally substituted alkenyl. In certain embodiments, $R^{B1}$ is optionally substituted alkynyl. In certain embodiments, $R^{B1}$ is optionally substituted aryl. In certain embodiments, $R^{B1}$ is optionally substituted carbocyclyl. In certain embodiments, $R^{B1}$ is optionally substituted heteroaryl. In certain embodiments, $R^{B1}$ is optionally substituted heterocyclyl. In certain embodiments, $R^{B1}$ is a small molecule.

In certain embodiments, $R^{B2}$ is hydrogen. In certain embodiments, $R^{B2}$ is optionally substituted alkyl. In certain embodiments, $R^{B2}$ is optionally substituted alkenyl. In certain embodiments, $R^{B2}$ is optionally substituted alkynyl. In certain embodiments, $R^{B2}$ is optionally substituted aryl. In certain embodiments, $R^{B2}$ is optionally substituted carbocyclyl. In certain embodiments, $R^{B2}$ is optionally substituted heteroaryl. In certain embodiments, $R^{B2}$ is optionally substituted heterocyclyl. In certain embodiments, $R^{B2}$ is a small molecule.

In certain embodiments, $R^{A1}$ and $R^{B1}$ are joined together via a linker to form a compound of Formula (A-B).

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 2,000 g/mol, not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, at least about 1,000 g/mol, or at least about 2,000 g/mol. Combinations of the above ranges (e.g., at least about 200 g/mol and not more than about 500 g/mol) are also possible.

Group $R^1$

As generally defined herein, $R^1$ is optionally substituted alkyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-3}$ alkyl. In certain embodiments, $R^1$ is unsubstituted $C_{1-3}$ alkyl. In certain embodiments, $R^1$ is selected from the group consisting of methyl, ethyl, n-propyl, iso-propyl, n-butyl, iso-butyl, sec-butyl, and tert-butyl. In certain embodiments, $R^1$ is ethyl.

Group $R^2$, $R^{P1a}$, and $R^N$

As generally defined herein, $R^2$ is —$OR^{P1a}$ or —$N(R^N)_2$. In certain embodiments, $R^2$ is —$OR^{P1a}$. In certain embodiments, $R^2$ is —$N(R^N)_2$. In certain embodiments, $R^2$ is —OH. In certain embodiments, $R^2$ is —O—silyl. In certain embodiments, $R^2$ is —O—Sit-BuMe$_2$.

As generally defined herein, each instance of $R^N$ is hydrogen, optionally substituted alkyl, or a nitrogen protecting group, or optionally two $R^N$ are joined together with the intervening atoms to form optionally substituted heterocyclyl or optionally substituted heteroaryl. In certain embodiments, at least one instance of $R^N$ is hydrogen. In certain embodiments, at least one instance of $R^N$ is optionally substituted alkyl. In certain embodiments, at least one instance of $R^N$ is a nitrogen protecting group.

As generally defined herein, $R^{P1a}$ is hydrogen, optionally substituted alkyl, or an oxygen protecting group, optionally wherein $R^{P1}$ and $R^{P1a}$ are taken together with the intervening atoms to form optionally substituted heterocyclyl. In certain embodiments, $R^{P1a}$ is hydrogen. In certain embodiments, $R^{P1a}$ is optionally substituted alkyl. In certain embodiments, $R^{P1a}$ is an oxygen protecting group. In certain embodiments, $R^{P1a}$ is silyl. In certain embodiments, $R^{P1a}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P1a}$ is 4-monomethoxytrityl (MMTr). In certain embodiments, $R^{P1a}$ is tert-butyl dimethylsilyl (—Sit-BuMe$_2$ (TBS or TBDMS)). In certain embodiments, $R^{P1a}$ is 4,4'-dimethoxytrityl (DMTr). In certain embodiments, $R^{P1}$ and $R^{P1a}$ are taken together with the intervening atoms to form optionally substituted heterocyclyl. In certain embodiments, $R^{P1}$ and $R^{P1a}$ are taken together with the intervening atoms to form optionally substituted five-membered heterocyclyl. In certain embodiments, $R^{P1}$ and $R^{P1a}$ are taken together with the intervening atoms to form a 1,3-dioxolane ring. In certain embodiments, $R^{P1}$ and $R^{P1a}$ are taken together with the intervening atoms to form the following structure:

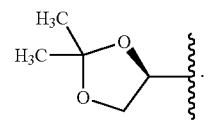

Group $R^3$

As generally defined herein, $R^3$ is hydrogen, optionally substituted alkyl, or an oxygen protecting group. In certain embodiments, $R^3$ is hydrogen. In certain embodiments, $R^3$ is optionally substituted alkyl. In certain embodiments, $R^3$ is an oxygen protecting group. In certain embodiments, $R^3$ is optionally substituted $C_{1-6}$ alkyl. In certain embodiments, $R^3$ is unsubstituted $C_{1-6}$ alkyl. In certain embodiments, $R^3$ is optionally substituted $C_{1-3}$ alkyl. In certain embodiments, $R^3$ is unsubstituted $C_{1-3}$ alkyl. In certain embodiments, $R^3$ is selected from the group consisting of methyl, ethyl, n-propyl, iso-propyl, n-butyl, iso-butyl, sec-butyl, and tert-butyl. In certain embodiments, $R^3$ is methyl.

Group $R^{P1}$

As generally defined herein, $R^{P1}$ is hydrogen, optionally substituted alkyl, or an oxygen protecting group; optionally wherein $R^{P1}$ and $R^{P1a}$ are taken together with the intervening atoms to form optionally substituted heterocyclyl. In certain embodiments, $R^{P1}$ is hydrogen. In certain embodiments, $R^{P1}$ is optionally substituted alkyl. In certain embodiments, $R^{P1}$ is an oxygen protecting group. In certain embodiments, $R^{P1}$ is silyl. In certain embodiments, $R^{P1}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P1}$ is tert-butyl dimethylsilyl (—Sit-BuMe$_2$ (TBS or TBDMS)). In certain embodiments, $R^{P1}$ is 4-monomethoxytrityl (MMTr). In certain embodiments, $R^{P1}$ is 4,4'-dimethoxytrityl (DMTr).

Group $R^{P2}$

As generally defined herein, $R^{P2}$ is hydrogen, optionally substituted alkyl, or an oxygen protecting group. In certain embodiments, $R^{P2}$ is hydrogen. In certain embodiments, $R^{P2}$ is optionally substituted alkyl. In certain embodiments, $R^{P2}$ is an oxygen protecting group. In certain embodiments, $R^{P2}$ is silyl. In certain embodiments, $R^{P2}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P2}$ is tert-butyl dimethylsilyl (—Sit-BuMe$_2$ (TBS or TBDMS)). In certain embodiments, $R^{P2}$ is 4-monomethoxytrityl (MMTr). In certain embodiments, $R^{P2}$ is 4,4'-dimethoxytrityl (DMTr).

Group $R^{P3}$

As generally defined herein, $R^{P3}$ is hydrogen, optionally substituted alkyl, or an oxygen protecting group. In certain embodiments, $R^{P3}$ is hydrogen. In certain embodiments, $R^{P3}$ is optionally substituted alkyl. In certain embodiments, $R^{P3}$ is an oxygen protecting group. In certain embodiments, $R^{P3}$ is silyl. In certain embodiments, $R^{P3}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P3}$ is tert-butyl dimethylsilyl (—Sit-BuMe$_2$ (TBS or TBDMS)). In certain embodiments, $R^{P3}$ is 4-monomethoxytrityl (MMTr). In certain embodiments, $R^{P3}$ is 4,4'-dimethoxytrityl (DMTr).

Groups $R^{P4a}$ and $R^{P4b}$

As generally defined herein, $R^{P4a}$ and $R^{P4b}$ are independently hydrogen, optionally substituted alkyl, or an oxygen protecting group; optionally wherein $R^{P4a}$ and $R^{P4b}$ are joined together with the intervening atoms to form optionally substituted heterocyclyl.

In certain embodiments, $R^{P4a}$ is hydrogen. In certain embodiments, $R^{P4a}$ is optionally substituted alkyl. In certain embodiments, $R^{P4a}$ is an oxygen protecting group. In certain embodiments, $R^{P4a}$ is silyl. In certain embodiments, $R^{P4a}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P4a}$ is tert-butyl dimethylsilyl (—Sit-BuMe$_2$ (TBS or TBDMS)). In certain embodiments, $R^{P4a}$ is 4-monomethoxytrityl (MMTr). In certain embodiments, $R^{P4a}$ is 4,4'-dimethoxytrityl (DMTr).

In certain embodiments, $R^{P4b}$ is hydrogen. In certain embodiments, $R^{P4b}$ is optionally substituted alkyl. In certain embodiments, $R^{P4b}$ is an oxygen protecting group. In certain embodiments, $R^{P4b}$ is silyl. In certain embodiments, $R^{P4b}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P4b}$ is tert-butyl dimethylsilyl (—Sit-BuMe$_2$ (TBS or TBDMS)). In certain embodiments, $R^{P4b}$ is 4-monomethoxytrityl (MMTr). In certain embodiments, $R^{P4b}$ is 4,4'-dimethoxytrityl (DMTr).

In certain embodiments, $R^{P4a}$ and $R^{P4b}$ are joined together with the intervening atoms to form optionally substituted heterocyclyl. In certain embodiments, $R^{P4a}$ and $R^{P4b}$ are joined together with the intervening atoms to form optionally substituted five-membered heterocyclyl. In certain embodiments, $R^{P4a}$ and $R^{P4b}$ are joined together with the intervening atoms to form a 1,3-dioxolane ring. In certain embodiments, $R^{P4a}$ and $R^{P4b}$ are joined together with the intervening atoms to form the following structure:

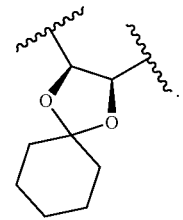

In certain embodiments, $R^{P4a}$ and $R^{P4b}$ are joined together with the intervening atoms to form the following structure:

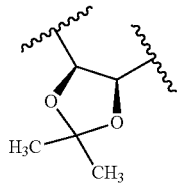

Groups $R^7$ and $R^{7a}$

As generally defined herein, $R^7$ is —CH$_2$OR$^{7a}$, —CO$_2$R$^{7a}$, or —C(O)H. In certain embodiments, $R^7$ is —CH$_2$OR$^7$a. In certain embodiments, $R^7$ is —CO$_2$R$^{7a}$. In certain embodiments, $R^7$ is —C(O)H.

As generally defined herein, $R^{7a}$ is hydrogen, optionally substituted alkyl, or an oxygen protecting group. In certain embodiments, $R^{7a}$ is hydrogen. In certain embodiments, $R^{7a}$ is optionally substituted alkyl. In certain embodiments, $R^{7a}$ is an oxygen protecting group.

In certain embodiments, $R^{7a}$ and $R^{P1}$ are joined together with the intervening atoms to form optionally substituted heterocyclyl. In certain embodiments, $R^{7a}$ and $R^{P1}$ are joined together with the intervening atoms to form optionally substituted 7-membered heterocyclyl. In certain embodiments, $R^{7a}$ and $R^{P1}$ are joined together with the intervening atoms to form the following structure:

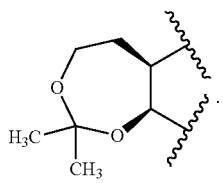

Group R⁴

As generally defined herein, each instance of $R^4$ is independently hydrogen, halogen, optionally substituted alkyl, or two $R^4$ groups are taken together to form:

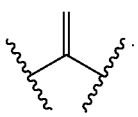 [SMILES: *C(*)=C]

In certain embodiments, at least one instance of $R^4$ is hydrogen. In certain embodiments, at least one instance of $R^4$ is halogen. In certain embodiments, at least one instance of $R^4$ is optionally substituted alkyl. In certain embodiments, two $R^4$ groups are taken together to form:

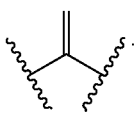 [SMILES: *C(*)=C]

Group R⁶

As generally defined herein, each instance of $R^6$ is independently hydrogen, halogen, optionally substituted alkyl, or two $R^6$ groups are taken together to form:

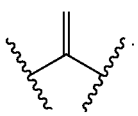 [SMILES: *C(*)=C]

In certain embodiments, at least one instance of $R^6$ is hydrogen. In certain embodiments, at least one instance of $R^6$ is halogen. In certain embodiments, at least one instance of $R^6$ is optionally substituted alkyl. In certain embodiments, two $R^6$ groups are taken together to form:

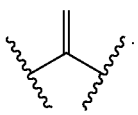 [SMILES: *C(*)=C]

Group R⁵

As generally defined herein, $R^5$ is hydrogen, halogen, or optionally substituted alkyl. In certain embodiments, $R^5$ is hydrogen. In certain embodiments, $R^5$ is halogen, In certain embodiments, $R^5$ is optionally substituted alkyl. In certain embodiments, $R^5$ is optionally substituted $C_{1-6}$ alkyl. In certain embodiments, $R^5$ is unsubstituted $C_{1-6}$ alkyl. In certain embodiments, $R^5$ is optionally substituted $C_{1-3}$ alkyl. In certain embodiments, $R^5$ is unsubstituted $C_{1-3}$ alkyl. In certain embodiments, $R^5$ is selected from the group consisting of methyl, ethyl, n-propyl, iso-propyl, n-butyl, iso-butyl, sec-butyl, and tert-butyl. In certain embodiments, $R^5$ is methyl.

Group $R^{P5}$

As generally defined herein, $R^{P5}$ is hydrogen, optionally substituted alkyl, or an oxygen protecting group. In certain embodiments, $R^{P5}$ is hydrogen. In certain embodiments, $R^{P5}$ is optionally substituted alkyl. In certain embodiments, $R^{P5}$ is an oxygen protecting group. In certain embodiments, $R^{P5}$ is silyl. In certain embodiments, $R^{P5}$ is trimethylsilyl (—SiMe₃ (TMS)), triethylsilyl (—SiEt₃ (TES)), tert-butyl dimethylsilyl (—Sit-BuMe₂ (TBS or TBDMS)), or tert-butyl diphenylsilyl (—Sit-BuPh₂ (TBDPS)). In certain embodiments, $R^{P5}$ is tert-butyl dimethylsilyl (—Sit-BuMe₂ (TBS or TBDMS)). In certain embodiments, $R^{P5}$ is 4-monomethoxytrityl (MMTr). In certain embodiments, $R^{P5}$ is 4,4'-dimethoxytrityl (DMTr).

Group Y¹

As generally defined herein, $Y^1$ is halogen, a leaving group, or silyl. In certain embodiments, $Y^1$ is halogen. In certain embodiments, $Y^1$ is a leaving group. In certain embodiments, $Y^1$ is silyl. In certain embodiments, $Y^1$ is trialkylsilyl. In certain embodiments, $Y^1$ is trimethylsilyl (—SiMe₃ (TMS)), triethylsilyl (—SiEt₃ (TES)), tert-butyl dimethylsilyl (—Sit-BuMe₂ (TBS or TBDMS)), or tert-butyl diphenylsilyl (—Sit-BuPh₂ (TBDPS)). In certain embodiments, $Y^1$ is trimethylsilyl (—SiMe₃ (TMS)).

Groups X', X², and X³

As generally defined herein, $X^1$ is halogen or a leaving group. In certain embodiments, $X^1$ is halogen. In certain embodiments, $X^1$ is chlorine (—Cl), bromine (—Br), iodine (—I), or fluorine (—F). In certain embodiments, $X^1$ is —Cl. In certain embodiments, $X^1$ is —I. In certain embodiments, $X^1$ is —Br. In certain embodiments, $X^1$ is —F. In certain embodiments, $X^1$ is a leaving group. In certain embodiments, $X^1$ is a sulfonate leaving group. In certain embodiments, $X^1$ is a mesylate (—OSO₂CH₃), tosylate (—OSO₂p-CH₃C₆H₄), or triflate (—OSO₂CF₃).

As generally defined herein, $X^2$ is halogen or a leaving group. In certain embodiments, $X^2$ is halogen. In certain embodiments, $X^2$ is chlorine (—Cl), bromine (—Br), iodine (—I), or fluorine (—F). In certain embodiments, $X^2$ is —Cl. In certain embodiments, $X^2$ is —I. In certain embodiments, $X^2$ is —Br. In certain embodiments, $X^2$ is —F. In certain embodiments, $X^2$ is a leaving group. In certain embodiments, $X^2$ is a sulfonate leaving group. In certain embodiments, $X^2$ is a mesylate (—OSO₂CH₃), tosylate (—OSO₂p-CH₃C₆H₄), or triflate (—OSO₂CF₃).

As generally defined herein, $X^3$ is halogen or a leaving group. In certain embodiments, $X^3$ is halogen. In certain embodiments, $X^3$ is chlorine (—Cl), bromine (—Br), iodine (—I), or fluorine (—F). In certain embodiments, $X^3$ is —Cl. In certain embodiments, $X^3$ is —I. In certain embodiments, $X^3$ is —Br. In certain embodiments, $X^3$ is —F. In certain embodiments, $X^3$ is a leaving group. In certain embodiments, $X^3$ is a sulfonate leaving group. In certain embodiments, $X^3$ is a mesylate (—OSO₂CH₃), tosylate (—OSO₂p-CH₃C₆H₄), or triflate (—OSO₂CF₃).

$R^X$, $R^Y$, $R^{Xa}$, and $R^{Ya}$

As generally defined herein, $R^X$ is hydrogen or —$OR^{Xa}$, wherein $R^{Xa}$ is hydrogen, optionally substituted alkyl, or an oxygen protecting group; optionally wherein $R^{Xa}$ and $R^{Ya}$ are joined together with their intervening atoms to form optionally substituted heterocyclyl. In certain embodiments, $R^X$ is hydrogen. In certain embodiments, $R^X$ is —$OR^{Xa}$. In certain embodiments, $R^X$ is —OH.

As generally defined herein, $R^{Xa}$ is hydrogen, optionally substituted alkyl, or an oxygen protecting group. In certain embodiments, $R^{Xa}$ is hydrogen. In certain embodiments, $R^{Xa}$ is optionally substituted alkyl. In certain embodiments, $R^{Xa}$ is an oxygen protecting group. In certain embodiments, $R^{Xa}$ is allyl. In certain embodiments, $R^{Xa}$ is silyl. In certain embodiments, $R^{Xa}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{Xa}$ is 4-monomethoxytrityl (MMTr). In certain embodiments, $R^{Xa}$ is 4,4'-dimethoxytrityl (DMTr).

As generally defined herein, $R^Y$ is hydrogen or —OR$^{Ya}$, wherein $R^{Ya}$ is hydrogen, optionally substituted alkyl, or an oxygen protecting group; optionally wherein $R^{Ya}$ and $R^{Xa}$ are joined together with their intervening atoms to form optionally substituted heterocyclyl. In certain embodiments, $R^Y$ is hydrogen. In certain embodiments, $R^Y$ is —OR$^{Xa}$. In certain embodiments, $R^Y$ is —OH.

As generally defined herein, $R^{Ya}$ is hydrogen, optionally substituted alkyl, or an oxygen protecting group. In certain embodiments, $R^{Ya}$ is hydrogen. In certain embodiments, $R^{Ya}$ is optionally substituted alkyl. In certain embodiments, $R^{Ya}$ is an oxygen protecting group. In certain embodiments, $R^{Ya}$ is allyl. In certain embodiments, $R^{Ya}$ is silyl. In certain embodiments, $R^{Ya}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{Ya}$ is 4-monomethoxytrityl (MMTr). In certain embodiments, $R^{Ya}$ is 4,4'-dimethoxytrityl (DMTr).

In certain embodiments, $R^{Xa}$ and $R^{Ya}$ are joined together with the intervening atoms to form optionally substituted heterocyclyl. In certain embodiments, $R^{Xa}$ and $R^{Ya}$ are joined together with the intervening atoms to form optionally substituted 5-membered heterocyclyl. In certain embodiments, $R^{Xa}$ and $R^{Ya}$ are joined together with the intervening atoms to form optionally substituted 1,3-dioxolane. In certain embodiments, $R^{Xa}$ and $R^{Ya}$ are joined together with the intervening atoms to form substituted 1,3-dioxolane. In certain embodiments, $R^{Xa}$ and $R^{Ya}$ are joined together with the intervening atoms to form one of the following structures:

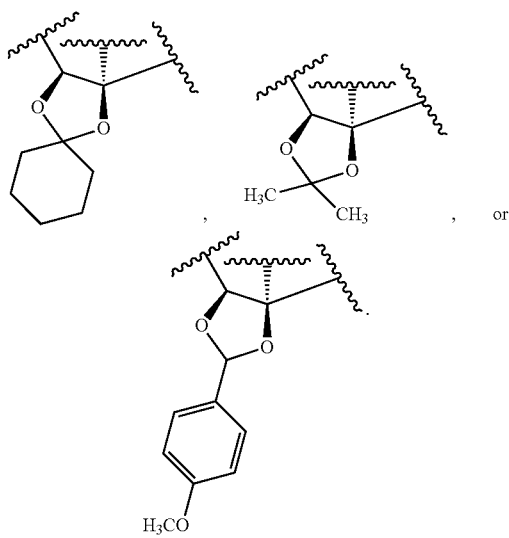

Groups $R^{P5}$, $R^{P6}$, $R^{P7}$

As generally defined herein, $R^{P5}$ is hydrogen, optionally substituted alkyl, or an oxygen protecting group. In certain embodiments, $R^{P5}$ is hydrogen. In certain embodiments, $R^{P5}$ is optionally substituted alkyl. In certain embodiments, $R^{P5}$ is an oxygen protecting group. In certain embodiments, $R^{P5}$ is silyl. In certain embodiments, $R^{P5}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P5}$ is tert-butyl dimethylsilyl (—Sit-BuMe$_2$ (TBS or TBDMS)). In certain embodiments, $R^{P5}$ is 4-monomethoxytrityl (MMTr). In certain embodiments, $R^{P5}$ is 4,4'-dimethoxytrityl (DMTr).

In certain embodiments, $R^{P5}$ and $R^{P6}$ are joined together with the intervening atoms to form optionally substituted heterocyclyl. In certain embodiments, $R^{P5}$ and $R^{P6}$ are joined together with the intervening atoms to form optionally substituted 5-membered heterocyclyl. In certain embodiments, $R^{P5}$ and $R^{P6}$ are joined together with the intervening atoms to form substituted 1,3-dioxolane.

As generally defined herein, $R^{P6}$ is hydrogen, optionally substituted alkyl, or an oxygen protecting group. In certain embodiments, $R^{P6}$ is hydrogen. In certain embodiments, $R^{P6}$ is optionally substituted alkyl. In certain embodiments, $R^{P6}$ is an oxygen protecting group. In certain embodiments, $R^{P6}$ is silyl. In certain embodiments, $R^{P6}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P6}$ is tert-butyl dimethylsilyl (—Sit-BuMe$_2$ (TBS or TBDMS)). In certain embodiments, $R^{P6}$ is 4-monomethoxytrityl (MMTr). In certain embodiments, $R^{P6}$ is 4,4'-dimethoxytrityl (DMTr).

As generally defined herein, $R^{P7}$ is hydrogen, optionally substituted alkyl, or an oxygen protecting group. In certain embodiments, $R^{P7}$ is hydrogen. In certain embodiments, $R^{P7}$ is optionally substituted alkyl. In certain embodiments, $R^{P7}$ is an oxygen protecting group. In certain embodiments, $R^{P7}$ is silyl. In certain embodiments, $R^{P7}$ is trimethylsilyl (—SiMe$_3$ (TMS)), triethylsilyl (—SiEt$_3$ (TES)), tert-butyl dimethylsilyl (—Sit-BuMe$_2$ (TBS or TBDMS)), or tert-butyl diphenylsilyl (—Sit-BuPh$_2$ (TBDPS)). In certain embodiments, $R^{P7}$ is tert-butyl dimethylsilyl (—Sit-BuMe$_2$ (TBS or TBDMS)). In certain embodiments, $R^{P7}$ is 4-monomethoxytrityl (MMTr). In certain embodiments, $R^{P7}$ is 4,4'-dimethoxytrityl (DMTr).

In certain embodiments, $R^{P6}$ and $R^{P7}$ are joined together with the intervening atoms to form optionally substituted heterocyclyl. In certain embodiments, $R^{P6}$ and $R^{P7}$ are joined together with the intervening atoms to form optionally substituted 5-membered heterocyclyl. In certain embodiments, $R^{P6}$ and $R^{P7}$ are joined together with the intervening atoms to form substituted 1,3-dioxolane.

Groups $R^8$, $R^9$, $R^{10}$

As generally defined herein, $R^8$ is hydrogen, halogen, or optionally substituted alkyl. In certain embodiments, $R^8$ is hydrogen. In certain embodiments, $R^8$ is halogen, In certain embodiments, $R^8$ is optionally substituted alkyl. In certain embodiments, $R^8$ is optionally substituted $C_{1-6}$ alkyl. In certain embodiments, $R^8$ is unsubstituted $C_{1-6}$ alkyl. In certain embodiments, $R^8$ is optionally substituted $C_{1-3}$ alkyl. In certain embodiments, $R^8$ is unsubstituted $C_{1-3}$ alkyl. In certain embodiments, $R^8$ is selected from the group consisting of methyl, ethyl, n-propyl, iso-propyl, n-butyl, iso-butyl, sec-butyl, and tert-butyl. In certain embodiments, $R^8$ is methyl.

As generally defined herein, $R^9$ is hydrogen, halogen, or optionally substituted alkyl. In certain embodiments, $R^9$ is hydrogen. In certain embodiments, $R^9$ is halogen, In certain embodiments, $R^9$ is optionally substituted alkyl. In certain embodiments, $R^9$ is optionally substituted $C_{1-6}$ alkyl. In certain embodiments, $R^9$ is unsubstituted $C_{1-6}$ alkyl. In certain embodiments, $R^9$ is optionally substituted $C_{1-3}$ alkyl. In certain embodiments, $R^9$ is unsubstituted $C_{1-3}$ alkyl. In certain embodiments, $R^9$ is selected from the group consisting of methyl, ethyl, n-propyl, iso-propyl, n-butyl, iso-butyl, sec-butyl, and tert-butyl. In certain embodiments, $R^9$ is methyl.

As generally defined herein, $R^{10}$ is hydrogen, halogen, or optionally substituted alkyl. In certain embodiments, $R^{10}$ is hydrogen. In certain embodiments, $R^{10}$ is halogen, In certain embodiments, $R^{10}$ is optionally substituted alkyl. In certain embodiments, $R^{10}$ is optionally substituted $C_{1-6}$ alkyl. In certain embodiments, $R^{10}$ is unsubstituted $C_{1-6}$ alkyl. In certain embodiments, $R^{10}$ is optionally substituted $C_{1-3}$ alkyl. In certain embodiments, $R^{10}$ is unsubstituted $C_{1-3}$ alkyl. In certain embodiments, $R^{10}$ is selected from the group consisting of methyl, ethyl, n-propyl, iso-propyl, n-butyl, iso-butyl, sec-butyl, and tert-butyl. In certain embodiments, $R^{10}$ is methyl.

Group $R^{11}$

As generally defined herein, $R^{11}$ is hydrogen, optionally substituted alkyl, or an oxygen protecting group. In certain embodiments, $R^{11}$ is hydrogen. In certain embodiments, $R^{11}$ is optionally substituted alkyl. In certain embodiments, $R^{11}$ is an oxygen protecting group. As generally defined herein, $R^{11}$ is hydrogen, halogen, or optionally substituted alkyl. In certain embodiments, $R^{11}$ is hydrogen. In certain embodiments, $R^{11}$ is halogen, In certain embodiments, $R^{11}$ is optionally substituted alkyl. In certain embodiments, $R^{11}$ is optionally substituted $C_{1-6}$ alkyl. In certain embodiments, $R^{11}$ is unsubstituted $C_{1-6}$ alkyl. In certain embodiments, $R^{11}$ is optionally substituted $C_{1-3}$ alkyl. In certain embodiments, $R^{11}$ is unsubstituted $C_{1-3}$ alkyl. In certain embodiments, $R^{11}$ is selected from the group consisting of methyl, ethyl, n-propyl, iso-propyl, n-butyl, iso-butyl, sec-butyl, and tert-butyl. In certain embodiments, $R^{11}$ is methyl. In certain embodiments, $R^{11}$ is tert-butyl.

Pharmaceutical Compositions and Administration

The present invention provides pharmaceutical compositions comprising a compound of Formula (H-1), (HH-1), or (NH-1), or a pharmaceutically acceptable salt thereof, as described herein, and optionally a pharmaceutically acceptable excipient.

The present disclosure provides pharmaceutical compositions comprising a compound of Formula (H-1), (HH-1), or (NH-1), or a pharmaceutically acceptable salt thereof, as described herein, and optionally a pharmaceutically acceptable excipient. It will be understood by one of ordinary skill in the art that the compound of Formula (H-1), (HH-1), or (NH-1), or a pharmaceutically acceptable salt thereof, may be present in various forms, such as amorphous forms, hydrates, solvates, or polymorphic forms. In certain embodiments, a provided composition comprises two or more compounds described herein. In certain embodiments, a compound of Formula (H-1), (HH-1), or (NH-1), or a pharmaceutically acceptable salt thereof, is provided in an effective amount in the pharmaceutical composition. In certain embodiments, the effective amount is a therapeutically effective amount. In certain embodiments, the effective amount is an amount effective for treating or preventing a condition associated with aberrant cell proliferation. In certain embodiments, the effective amount is an amount effective for treating or preventing cancer. In certain embodiments, the effective amount is an amount effective for treating or preventing metastatic breast cancer. In certain embodiments, the effective amount is an amount effective for treating or preventing non-small cell lung cancer. In certain embodiments, the effective amount is an amount effective for treating or preventing prostate cancer. In certain embodiments, the effective amount is an amount effective for treating or preventing a sarcoma. In certain embodiments, the effective amount is an amount effective for inhibiting mitosis in a cancer cell in a subject. In certain embodiments, the effective amount is an amount effective for inducing apoptosis in a cancer cell in a subject. In certain embodiments, the effective amount is an amount effective for binding to microtubules in a cancer cell in a subject. In certain embodiments, the effective amount is an amount effective for inhibiting microtubule dynamics in a cancer cell in a subject.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the compound of Formula (H-1), (HH-1), or (NH-1), or a pharmaceutically acceptable salt thereof, of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the compound of Formula (H-1), (HH-1), or (NH-1), or a pharmaceutically acceptable salt thereof. The amount of the compound of Formula (H-1), (HH-1), or (NH-1), or a pharmaceutically acceptable salt thereof, is generally equal to the dosage of the compound of Formula (H-1), (HH-1), or (NH-1), or a pharmaceutically acceptable salt thereof, which would be administered to a subject and/or a convenient fraction of such a dosage, such as, for example, one-half or one-third of such a dosage.

Relative amounts of the compound of Formula (H-1), (HH-1), or (NH-1), or pharmaceutically acceptable salt thereof, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the compound of Formula (H-1), (HH-1), or (NH-1), or a pharmaceutically acceptable salt thereof.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether (Brij 30), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the compound of Formula (H-1), (HH-1), or (NH-1), or pharmaceutically acceptable salt thereof, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds of the invention with suitable non-irritating excipients or carriers such as cocoa butter, polyethylene glycol, or a suppository wax which are solid at ambient temperature but liquid at body temperature and therefore melt in the rectum or vaginal cavity and release the compound of Formula (H-1), (HH-1), or (NH-1), or a pharmaceutically acceptable salt thereof.

Solid dosage forms for oral administration include capsules, tablets, pills, powders, and granules. In such solid dosage forms, the compound of Formula (H-1), (HH-1), or (NH-1), or pharmaceutically acceptable salt thereof, is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical Formulating art. They may optionally comprise opacifying agents and can be of a composition that they release the compound of Formula (H-1), (HH-1), or (NH-1), or pharmaceutically acceptable salt thereof only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The compound of Formula (H-1), (HH-1), or (NH-1), or pharmaceutically acceptable salt thereof, can be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the compound of Formula (H-1), (HH-1), or (NH-1), or pharmaceutically acceptable salt thereof, can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the compound of Formula (H-1), (HH-1), or (NH-1), or pharmaceutically acceptable salt thereof, only, or preferentially, in a certain part of the intestinal tract, optionally, in a delayed manner. Examples of embedding compositions which can be used include polymeric substances and waxes.

Dosage forms for topical and/or transdermal administration of a the compound of Formula (H-1), (HH-1), or (NH-1), or pharmaceutically acceptable salt thereof, of this invention may include ointments, pastes, creams, lotions, gels, powders, solutions, sprays, inhalants and/or patches. Generally, the compound of Formula (H-1), (HH-1), or (NH-1), or pharmaceutically acceptable salt thereof, is admixed under sterile conditions with a pharmaceutically acceptable carrier and/or any needed preservatives and/or buffers as can be required. Additionally, the present invention contemplates the use of transdermal patches, which often have the added advantage of providing controlled delivery of a the compound of Formula (H-1), (HH-1), or (NH-1), or pharmaceutically acceptable salt thereof, to the body. Such dosage forms can be prepared, for example, by dissolving and/or dispensing the compound of Formula (H-1), (HH-1), or (NH-1), or pharmaceutically acceptable salt thereof, in the proper medium. Alternatively or additionally, the rate can be controlled by either providing a rate controlling membrane and/or by dispersing the compound of Formula (H-1), (HH-1), or (NH-1), or pharmaceutically acceptable salt thereof, in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) of the compound, although the concentration of the compound of Formula (H-1), (HH-1), or (NH-1), or pharmaceutically acceptable salt thereof, can be as high as the solubility limit of the compound in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the compound of Formula (H-1), (HH-1), or (NH-1), or pharmaceutically acceptable salt thereof, and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the compound of Formula (H-1), (HH-1), or (NH-1), or pharmaceutically acceptable salt thereof, dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the compound may constitute 0.1 to 20% (w/w) of the composition. The propellant may further comprise additional ingredients such as a liquid non-ionic and/or solid anionic surfactant and/or a solid diluent (which may have a particle size of the same order as particles comprising the compound).

Pharmaceutical compositions of the invention formulated for pulmonary delivery may provide the compound of Formula (H-1), (HH-1), or (NH-1), or pharmaceutically acceptable salt thereof, in the form of droplets of a solution and/or suspension. Such formulations can be prepared, packaged, and/or sold as aqueous and/or dilute alcoholic solutions and/or suspensions, optionally sterile, comprising the compound of Formula (H-1), (HH-1), or (NH-1), or pharmaceutically acceptable salt thereof, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the compound and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the compound of Formula (H-1), (HH-1), or (NH-1), or pharmaceutically acceptable salt thereof, and may comprise one or more of the additional ingredients described herein. A pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) of the compound, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the compound. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation for ophthalmic administration. Such formulations may, for example, be in the form of eye drops including, for example, a 0.1/1.0% (w/w) solution and/or suspension of the compound of Formula (H-1), (HH-1), or (NH-1), or pharmaceutically acceptable salt thereof, in an aqueous or oily liquid carrier. Such drops may further comprise buffering agents, salts, and/or one or more other of the additional ingredients described herein. Other opthalmically-administrable formulations which are useful include those which comprise the compound of Formula (H-1), (HH-1), or (NH-1), or pharmaceutically acceptable salt thereof, in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds of Formula (H-1), (HH-1), or (NH-1), or pharmaceutically acceptable salts thereof, provided herein are typically formulated in dosage unit form for ease of administration and uniformity of dosage. It will be understood, however, that the total daily amount of the compound will be decided by the attending physician within the scope of sound medical judgment. The specific therapeutically effective dose level for any particular subject will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compound of Formula (H-1), (HH-1), or (NH-1), or pharmaceutically acceptable salt thereof, and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

The exact amount of a compound of Formula (H-1), (HH-1), or (NH-1), or pharmaceutically acceptable salt thereof, required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound of Formula (H-1), (HH-1), or (NH-1), or pharmaceutically acceptable salt thereof, for administration one or more times a day to a 70 kg adult human may comprise about 0.1 mg to about 3000 mg, about 0.1 mg to about 2000 mg, about 0.1 mg to about 1000 mg, about 0.1 mg to about 100 mg, about 1 mg to about 100 mg, or about 10 mg to about 100 mg, of a compound of Formula (H-1), (HH-1), or (NH-1), or pharmaceutically acceptable salt thereof, per unit dosage form.

In certain embodiments, the compound of Formula (H-1), (HH-1), or (NH-1), or pharmaceutically acceptable salt thereof, of the present invention may be administered at dosage levels sufficient to deliver from about 0.001 mg/kg to about 100 mg/kg, from about 0.01 mg/kg to about 100 mg/kg, from about 0.1 mg/kg to about 100 mg/kg, from about 0.5 mg/kg to about 100 mg/kg, from about 10 mg/kg to about 100 mg/kg, from about 20 mg/kg to about 100 mg/kg, and from about 25 mg/kg to about 100 mg/kg, of subject body weight per day, one or more times a day, to obtain the desired therapeutic effect.

It will be also appreciated that a compound of Formula (H-1), (HH-1), or (NH-1), or pharmaceutically acceptable salt thereof, as described herein, can be administered in combination with one or more additional therapeutically active agents. compound or composition thereof can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

In any of the above described methods, one or more additional therapeutic agents (also referred to as the "agent") may be administered concurrently with, prior to, or subsequent to, the compound of the present invention, as described herein. The agent may be added at the same time as the compound of the present invention (simultaneous administration), before or after administration of the compound of the present invention (sequential administration), or any combination thereof. For example, in certain embodiments, the agent is administered first, followed by simultaneous administration of the agent and the compound of the present invention. In certain embodiments, the compound is administered first, followed by simultaneous administration of the agent and the compound of the present invention. In any of the above embodiments, either the agent or the compound of the present invention may be further administered alone after the simultaneous administration.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically agent is another anti-cancer agent. Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g.,hydroxyurea and deferoxamine), uracil analogs (e.g., 5-fluorouracil (5-FU), floxuridine, doxifluridine, ratitrexed, tegafur-uracil, capecitabine), cytosine analogs (e.g.,cytarabine (ara C), cytosine arabinoside, and fludarabine), purine analogs (e.g.,mercaptopurine and Thioguanine), Vitamin D3 analogs (e.g.,EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (Astra-Zeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Also encompassed by the invention are kits (e.g., pharmaceutical packs). The kits provided may comprise an inventive pharmaceutical composition or compound of Formula (H-1), (HH-1), or (NH-1), or pharmaceutically acceptable salt thereof, and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Treatment

The present invention also provides methods of using a compound of Formula (H-1), (HH-1), or (NH-1), or pharmaceutically acceptable salt thereof, e.g., by treating or preventing a condition associated with aberrant cell proliferation in a subject in need thereof, or by inhibiting mitosis or inducing cell apoptosis in a subject in need thereof, comprising administering to the subject a compound of Formula (H-1), (HH-1), or (NH-1), or pharmaceutically acceptable salt thereof, or a pharmaceutical composition thereof, in an amount sufficient to treat the condition. In certain embodiments, a compound of Formula (H-1), (HH-1), or (NH-1), or pharmaceutically acceptable salt thereof, binds to microtubules and inhibits mitosis or induces cell apoptosis through inhibition of microtubule dynamics in a subject in need thereof. In certain embodiments, a compound of Formula (H-1), (HH-1), or (NH-1), or pharmaceutically acceptable salt thereof, binds to high affinity sites at the plus end of existing microtubules.

In certain embodiments, compounds of Formula (H-1), (HH-1), or (NH-1), or pharmaceutically acceptable salts thereof, are useful for treatment of a proliferative disease. Exemplary proliferative diseases include, but are not limited to, tumors, begnin neoplasms, pre-malignant neoplasms (carcinoma in situ), and malignant neoplasms (cancers). Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familial hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematological malignancy (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described herein; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma, sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the cancer is a hematological malignancy. In certain embodiments, the cancer is lymphoma. In certain embodiments, the cancer is leukemia. In certain embodiments, the cancer is breast cancer.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, and unless otherwise specified, the terms "treat," "treating," and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder, or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein "inhibition", "inhibiting", "inhibit" and "inhibitor", and the like, refer to the ability of a compound to reduce, slow, halt or prevent activity of a particular biological process (e.g., microtubule dynamics or growth) in a cell relative to vehicle.

EXAMPLES

Palladium-Mediated Ketone Synthesis

A ketone synthesis has been developed involving in situ activation of alkyl halides to alkylzinc halides in the presence of thioesters and palladium. The new method provides a reliable option for coupling at a late stage in a convergent synthesis of complex molecules. In certain embodiments, the ketone synthesis is a one-pot synthesis. In some cases, the reaction is efficient with use of a near 1:1 molar ratio of coupling partners.

Two facile, orthogonal methods were developed for the preparation of alkylzinc halides: (1) direct insertion of zinc dust to 1°- and 2°-alkyl halides in the presence of LiI in DMI; and (2) early transition-metal assisted activation of alkyl halides via a single electron transfer (SET) process. $CrCl_2$ has been found as an unprecedented, inevitable mediator for-preparation of alkylzinc halides from alkyl halides, where $CrCl_2$ likely functions to trap carbon-based radicals, generated via a SET process, and transfer it to Zn(II) to form RZnX. In addition to a commonly used CoPc, a new radical initiator $NbCpCl_4$ has been discovered through the study presented here. Further, with use of the two orthogonal methods, three sets of coupling conditions are exemplified which complete one-pot ketone synthesis: Condition A ($Pd_2dba_3$, $PR_3$, Zn, LiI, TESCl, DMI); Condition B (A+$CrCl_2$); and Condition C (B+$NbCpCl_4$ or CoPc) being useful for simple linear and α-substituted substrates, simple linear and (β-substituted substrates, and complex substrates. Controlled formation of alkylzinc halides by a combination of $CrCl_2$ and $NbCpCl_4$ or CoPc was used in the application to complex substrates. Interestingly, the ketone synthesis did not suffer from chemical instability due to the inevitable radical pathway(s) during the single electron transfer process, for example, a 1,5-H shift. Notably, even with the increase in molecular size, no significant decrease in coupling efficiency was seen in the reaction of complex substrates. To illustrate the synthetic value at a late stage in a complex molecule synthesis, ketone 4sc, containing all the carbons of Eribulin, was synthesized from is and 3c (FIG. 8).

Figure 10:
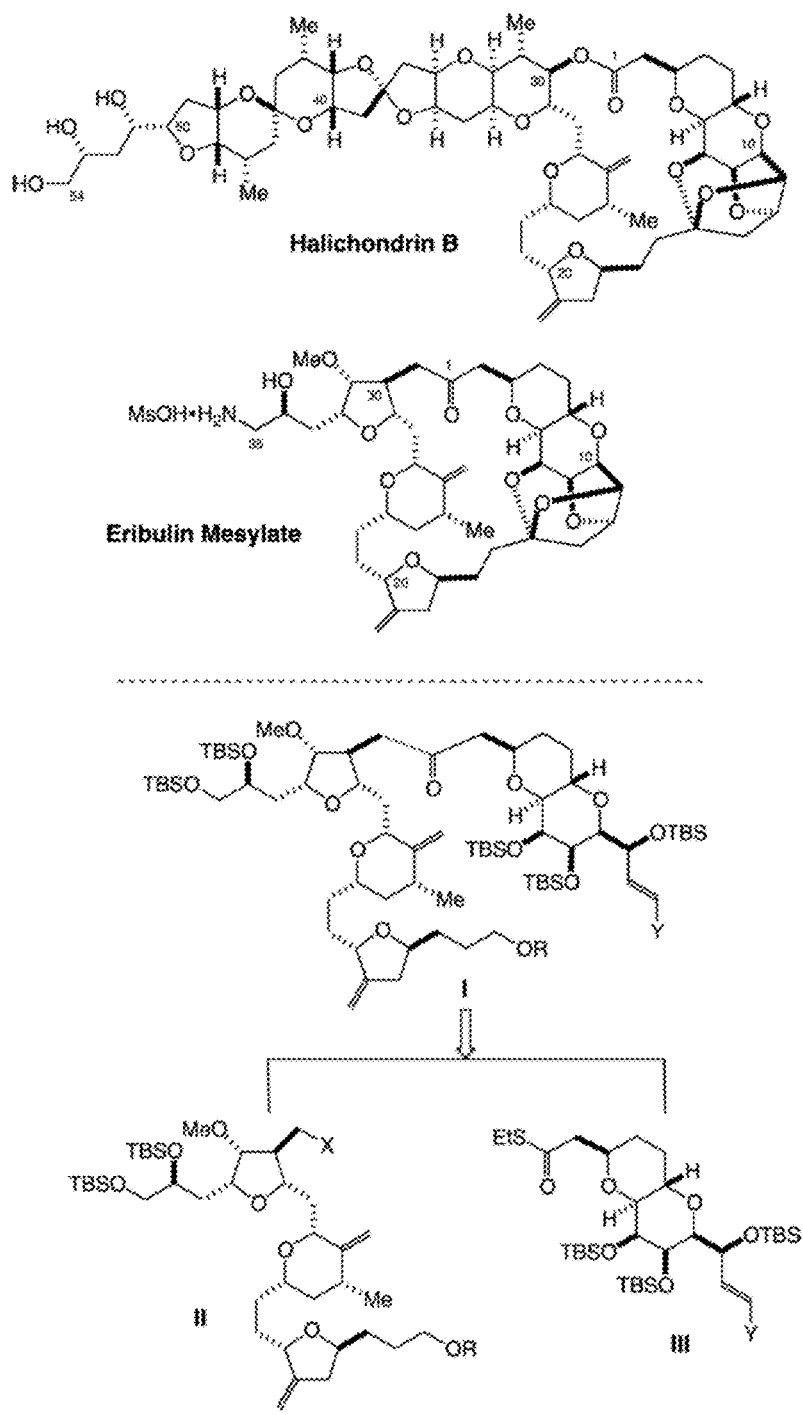
FIG. 10 shows the structure of halichondrin B and Eribulin mesylate and retrosynthesis.
Figure 11:
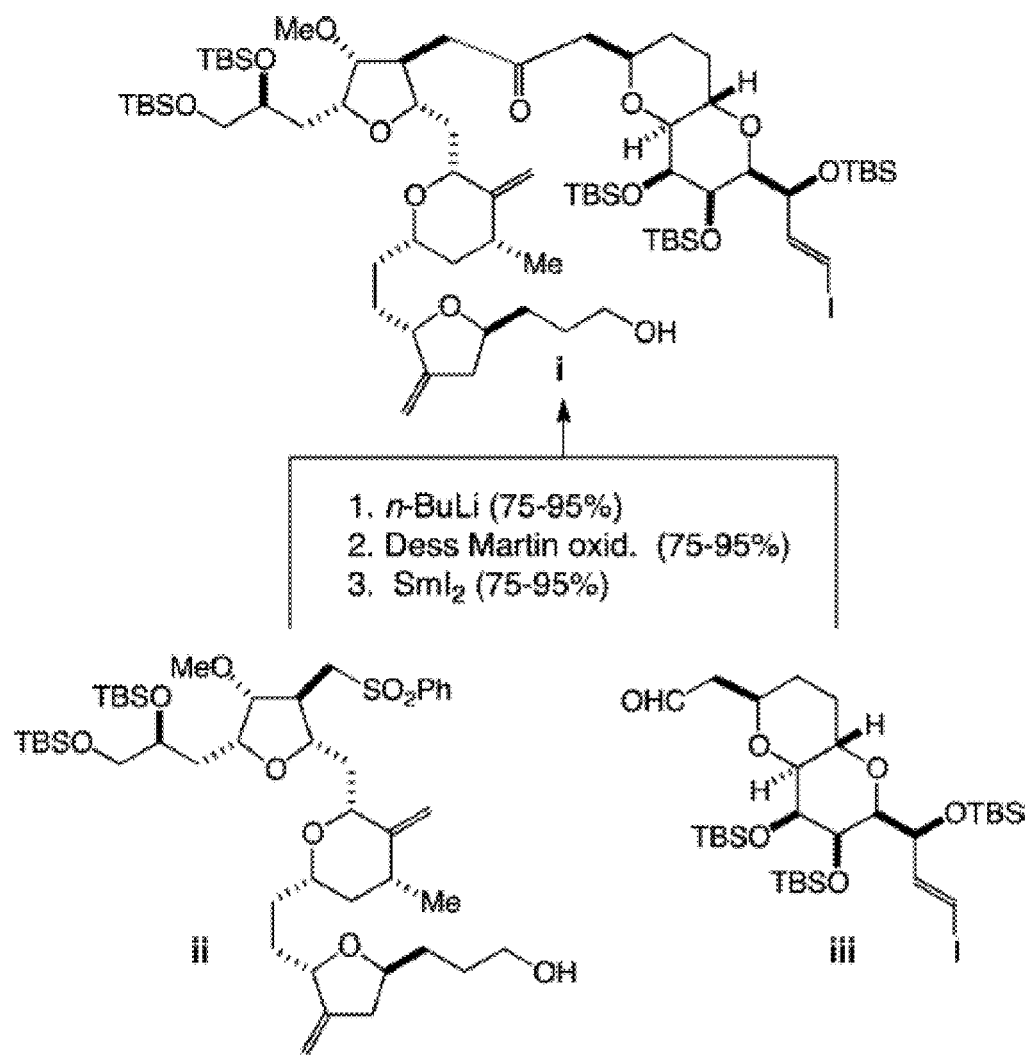
FIG. 11 is a structure showing of the results of retrosynthesis.

Related to the synthesis of Eribulin a totally synthetic anticancer drug developed through structure modification of the right half of the marine natural product halichondrin B, there was interest in the possibility of synthesizing ketone I or its synthetic equivalent via a coupling of two advanced building blocks II and III in one step (FIG. 10). Commercial Eribulin is produced via ketone i, which is synthesized by coupling phenylsulfone ii and aldehyde iii. This coupling was originally used in drug-discovery efforts and then optimized in process-development effort (see, e.g., Zheng et al., *J. Bioorg. Med. Chem. Lett.* 2004, 14, 5551, Yu et al., *Anticancer Agents from Natural Products*; CRC Press: 2005; p 241, Yu et al., In Annual Reports in Medicinal Chemistry; John, E. M., Ed.; Academic Press: 2011; Vol. 46, p 227, and Austad et al., *Synlett* 2013, 24, 333). Recently, the efficiency of phenylsulfone-aldehyde coupling was dramatically improved by use of a flow system even at 10° C.; 96% HPLC yield; 1.1 equiv of iii at 10° C. (see, e.g., Fukuyama et al., *Org. Process Res. Dev.* 2016, 20, 503, Inanaga et al., *Org. Lett.* 2015, 17, 3158, and Fukuyama et al., *Org. Process Res. Dev.* 2016, 20, 100) (FIG. 11).This retrosynthesis was attractive because of its high degree of convergency. In order to realize the proposed synthesis efficiently, however, a ketone synthesis with good functional-group tolerance, desirably with use of an approximately 1:1 molar ratio of coupling partners, was needed. During analysis it was found that none of the known ketone synthesis satisfactorily met these needs. To achieve this goal, a one-pot synthesis, which could be achieved by generating an alkylzinc species from an alkyl halide in the presence of a thioester and a Pd-catalyst, was considered. Interestingly, Ni-mediated one-pot ketone syntheses from alkyl halides and acid derivatives are known (see, e.g., Onaka et al., *Chem. Lett.* 1981, 10, 531, Wotal et al., *J. Org. Lett.* 2012, 14, 1476, Wotal et al., *Organometallics* 2014, 33, 5874, Weix, *Acc. Chem. Res.* 2015, 48, 1767, Yin et al., Chem. Commun. 2012, 48, 7034, Zhao et al., *J. Am. Chem. Soc.* 2014, 136, 17645, Cherney et al., *J. Am. Chem. Soc.* 2013, 135, 7442, Krasovskiy et al., *J. Am. Chem. Soc.* 2009, 131, 15592, and Duplais et al., *Organometallics* 2011, 30, 6090), but they have not been used at a late stage in a convergent synthesis of complex molecules. Reported here is a highly efficient ketone synthesis by using alkylzinc halides prepared from alkyl halides via direct Zn insertion or a SET process, followed by Pd-catalyzed coupling with a thioester. This method has a few appealing features, including (1) excellent functional group tolerance; (2) excellent coupling efficiency with use of a near 1:1 molar ratio of coupling partners; and (3) experimental convenience, among other considerations.

Activation of Alkyl Halides via Direct Zn Insertion and Single Electron Transfer Palladium-mediated ketone synthesis is generally considered to involve three distinct steps: (1) oxidative addition of a Pd(0)-catalyst to a thioester, (2) transmetalation from a preprepared alkylzinc halide to the resultant Pd(II) species, and (3) reductive elimination leading to a ketone and simultaneously regenerating the Pd(0)-catalyst (see, e.g., Fukuyama et al., Aldrichimica Acta 2004, 37, 87). In order to achieve the proposed one-pot ketone synthesis, a method to prepare alkylzinc halides from alkyl halides was sought.

There may be an additional benefit in one-pot ketone synthesis. Alkylzinc halides are known to exhibit a radical character (see, e.g., Guijarro et al., J. Am. Chem. Soc. 1999, 121, 4155); for example, a trace amount of oxygen was suggested to break down alkylzinc halides to alkyl radicals (see, e.g., Cohen et al., J. Am. Chem. Soc. 2007, 129, 15405), thereby hinting at a potential issue; namely, some alkylzinc halides might suffer from the chemical instability due to the inevitable radical pathway(s), for example a 1,5-H shift. By adjusting the rate of alkylzinc-halide generation relative to the rate of Zn→Pd transmetalation, one could imagine the possibility of avoiding accumulation of generated alkylzinc halides so that such an inherent problem might be suppressed or eliminated. Thus, one-pot ketone synthesis could allow for the expansion of the substrate scope of the ketone synthesis and, at the same time, minimize the waste of organozinc species.

The direct insertion of zinc into alkyl halides gives the simplest solution for preparation of alkylzinc halides. However, this process is known to be relatively inefficient with commercially available zinc (see, e.g., Knochel et al., PATAI'S Chemistry of Functional Groups; John Wiley & Sons, Ltd: 2009). Several methods for activating non-activated alkyl halides with zinc have been developed, including preactivation of zinc (see, e.g., Knochel et al., J. Org. Chem. 1988, 53, 2390), Rieke-zinc (see, e.g., Rieke, Science 1989, 246, 1260 and Zhu et al., J. Org. Chem. 1991, 56, 1445), and Zn/I₂/DMA/70° C. (see, e.g., Huo, Org. Lett. 2003, 5, 423). Recently, it was reported LiCl-acceleration of zinc insertion to alkyl halides, to form organozinc halides (Zn/LiCl/THF/50° C., and Mg/ZnCl₂/LiCl/THF) (see, e.g., Krasovskiy et al., Angew. Chem., Int. Ed. 2006, 45, 6040 and Blümke et al., Chem. Commun. 2010, 46, 4082). However, it appears that these methods have not yet been tested for preparation of highly functionalized and/or sterically demanding alkylzinc halides.

To prepare alkylzinc halides in situ, two methods were studied: (1) direct insertion of zinc dust to alkyl halides and (2) early transition-metal assisted alkyl halide activation via a SET process (see, e.g., Jahn, Top. Curr. Chem. 2011, 320, 121, Top. Curr. Chem. 2011, 320, 191; Top. Curr. Chem. 2011, 320, 323, Gansäuer et al., Chem. Rev. 2000, 100, 2771, Hackmann et al., Tetrahedron 1993, 49, 4559, MacLeod et al., Organometallics 2010, 29, 6639, and Zhou et al., J. Org. Chem. 2003, 68, 1633). Although alkyl-halide activation by early transition metals such as CoPc or Fe(acac)₃ was known, preparation of alkylzinc halides via a SET process had not yet been demonstrated. This process was effective to generate alkylchromium intermediates from alkyl halides for the Co/Cr- and Fe/Cr-mediated couplings (see, e.g., Takai et al., J. Org. Chem. 1989, 54, 4732, Takai, Organic Reactions; John Wiley & Sons, Inc.: 2004; Chapter 3, p 253, Choi et al., Org. Lett. 2002, 4, 4435, and Guo et al., J. Am. Chem. Soc. 2009, 131, 15387).

Figure 12:
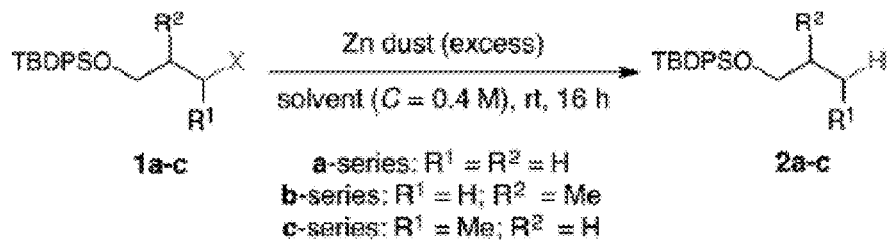
FIG. 12 shows the activation of alkyl halides to alkylzinc halides. The conditions for this experiment were as follows: unless indicated, the reactions were run with 1 (0.04 mmol), Zn(0) (>5 equiv), and an additive(s) in solvent (0.4 M) at room temperature in a glovebox. [b]Product distribution was estimated from $^1H$ NMR of crude products. [c]Full conversion was achieved in other aprotic polar solvents such as DMA and NMP. [d]2b was not formed in DMA or NMP. Abbreviations: DMI=1,3-dimethyl-2-imidazolidinone; DMA=N,N-dimethylacetamide; NMP=N-methyl-2-pyrrolidone; CoPc=Cobalt(II) phthalocyanine; $NbCpCl_4$=cyclopentadienylniobium(V) tetrachloride; NR=no reaction.

At the onset, alkyl bromides were used, instead of the corresponding alkyl iodides, considering the fact that alkyl bromides generally tolerate better in various organic transformations than alkyl iodides do. Later, it was discovered that the best activation condition utilizes LiI so that alkyl bromides were transformed to the corresponding alkyl iodides in situ. For the screening, a linear-chain alkyl bromide 1a, as well as β- and α-methyl substituted bromides 1b and 1c were chosen. Experimentally, 1a-1c were subjected to the specified conditions and the extent of Zn-activation was estimated from the product distribution after aqueous workup (FIG. 12). For these experiments, commercial zinc dust was used without any pretreatment. The general procedure for the activation of alkyl halides was as follows: to alkyl halide 1 (0.04 mmol) and Zn (0) (>12.4 mg, 5 eq.) in solvent (0.1 mL) was added additive(s) at room temperature in a glove box. After stirring the reaction mixture for 16 hours, it was diluted with Et₂O and quenched with saturated aqueous Rochelle salt. After being stirred for 30 minutes, it was extracted with Et₂O and the extract was washed with water. After concentration, ¹H NMR was taken to obtain the ratio of compounds as provided in FIG. 12.

First studied was the direct insertion of zinc dust to alkyl bromides. Activation of linear-chain bromide 1a was observed. Namely, in the presence of LiI (see, e.g., Jubert et al., J. Org. Chem. 1992, 57, 5425), zinc insertion smoothly took place at room temperature in aprotic polar solvents such as 1,3-dimethyl-2-imidazolidinone (DMI), N,N-dimethylacetamide (DMA), and N-methyl-2-pyrrolidone (NMP) (FIG. 12, entry 2). Even in THF, zinc insertion was observed, although it was significantly slower (FIG. 12, entry 1). On the basis of two pieces of literature information, the observed results were not totally surprising. First, polar solvents such as DMA, HMPA, and DMF are known to facilitate Zn insertion, although harsher conditions (heating and ultrasound) are usually employed (see, e.g., Jubert et al., J. Org. Chem. 1992, 57, 5425, Sato et al., Chem. Lett. 1982, 11, 157, Oh et al., Tetrahedron 2009, 65, 2966, and Roskamp et al., J. Am. Chem. Soc. 1987, 109, 3152). Second, lithium salts are known to exhibit a significant accelerating effect for Zn insertion (see, e.g., Krasovskiy et al., Angew. Chem., Int. Ed. 2006, 45, 6040 and Blümke et al., Chem. Commun. 2010, 46, 4082). Interestingly, for activation of 1a at room temperature, LiBr and LiCl were found to be much less effective than LiI (FIG. 12, entries 3 and 4). It was assumed that LiI played two roles, i.e., in situ formation of the iodide corresponding to 1a and Zn insertion acceleration by lithium salt.

Activation of β-substituted bromide 1b was occurred with DMI (solvent) and LiI (additive, 1 equiv) at room temperature (FIG. 12, entry 5). In order to gain structure information on the "alkylzinc halide" prepared under the conditions of FIG. 12, entry 5, electrospray-ionization negative-ion mass spectroscopy was used, thereby demonstrating that the major species present in the solution corresponded to the expected alkylzinc halides. See FIG. 19 for details. Overall, these results indicated that the Zn-insertion involves: (1) alkyl bromide 1a was first converted to the corresponding iodide and (2) lithium iodide or bromide accelerated Zn-insertion to the resultant alkyl iodide. Experimental results given under FIG. 12, entries 3-5, 7, and 8 support the first step. However, mechanistic insight into the remarkable acceleration effect observed with LiI in DMI was not clear at that time. A decrease in the amount of LiI from 1.0 to 0.5 equiv caused a sharp drop in activation (FIG. 12, entry 6 versus 5). Intriguingly, addition of TESCl restored smooth zinc insertion (FIG. 12, entry 9). It is speculated that the major role of TESCl was cleaning the surface of commercial zinc dust.

As mentioned above, interest was in the possibility of generating alkylzinc species via a SET process. It was found that a radical initiator CoPc activated 1b without assistance of LiI (FIG. 12, entry 10). Interestingly, it was found that NbCpCl$_4$ was also an effective initiator (FIG. 12, entry 11). Literature search revealed that low-valent niobium was used for radical-based transition metal catalyzed reactions (see, e.g., Sato et al., *Chem. Lett.* 1982, 11, 157, Oh et al., *Tetrahedron* 2009, 65, 2966, and Roskamp et al., *J. Am. Chem. Soc.* 1987, 109, 3152), but not for alkyl-halide activation. Nonetheless, it was suggested that the low-valent niobium, generated by reduction of NbCpCl$_4$ with Zn in situ, worked as a radical initiator. NbCpCl$_4$ appeared to be a slower initiator than CoPc, which might be an advantage in a one-pot Pd-catalyzed ketone synthesis with use of a 1:1 molar ratio of alkyl bromide and thioester for the reason mentioned above.

α-Substituted bromide 1c (X═Br) was found to behave as predicted on the basis of the results observed on 1a and 1b. Direct zinc insertion to 1c with X═Br was sluggish (FIG. 12, entry 12 versus entries 2 and 5), which was expected because of the slower rate of Br→I displacement. Indeed, facile activation of 1c (X═I) was observed (FIG. 12, entry 13). Direct insertion of zinc to 2°-alkyl halides compared to 1°-alkyl halides is known to be faster (see, e.g., Guijarro et al., *J. Am. Chem. Soc.* 1999, 121, 4155 and Knochel et al., PATAI'S Chemistry of Functional Groups; John Wiley & Sons, Ltd: 2009). SET activation behaviors of 1c were found almost identical to those observed for 1b (FIG. 12, entries 14 and 15 versus entries 10 and 11).

Before shifting focus to the carbon-carbon bond-forming step, the stability of alkylzinc halide, prepared via direct Zn-insertion of an alkyl bromide at room temperature was tested, thereby demonstrating that it was stable at room temperature at least for 2 weeks. The same yield was obtained in the coupling using 2-week old or freshly prepared RZnX in the two-step procedure given in FIG. 15.

One Pot Ketone Synthesis from Alkyl Halides and Thioesters

Known ketone syntheses has a number of appealing aspects, including the nearly neutral conditions employed for coupling alkylzinc halides with thioesters with good functional group compatibility. However, application is often limited to relatively small nucleophiles. It is thought that in situ preparation of alkylzinc halides could allow for a one-pot ketone synthesis in one-pot, thereby not only giving experimental convenience but also adding a new dimension in organic synthesis. Particular interest was in the possibility of employing one-pot ketone synthesis at a late stage in a convergent synthesis of complex molecules. For this reason, the aim was toward one-pot ketone synthesis, which could meet with several criteria including the synthetic efficiency, the functional group tolerance, and the use of a near 1:1 molar ratio of coupling partners.

With two orthogonal methods for activation of alkyl halides with zinc dust at room temperature, the feasibility of one-pot ketone synthesis was examined. For this study, the coupling of 1a-1c+3a→4aa-4ca was selected (FIG. 13). The general procedure for Ketone synthesis was as follows: Pre-mixture I [Pd$_2$dba$_3$(0.02 M), Ligand (0.04 M) in DMI]: In a vial, phosphine ligand (0.1 mmol) and tris(dibetazylideneacetone)dipalladium(0) (Pd$_2$dba$_3$, 46 mg, 0.05 mmol) were dissolved in 1,3-dimethyl-2-imidazolidinone (DMI) (2.5 mL) in a glove box. Pre-mixture II-A [LiI (0.4 M)]: LiI (133 mg, 1 mmol) was dissolved in DMI (2.5 mL) in a vial in a glove box. Pre-mixture II-B [CrCl$_2$ (0.1 M) and LiI (0.4 M)]: LiI (133 mg, 1 mmol) and CrCl$_2$ (30 mg, 0.25 mmol) were dissolved in DMI (2.5 mL) in a vial in a glove box to give a homogeneous blue solution. To thioester 3a (9 mg, 0.04 mmol), alkyl halide 1 (0.048 mmol), and zinc (13 mg, 5 eq.) was added pre-mixture II-A [0.1 mL, LiI (1.0 eq., 0.4 M) in DMI] or pre-mixture II-B [0.1 mL, CrCl$_2$ (0.25 eq., 0.1 M), LiI (1 eq., 0.4 M) in DMI]. Then pre-mixture I [0.1 mL, Pd$_2$dba$_3$ (5 mol %, 0.02 M), Ligand (10 mol %, 0.04 M) in DMI], the additive(s), and TESCl (10 μL, 1.5 eq.) were added to the reaction mixture and stirred for 17 hours at room temperature in a glove box. Et$_2$O and saturated aqueous Rochelle salt were added and stirred for 30 min. Then, it was extracted with Et$_2$O and the extract was washed with water. After concentration, $^1$H NMR was taken to obtain the ratio of compounds as provided in FIG. 13. Experimentally, palladium catalyst/phosphine ligand and lithium salt, dissolved in DMI separately, were added to substrates and Zn dust, and the product distribution was estimated from $^1$H NMR analysis of crude products (FIG. 13).

Knowing that the activation of bromide 1a was effectively achieved in DMI in the presence of LiI (FIG. 12, entry 2), this condition was first tested for one-pot ketone synthesis and succeeded in isolation of the expected ketone 4aa (FIG. 13, entry 1). This experiment demonstrated the feasibility of one-pot ketone synthesis. Next, the goal was to improve the coupling yield and it was speculated that the observed modest yield could be attributed to either (1) poor efficiency for zinc insertion and/or (2) poor efficiency for a Pd-mediated carbon-carbon bond-forming step. To address this question, the coupling was tested in the presence of LiI and TESCl (FIG. 13, entry 2), cf., entry 9 in FIG. 12, and found the coupling efficiency was significantly improved, thereby suggesting that the former reason was more likely. In other words, the thioester, Pd-catalyst, and/or phosphorus ligand appeared to slow down the direct Zn-insertion step.

Using 1.0 equiv of LiI and 1.5 equiv of TESCl in DMI, the coupling conditions were then optimized, including the Pd-catalyst and phosphorus ligand, and it was found that the phosphorus ligand had a significant effect; bulky and electron-rich tricyclohexylphosphine (PCy$_3$) was found to be effective. Several Pd catalysts, including Pd/C D1 (see, e.g., Shimizu et al., *Tetrahedron Lett.* 2001, 42, 429 and Mori et al., *Adv. Synth. Catal.* 2007, 349, 2027), were tested, but it was discovered that Pd$_2$dba$_3$ was best for screening ligands, although Pd(PCy$_3$)Cl$_2$ gave similar results. Other ligands tested included t-Bu$_3$P, SPhos, and PEPPSI-IPr.

The reaction mechanism for Pd-catalyzed cross-coupling reactions appears to be more complex than the generally accepted catalytic cycle, i.e. oxidative addition, transmetalation, and reductive elimination. For example, previous research has shown the involvement of higher-order organozincates in the alkyl-alkyl Negishi cross-coupling; previous research has also suggested that a less active Zn—Pd dimer could be formed in the Negishi coupling, but lithium salt could prevent the dimerization of Zn—Pd by forming anionic organozincates (Achonduh et al., J.; Organ, M. G. *Chem. Commun.* 2010, 46, 4109, McCann et al., J. A. C.; Organ, M. G. *Angew. Chem., Int. Ed.* 2012, 51, 7024, and Böck et al., *Chem.-Eur. J.* 2015, 21, 5548). With this information, the effect of lithium salt was tested, but it was found that an increase of lithium salt did not improve the efficiency of 1b+3a→4ba. See below for details. An extensive search for a second metal promoter was then conducted, leading to the discovery that CrCl₂ significantly improved the coupling efficiency (FIG. 13, entry 5). A similar improvement by CrCl₂ was observed with 1b (X=I) (FIG. 13, entries 10 and 11). It was assumed that chromium salt might shift the equilibrium toward higher-order organozincates and/or might break Pd—Zn to restore palladium reactivity.

Next, the feasibility of one-pot ketone synthesis with an alkylzinc halide prepared via a SET process was studied. The first attempt with CoPc (cf., entry 10, FIG. 12) was disappointing; the desired product 4ba was not detected in either the presence or absence of LiI (FIG. 13, entry 6). On the addition of 25 mol % CrCl₂, the desired ketone 4ba was formed with excellent efficiency (FIG. 13, entry 7). The same results were observed with NbCpCl₄ (FIG. 13, entries 8 and 9). It was suggested that CrCl₂ played a role in trapping the alkyl radical, generated by CoPc or NbCpCl₄, and transferring it to the zinc halide.

Figure 14:
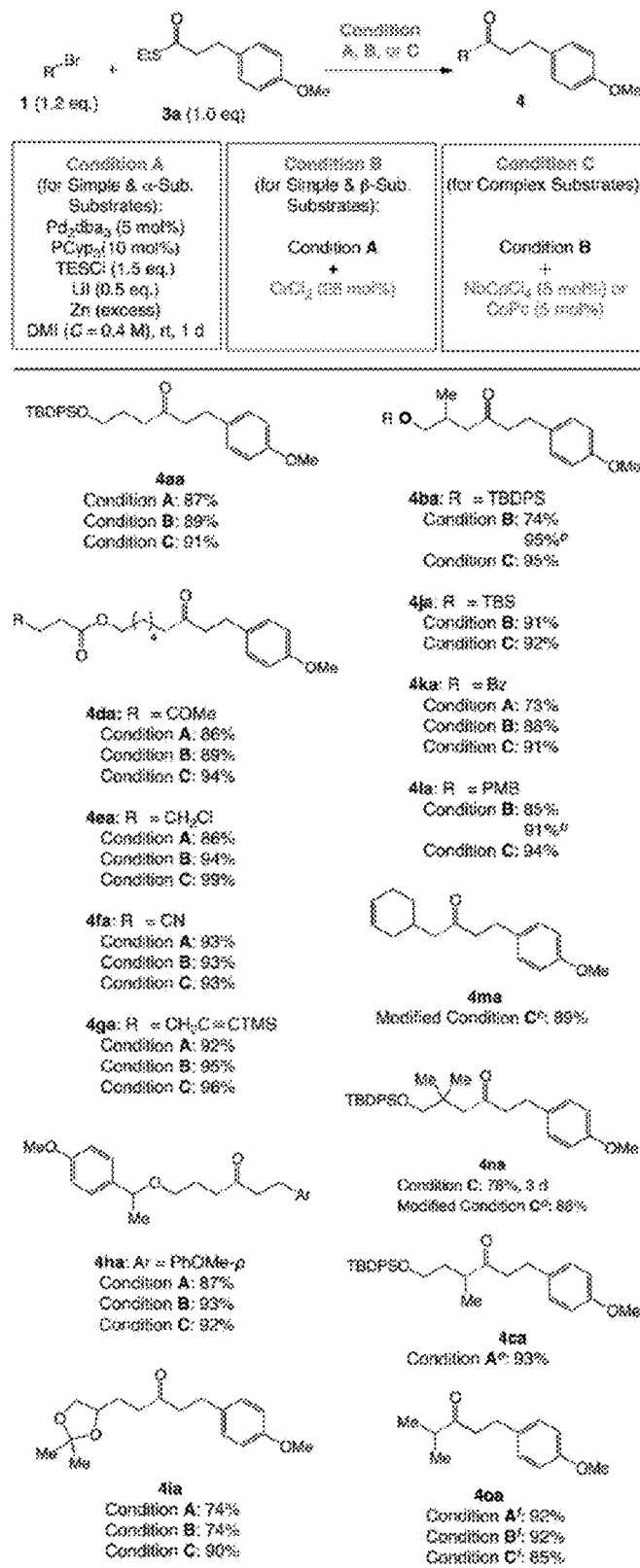
FIG. 14 shows one-pot ketone synthesis with arbitrarily chosen nucleophiles. The conditions for this experiment were as follows: the couplings were done in a scale of 3a (0.20 mmol) and 1 (0.24 mmol), and the yields are based on chromatographically isolated products. In general, tricyclohexylphosphine ($PCy_3$) is more effective than tricyclopentylphosphine ($PCyp_3$) for simple substrates (FIG. 20) (See Materials and Methods for details) but $PCyp_3$ was found to be the optimal choice of ligand for complex substrates (FIG. 17 and FIG. 18). Thus, $PCyp_3$ was used to study functional group tolerance in FIG. 14. Higher yields were expected with most substrates if $PCy_3$ was used rather than $PCyp_3$ as shown with 1b and 1l, especially under Condition A. [b]PCy3 instead of PCyp3. [c]Pd2dba3 (10 mol %), PCyp3 (20 mol %), CrCl2 (50 mol %), LiI (1 equiv), NbCpCl4 (10 mol %), DMI (C=0.4 M). [d]CoPc (5 mol %) instead of NbCpCl4 (5 mol %). [e]1c equiv) and PCy3 used. [f]1o (1.5 equiv) and PCy3 used. Abbreviation: PCyp3=tricyclopentylphosphine.

The behavior of α-substituted bromide 1c was intriguing. Based on the steric reason, it was anticipated that α-substituted halide 1c would behave similarly to β-substituted bromide 1b rather than nonsubstituted bromide 1a. Experimentally, however, the best conditions for 1c were found to be the best conditions for 1a (FIG. 13, entry 12) rather than the best conditions for 1b (FIG. 13, entry 5). The coupling with isopropyl iodide exhibited the overall profile similar to that with 1c (FIG. 14). It was speculated that this observation related to the relative stability or reactivity of secondary versus primary alkylchromium halides. The thermal stability of the Cr—C σ-bond is reported to decrease in the order of primary>secondary>tertiary (see, e.g., Takai et al., *J. Org. Chem.* 1989, 54, 4732, Sneeden et al., *J. Organomet. Chem.* 1969, 16, 449, Baird, *J. Organomet. Chem.* 1974, 64, 289, and Nishimura et al., *J. Organomet. Chem.* 1972, 37, 317).

In order to demonstrate that these screening results are translated to a useful synthetic method, one-pot ketone synthesis 1a–1c+3a→4aa–4ca in a 0.2 mmol scale was carried out, to isolate ketone 4aa–4ca in 87% (FIG. 14, entry 3), 95% (FIG. 14, entry 5), and 93% yields (FIG. 14, entry 12), respectively.

General Procedure for Ketone Synthesis Shown in FIG. 14

Pre-mixture I: To a vial were added tricyclopentylphoshine (PCyp₃, 144 mg, 0.6 mmol), tris(dibenzylideneacetone)dipalladium(O) (Pd₂dba₃, 276 mg, 0.3 mmol, 0.06 M), and 1,3-dimethyl-2-imidazolidinone (DMI) (5 mL) in a glove box. Condition A: In a separate vial, LiI (400 mg, 3 mmol, 0.6 M) was dissolved in DMI (5 mL) in a glove box (pre-mixture II-A). To thioester 3a (0.2 mmol), alkyl halide 1 (0.24 mmol), and zinc (1 mmol) were added LiI (333 µL, 0.6 M, 1 eq.), pre-mixture I [166 µL, Pd₂dba₃ (0.01 mmol, 0.06 M), PCyp₃ (0.02 mmol, 0.12 M) in DMI], and TESCl (50 µL, 0.3 mmol). The reaction mixture was stirred vigorously for 1 d. Upon completion of reaction, Et₂O and saturated aqueous Rochelle salt were added and stirred for 30 min. Then, it was extracted with Et₂O and the extract was washed with water to remove DMI. After concentration, a silica gel column chromatography was conducted to yield the desired ketone. Condition B: In a separate vial, CrCl₂ (91 mg, 0.75 mmol) and LiI (300 mg, 3 mmol) were dissolved in DMI (5 mL) in a glove box to give a homogeneous blue solution (pre-mixture II-B). To thioester 3a (0.2 mmol), alkyl halide 1 (0.24 mmol), and zinc (1 mmol) were added premixture II-B [333 µL, CrCl₂ (0.15 M, 0.05 mmol, 0.25 eq.), LiI (0.6 M, 0.2 mmol, 1.0 eq) in DMI], pre-mixture I [166 µL, Pd₂dba₃ (0.01 mmol, 0.06 M), PCyp₃ (0.02 mmol, 0.12 M) in DMI], and TESCl (50 µL, 0.3 mmol). The reaction mixture was stirred vigorously for 1 d. Upon completion of the reaction, Et₂O and saturated Rochelle salt solution were added and stirred for 30 min. Then, it was extracted with Et₂O and the extract was washed with water to remove DMI. After concentration, it was purified by a silica gel column chromatography to provide the desired ketone. Condition C: To thioester 3a (0.2 mmol), alkyl halide 1 (0.24 mmol), and zinc (1 mmol) were added pre-mixture II-B [333 µL, CrCl₂ (0.15 M, 0.25 eq.), LiI (0.6 M, 1 eq.)], pre-mixture I [166 µL, Pd₂dba₃ (0.01 mmol, 0.06 M), PCyp₃ (0.02 mmol, 0.12 M) in DMI], and TESCl (50 µL, 0.3 mmol). Then, NbCpCl₄ (3 mg, 0.01 mmol) or CoPc (5.7 mg, 0.01 mmol) was added to the reaction mixture and the reaction mixture was stirred vigorously for 1 d. Upon completion of the reaction, Et₂O and saturated Rochelle salt solution was added and stirred for 30 min. Then, it was extracted with Et₂O and the extract was washed with water to remove DMI. The desired ketone was obtained by silica gel column chromatography purification. Alternative Condition C: To a 20 mL vial were added tricyclopentylphoshine (24 mg, 0.1 mmol), tris(dibenzylideneacetone)dipalladium (0) (56 mg, 0.05 mmol), CrCl₂ (30 mg, 0.25 mmol), Zinc (32 mg, 0.5 mmol), cyclopentadienylniobium(V) tetrachloride (NbCpCl₄, 15 mg, 0.05 mmol), and 1,3-dimethyl-2-imidazolidinone (DMI) (2.5 mL) in a glove box. The mixture was stirred to dissolve all solids except Zn for 1 h at room temperature. Then LiI (67 mg, 0.5 mmol) was added to the mixture and stirred for 1 h to give a homogeneous dark-brown solution except Zn. Thioester 3a (0.2 mmol), alkyl bromide 1 (0.24 mmol), and Zinc (1 mmol) were added to a second vial. Then the pre-mixture (0.5 mL, 0.02 M, 5 mol % based on NbCpCl₄ and Pd₂dba₃) and TESCl (50 µL, 0.3 mmol) were added subsequently. The reaction mixture was stirred vigorously for 1 d.

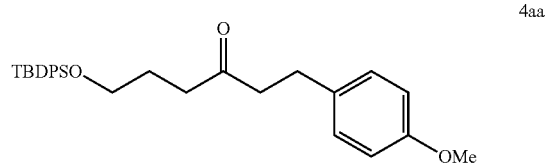

4aa

4aa: 87% (Condition A), 89% (Condition B), 91% (Condition C) as a clear liquid; ¹H NMR (600 MHz, CDCl₃) δ7.66-7.59 (m, 4H), 7.44-7.35 (m, 6H), 7.11-7.06 (m, 2H), 6.83-6.79 (m, 2H), 3.78 (s, 3H), 3.65 (t, J=6.1 Hz, 2H), 2.82 (t, J=7.7 Hz, 2H), 2.68 (t, J=7.7 Hz, 2H), 2.49 (t, J=7.3 Hz, 2H), 1.86-1.77 (m, 2H), 1.04 (s, 9H); ¹³C NMR (126 MHz, CDCl₃) δ210.07, 157.89, 135.50, 133.75, 133.13, 129.59, 129.19, 127.62, 113.85, 62.97, 55.23, 44.59, 39.34, 28.92, 26.84, 26.54, 19.19; IR (neat) v 931, 2856, 1712, 1513, 1246, 1300, 1111, 702; HRMS (ESI) calculated for (C₂₉H₃₆O₃Si+H⁺): 461.2506 found 461.2501.

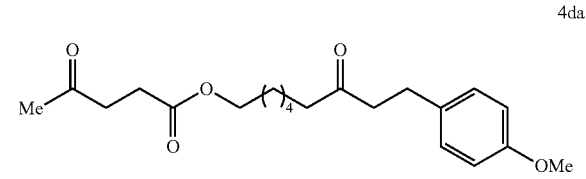

4da

4da: 86% (Condition A), 89% (Condition B), 94% (Conditions C) as a clear liquid; ¹H NMR (500 MHz, CDCl₃) δ7.14-7.04 (m, 2H), 6.87-6.78 (m, 2H), 4.05 (t, J=6.6 Hz, 2H), 3.78 (s, 3H), 2.83 (t, J=7.6 Hz, 2H), 2.74 (t, J=6.6 Hz, 2H), 2.69 (t, J=7.6 Hz, 2H), 2.57 (t, J=6.6 Hz, 2H), 2.37 (t, J=7.4 Hz, 2H), 2.19 (s, 3H), 1.66-1.50 (m, 4H), 1.38-1.22 (m, 4H); ¹³C NMR (126 MHz, CDCl₃) δ210.29, 206.66, 172.79, 157.89, 133.13, 129.21, 113.84, 64.62, 55.24, 44.53, 42.86, 37.94, 29.88, 28.91, 28.74, 28.37, 27.96, 25.66, 23.53; IR (neat) v 2934, 1731, 1713, 1512, 1357, 1244, 1157; HRMS (ESI) calculated for ($C_{21}H_{30}O_5$+Na⁺): 385.1985 found 385.1983.

δ7.11-7.05 (m, 2H), 6.84-6.79 (m, 2H), 4.05 (t, J=6.7 Hz, 2H), 3.78 (s, 3H), 2.83 (t, J=7.6 Hz, 2H), 2.68 (t, J=7.4 Hz, 2H), 2.42 (t, J=7.5 Hz, 2H), 2.37 (t, J=7.4 Hz, 2H), 2.29 (t, J=7.0 Hz, 2H), 1.83 (p, J=7.1 Hz, 2H), 1.66-1.49 (m, 4H), 1.38-1.23 (m, 4H), 0.14 (s, 9H); ¹³C NMR (126 MHz, CDCl₃) δ210.24, 173.20, 157.90, 133.12, 129.22, 113.85, 106.01, 85.37, 64.36, 55.23, 44.54, 42.88, 33.00, 28.92, 28.78, 28.42, 25.72, 23.77, 23.54, 19.28, 0.11; IR (neat) v 2937, 2858, 2174, 1732, 1714, 1513, 1247, 842; HRMS (ESI) calculated for ($C_{25}H_{38}O_4Si$+Na⁺): 453.2432 found 453.2417.

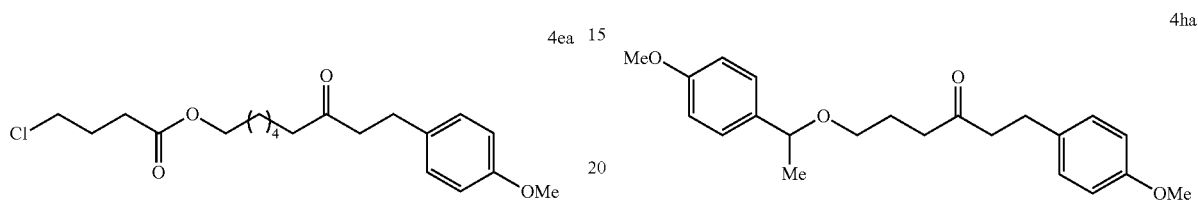

4ea

4ha

4ea: 86% (Condition A), 94% (Condition B), 99% (Conditions C) as a clear liquid; ¹H NMR (600 MHz, CDCl₃) δ7.15-7.05 (m, 2H), 6.88-6.78 (m, 2H), 4.06 (t, J=6.7 Hz, 2H), 3.78 (s, 3H), 3.60 (t, J=6.4 Hz, 2H), 2.83 (t, J=7.6 Hz, 2H), 2.69 (t, J=7.6 Hz, 2H), 2.49 (t, J=7.2 Hz, 2H), 2.37 (t, J=7.3 Hz, 2H), 2.13-2.06 (m, 2H), 1.66-1.49 (m, 4H), 1.38-1.24 (m, 4H); ¹³C NMR (126 MHz, CDCl₃) δ210.23, 172.70, 157.92, 133.12, 129.21, 113.85, 64.55, 55.24, 44.53, 44.09, 42.86, 31.22, 28.93, 28.75, 28.39, 27.66, 25.71, 23.52; IR (neat) v 2935, 1731, 1713, 1513, 1300, 1245, 1178; HRMS (ESI) calculated for ($C_{20}H_{29}ClO_4$+H⁺): 369.1827 found 369.1827.

4ha: 87% (Condition A), 93% (Condition B), 92% (Condition C) as a clear liquid; ¹H NMR (600 MHz, CDCl₃) δ7.14 (dd, J=68.5, 8.5 Hz, 4H), 6.89-6.78 (m, 4H), 4.29 (q, J=6.4 Hz, 1H), 3.80 (s, 3H), 3.78 (s, 3H), 3.29-3.19 (m, 2H), 2.86-2.78 (m, 2H), 2.73-2.64 (m, 2H), 2.52-2.38 (m, 2H), 1.85-1.76 (m, 2H), 1.38 (d, J=6.5 Hz, 3H); ¹³C NMR (126 MHz, CDCl₃) δ209.96, 158.90, 157.90, 135.95, 133.17, 129.19, 127.29, 113.85, 113.73, 67.29, 55.23, 44.54, 39.74, 28.88, 24.00, 23.90; IR (neat) v 2953, 1712, 1612, 1513, 1245, 1036, 832; HRMS (ESI) calculated for ($C_{22}H_{28}O_4$+Na⁺): 378.1880 found 378.1867.

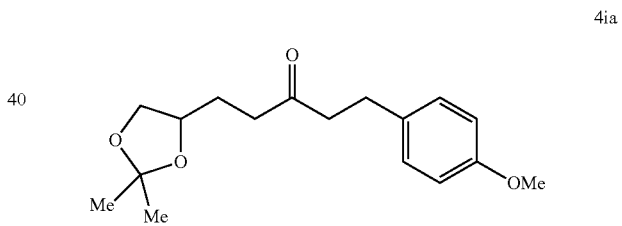

4fa

4ia

4fa: 93% (Condition A), 93% (Condition B), 93% (Conditions C) as a clear liquid; ¹H NMR (500 MHz, CDCl₃) δ7.16-7.01 (m, 2H), 6.89-6.78 (m, 2H), 4.12 (t, J=6.7 Hz, 2H), 3.78 (s, 3H), 2.83 (t, J=7.5 Hz, 2H), 2.75-2.59 (m, 6H), 2.37 (t, J=7.3 Hz, 2H), 1.71-1.48 (m, 4H), 1.41-1.22 (m, 4H); ¹³C NMR (126 MHz, CDCl₃) δ210.21, 170.03, 157.90, 133.10, 129.22, 118.43, 113.84, 65.43, 55.24, 44.53, 42.82, 29.96, 28.91, 28.69, 28.28, 25.64, 23.47, 12.97; IR (neat) v 2937, 2250, 1737, 1711, 1693, 1513, 1246, 1178; HRMS (ESI) calculated for ($C_{20}H_{27}NO_4$+H⁺): 346.2013 found 346.2008.

4ia: 74% (Condition A), 74% (Condition B), 90% (Condition C) as a clear liquid; ¹H NMR (500 MHz, CDCl₃) δ7.19-7.04 (m, 2H), 6.91-6.77 (m, 2H), 4.10-4.01 (m, 2H), 3.80 (s, 3H), 3.52 (dd, J=7.7, 6.7 Hz, 1H), 2.86 (t, J=7.6 Hz, 2H), 2.77-2.70 (m, 2H), 2.62-2.46 (m, 2H), 1.92-1.83 (m, 1H), 1.81-1.72 (m, 1H), 1.40 (s, 3H), 1.34 (s, 3H); ¹³C NMR (126 MHz, CDCl₃) δ209.42, 157.94, 132.99, 129.20, 113.88, 108.90, 77.25, 76.99, 76.74, 75.04, 69.18, 55.24, 44.59, 38.89, 28.93, 27.33, 26.88, 25.60, 25.58; IR (neat) v 2934, 1713, 1612, 1513, 1370, 1246, 1066; HRMS (ESI) calculated for ($C_{17}H_{24}O_4$+Na⁺): 315.1567 found 315.1572.

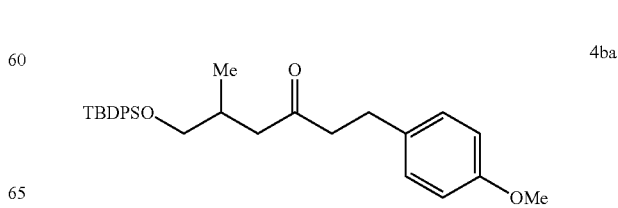

4ga

4ba

4ga: 92% (Condition A), 95% (Condition B), 96% (Condition C) as a clear liquid; ¹H NMR (500 MHz, CDCl₃)

4ba: 74% (Conditions B), 95% (Conditions B with PCy$_3$), 95% (Conditions C) as a clear liquid; $^1$H NMR (600 MHz, CDCl$_3$) δ7.65-7.60 (m, 4H), 7.44-7.34 (m, 6H), 7.10-7.06 (m, 2H), 6.83-6.78 (m, 2H), 3.78 (s, 3H), 3.51 (dd, J=9.9, 5.3 Hz, 1H), 3.42 (dd, J=9.9, 6.4 Hz, 1H), 2.85-2.79 (m, 2H), 2.70-2.59 (m, 3H), 2.30-2.21 (m, 1H), 2.18 (dd, J=15.9, 8.2 Hz, 1H), 1.04 (s, 9H), 0.87 (d, J=6.6 Hz, 3H); $^{13}$C NMR (126 Hz, CDCl$_3$) δ 209.93, 157.90, 135.57, 135.55, 133.68, 133.17, 129.60, 129.21, 127.63, 113.86, 68.26, 55.25, 46.78, 45.04, 31.93, 28.89, 26.88, 26.85, 19.28, 16.77; IR (neat) v 2956, 2857, 1712, 1512, 1463, 1245, 1106, 700; HRMS (ESI) calculated for (C$_{30}$H$_{38}$O$_4$Si+H$^+$): 475.2663 found 475.2684.

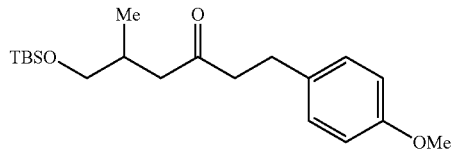

4ja

4ja: 91% (Condition B), 92% (Condition C) as a clear liquid; $^1$H NMR (500 MHz, CDCl$_3$) δ7.12-7.07 (m, 2H), 6.82 (m, 2H), 3.78 (s, 3H), 3.46 (dd, J=9.8, 5.1 Hz, 1H), 3.39-3.29 (m, 1H), 2.86-2.80 (m, 2H), 2.72-2.67 (m, 2H), 2.60-2.51 (m, 1H), 2.22-2.09 (m, 2H), 0.88 (s, 9H), 0.85 (d, J=6.5 Hz, 3H), 0.02 (s, 3H), 0.02 (s, 3H); $^{13}$C NMR (126 MHz, CDCl$_3$) δ210.06, 157.87, 133.20, 129.20, 113.83, 67.51, 55.23, 46.75, 45.05, 32.03, 28.88, 25.89, 18.28, 16.72, −5.44, −5.47; IR (neat) v 2954, 2856, 1712, 1513, 1247, 1095, 836; HRMS (ESI) calculated for (C$_{20}$H$_{34}$O$_3$Si+H$^+$): 351.2350 found 351.2333.

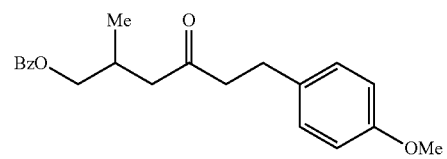

4ka

4ka: 73% (Condition A), 88% (Condition B), 91% (Condition C) as a clear liquid; $^1$H NMR (500 MHz, CDCl$_3$) δ8.04-7.99 (m, 2H), 7.59-7.54 (m, 1H), 7.47-7.41 (m, 2H), 7.09-7.03 (m, 2H), 6.83-6.76 (m, 2H), 4.19 (dd, J=10.8, 5.4 Hz, 1H), 4.13 (dd, J=10.8, 6.2 Hz, 1H), 3.77 (s, 3H), 2.87-2.78 (m, 2H), 2.75-2.65 (m, 2H), 2.62-2.50 (m, 2H), 2.39-2.28 (m, 1H), 1.02 (d, J=6.7 Hz, 3H); $^{13}$C NMR (126 MHz, CDCl$_3$) δ 208.79, 166.45, 157.94, 132.97, 132.92, 130.15, 129.52, 129.19, 128.38, 113.87, 68.97, 55.23, 46.79, 45.17, 28.84, 17.05; IR (neat) v 2957, 1716, 1612, 1513, 1274, 1247, 713; HRMS (ESI) calculated for (C$_{21}$H$_{24}$O$_4$+Na$^+$): 363.1567 found 363.1573.

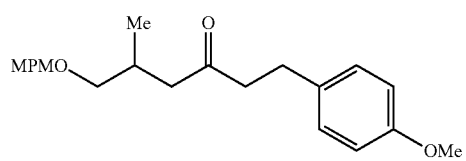

4la

4la: 85% (Condition B), 91% (Condition B, PCy$_3$ instead of PCyp$_3$), 94% (Condition C) as a clear liquid after a silica gel column chromatography (EtOAc/Hexanes=1/20); $^1$H NMR (600 MHz, CDCl$_3$) δ7.22 (m, 2H), 7.06 (m, 2H), 6.87 (m, 2H), 6.81 (m, 2H), 4.38 (s, 2H), 3.80 (s, 3H), 3.77 (s, 3H), 3.30 (dd, J=9.2, 5.4 Hz, 1H), 3.19 (dd, J=9.2, 7.2 Hz, 1H), 2.80 (dd, J=11.5, 4.5 Hz, 2H), 2.70-2.64 (m, 2H), 2.54 (dd, J=16.1, 5.9 Hz, 1H), 2.34 (td, J=12.9, 6.8 Hz, 1H), 2.19 (dd, J=16.1, 7.5 Hz, 1H), 0.89 (d, J=6.8 Hz, 3H); $^{13}$C NMR (126 MHz, CDCl$_3$) δ209.79, 159.09, 157.87, 133.22, 130.54, 129.21, 129.16, 113.82, 113.71, 74.70, 72.57, 55.24, 47.28, 45.02, 29.83, 28.81, 17.17; IR (neat) v 2955, 2836, 1710, 1612, 1511, 1244, 1034; HRMS (ESI) calculated for (C$_{22}$H$_{28}$O$_4$+H$^+$): 357.2060 found 357.2075.

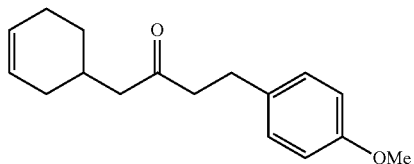

4ma

4ma: To a 20 mL vial were added tricyclopentylphoshine (9.5 mg, 0.04 mmol), tris(dibenzylideneacetone)dipalladium (0) (18.4 mg, 0.02 mmol), CrCl$_2$ (12 mg, 0.1 mmol), Zinc (6 mg, 0.1 mmol), cyclopentadienylniobium(V) tetrachloride (NbCpCl$_4$, 6 mg, 0.02 mmol), and 1,3-dimethyl-2-imidazolidinone (DMI) (0.5 mL) in a glove box. The mixture was stirred to dissolve all solids except Zn for 1 h at room temperature. Then LiI (26.6 mg, 0.2 mmol) was added to the mixture and stirred for 1 h to give a thick dark-brown solution. To a second vial containing thioester 3a (45 mg, 0.2 mmol), alkyl bromide 1m (42 mg, 0.24 mmol), and Zinc (64 mg, 1 mmol), the pre-mixture and TESCl (50 μL, 0.3 mmol) were added subsequently. The reaction mixture was stirred vigorously for 1 d. After work-up and purification, 4ma was obtained in 89% yield as a liquid. $^1$H NMR (500 MHz, CDCl$_3$) δ7.13-7.04 (m, 2H), 6.86-6.78 (m, 2H), 5.68-5.57 (m, 2H), 3.78 (s, 3H), 2.84 (t, J=7.6 Hz, 2H), 2.69 (t, J=7.7 Hz, 2H), 2.38-2.31 (m, 2H), 2.17-1.98 (m, 4H), 1.70-1.60 (m, 2H), 1.29-1.18 (m, 1H); $^{13}$C NMR (126 MHz, CDCl$_3$) δ209.86, 157.90, 133.13, 129.23, 126.83, 125.85, 113.84, 55.25, 49.66, 45.08, 31.42, 29.52, 28.87, 28.54, 24.70; IR (neat) v 2914, 2835, 1711, 1512, 1246, 1036; HRMS (ESI) calculated for (C$_{17}$H$_{22}$O$_2$+Na$^+$): 281.1512 found 281.1523.

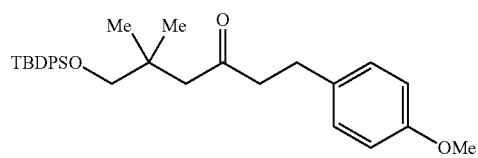

4na

4na: 3 d, 78% (Condition C), 1 d, 88% (CoPc instead of NbCpCl$_4$, Condition C) as a clear liquid; $^1$H NMR (600 MHz, CDCl$_3$) δ7.66-7.61 (m, 4H), 7.44-7.34 (m, 6H), 7.09-7.04 (m, 2H), 6.83-6.78 (m, 2H), 3.77 (s, 3H), 3.39 (s, 2H), 2.79 (t, J=7.6 Hz, 2H), 2.68 (t, J=7.6 Hz, 2H), 2.42 (s, 2H), 1.06 (s, 9H), 0.97 (s, 6H); $^{13}$C NMR (126 MHz, CDCl$_3$) δ210.04, 157.82, 135.63, 133.60, 133.23, 129.57, 129.22, 127.58, 113.81, 72.00, 55.22, 49.96, 46.72, 36.14, 28.81, 26.92, 26.88, 24.36, 19.39; IR (neat) v 2957, 2857, 1712, 1513, 1247, 1112, 702; HRMS (ESI) calculated for $(C_{31}H_{40}O_3Si+H^+)$: 489.2819 found 489.2811.

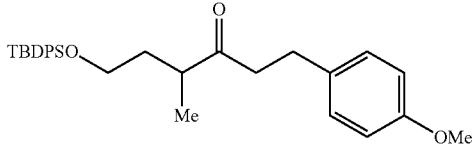

4ca

4ca: 1 d, 93% [Condition A with 1c (2.0 eq.)] as a clear liquid; $^1$H NMR (500 MHz, CDCl$_3$) δ; 7.69-7.64 (m, 4H), 7.47-7.37 (m, 6H), 7.12-7.07 (m, 2H), 6.86-6.81 (m, 2H), 3.80 (s, 3H), 3.66 (t, J=6.1 Hz, 2H), 2.87-2.72 (m, 5H), 2.00-1.89 (m, 1H), 1.56-1.47 (m, 1H), 1.07 (s, 9H), 1.03 (d, J=7.0 Hz, 3H); $^{13}$C NMR (126 MHz, CDCl$_3$) δ 213.55, 157.87, 135.01, 133.69, 133.65, 133.33, 129.64, 129.23, 127.65, 113.81, 61.55, 55.22, 43.07, 42.81, 35.28, 28.87, 26.85, 19.17, 16.11; IR (neat) v 2931, 2857, 1711, 1513, 1246, 1111, 702; HRMS (ESI) calculated for $(C_{30}H_{38}O_3Si+H^+)$: 475.2663 found 475.2656.

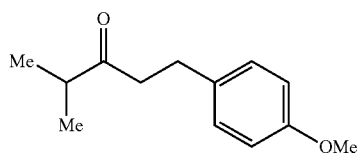

4oa

4oa (see, e.g., Zheng et al., J. Bioorg. Med. Chem. Lett. 2004, 14, 5551, Yu et al., Anticancer Agents from Natural Products; CRC Press: 2005; p 241, Yu et al., In Annual Reports in Medicinal Chemistry; John, E. M., Ed.; Academic Press: 2011; Vol. 46, p 227, Austad et al., Synlett 2013, 24, 333) was obtained as a clear liquid from 1° (1.5 eq.). 92% (Condition A), 92% (Condition B), 85% (Condition C).

One-Step vs Two-Step Procedure

Alkylzinc halides prepared via direct zinc insertion were stable at room temperature at least for 2 weeks. That observation suggested the possibility of utilizing alkylzinc halides thus prepared for Fukuyama ketone synthesis in a two-step procedure similar to the original Fukuyama protocol. To address this notion, the efficiency of the one-step procedure (one-pot) and that of a two-step procedure were compared. As an example for the direct zinc insertion method, we chose the coupling 1b+3a→4ba was selected (FIG. 15). No difference in the overall yield between the one- and two-step procedures was observed, as expected. TESCl was not required and was omitted for two-step procedures.

One-Step Procedure

To a 8 mL vial were added PCy$_3$ (5.6 mg, 0.02 mmol), Pd$_2$dba$_3$(0) (9.1 mg, 0.01 mmol), and DMI (0.5 mL) in a glove box at room temperature. After 30 min, CrCl$_2$ (6 mg, 0.05 mmol) and LiI (26 mg, 0.2 mmol) were added to the mixture and stirred for 1 h to give a homogeneous dark solution. To a second vial containing thioester 3a (45 mg, 0.2 mmol), alkyl bromide 1b (94 mg, 0.24 mmol), and Zn (64 mg, 1.0 mmol), pre-mixture and TESCl (50 μL, 0.3 mmol) were added. The reaction mixture was stirred vigorously for 1 d. Et$_2$O and saturated Rochelle salt solution were added and stirred for 30 min. Then, it was extracted with Et$_2$O and the extract was washed with water. After concentration, a SiO$_2$ column chromatography (EtOAc/Hexanes=1/20) was performed to give the desired ketone 4ba in 95% yield.

Two-Step Procedure

To alkyl bromide 1b (94 mg, 0.24 mmol) and Zn (64 mg, 1.0 mmol) were added LiI (26.6 mg, 0.2 mmol) and DMI (0.25 mL). After 20 hrs with vigorous stirring, CrCl$_2$ (6 mg, 0.05 mmol), pre-mixture I [0.25 mL, Pd$_2$dba$_3$ (0.01 mmol, 0.04 M), PCy$_3$ (0.02 mmol, 0.08 M) in DMI], and thioester 3a (45 mg, 0.2 mmol) were added to the reaction mixture subsequently and stirred at rt in a glove box until 3a was consumed. After work-up and a SiO$_2$ column chromatography, ketone 4ba was obtained in 91% yield.

For the study on alkylzinc halides generated via a SET process, the conditions with CoPc for the coupling 1b+3a→4ba were first studied (FIG. 15). As discussed previously, CrCl$_2$ plays a role in achieving an efficient one-pot ketone synthesis of β-substituted bromide 1b. Then, there are two possibilities in the timing of the addition of this key additive, i.e., addition of CrCl$_2$ in the first or second step. Experimentally, it was found that its addition in the first step gave the expected ketone in the yield comparable to that in the one-step procedure, whereas its addition in the second step gave virtually no expected ketone. This experiment established the experimental protocol for preparation of alkylzinc halides with use of a SET process. At the same time, it provided the evidence that CrCl$_2$ is involved in the process from alkyl halides to the alkylzinc halide. This observation was consistent with the assumption that the role of CrCl$_2$ was to trap the alkyl radical, generated via a CoPc-mediated SET process, and transmetallate it to Zn(II) to form RZnX. After step one in the two-step procedures, each supernatant solution was diluted and subjected to ESI mass spectroscopy in negative ionic mode. Besides ZnX$_3^-$, RZnX$_2^-$ ions were observed at higher m/z ratios for following conditions: (1) direct Zn insertion: (Zn, LiI); (2) SET with CrCl$_2$: (CoPc, Zn, CrCl$_2$) and (NbCpCl$_4$, Zn, CrCl$_2$). See below for details. In addition, CrCl$_2$ may have an additional role as noticed in the coupling under the conditions that included LiI, TESCl, and CrCl$_2$ (FIG. 13, entry 5). The overall profile for the coupling with an alkylzinc halide, generated with NbCpCl$_4$ and zinc dust, was the same as that observed for the coupling with an alkylzinc halide, generated with CoPc.

One-Step Procedure

To thioester 3a (45 mg, 0.2 mmol), alkyl bromide 1b (94 mg, 0.24 mmol), and Zn (64 mg, 1.0 mmol) in DMI (0.25 mL) was added CrCl$_2$ (6 mg, 0.05 mmol) with vigorous stirring. After 5 min, CoPc (5.7 mg, 0.01 mmol) or NbCpCl$_4$ (3 mg, 0.01 mmol) was added followed by premixture I [0.25 mL, Pd$_2$dba$_3$ (0.01 mmol, 0.04 M), PCy$_3$ (0.02 mmol, 0.08 M) in DMI] and TESCl (50 μL, 0.3 mmol). After 2 days for the reaction with CoPc or 1 day for the reaction with NbCpCl$_4$, above mentioned work-up and a SiO$_2$ column chromatography were performed to provide ketone 4ba in 96% yield (CoPc) and 95% yield (NbCpCl$_4$), respectively.

Two-Step Procedure: First Step in the Absence of CrCl$_2$

To alkyl bromide 1b (94 mg, 0.24 mmol) and Zn (64 mg, 1.0 mmol) in DMI (0.25 mL) was added CoPc (5.7 mg, 0.01 mmol) or NbCpCl$_4$ (3 mg, 0.01 mmol) and stirred for 20 h. Then, CrCl$_2$ (6 mg, 0.05 mmol), pre-mixture I [0.25 mL, Pd$_2$dba$_3$ (0.01 mmol, 0.04 M), PCy$_3$ (0.02 mmol, 0.08 M) in DMI], and thioester 3a (45 mg, 0.2 mmol) were added to the reaction mixture subsequently and stirred at room temperature in a glove box for 1 d (for both CoPc and NbCpCl$_4$). After workup, less than 5% of ketone 4ba was detected by crude $^1$H NMR.

Two-Step Procedure: First Step in the Presence of $CrCl_2$

To alkyl bromide 1b (94 mg, 0.24 mmol) and Zn (64 mg, 1.0 mmol) in DMI (0.25 mL) was added $CrCl_2$ (6 mg, 0.05 mmol) and dissolved (about 5 min). Then CoPc (5.7 mg, 0.01 mmol) or $NbCpCl_4$ (3 mg, 0.01 mmol) was added and stirred for 20 h. Pre-mixture I [0.25 mL, $Pd_2dba_3$ (0.01 mmol, 0.04 M), $PCy_3$ (0.02 mmol, 0.08 M) in DMI] and thioester 3a (45 mg, 0.2 mmol) were added to the reaction mixture and stirred at room temperature in a glove box for 1 d (for both CoPc and $NbCpCl_4$). After work-up and a $SiO_2$ column chromatography, ketone 4ba was obtained in 85% (CoPc) and in 95% ($NbCpCl_4$) yield.

Three Coupling Conditions

Figure 17:
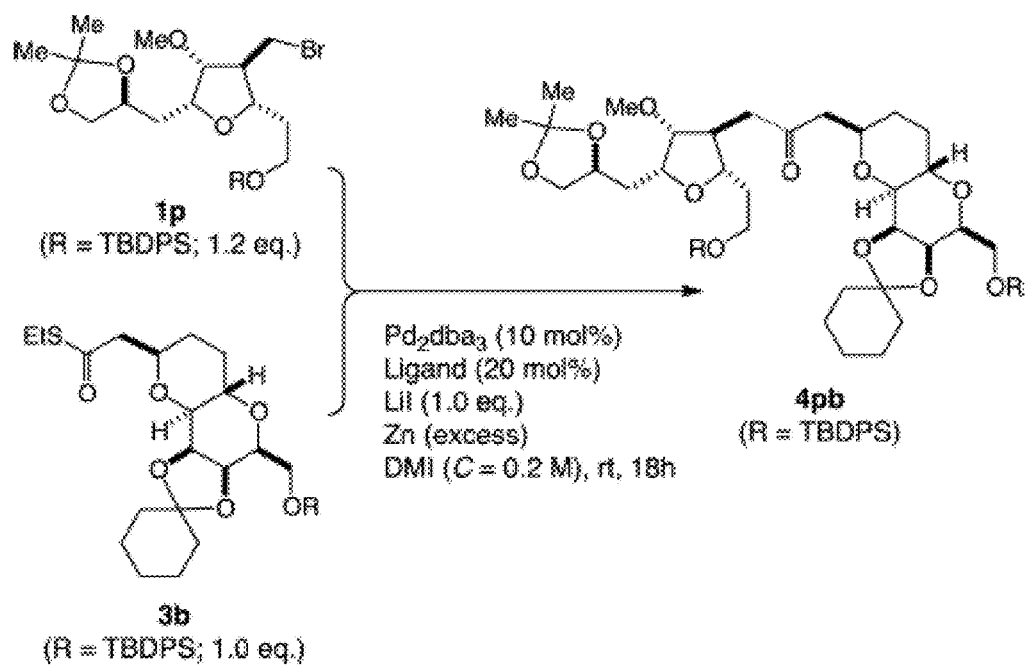
FIG. 17 is a schematic showing one-pot ketone synthesis with complex nucleophile and electrophile. Screening was done with a scale of 1p (0.012 mmol) and 3b (0.010 mmol). Conversion was estimated by crude $^1$H NMR.
Figure 18:
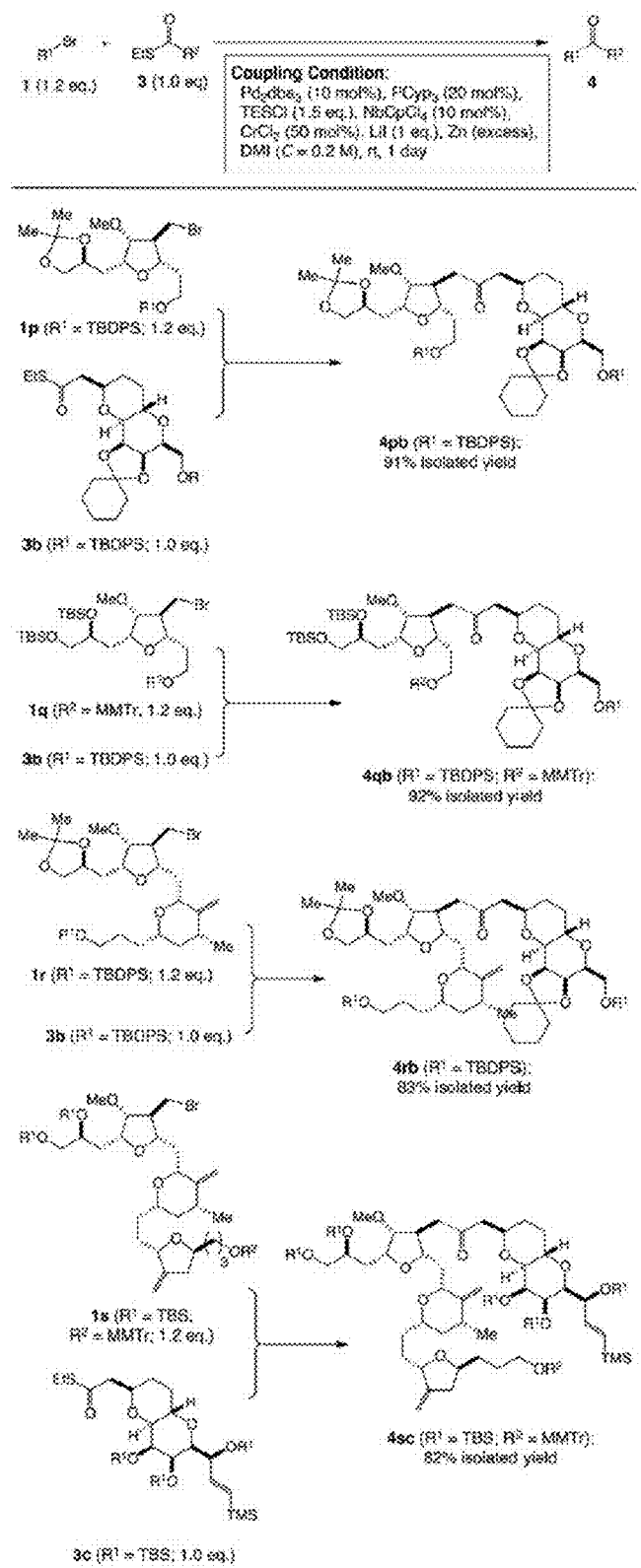
FIG. 18 shows the application of Eribulin synthesis. Couplings were done in 0.10 mmol scale, except for 1s+3→4sc in a 0.05 mmol scale. Yields were based on the products isolated by column chromatography.

As summarized in FIG. 13, three different types of coupling conditions for one-pot ketone synthesis are exemplified (FIG. 14). In general, tricyclohexylphosphine ($PCy_3$) is more effective than tricyclopentylphosphine ($PCyp_3$) for simple substrates (FIG. 20) but $PCyp_3$ was found to be the optimal choice of ligand for complex substrates (FIG. 17 and FIG. 18). Thus, $PCyp_3$ was used to study functional group tolerance in FIG. 14. Higher yields were expected with most substrates if $PCy_3$ was used rather than $PCyp_3$ as shown with 1b and 1l, especially under Condition A. These three coupling conditions were applied to arbitrarily chosen substrates, with the hope that this study should demonstrate functional-group tolerance and, at the same time, give a guideline in selecting the coupling conditions for a given substrate.

Overall, one-pot ketone synthesis was effective for all the arbitrarily chosen substrates, and Condition C worked best for the substrates tested, except for a-substituted iodides, cf., 4ca and 4oa (FIG. 14). Thus, with use of Condition C, it can be tested whether one-pot ketone synthesis is applicable to a given substrate. A glance of the results given in FIG. 13 and FIG. 14 gives a rough guideline for predicting the effectiveness of Conditions A and B for a given substrate. The results given in FIG. 14 show that common functional groups were well tolerated in one-pot ketone synthesis, including silyl protecting groups, p-methoxybenzyl (PMB), acetonide, ester, cyanide, ketone, chloride, olefin, and TMS-protected acetylene.

In order to test for leakage of alkyl bromide via a radical process such as a 1,5-H shift, the alkyl halides leading to 4ha and 4la were chosen. Even under Condition C, using a SET process for preparation of alkylzinc halides, the reductive radical quenching did not override the desired Pd-catalyzed coupling pathway.

Coupling Efficiency vs Molar Ratio of Coupling Partners

Under coupling Condition C, the coupling efficiency versus the molar ratio of coupling partners was examined. For this test, the coupling of 1b+3a→4ba was chosen, where 4ba was isolated in 95%, 93%, 88%, 82%, and 87% yields with 1b:3a=1.2:1.0, 1.1:1.0, 1.0:1.0, 1.0:1.1, and 1.0:1.2, respectively. This experiment demonstrated that one-pot ketone synthesis is effective even with an ~1:1 molar ratio of coupling partners.

Application to Syntheses of Complex Molecules

Having demonstrated the feasibility of a one-pot ketone synthesis from alkyl halides and thioesters, the next phase of study began, namely a test of the coupling efficiency with both nucleophile and electrophile bearing structure complexity (FIG. 17). For this test, the coupling of 1p+3b→4pb was chosen and the coupling efficiency under three different types of coupling conditions, i.e., Conditions A-C was studied.

One-pot ketone synthesis under Condition C, particularly with $NbCpCl_4$, gave a clean, complete conversion to furnish the desired ketone in 91% isolated yield (FIG. 18). Overall, these observations demonstrated once again that one-pot ketone synthesis via a SET process gives excellent efficiency even for complex substrates.

General Conditions for FIG. 18

Pre-mixture I [$Pd_2dba_3$ (0.04 M), $PCyp_3$ (0.08 M) in DMI]: To a vial were added $PCyp_3$ (24 mg, 0.1 mmol), tris(dibenzylideneacetone)dipalladium(0) ($Pd_2dba_3$, 46 mg, 0.05 mmol), and 1,3-dimethyl-2-imidazolidinone (DMI) (1.25 mL) in a glove box. Pre-mixture II-B [$CrCl_2$ (0.2 M) and LiI (0.4 M)]: LiI (133 mg, 1 mmol) and $CrCl_2$ (60 mg, 0.5 mmol) were dissolved in DMI (2.5 mL) in a vial in a glove box to give a homogeneous blue solution. To a 10 mL round-bottom flask were added 3 (0.1 mmol), 1 (0.12 mmol) and azeotroped with PhH (4 mL) (3 times) and then it was dried under vacuum for a least 2 h. Following the standard Condition C, Zn (>5 eq.), in a glovebox, premixture-I (0.25 mL) [$Pd_2dba_3$ (10 mol %, 0.04 M), $PCyp_3$ (20 mol %)], premixture-II-B (0.25 mL) [$CrCl_2$ (0.05 mmol, 0.5 eq., 0.2 M), LiI (0.1 mmol, 1 eq., 0.4 M)], $NbCpCl_4$ (3 mg, 0.01 mmol, 10 mol %) and TESCl (25 µL, 1.5 eq.) were added to the flask and stirred vigorously for 1 day. Upon completion of the reaction, the mixture was diluted with $Et_2O$, quenched with saturated aqueous Rochelle salt and stirred for 30 min. Then it was extracted with $Et_2O$ (3 times) and the organic layer was washed with water, dried over $Na_2SO_4$, and purified by a flash column chromatography to give the desired ketone.

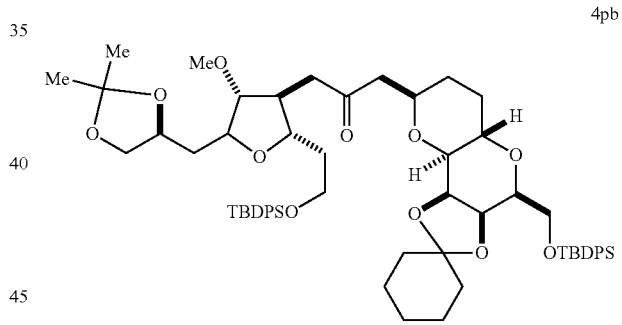

4pb

4pb (98 mg, 91%, a clear liquid) from 3b (62.4 mg, 0.1 mmol) and 1p (70 mg, 0.12 mmol); $[\alpha]_D^{20}=-29.3°$ (c 1.0, $CH_2Cl_2$); $^1$H NMR (500 MHz, $C_6D_6$) δ7.90-7.78 (m, 8H), 7.33-7.21 (m, 12H), 4.47 (dd, J=8.4, 1.6 Hz, 1H), 4.33-4.24 (m, 2H), 4.18 (dd, J=9.4, 8.1 Hz, 1H), 4.06-3.97 (m, 4H), 3.97-3.89 (m, 2H), 3.84-3.68 (m, 3H), 3.56 (t, J=7.6 Hz, 1H), 3.33 (dd, J=3.9, 1.3 Hz, 1H), 3.27 (s, 3H), 3.15 (dd, J=10.1, 3.1 Hz, 1H), 2.56-2.46 (m, 1H), 2.37 (dd, J=16.0, 8.3 Hz, 1H), 2.25-2.09 (m, 3H), 2.09-1.98 (m, 4H), 1.87-1.75 (m, 3H), 1.62 (m, 3H), 1.58-1.10 (m, 8H), 1.46 (s, 3H), 1.37 (s, 3H), 1.22 (s, 18H); $^{13}$C NMR (126 MHz, $C_6D_6$) δ205.97, 136.07, 136.02, 135.98, 134.42, 133.96, 133.93, 129.98, 129.90, 128.07, 110.18, 108.76, 86.94, 80.69, 78.20, 76.62, 74.45, 74.06, 73.98, 71.41, 70.61, 69.80, 66.05, 63.66, 61.73, 56.67, 48.47, 46.29, 44.82, 39.22, 36.29, 33.91, 33.56, 31.22, 30.44, 27.33, 27.18, 27.07, 26.20, 25.54, 24.29, 23.92, 19.54; IR (neat) v 2932, 2857, 1717, 1428, 1369, 1104, 703; HRMS (ESI) calculated for ($C_{63}H_{86}O_{11}Si_2+Na^+$): 1097.5601 found 1097.5655.

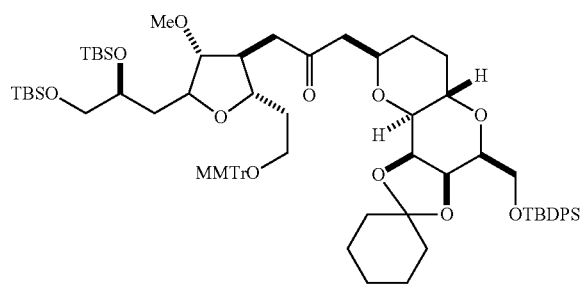

4qb (119 mg, 92%, a clear liquid) from 3b (62.4 mg, 0.1 mmol) and 1q (98 mg, 0.12 mmol); [α]$_D^{20}$=−28.0° (c 1.0, CH$_2$Cl$_2$); 1H NMR (600 MHz, C$_6$D$_6$) δ7.90-7.84 (m, 2H), 7.84-7.78 (m, 2H), 7.69-7.62 (m, 4H), 7.52-7.43 (m, 2H), 7.31-7.18 (m, 10H), 7.12-7.07 (m, 2H), 6.81-6.73 (m, 2H), 4.47 (dd, J=8.4, 1.7 Hz, 1H), 4.30-4.25 (m, 1H), 4.18 (dd, J=9.5, 8.1 Hz, 1H), 4.15-4.07 (m, 2H), 4.07-3.99 (m, 2H), 3.86-3.77 (m, 3H), 3.76-3.67 (m, 2H), 3.49-3.41 (m, 2H), 3.40 (dd, J=4.0, 1.7 Hz, 1H), 3.35 (s, 3H), 3.33 (s, 3H), 3.18 (dd, J=10.1, 3.1 Hz, 1H), 2.57-2.51 (m, 1H), 2.46 (dd, J=16.3, 8.0 Hz, 1H), 2.24-2.14 (m, 4H), 2.14-2.04 (m, 2H), 2.04-1.98 (m, 1H), 1.89 (dd, J=16.3, 4.2 Hz, 1H), 1.87-1.74 (m, 2H), 1.64-1.58 (m, 3H), 1.58-1.40 (m, 4H), 1.38-1.29 (m, 2H), 1.22 (s, 9H), 1.20-1.13 (m, 2H), 1.03 (s, 9H), 1.00 (s, 9H), 0.20 (s, 3H), 0.17 (s, 3H), 0.10 (s, 6H); 13C NMR (126 MHz, C$_6$D$_6$) δ205.94, 159.05, 145.63, 145.55, 136.55, 136.07, 135.97, 133.97, 133.93, 130.80, 129.97, 129.02, 128.98, 128.06, 127.02, 113.49, 110.16, 87.41, 86.76, 81.33, 78.10, 76.63, 74.40, 74.00, 72.14, 71.43, 70.60, 68.38, 66.08, 63.65, 61.48, 56.98, 54.72, 48.48, 46.38, 45.31, 36.91, 36.29, 34.72, 33.93, 31.23, 30.46, 27.07, 26.25, 25.55, 24.29, 23.92, 19.54, 18.64, 18.46, −3.90, −4.42, −5.09, −5.11; IR (neat) ν 2930, 2856, 1716, 1510, 1251, 1102, 833; HRMS (ESI) calculated for (C$_{76}$H$_{108}$O$_{12}$Si$_3$+Na$^+$): 1319.7041 found 1319.7028.

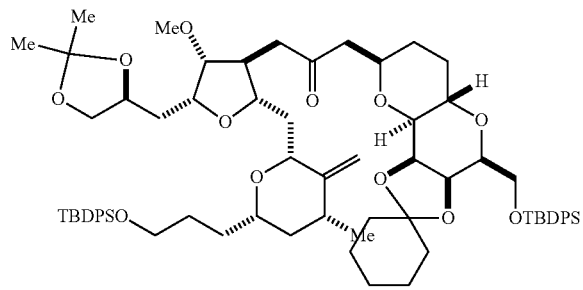

4rb (101 mg, 83%, a clear liquid) from 3b (62.4 mg, 0.1 mmol) and 1r (87 mg, 0.12 mmol) which was azeotroped with PhH (4 mL) (at least 5 times); [α]$_D^{20}$=−18.4° (c 1.0, CH$_2$Cl$_2$); 1H NMR (600 MHz, C$_6$D$_6$) δ7.89-7.79 (m, 8H), 7.32-7.21 (m, 12H), 4.98 (s, 1H), 4.82 (d, J=1.8 Hz, 1H), 4.48 (dd, J=8.4, 1.7 Hz, 1H), 4.37-4.27 (m, 2H), 4.19 (dd, J=9.5, 8.2 Hz, 1H), 4.08-4.00 (m, 3H), 4.00-3.91 (m, 3H), 3.85-3.72 (m, 4H), 3.59 (t, J=7.6 Hz, 1H), 3.40 (d, J=3.7 Hz, 1H), 3.34-3.29 (m, 1H), 3.31 (s, 3H), 3.19 (dd, J=10.2, 3.1 Hz, 1H), 2.76-2.68 (m, 1H), 2.52-2.42 (m, 2H), 2.41-2.28 (m, 3H), 2.28-2.22 (m, 1H), 2.16 (dd, J=17.7, 9.3 Hz, 1H), 2.05-1.97 (m, 2H), 1.91 (dd, J=16.2, 4.0 Hz, 1H), 1.88-1.81 (m, 2H), 1.81-1.75 (m, 1H), 1.72-1.48 (m, 8H), 1.47 (s, 3H), 1.46-1.40 (m, 2H), 1.38 (s, 3H), 1.37-1.26 (m, 3H), 1.22 (s, 9H), 1.21 (s, 9H), 1.20-1.10 (m, 3H), 0.98 (d, J=6.5 Hz, 3H); 13C NMR (126 MHz, C$_6$D$_6$) δ206.16, 151.70, 136.06, 136.00, 135.96, 134.43, 133.95, 133.91, 129.98, 129.94, 128.09, 128.07, 110.18, 108.79, 104.44, 87.33, 81.40, 78.23, 77.11, 76.70, 76.07, 74.49, 74.11, 74.00, 71.39, 70.61, 69.81, 66.04, 64.46, 63.62, 60.02, 56.76, 48.58, 46.56, 44.62, 43.40, 38.52, 36.29, 36.06, 33.93, 33.51, 32.79, 31.23, 30.40, 29.44, 27.35, 27.16, 27.13, 27.06, 26.18, 25.58, 24.28, 23.94, 20.51, 19.53, 19.50, 18.14, 14.18; IR (neat) ν 2931, 2857, 1716, 1472, 1428, 1369, 1092, 702; HRMS (ESI) calculated For (C$_{72}$H$_{100}$O$_{12}$Si$_2$+H$^+$): 1213.6826 found 1213.6811.

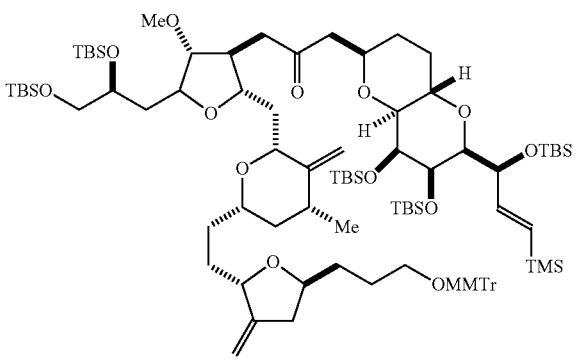

4sc (68 mg, 82%, a foamy solid) from 3c (37 mg, 0.05 mmol) and is (63.4 mg, 0.06 mmol) which was azeotroped with PhH (4 mL) (at least 5 times); [α]$_D^{20}$=−26.3° (c 1.0, CH$_2$Cl$_2$); 1H NMR (500 MHz, C$_6$D$_6$) δ7.63 (dd, J=8.4, 1.3 Hz, 4H), 7.49-7.41 (m, 2H), 7.18 (d, J=7.7 Hz, 4H), 7.10-7.04 (m, 2H), 6.77-6.70 (m, 2H), 6.52 (dd, J=18.8, 8.3 Hz, 1H), 6.16 (dd, J=18.9, 0.7 Hz, 1H), 5.29 (dd, J=8.3, 4.8 Hz, 1H), 5.00 (s, 1H), 4.95 (q, J=2.1 Hz, 1H), 4.87 (q, J=2.1 Hz, 1H), 4.82 (s, 1H), 4.48 (s, 1H), 4.27 (t, J=2.4 Hz, 1H), 4.24-4.09 (m, 3H), 4.09-3.97 (m, 3H), 3.97-3.86 (m, 2H), 3.82 (dd, J=10.3, 5.7 Hz, 1H), 3.78-3.68 (m, 2H), 3.59-3.51 (m, 1H), 3.44-3.38 (m, 1H), 3.36-3.29 (m, 1H), 3.34 (s, 3H), 3.31 (s, 3H), 3.22 (t, J=6.2 Hz, 2H), 2.99 (dd, J=9.5, 2.3 Hz, 1H), 2.82-2.72 (m, 1H), 2.65 (dd, J=16.7, 6.7 Hz, 1H), 2.54-2.37 (m, 4H), 2.36-2.18 (m, 4H), 2.14-2.04 (m, 2H), 2.00-1.92 (m, 1H), 1.90-1.77 (m, 3H), 1.75-1.63 (m, 4H), 1.62-1.56 (m, 1H), 1.52-1.46 (m, 2H), 1.46-1.36 (m, 1H), 1.30-1.18 (m, 2H), 1.17 (s, 9H), 1.16-1.06 (m, 2H), 1.05 (s, 18H), 1.00 (s, 9H), 0.97 (s, 9H), 0.35 (s, 3H), 0.34 (s, 3H), 0.26 (s, 3H), 0.23 (s, 6H), 0.21 (s, 3H), 0.20 (s, 9H), 0.17 (s, 3H), 0.16 (s, 3H), 0.12 (s, 3H), 0.11 (s, 3H); 13C NMR (126 MHz, C$_6$D$_6$) δ205.32, 159.07, 152.91, 151.72, 147.89, 145.62, 136.54, 131.37, 130.77, 128.93, 127.00, 113.43, 104.52, 104.42, 87.97, 86.57, 81.40, 81.34, 79.70, 79.66, 77.99, 77.23, 77.17, 76.21, 76.05, 73.77, 73.62, 72.25, 71.57, 68.41, 63.80, 63.76, 56.92, 54.72, 49.32, 46.12, 44.45, 43.37, 39.30, 38.84, 36.19, 34.70, 32.53, 32.47, 31.92, 31.12, 29.26, 27.15, 26.99, 26.72, 26.64, 26.29, 26.27, 19.56, 19.10, 18.65, 18.50, 18.15, −1.29, −2.32, −2.66, −3.42, −3.84, −3.97, −4.06, −4.35, −4.39, −5.08, −5.11; IR (neat) ν 2931, 2857, 1716, 1472, 1428, 1369, 1092, 702; HRMS (ESI) calculated for (C$_9$H$_{158}$O$_{14}$Si$_6$+Na$^+$): 1690.0159 found 1690.0164.

Application to Synthesis of Eribulin

Lastly, Eribulin was used as an example to illustrate that one-pot ketone synthesis is a reliable option for a late stage coupling in a convergent synthesis of complex molecules (FIG. 18). No significant difference in coupling efficiency were found, with the increase in molecular size. The halides having an allylic tertiary hydrogen positioned for the 1,5-H shift did not show obvious leakage through a radical species (1r, 1s). Finally, one-pot ketone synthesis was successfully applied to a synthesis of ketone 4sc containing all the carbons of Eribulin.

A facile activation of nonactivated 1°- and 2°-alkyl halides was achieved via (1) direct Zn insertion or (2) early transition-metal assisted SET-activation. For alkyl bromides, lithium iodide in DMI was found to be an effective combination for efficient insertion of zinc dust into alkyl bromides at room temperature. Mechanistically, alkyl bromides were first transformed to the corresponding alkyl iodides, which then reacted with zinc dust. An orthogonal, unprecedented method was developed, to prepare alkylzinc halides with use of a combination of CoPc or NbCpCl$_4$ and CrCl$_2$, where the former served as a radical initiator whereas the latter served to trap and transfer the generated radical to zinc halide. Through this study, a new radical initiator, generated from NbCpCl$_4$ and zinc dust, was discovered.

Controlled formation of alkylzinc halides by a combination of CrCl$_2$ and NbCpCl$_4$ or CoPc was crucial for its application to complex substrates. Interestingly, one-pot ketone synthesis did not suffer from the chemical instability due to the inevitable radical pathway(s), for example a 1,5-H shift. Notably, even with the increase in molecular size, no significant decrease in coupling efficiency was noticed. For these reasons, one-pot ketone synthesis was a reliable option for coupling at a late stage in a convergent synthesis of complex molecules, as exemplified in a synthesis of 4sc containing all the carbons of Eribulin.

All of the required reagents were commercially available and were conveniently premixed and stored without loss of activity. The facile preparation of alkylzinc halides at room temperature will find various applications beyond this work.

Materials and Methods for Intermolecular Couplings

General Procedure

NMR spectra were recorded on a Varian Inova 600 MHz, 500 MHz, or 400 MHz spectrometer. Chemical shifts are reported in parts per million (ppm). For $^1$H NMR spectra (CDCl$_3$ and C$_6$D$_6$), the residual solvent peak was used as the internal reference (7.26 ppm in CDCl$_3$; 7.16 ppm in C$_6$D$_6$), while the central solvent peak as the reference (77.0 ppm in CDCl$_3$; 128.0 ppm in C$_6$D$_6$) for $^{13}$C NMR spectra. In reporting spectral data, the following abbreviations were used: s=singlet, d=doublet, t=triplet, q=quartet, m=multiplet, dd=doublet, td=triplet doublet, qd=quartet doublet. High resolution mass spectra (HRMS) were obtained on an Agilent 6210 Time-of-Flight LC/MC Machine and were reported in units of m/e. Optical rotations were measured at 20° C. using a Perkin-Elmer 241 polarimeter. IR spectra were recorded on a Bruker Alpha FT-IR spectrometer. Analytical and semi-preparative thin layer chromatography (TLC) was performed with E. Merck precoated TLC plates, silica gel 60 F254, layer thickness 0.25 and 1.00 mm, respectively. TLC plates were visualized by staining with p-anisaldehyde or phosphomolybdic acid stain. Flash chromatography separations were performed on E. Merck Kieselgel 60 (230-400) mesh silica gel. All moisture sensitive reactions were conducted under an inert atmosphere.

Materials

Tris(dibenzylideneacetone)dipalladium(0) (Pd$_2$dba$_3$, 97%, Sigma-Aldrich), Lithium iodide (Sigma-Aldrich), Chromium(II) chloride (CrCl$_2$, 99.9%, Strem Chemicals), Cyclopentadienylniobium(V) tetrachloride (NbCpCl$_4$, 98%, Strem Chemicals), Zinc (~325 mesh, 99.9%, Strem Chemicals), 1,3-Dimethyl-2-imidazolidinone (DMI) (>99.5%, Sigma-Aldrich) were purchased as indicated and used without further purification. Others were commercial grade and were used as supplied.

Synthesis of Substrates: Alkyl Halides

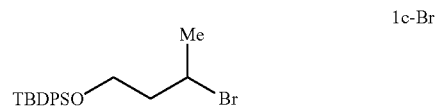

1c-Br was prepared from butane-1,3-diol by TBDPS protection (TBDPSCl, imidazole, CH$_2$Cl$_2$) followed by Appel reaction (CBr$_4$, PPh$_3$, CH$_2$Cl$_2$/Pyr=3/1). $^1$H NMR (500 MHz, CDCl$_3$) δ: 7.73-7.66 (m, 4H), 7.48-7.38 (m, 6H), 4.49-4.40 (m, 1H), 3.88-3.75 (m, 2H), 2.03 (dt, J=7.2, 5.6 Hz, 2H), 1.76 (d, J=6.7 Hz, 3H), 1.07 (s, 9H); $^{13}$C NMR (126 MHz, CDCl$_3$) δ135.59, 135.52, 133.699, 133.53, 129,66, 127.67, 61.74, 48.11, 43.68, 26.83, 26.61, 19.22; IR (neat) v 3071, 2858, 1472, 1428, 1112, 701; HRMS (ESI) calculated for (C$_{20}$H$_{27}$BrOSi+H+): 391.1087 found 391.1087.

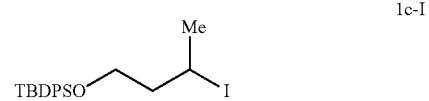

1c-I was prepared from butane-1,3-diol by TBDPS protection (TBDPSCl, imidazole, CH$_2$Cl$_2$) followed by Appel reaction (I$_2$, PPh$_3$, imidazole, CH$_2$Cl$_2$). $^1$H NMR (500 MHz, CDCl$_3$) δ; 7.79-7.61 (m, 4H), 7.51-7.37 (m, 6H), 4.54-4.41 (m, 1H), 3.87-3.66 (m, 2H), 2.05 (ddt, J=14.1, 9.4, 4.8 Hz, 1H), 1.97 (d, J=6.9 Hz, 3H), 1.93-1.82 (m, 1H), 1.07 (s, 9H); $^{13}$C NMR (126 MHz, CDCl$_3$) δ135.62, 135.50, 133.67, 133.50, 129.65, 127.66, 63.37, 45.31, 29.06, 26.84, 26.34, 19.22; IR (neat) v 3071, 2857, 1472, 1428, 1112, 688; HRMS (ESI) calculated for (C$_{20}$H$_{27}$IOSi+H+): 439.0949 found 439.0949.

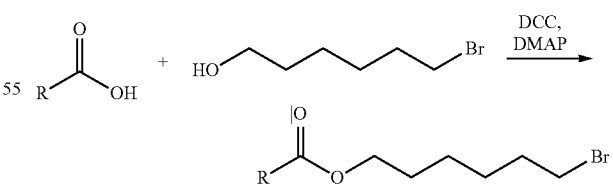

6-bromohexan-1-ol (1.0 g, 5.56 mmol) and the corresponding acid (1.5 eq.) were dissolved in CH$_2$Cl$_2$ (5 mL) in a vial. DMAP (5 mol %) and DCC (1.5 eq.) were added and stirred for 2 hrs. When the reaction was completed, hexanes (3 mL) were added and the mixture was filtered through a short SiO$_2$ pad with Et$_2$O. A flash column chromatography provided the desired ester in a quantitative yield.

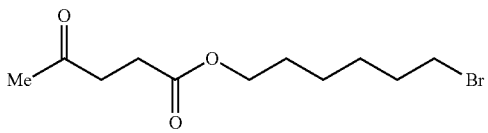
1d

¹H NMR (500 MHz, CDCl₃) δ4.07 (t, J=6.6 Hz, 2H), 3.40 (t, J=6.7 Hz, 2H), 2.74 (t, J=6.5 Hz, 2H), 2.57 (d, J=6.5 Hz, 2H), 2.19 (s, 3H), 1.90-1.82 (m, 2H), 1.68-1.59 (m, 2H), 1.51-1.32 (m, 4H); ¹³C NMR (126 MHz, CDCl₃) δ206.61, 172.76, 64.49, 37.91, 33.69, 32.55, 29.85, 28.37, 27.93, 27.72, 25.06; IR (neat) v 2937, 2860, 1733, 1719, 1357, 1158; HRMS (ESI) calculated for $(C_{11}H_{19}BrO_3+Na^+)$: 301.0410 found 301.0414.

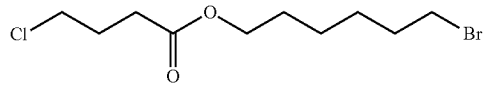
1e

¹H NMR (600 MHz, CDCl₃) δ4.09 (t, J=6.6 Hz, 2H), 3.60 (t, J=6.3 Hz, 2H), 3.41 (t, J=6.8 Hz, 2H), 2.50 (t, J=7.2 Hz, 2H), 2.13-2.06 (m, 2H), 1.91-1.83 (m, 2H), 1.68-1.62 (m, 2H), 1.51-1.44 (m, 2H), 1.42-1.35 (m, 2H); ¹³C NMR (126 MHz, CDCl₃) δ172.70, 77.25, 76.99, 76.74, 64.45, 44.08, 33.66, 32.56, 31.21, 28.41, 27.75, 27.64, 25.13; IR (neat) v 2936, 2859, 1732, 1457, 1201, 1176, 1146; HRMS (ESI) calculated For $(C_{10}H_{18}BrClO_2+Na^+)$: 307.0071 found 307.0060.

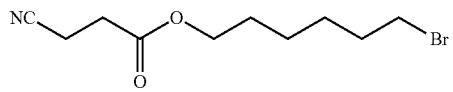
1f

¹H NMR (600 MHz CDCl₃) δ4.15 (t, J=6.7 Hz, 2H), 3.41 (t, J=6.7 Hz, 2H), 2.72-2.62 (m, 4H), 1.91-1.83 (m, 2H), 1.71-1.63 (m, 2H), 1.52-1.43 (m, 2H), 1.43-1.34 (m, 2H); ¹³C NMR (126 MHz, CDCl₃) δ170.03, 118.41, 65.33, 33.66, 32.49, 29.95, 28.30, 27.68, 25.04, 12.97; IR (neat) v 2938, 2860, 2251, 1734, 1248, 1179; HRMS (ESI) calculated for $(C_{10}H_{16}BrNO_2+Na^+)$: 284.0257 found 284.0255.

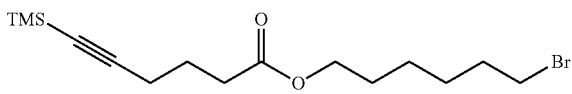
1g

From the known acid which was prepared by literature (see, e.g., Zheng et al., J. Bioorg. Med. Chem. Lett. 2004, 14, 5551, Yu et al., Anticancer Agents from Natural Products; CRC Press: 2005; p 241, Yu et al., In Annual Reports in Medicinal Chemistry; John, E. M., Ed.; Academic Press: 2011; Vol. 46, p 227, Austad et al., Synlett 2013, 24, 333, see, e.g., Fukuyama et al., Org. Process Res. Dev. 2016, 20, 503, Inanaga et al., Org. Lett. 2015, 17, 3158, and Fukuyama et al., Org. Process Res. Dev. 2016, 20, 100). ¹H NMR (500 MHz, CDCl₃) δ4.08 (t, J=6.7 Hz, 2H), 3.41 (t, J=6.8 Hz, 2H), 2.43 (t, J=7.5 Hz, 2H), 2.29 (t, J=7.0 Hz, 2H), 1.91-1.78 (m, 4H), 1.70-1.60 (m, 2H), 1.52-m, 4H), 0.14 (s, 9H); ¹³C NMR (126 MHz, CDCl₃) δ173.19, 105.98, 85.39, 76.74, 64.26, 33.67, 32.99, 32.58, 28.43, 27.76, 25.14, 23.76, 19.27, 0.10; IR (neat) v 2957, 2938, 2174, 1733, 1248, 1158, 840; HRMS (ESI) calculated for $(C_{15}H_{27}BrO_2Si+Na^+)$: 369.0856 found 369.0852.

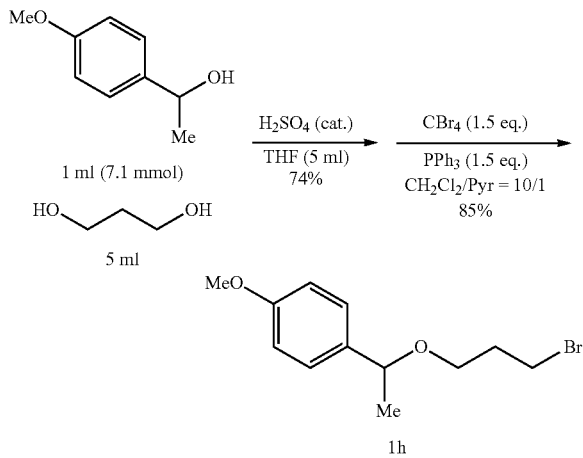
1h

To a solution of 1-(4-methoxyphenyl)ethan-1-ol and 1,3-propanediol in THF was added catalytic amount of H2SO4 at room temperature and stirred. After completion of the reaction, the mixture was diluted with water, extracted with EtOAc, and purified by a flash column chromatography (EtOAc/Hexanes=1/2) to give the desired alcohol (1.11 g, 74%). Subsequently, to the alcohol in Pyr/CH₂Cl₂ (1/10) were added CBr₄ (1.5 eq.) and PPh₃ (1.5 eq.). Upon completion of the reaction, saturated Na₂S₂O₃ was added and extracted with CH₂Cl₂. A flash column chromatography (EtOAc/Hexanes=1/20) provided bromide 1 h as a clear liquid in 85% yield. ¹H NMR (500 MHz, CDCl₃) δ7.25-7.20 (m, 2H), 6.91-6.86 (m, 2H), 4.36 (q, J=6.4 Hz, 1H), 3.81 (s, 3H), 3.56-3.44 (m, 2H), 3.44-3.35 (m, 2H), 2.13-2.00 (m, 2H), 1.42 (d, J=6.4 Hz, 3H); ¹³C NMR (126 MHz, CDCl₃) δ158.94, 135.75, 127.29, 113.76, 77.70, 65.73, 55.24, 33.08, 30.80, 23.88; IR (neat) v 2972, 1612, 1512, 1245, 1100, 1036, 832; HRMS (ESI) calculated For $(C_{12}H_{17}BrO_2+Na^+)$: 295.0304 found 295.0310.

1j 1j was prepared from 3-bromo-2-methylpropan-1-ol by TBS protection [TBSCl (1.5 eq.), imidazole (3 eq.), and CH₂Cl₂]. ¹H NMR (500 MHz, CDCl₃) δ3.61-3.40 (m, 4H), 2.02-1.92 (m, 1H), 0.99 (d, J=6.8 Hz, 3H), 0.89 (s, 9H), 0.06 (s, 6H); ¹³C NMR (126 MHz, CDCl₃) δ65.31, 38.03, 37.77, 25.87, 18.26, 15.45, −5.44, −5.46; IR (neat) v 2955, 2929, 2857, 1472, 1251, 1095, 1020, 833; HRMS (ESI) calculated for $(C_{10}H_{23}BrOSi+H^+)$: 267.0774 found 267.0767.

1k 1k was prepared from 3-bromo-2-methylpropan-1-ol by benzoylation [BzCl (1.5 eq.), DMAP (cat.), and Et$_3$N/CH$_2$Cl$_2$ (1/3)]. $^1$H NMR (500 MHz, CDCl$_3$) δ8.12-7.99 (m, 2H), 7.65-7.41 (m, 3H), 4.39-4.27 (m, 2H), 3.61-3.49 (m, 2H), 2.44-2.28 (m, 1H), 1.18 (d, J=6.8 Hz, 3H); $^{13}$C NMR (126 MHz, CDCl$_3$) δ166.28, 133.05, 129.99, 129.54, 128.40, 77.25, 76.99, 76.74, 66.96, 36.78, 34.84, 15.86; IR (neat) v 2967, 1719, 1451, 1271, 1113, 710; HRMS (ESI) calculated for (C$_{11}$H$_{13}$BrO$_2$+Na$^+$): 278.9991 found 278.9994.

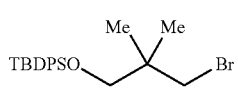

1n 1n was prepared from 3-bromo-2,2-dimethylpropan-1-ol TBDPS protection [TBDPSCl (1.5 eq.), imidazole (3 eq.), and CH$_2$Cl$_2$]. $^1$H NMR (500 MHz, CDCl$_3$) δ7.70-7.65 (m, 4H), 7.46-7.35 (m, 6H), 3.48 (s, 2H), 3.44 (s, 2H), 1.06 (s, 9H), 1.01 (s, 6H); $^{13}$C NMR (126 MHz, CDCl$_3$) δ135.66, 133.42, 129.62, 127.62, 69.60, 43.51, 37.27, 26.85, 26.82, 23.12, 23.09, 19.38; IR (neat) v 2960, 2931, 2858, 1473, 1428, 1112, 701; HRMS (ESI) calculated For (C$_{21}$H$_{29}$BrOSi+H$^+$): 405.1244 found 405.1234.

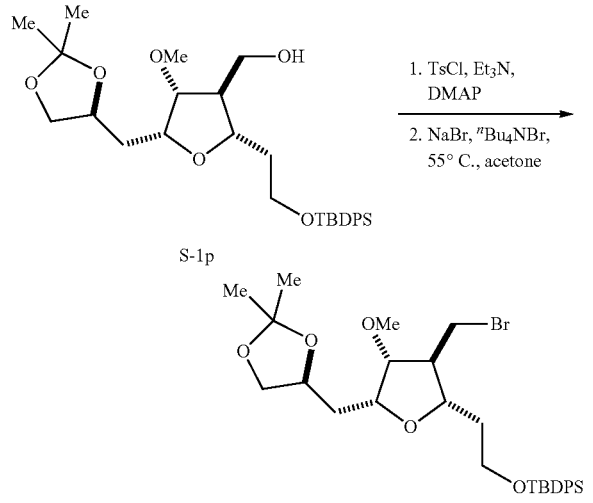

S-1p

1p

To alcohol S-1p (see, e.g., Onaka et al., Chem. Lett. 1981, 10, 531, Wotal et al., J. Org. Lett. 2012, 14, 1476, Wotal et al., Organometallics 2014, 33, 5874, Weix, Acc. Chem. Res. 2015, 48, 1767, Yin et al., Chem. Commun. 2012, 48, 7034, Zhao et al., J. Am. Chem. Soc. 2014, 136, 17645, Cherney et al., J. Am. Chem. Soc. 2013, 135, 7442, Krasovskiy et al., J. Am. Chem. Soc. 2009, 131, 15592, and Duplais et al., Organometallics 2011, 30, 6090) (1 eq.) in Et$_3$N/CH$_2$Cl$_2$ (1/5) were added DMAP (cat.) and TsCl (2 eq.). After 1 day, saturated NaHCO$_3$ was added and extracted with CH$_2$Cl$_2$. A short SiO$_2$ column chromatography (EtOAc/Hexanes=1/10) provided the tosylated compound. NaBr (>10 eq.) and n-Bu4NBr (cat.) were added to the tosyalte in acetone and heated to 55° C. Upon completion of the reaction, the mixture was subjected to filtration (short pad of SiO$_2$, Et$_2$O) and a SiO$_2$ column chromatography to give the desired bromide 1p (>80% yield for 2 steps). [α]$_D^{20}$=−31.4° (c 1.0, CH$_2$Cl$_2$); $^1$H NMR (500 MHz, C$_6$D$_6$) δ7.81-7.75 (m, 4H), 7.29-7.22 (m, 6H), 4.26-4.19 (m, 1H), 3.92-3.84 (m, 2H), 3.83-3.75 (m, 2H), 3.68-3.60 (m, 1H), 3.51 (dd, J=8.0, 7.3 Hz, 1H), 3.39 (dd, J=4.3, 1.7 Hz, 1H), 3.01 (s, 3H), 2.94 (dd, J=10.4, 5.8 Hz, 1H), 2.78 (dd, J=10.5, 8.2 Hz, 1H), 2.18-2.10 (m, 2H), 2.03 (ddd, J=13.5, 7.0, 5.8 Hz, 1H), 1.86-1.78 (m, 2H), 1.44 (s, 3H), 1.36 (s, 3H), 1.18 (s, 9H); $^{13}$C NMR (126 MHz, C$_6$D$_6$) δ135.98, 135.95, 134.22, 134.16, 129.95, 128.06, 108.74, 86.29, 79.37, 78.26, 73.85, 69.65, 61.24, 56.36, 52.77, 38.64, 33.27, 33.09, 27.28, 27.12, 26.12, 19.45; IR (neat) v 2957, 2857, 1472, 1369, 1112, 702; HRMS (ESI) calculated for (C$_{30}$H$_{43}$BrO$_5$Si+H$^+$): 591.2136 found 591.2164.

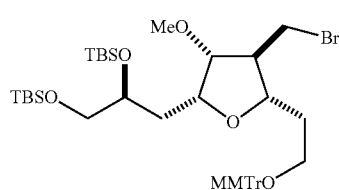

1q

Partial deprotection of MMTr observed during substitution of the tosylate to bromide, but it was not optimized (46% yield). [α]$_D^{20}$=−29.5° (c 1.0, CH$_2$Cl$_2$); $^1$H NMR (500 MHz, C$_6$D$_6$) δ7.65-7.60 (m, 4H), 7.47-7.42 (m, 2H), 7.23-7.17 (m, 4H), 7.10-7.04 (m, 2H), 6.80-6.73 (m, 2H), 4.09-4.02 (m, 1H), 4.02-3.96 (m, 1H), 3.75 (dd, J=10.3, 5.6 Hz, 1H), 3.70-3.62 (m, 2H), 3.53 (dd, J=4.2, 1.6 Hz, 1H), 3.41-3.32 (m, 2H), 3.31 (s, 3H), 3.09 (s, 3H), 3.01 (dd, J=10.5, 5.2 Hz, 1H), 2.88 (dd, J=10.5, 8.5 Hz, 1H), 2.24-2.08 (m, 3H), 2.08-1.99 (m, 1H), 1.94-1.84 (m, 1H), 1.01 (s, 9H), 0.98 (s, 9H), 0.18 (s, 3H), 0.15 (s, 3H), 0.09 (s, 6H); $^{13}$C NMR (126 MHz, C$_6$D$_6$) δ159.11, 145.51, 145.36, 136.31, 130.75, 128.90, 128.84, 128.08, 127.05, 127.03, 113.48, 86.82, 86.62, 79.91, 78.31, 71.88, 68.28, 61.01, 56.47, 54.68, 52.89, 36.41, 34.36, 33.56, 26.19, 26.18, 18.59, 18.40, −3.94, −4.51, −5.16; IR (neat) v 2928, 2856, 1510, 1463, 1251, 1082, 834; HRMS (ESI) calculated for (C$_{43}$H$_{65}$BrO$_6$Si$_2$+Na$^+$): 835.3395 found 835.3417.

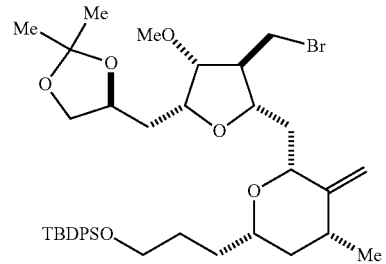

1r

86% yield. [α]$_D^{20}$=−8.7° (c 1.0, CH$_2$Cl$_2$); $^1$H NMR (500 MHz, C$_6$D$_6$) δ7.86-7.73 (m, 4H), 7.32-7.22 (m, 6H), 4.86 (s, 1H), 4.73 (d, J=1.9 Hz, 1H), 4.32-4.21 (m, 1H), 3.89 (dd, J=7.9, 5.9 Hz, 1H), 3.87-3.78 (m, 2H), 3.77-3.69 (m, 4H), 3.54 (dd, J=8.0, 7.3 Hz, 1H), 3.50 (dd, J=4.1, 1.3 Hz, 1H), 3.20 (m, 2H), 3.12 (s, 3H), 3.12-3.10 (m, 1H), 2.85 (dd, J=10.4, 9.2 Hz, 1H), 2.41 (m, 1H), 2.34 (ddd, J=13.4, 8.2, 5.0 Hz, 1H), 2.26 (m, 1H), 2.17-2.08 (m, 1H), 1.95-1.85 (m, 1H), 1.84-1.73 (m, 1H), 1.68-1.49 (m, 2H), 1.49-1.41 (m, 1H), 1.45 (s, 3H), 1.35 (s, 3H), 1.20 (s, 9H), 0.91 (d, J=6.5 Hz, 3H); $^{13}$C NMR (126 MHz, C$_6$D$_6$) δ151.22, 136.01, 134.40, 129.94, 128.06, 108.79, 104.60, 86.61, 79.91, 78.21, 77.14, 75.74, 73.92, 69.66, 64.34, 56.44, 53.10, 43.06, 37.63, 35.85, 33.55, 33.08, 32.70, 29.38, 27.30, 27.15, 26.09, 19.49, 18.04; IR (neat) v 2951, 2855, 1456, 1428, 1389, 1091, 702; HRMS (ESI) calculated for ($C_{39}H_{57}BrO_6Si+Na^+$): 751.3000 found 751.3003.

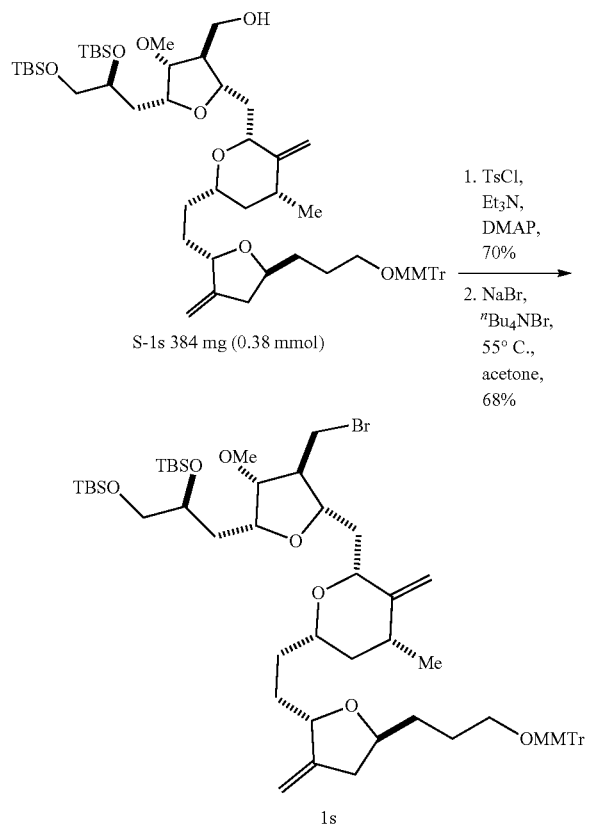

S-1s 384 mg (0.38 mmol)

1. TsCl, Et$_3$N, DMAP, 70%
2. NaBr, $^n$Bu$_4$NBr, 55° C., acetone, 68%

1s

To alcohol S-1s (see, e.g., Onaka et al., Chem. Lett. 1981, 10, 531, Wotal et al., J. Org. Lett. 2012, 14, 1476, Wotal et al., Organometallics 2014, 33, 5874, Weix, Acc. Chem. Res. 2015, 48, 1767, Yin et al., Chem. Commun. 2012, 48, 7034, Zhao et al., J. Am. Chem. Soc. 2014, 136, 17645, Cherney et al., J. Am. Chem. Soc. 2013, 135, 7442, Krasovskiy et al., J. Am. Chem. Soc. 2009, 131, 15592, and Duplais et al., Organometallics 2011, 30, 6090) (384 mg, 0.38 mmol) in Et$_3$N/CH$_2$Cl$_2$ (1/5) were added DMAP (cat.) and TsCl (2 eq.). After 1 day (~10% S.M. left), saturated NaHCO$_3$ was added and extracted with CH$_2$Cl$_2$. A SiO$_2$ column chromatography (EtOAc/Hexanes=1/10) provided the tosylated compound (310 mg, 70%). NaBr (>10 eq.) and n-Bu$_4$NBr (cat.) were added to the tosylate in acetone and heated to 55° C. Partial decomposition of MMTr group was observed and the reaction was stopped at ~60% conversion (6 h) by TLC. After a filtration (short pad of SiO$_2$, Et$_2$O) and a column chromatography (EtOAc/Hexanes=1/50, 1/20 to 1/10), the desired bromide was separated from S.M. The recovered S.M. was re-subjected to the above conditions. 1s was obtained in 68% combined yield (195 mg). $[\alpha]_D^{20}$=−20.0° (c 1.0, CH$_2$Cl$_2$); $^1$H NMR (600 MHz, C$_6$D$_6$) δ 7.65-7.60 (m, 4H), 7.47-7.43 (m, 2H), 7.18-7.15 (m, 4H), 7.08-7.03 (m, 2H), 6.75-6.70 (m, 2H), 4.92 (q, J=2.1 Hz, 1H), 4.90 (br s, 1H), 4.86 (q, J=2.2 Hz, 1H), 4.76 (d, J=1.9 Hz, 1H), 4.48-4.43 (m, 1H), 4.12-4.03 (m, 2H), 4.00-3.89 (m, 2H), 3.83 (dd, J=8.0, 4.4 Hz, 1H), 3.78 (dd, J=10.3, 5.5 Hz, 1H), 3.69 (dd, J=10.3, 4.9 Hz, 1H), 3.63 (dd, J=4.1, 1.6 Hz, 1H), 3.37 (m, 5.1 Hz, 2H), 3.30 (s, 3H), 3.22 (t, J=6.3 Hz, 2H), 3.20 (s, 3H), 3.09 (dd, J=10.6, 8.8 Hz, 1H), 2.51-2.33 (m, 3H), 2.28-2.14 (m, 3H), 2.09-2.05 (m, 1H), 2.00-1.96 (m, 1H), 1.89-1.74 (m, 4H), 1.71-1.64 (m, 3H), 1.59-1.52 (m, 1H), 1.50-1.40 (m, 2H), 1.02 (s, 9H), 0.99 (s, 9H), 0.93 (d, J=6.5 Hz, 3H), 0.20 (s, 3H), 0.19 (s, 3H), 0.11 (s, 3H), 0.10 (s, 3H); $^{13}$C NMR (126 MHz, C$_6$D$_6$) δ159.05, 152.74, 151.32, 145.63, 136.54, 130.76, 128.92, 126.97, 113.41, 104.57, 104.52, 86.98, 86.56, 79.73, 79.56, 78.19, 77.25, 77.18, 75.85, 72.00, 68.28, 63.81, 56.64, 54.70, 52.86, 43.09, 39.25, 37.79, 36.78, 35.97, 34.31, 33.87, 32.50, 32.29, 31.84, 30.17, 27.13, 26.22, 26.20, 24.98, 23.50, 18.61, 18.42, 18.07, −3.91, −4.48, −5.13, −5.15; IR (neat) v 2928, 2855, 1509, 1463, 1447, 1251, 1087, 834; HRMS (ESI) calculated for ($C_{59}H_{89}O_8Si_2+K^+$): 1099.4911 found 1099.4888.

Synthesis of Substrates: Thioesters

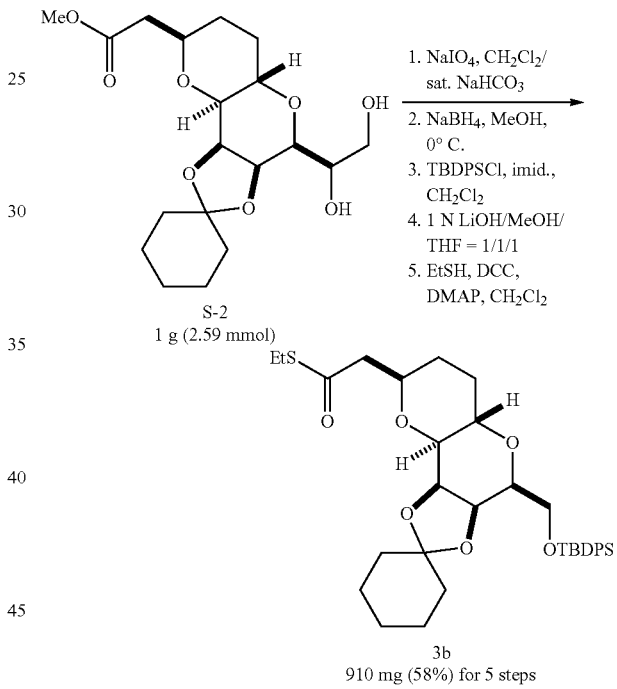

S-2
1 g (2.59 mmol)

1. NaIO$_4$, CH$_2$Cl$_2$/sat. NaHCO$_3$
2. NaBH$_4$, MeOH, 0° C.
3. TBDPSCl, imid., CH$_2$Cl$_2$
4. 1 N LiOH/MeOH/THF = 1/1/1
5. EtSH, DCC, DMAP, CH$_2$Cl$_2$ 3b
910 mg (58%) for 5 steps The first 2 steps were conducted following literature (see, e.g., Guijarro et al., J. Am. Chem. Soc. 1999, 121, 4155) and the crude alcohol was subjected to TBDPS protection conditions [TBDPSCl (1.5 eq), imidazole (3 eq.), CH$_2$Cl$_2$]. Again, without purification, the crude ester was hydrolyzed in MeOH/THF/1 N LiOH at room temperature. Upon completion of hydrolysis, it was acidified with 3 N HCl and extracted with EtOAc. After drying over MgSO$_4$, to the crude acid in CH$_2$Cl$_2$ were added EtSH (excess), DMAP (cat.), and DCC (1.5 eq.) subsequently. After 2 hrs, the reaction mixture was concentrated, diluted with (Et$_2$O) and filtered through a short silica gel pad. The crude was purified by a SiO$_2$ column chromatography to yield 3b (920 mg, 58%) as a sticky liquid. $[\alpha]_D^{20}$=−36.9° (c 1.0, CH$_2$Cl$_2$); $^1$H NMR (500 MHz, C$_6$D$_6$) δ7.91-7.75 (m, 4H), 7.31-7.18 (m, 6H), 4.41 (dd, J=8.4, 1.7 Hz, 1H), 4.30 (dd, J=8.4, 2.9 Hz, 1H), 4.16 (dd, J=9.5, 8.0 Hz, 1H), 4.05-3.96 (m, 2H), 3.86-3.79 (m, 1H), 3.77-3.72 (m, 1H), 3.10 (dd, J=10.1, 3.0

Hz, 1H), 2.80-2.71 (m, 2H), 2.68-2.59 (m, 1H), 2.24 (dd, J=15.4, 4.8 Hz, 1H), 1.96-1.88 (m, 1H), 1.87-1.75 (m, 2H), 1.64-1.56 (m, 3H), 1.56-1.43 (m, 3H), 1.39-1.26 (m, 2H), 1.25-1.04 (m, 12H), 1.00 (t, J=7.4 Hz, 3H); $^{13}$C NMR (126 MHz, $C_6D_6$) δ195.99, 136.07, 135.97, 133.99, 133.96, 129.95, 128.05, 110.21, 76.67, 74.80, 74.07, 71.47, 70.64, 66.03, 63.66, 49.90, 36.28, 33.97, 31.09, 30.14, 27.06, 25.56, 24.27, 23.91, 23.40, 19.53, 14.77; IR (neat) v 2933, 2857, 1686, 1428, 1103, 743; HRMS (ESI) calculated for ($C_{35}H_{48}O_6SSi+Na^+$): 647.2833 found 647.2856.

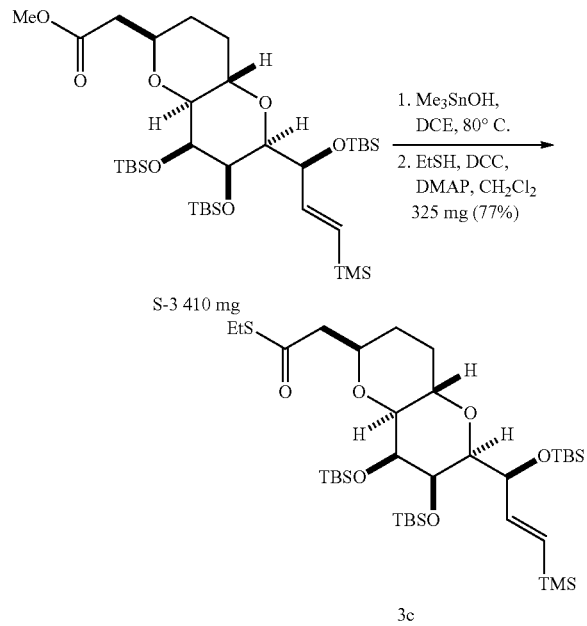

To methyl ester S-3 (410 mg, 0.57 mmol) (see, e.g., Guijarro et al., J. Am. Chem. Soc. 1999, 121, 4155) were added $Me_3SnOH$ (10 eq., 905 mg) and dichloroethane (3 mL) (see, e.g., Cohen et al., J. Am. Chem. Soc. 2007, 129, 15405). The mixture was stirred at 80° C. for 1 d and cooled down to room temperature upon completion of reaction. The reaction was diluted with EtOAc and quenched with 0.1 N HCl. After extraction (EtOAc) and drying over $Na_2SO_4$, the crude acid was used for the next step without further purification. To the crude acid in $CH_2Cl_2$ were added EtSH (excess), DMAP (cat.), and DCC (1.5 eq.) subsequently. After 2 hrs, the reaction mixture was concentrated, diluted (EtOAc/Hx=1/5) and filtered through a short silica gel pad. Purification with a $SiO_2$ column chromatography provided 3c (327 mg, 77%) as a foamy solid. ($[\alpha]_D^{20}$=−37.7° (c 1.0, $CH_2Cl_2$); $^1$H NMR (500 MHz, $C_6D_6$) δ6.49 (dd, J=18.9, 8.3 Hz, 1H), 6.14 (dd, J=18.9, 0.7 Hz, 1H), 5.28 (dd, J=8.3, 4.7 Hz, 1H), 4.25-4.22 (m, 1H), 4.14 (dd, J=6.6, 4.7 Hz, 1H), 3.96 (dd, J=6.7, 2.5 Hz, 1H), 3.87-3.80 (m, 1H), 3.66 (ddd, J=11.0, 9.5, 4.7 Hz, 1H), 2.91 (dd, J=9.6, 2.3 Hz, 1H), 2.75-2.64 (m, 3H), 2.30 (dd, J=15.1, 4.8 Hz, 1H), 1.91-1.84 (m, 1H), 1.40-1.23 (m, 2H), 1.19-1.17 (m, 1H), 1.15 (s, 9H), 1.05 (s, 9H), 1.02 (t, J=7.3 Hz, 3H), 0.94 (s, 9H), 0.34 (s, 3H), 0.31 (s, 3H), 0.25 (s, 3H), 0.22 (s, 3H), 0.18 (s, 9H), 0.14 (s, 3H), 0.12 (s, 3H); $^{13}$C NMR (126 MHz, $C_6D_6$) δ195.48, 147.86, 131.32, 81.35, 79.63, 76.00, 74.34, 73.57, 71.54, 63.63, 50.08, 30.76, 29.18, 26.95, 26.73, 26.64, 23.45, 19.51, 19.08, 18.50, 14.89, −1.32, −2.34, −2.66, −3.46, −4.08, −4.12, −4.36; IR (neat) v 2929, 2855, 2119, 1691, 1472, 1360, 1248, 1135, 835; HRMS (ESI) calculated for ($C_{36}H_{74}O_6SSi_4+Na^+$): 769.4175 found 769.4143.

Intramolecular, palladium-Mediated Macroketolization

Recently, a unified, convergent synthesis of halichondrin natural products was reported, using: (1) Ni/Cr-mediated coupling to form the C19-C20 bond, (2) THF $S_N2$ cyclization between C17-Cl and C20-OH, and (3) macrolactonization (FIG. 2) (see, e.g., Ueda et al., J. Am. Chem. Soc. 2014, 136, 5171 and Li et al., J. Am. Chem. Soc. 2015, 137, 6226). As described herein, this synthetic strategy can be extended to the synthesis of Eribulin, in which the first two key synthetic transformations could be achieved by use of the chemistry developed for the unified synthesis of halichondrins. The third key synthetic transformation is the cyclization to form the macrolactone in the halichondrin series, whereas it is the cyclization to form the macrocyclic ketone in the Eribulin serie using the methods for ketone formation provided herein.

Macrolactonization is a well-precedented synthetic transformation. However, except for a few limited cases (see, e.g., Nishikawa et al., J. Org. Chem. 2013, 78, 582, Tsuna et al., Tetrahedron Lett. 2011, 52, 7202; Porter et al., J. Am. Chem. Soc. 1988, 110, 3554, Kong et al., Angew. Chem., Int. Ed. 2009, 48, 7402, Boger et al., J. Am. Chem. Soc. 1990, 112, 4008, Kende et al., J. Am. Chem. Soc. 1995, 117, 8258, Wu et al., J. Org. Chem. 2011, 76, 9900, and Lowe et al., Org. Lett. 2008, 10, 3813), cyclization to form a macrocyclic ketone, referred to as macroketocyclization here, is an unexploited synthetic transformation (see, e.g., Zheng et al., J. Bioorg. Med. Chem. Lett. 2004, 14, 5551, Namba, K.; Kishi, Y. J. Am. Chem. Soc. 2005, 127, 15382, Austad et al., Synlett 2013, 24, 333, and Inanaga et al., Org. Lett. 2015, 17, 3158). Reported here is a macroketocyclization between a non-activated alkylbromide with a thioester and its application to a synthesis of Eribulin. A new convergent synthesis of Eribulin has been achieved, using: (1) catalytic asymmetric Ni/Cr-mediated coupling to form the C19-C20 bond, (2) base-induced cyclization to form the methylenetetrahydrofuran ring, and (3) Pd-mediated one-pot ketone synthesis to form the macrocyclic ketone. However, in order to translate the one-pot intermolecular ketone synthesis described herein to an intramolecular macroketocyclization, intermolecular coupling needs to be eliminated or suppressed. For the case of intramolecular transformations (e.g., macrolactonization), a high-dilution technique is commonly employed to achieve this goal.

Pd-mediated ketone synthesis is generally considered to involve three distinct steps: (1) oxidative addition of a Pd(0)-catalyst to a thioester to form RCO—Pd(II)X, (2) transmetallation from an alkylzinc halide to the resultant Pd(II) species, and (3) reductive elimination, leading to a ketone and re-generating the Pd(0)-catalyst. Among these steps, the second step (transmetallation) has been speculated to be most critical to effectively achieve the macroketocyclization under a high-dilution condition. Upon dilution, an intra-molecular transmetallation would be favored over the inter-molecular transmetallation, but would be disfavored over undesired side-reactions due to a higher probability of wasting radical and/or organometallic species. The goal of this experiment was to suppress undesired side-reactions by either slow activation of RX and/or acceleration of transmetallation to avoid accumulation of generated alkylzinc halides. Experimentally, it was found that catalytic intermolecular ketone synthesis proceeded well even at 25 mM. Among three conditions, Condition C [($Pd_2dba_3$ (10 mol %), $PCy_3$ (20 mol %), $CrCl_2$ (0.5 equiv), $NbCpCl_4$ (10 mol %), LiI (1 equiv), TESCl (1.5 equiv), Zn (xs) in DMI)] gave the best conversion. The conversion was 58%, 71%, and 80% under Conditions A, B, and C, respectively.

Encouraged by this observation, substrate 4a was chosen to study the feasibility of macroketocyclization (FIG. 3). Substrate 4a was subjected to a specified condition, and a yield of 5a was estimated from a $^1$H—NMR analysis of crude product. The general procedure for this experiment was as follows: PCy$_3$ (23 mg, 0.08 mmol), Pd$_2$dba$_3$(0) (36.6 mg, 0.04 mmol), and DMI (4 mL) were added to a vial in a glove box at room temperature. Then, CrCl$_3$ (32 mg, 0.2 mmol), Zn metal (204 mg, 3.2 mmol), NbCpCl$_4$ (12 mg, 0.04 mmol) were added to give a homogeneous dark solution except Zn. If needed, LiI (0.5 mmol) and TESCl (0.15 mmol) were added to the reaction mixture. Substrate 4a (21 mg, 0.04 mmol) in THF (4 mL) was added to this mixture and stirred vigorously at room temperature overnight. Et$_2$O and florisil were added and stirred for 30 min and it was filtered (SiO$_2$, Et$_2$O). The filtrate was washed with water, dried over Na$_2$SO$_4$, and concentrated. The crude $^1$H NMR and mass spectroscopy were taken and, if necessary, a silica gel chromatography (EtOAc/Hexanes=1/20, 1/10, then 1/7) was executed to give 5a. At 50 mM concentration, which was effective for inter-molecular ketone synthesis, 4a gave the debrominated product and dimer as major products (FIG. 3, entry 1). Considering that the activity of reagents might diminish by dilution, macroketocyclization was then tested in the presence of a stoichiometric amount of metals, thereby demonstrating that the desired ketone 5a was indeed formed as a major product at 10 mM concentration with only a small amount of debrominated product, although the dimer was still detected in more than 10% (FIG. 3, entry 2). Under the stoichiometric condition, CrCl$_2$ and NbCpCl$_4$ were essential (FIG. 3, entries 4 & 5), but LiI and TESCl were not (FIG. 3, entry 3). Also, reducing the amount of NbCpCl$_4$ resulted in a lower yield (FIG. 3, entry 6). These observations implicate that SET activation and the early transition metals (TM) are critical for macroketocyclization. Interestingly, this coupling condition corresponds to Condition C for inter-molecular one-pot ketone synthesis. Currently, there are no experimental supports to suggest a specific role(s) of early transition metals. However, it has been speculated that both metals play the same role(s) in both intra- and inter-molecular couplings. For the case of intermolecular ketone coupling, it is possible that the early transition metals might shift equilibrium from stable RZnX to higher-order organozincates and/or might break Pd—Zn to restore Pd reactivity, respectively. Lastly, it was found that Cr(III)Cl$_3$ was more effective than Cr(II)Cl$_2$ to lower the concentration further (FIG. 3, entries 9-11). Under these conditions, the desired product was formed, accompanied with only a trace amount of debrominated product.

Macroketocyclization of 4a was then carried out under the condition of entry 10 (FIG. 3) in a preparative scale (0.2 mmol) (FIG. 4). In order to achieve the macroketocyclization effectively, it has become evident that two conditions must be met: (1) to maintain Pd-, Nb- and Cr-reagents in a stoichiometric amount and (2) to maintain the substrate-concentration above 5 mmol. From a practical point of view, it would be more attractive if an amount of Pd-, Nb- and Cr-reagents could be reduced. One benefit in reducing an amount of the reagent is that the isolation of the product is much easier with a lesser amount of the reagent. To address this issue, the possibility of recycling the reagents mixture in one-pot was tested. Specifically, one-half of substrate 4a was added into one-half amount of the reagent mixture used for the stoichiometric conditions and, after 7 hours, the remaining half of 4a was added to the same reaction mixture. Under this setting, the cyclization completed to give 5a in 58% isolated yield after chromatographic purification. Thus, the macroketocyclization was effected with use of one-half of the reagents mixture in the price of time, i.e., 7 vs. 14 hours. Similarly, the macroketocyclization was tested by adding 1/4- and 1/8-amounts of 4a into a 1/4- and 1/8-amount of the reagents mixture, respectively, every 7 hours, to give 5a in 55%. Overall, under these conditions, the cyclization was achieved with use of ~30% and ~15% of the reagents mixture, in the price of time, i.e., 7 hours vs. 28 and 56 hours. These experimental data should allow for the identification of a proper setting for use of a syringe-pump. This procedure was also found effective for 16-membered ketone 5b to give 57% yield from 4b. In both cases, dimers and debrominated products were detected, but only in insignificant amounts (<10%).

Figure 5A:
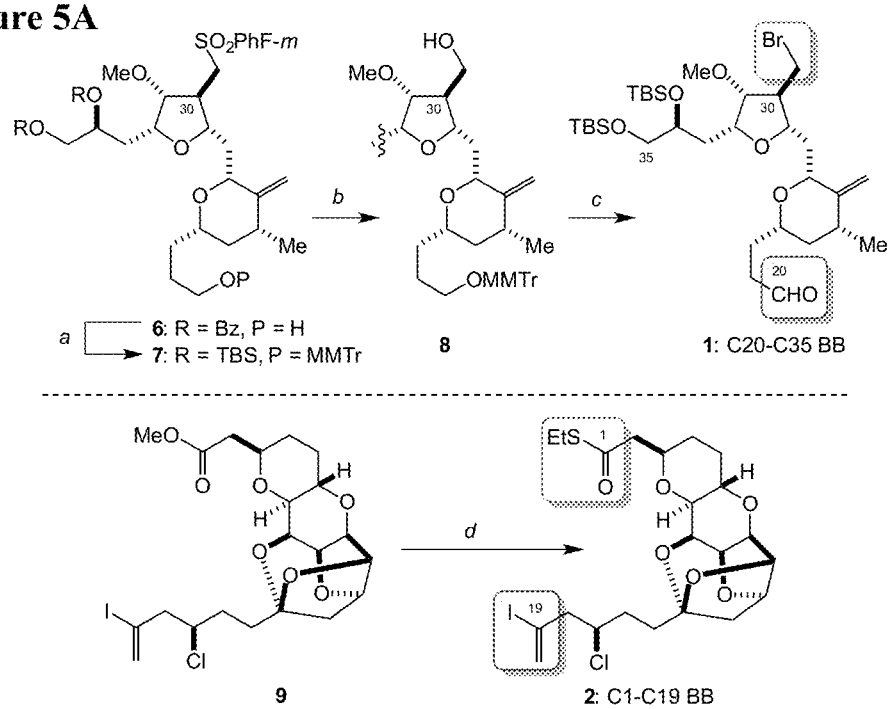
FIGS. 5A and 5B show a new convergent synthesis of Eribulin. The reagents and conditions of this experiement were as follows: a. 1. MMTrCl, i-$Pr_2NEt$, $CH_2Cl_2$, 93%. 2. $K_2CO_3$, MeOH. 3. TBSCl, imidazole, 88% for 2 steps. b. n-BuLi, THF, −78° C.; $HBSia_2$, −10° C. to room temperature, >12 h; $H_2O_2$, 3M NaOH, 0° C., 81%. c. 1. TsCl, DMAP (cat.), $Et_3N$, $CH_2Cl_2$, 88%. 2. NaBr, $Bu_4NBr$ (cat.), acetone, reflux, 90%. 3. $(CF_3)_2CHOH/H_2O=40/1$, 3 h, 90%. 4. Dess-Martin Ox., 90%. d. 1. $Me_3SnOH$, 80~85° C., DCE; 0.1 N HCl. 2. EtSH, DCC, DMAP, 94%. e. $CrCl_2$ (20 mol %), Cr-Ligand I (24 mol %), proton sponge (24 mol %), Ni-complex II (5 mol %), LiCl, Mn, $ZrCp_2Cl_2$, $CH_3CN$/EtOAc=3/1 (0.15 M), 86%. f $SrCO_3$ (xs), t-BuOH/$H_2O$=20/1 (4 mM), 95° C., open to air, 87%. g. $Pd_2dba_3$ (1 equiv), $PCyp_3$ (2 equiv) ($PCyp_3$ is better than $PCy_3$ for this type of substrate see, e.g., Lee et al., J. Am. Chem. Soc. 2016, 138, 7178), $CrCl_3$ (5 equiv), $NbCpCl_4$ (1 equiv), Zn (0) (xs), DMI/THF (1/1, 27 mM), 64%. h. Abbreviation: DCC=dicyclohexylcarbodiimide; $PCyp_3$=tricyclopentylphosphine.
Figure 5B:
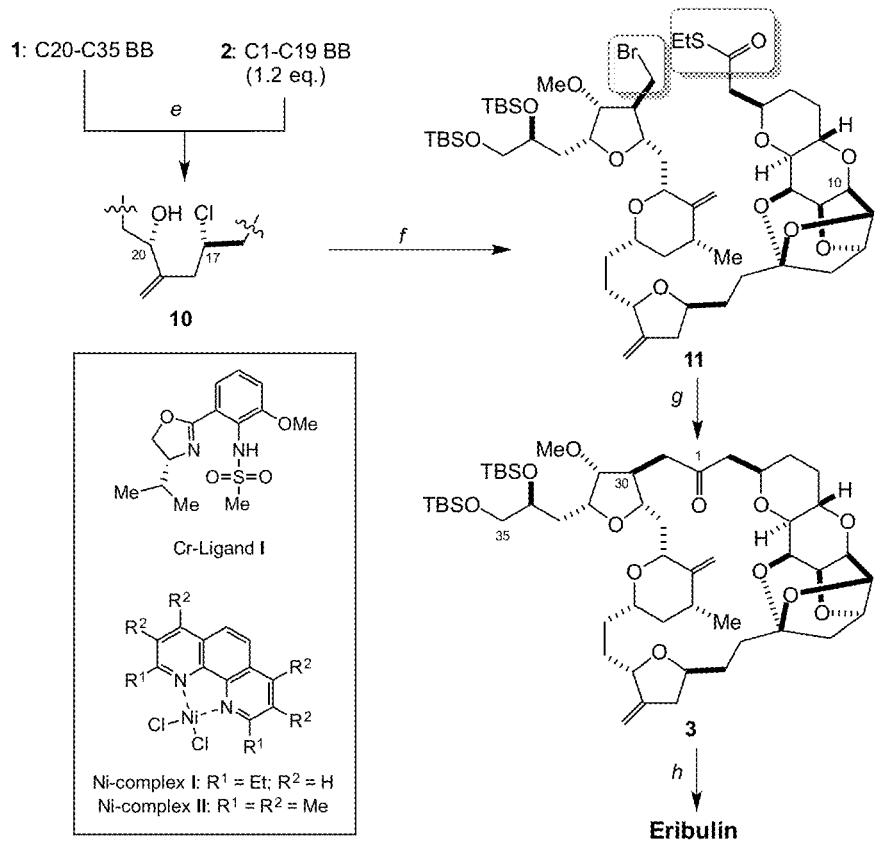
Figure 6A:
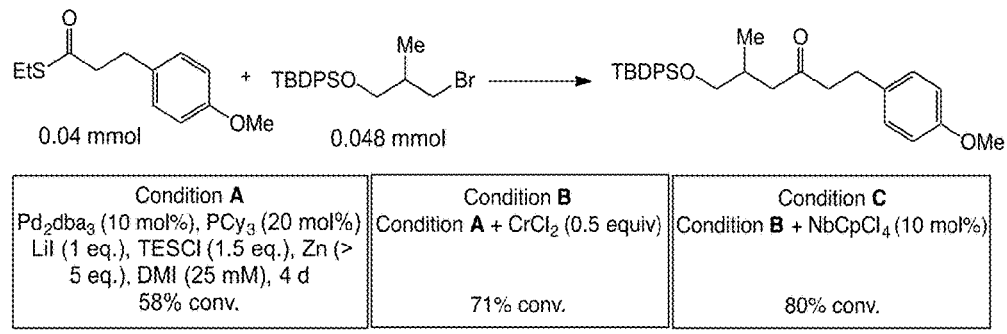
FIGS. 6A and 6B show intermolecular ketone synthesis under diluted concentration (see, e.g., Lee et al., J. Am. Chem. Soc. 2016, 138, 7178).
Figure 6B:
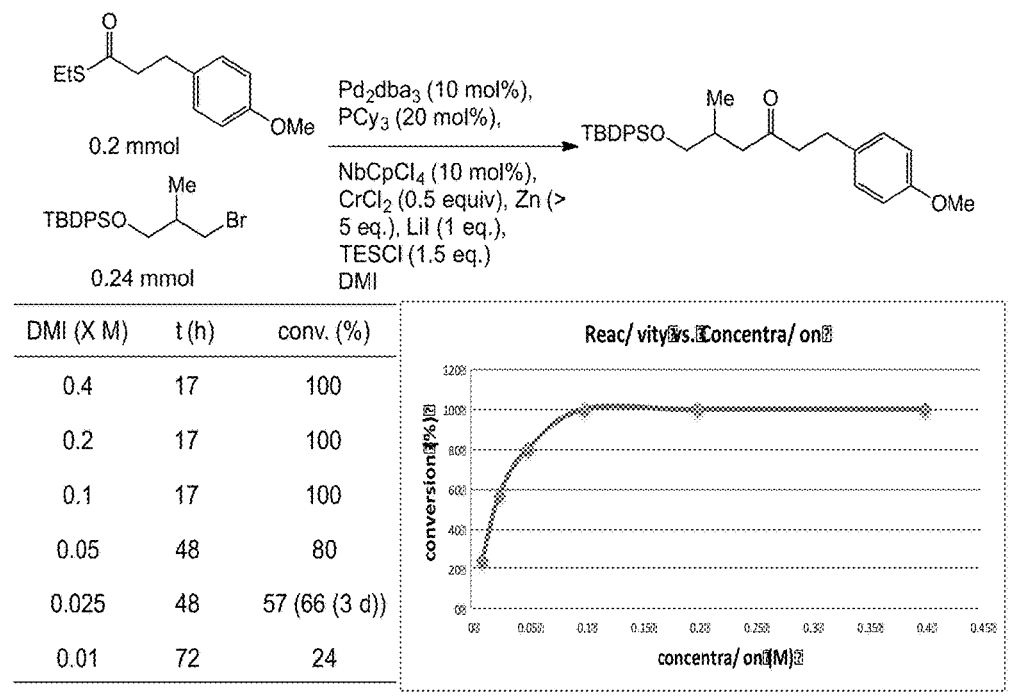

Having demonstrated the feasibility of one-pot macroketocyclization, focus was shifted onto its application to a synthesis of Eribulin (FIG. 2). The synthesis of aldehyde 1 was started from the known sulfone 6 (see, e.g., Liu et al., Org. Lett. 2012, 14, 2262). Protecting group manipulation, hydroxylation of sulfone 7 to alcohol 8, followed by tosylation and bromide substitution proceeded uneventfully (FIGS. 5A and 5B). However, deprotection of 4-methoxytrityl (MMTr) ether required an optimization, because of a concomitant deprotection of the primary TBS group; 1,1,1,3,3,3-hexafluoro-2-propanol (HFIP), which was known effective for selective deprotection of 4,4-dimethoxytrityl (DMTr) (see, e.g., Leonard et al., *Tetrahedron Lett.* 1995, 36, 7833), resulted in only partial deprotection of MMTr at 40° C. Assuming that a MMTr-cation acceptor might enhance the deprotection, it was eventually found that an addition of water (HFIP/H$_2$O=40/1) allowed for selective the required deprotection at room temperature. Then, the resulting alcohol was oxidized to aldehyde 1. On the other hand, thioester 2 was straightforwardly prepared from the known methyl ester 9 in two-steps (see, e.g., Ueda et al., *J. Am. Chem. Soc.* 2014, 136, 5171 and Li et al., *J. Am. Chem. Soc.* 2015, 137, 6226): hydrolysis by Me$_3$SnOH (see, e.g., Nicolaou et al., *Angew. Chem., Int. Ed.* 2005, 44, 1378) and coupling with EtSH by DCC.

With both aldehyde 1 and vinyl iodide 2 in hand, the C19-20 Ni/Cr-mediated coupling was studied. Initially, the condition optimized for the synthesis of halichondrin A was applied for coupling of 1 and 2 with Ni-complex I (see, e.g., Ueda et al., *J. Am. Chem. Soc.* 2014, 136, 5171), but gave the desired product 10 only in a modest yield (~40%). It was speculated that the low yield might be attributed to a poor selectivity in activation of the C$_{19}$-vinyl iodide—note the presence of an alkyl bromide as well as a thioester, which might potentially be activated with low-valent Ni. With this speculation, a Ni-catalyst which would allow for selective activation of the C19-vinyl iodide and consequently improve the efficiency of Ni/Cr-mediated coupling of 2 with 1, was sought. Through this search, it was found that a combination of Ni-complex II, prepared from electron-rich 2,3,4,7,8,9-hexamethyl-1,10-phenanthroline, and Cr-catalyst, prepared from unnat-i-Pr/Me/OMe sulfonamide I, gave a satisfactorily high coupling yield (86% yield; dr=~10:1 ($^1$H—NMR)). With the Cr-catalyst derived from unnat-i-Pr/PhCl$_2$/OCy (Me)$_2$ sulfonamide, the dr observed for this Ni/Cr-mediated coupling was around 20:1 in the halichondrin series. See e.g., Ueda et al., *J. Am. Chem. Soc.* 2014, 136, 5171 and Guo et al., *J. Am. Chem. Soc.* 2009, 131, 15387.

The next task was to cyclize 10 to 11, which had been done with AgOTf/Ag$_2$O in the synthesis of halichondrin A. This condition was not suitable to the present substrate, because of the presence of thioester- and bromide-groups. Thus, cyclization conditions reported previously were tested (100° C. in water) (see, e.g., Kang et al., Org. Lett. 2010, 12, 1716), which gave the desired product 11, although accompanied with a large amount of unidentified decomposition products. It was speculated that the liberated HCl might have caused the decomposition, and an extensive search for a suitable base began, leading to a satisfactory condition: SrCO$_3$(s) at 95° C. Interestingly, soluble amine bases gave complicated side reactions such as halide exchange. Under the optimized conditions, 11 was isolated in 87% yield and fully characterized.

Finally, 11 was subjected to macroketocyclization under the stoichiometric conditions. It is worthwhile noting that, contrary to model compounds 4a and 4b, the major side-reaction in this series was the reductive quentching of —CH$_2$Br to CH$_3$ rather than the dimerization, thereby suggesting the possibility of using a higher concentration. It was assumed that the difference in behavior might be attributed to the difference in conformational property of 11, compared to 4; specifically, 11 might have adopted a favorable conformation required for the macroketocycization. Consistent with this assumption, the macroketocyclization was achieved, without noticeable dimerization, even at 27 mM concentration, to furnish ketone 3 in 64% yield (52 mg scale). Reductive debromination was observed at 18 mM concentration, but not at 25 mM concentration. On the other hand, dimerization was not observed even at 27 mM concentration. Spectroscopic comparisons ($^1$H— and $^{13}$C— NMR, HR-MS) firmly established that 3 thus obtained was identical with the authentic sample (see, e.g., Zheng et al., J. Bioorg. Med. Chem. Lett. 2004, 14, 5551 and Austad et al., Synlett 2013, 24, 333). Lastly, macrocyclic ketone 3 was converted into Eribulin in three steps (see, e.g., Zheng et al., J. Bioorg. Med. Chem. Lett. 2004, 14, 5551, Austad et al., Synlett 2013, 24, 333, and Kaburagi et al., Tetrahedron Lett. 2007, 48, 8967).

In summary, a method was developed for macroketocyclization between an alkyl bromide and a thioester under mild conditions. NbCpCl$_4$ and CrCl$_3$ are key components not only for in-situ activation of alkyl bromide to alkylzinc halide via a SET process but also for acceleration of Pd-mediated coupling. Notably, this unique macroketocyclization does not require any special template or functional group to be removed after cyclization. Overall, the newly-developed macroketocyclization allowed for the synthesis of Eribulin with the same synthetic strategy as the one used in the halichondrins.

Materials and Methods for Intramolecular Macroketolization

General Procedures

NMR spectra were recorded on a Varian Inova 600 MHz, 500 MHz, or 400 MHz spectrometer. Chemical shifts are reported in parts per million (ppm). For $^1$H NMR spectra (CDCl$_3$ and C$_6$D$_6$), the residual solvent peak was used as the internal reference (7.26 ppm in CDCl$_3$; 7.16 ppm in C$_6$D$_6$), while the central solvent peak as the reference (77.0 ppm in CDCl$_3$; 128.0 ppm in C$_6$D$_6$) for $^{13}$C NMR spectra. In reporting spectral data, the following abbreviations were used: s=singlet, d=doublet, t=triplet, q=quartet, m=multiplet, dd=doublet, td=triplet doublet, qd=quartet doublet. High resolution mass spectra (HRMS) were obtained on an Agilent 6210 Time-of-Flight LC/MC Machine and were reported in units of m/e. Optical rotations were measured at 20° C. using a Perkin-Elmer 241 polarimeter. IR spectra were recorded on a Bruker Alpha FT-IR spectrometer. Analytical and semi-preparative thin layer chromatography (TLC) was performed with E. Merck pre-coated TLC plates, silica gel 60 F254, layer thickness 0.25 and 1.00 mm, respectively. TLC plates were visualized by staining with p-anisaldehyde or phosphomolybdic acid stain. Flash chromatography separations were performed on E. Merck Kieselgel 60 (230-400) mesh silica gel. All moisture sensitive reactions were conducted under an inert atmosphere.

Materials

Tris(dibenzylideneacetone)dipalladium(0) (Pd$_2$dba$_3$, 97%, Sigma-Aldrich), Lithium iodide (Sigma-Aldrich), Chromium (II) chloride (CrCl$_2$, 99.9%, Strem Chemicals), Chromium (III) chloride (CrCl$_3$, 99.9%, Strem Chemicals), Cyclopentadienylniobium(V) tetrachloride (NbCpCl$_4$, 98%, Strem Chemicals), Zinc (~325 mesh, 99.9%, Strem Chemicals), 1,3-Dimethyl-2-imidazolidinone (DMI) (>99.5%, Sigma-Aldrich) were purchased as indicated and used as received. Others were commercial grade and were used as supplied.

General Macroketocyclization with Model Compounds

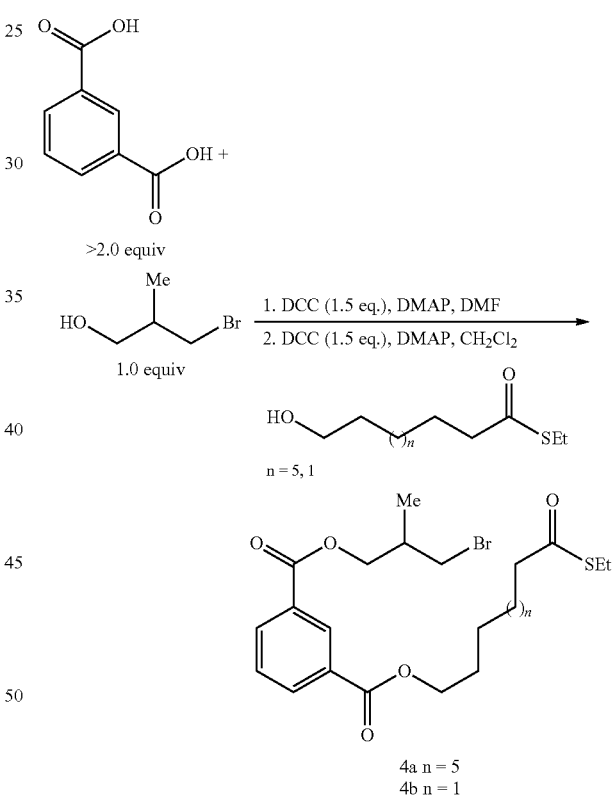

To isophthalic acid (excess) in DMF were added the alcohol (1 equiv), DMAP (cat.), and DCC (1.5 equiv). The mixture was stirred at room temperature for 4 h, diluted with EtOAc, filtered (SiO$_2$, EtOAc), and purified by a column chromatography (EtOAc/Hexanes=1/3 to 1/1). On the other hand, a hydroxyl thioester was prepared with EtSH (excess), DCC (1.5 equiv) in CH$_2$Cl$_2$. To the mono-acid in CH$_2$Cl$_2$ were added a hydroxyl thioester, DMAP, and DCC. After stirring for 4 h, the mixture was filtered (SiO$_2$, Et$_2$O), and purified by a column chromatography (EtOAc/Hexanes=1/20 to 1/10) to give 4.

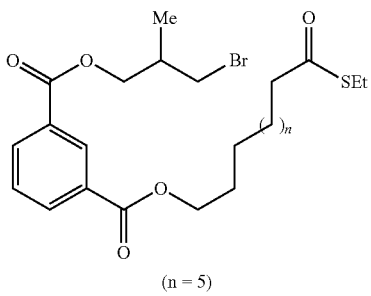

4a (n = 5)

A colorless liquid; $^1$H NMR (500 MHz, CDCl$_3$) δ8.69-8.65 (m, 1H), 8.27-8.18 (m, 2H), 7.59-7.49 (m, 1H), 4.40-4.26 (m, 4H), 3.52 (d, J=5.4 Hz, 2H), 2.87 (q, J=7.4 Hz, 2H), 2.53 (t, J=7.4 Hz, 2H), 2.42-2.29 (m, 1H), 1.84-1.72 (m, 2H), 1.71-1.60 (m, 2H), 1.49-1.40 (m, 2H), 1.40-1.28 (m, 8H), 1.24 (t, J=7.4 Hz, 3H), 1.17 (d, J=6.8 Hz, 3H); $^{13}$C NMR (126 MHz, CDCl$_3$) δ165.75, 165.53, 133.90, 133.65, 131.04, 130.64, 130.43, 128.64, 67.35, 65.50, 44.08, 36.64, 34.78, 29.26, 29.18, 29.16, 28.89, 28.66, 25.98, 25.62, 23.19, 15.89, 14.78; IR (neat) v 2930, 1724, 1689, 1304, 1237, 730; HRMS (ESI) calculated for (C$_{24}$H$_{35}$BrO$_5$S+H$^+$): 515.1461 found 515.1452.

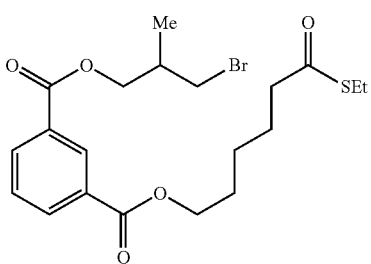

4b

A colorless liquid; $^1$H NMR (500 MHz, CDCl$_3$) δ8.68-8.63 (m, 1H), 8.27-8.18 (m, 2H), 7.60-7.49 (m, 1H), 4.42-4.25 (m, 4H), 3.52 (d, J=5.4 Hz, 2H), 2.87 (q, J=7.4 Hz, 2H), 2.58 (t, J=7.4 Hz, 2H), 2.42-2.30 (m, 1H), 1.89-1.68 (m, 4H), 1.58-1.46 (m, 2H), 1.24 (t, J=7.4 Hz, 3H), 1.17 (d, J=6.8 Hz, 3H); $^{13}$C NMR (126 MHz, CDCl$_3$) δ199.31, 165.64, 165.46, 133.87, 133.67, 130.88, 130.61, 130.43, 128.63, 67.33, 65.07, 43.78, 36.63, 34.74, 28.36, 25.38, 25.21, 23.21, 15.86, 14.73; IR (neat) v 2933, 1720, 1685, 1302, 1229, 729; HRMS (ESI) calculated for (C$_{20}$H$_{27}$BrO$_5$S+H$^+$): 459.0835 found 459.0828.

Macroketocyclization Procedure for FIG. 4

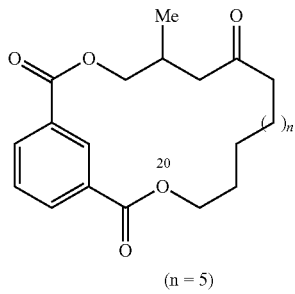

5a (n = 5)

Two portionwise addition of starting material: To a round-bottom flask were added PCy$_3$ (61 mg, 0.22 mmol), Pd$_2$dba$_3$(0) (91.5 mg, 0.1 mmol), and DMI (10 mL) in a glove box at room temperature. Then, CrCl$_3$ (79 mg, 0.5 mmol), Zn metal (640 mg, 10 mmol), NbCpCl$_4$ (30 mg, 0.1 mmol), and THF (5 mL) were added to give a homogeneous dark solution except Zn. To the mixture was added 4a (51.5 mg, 0.1 mmol) in THF (2.5 mL) and stirred vigorously at room temperature. After 7 h, to the mixture was added another portion of 4a (51.5 mg, 0.1 mmol) in THF (2.5 mL) and stirred vigorously at room temperature overnight. Et$_2$O and florisil were added and stirred for 30 min and it was filtered (SiO$_2$, Et$_2$O). The filtrate was washed with water, dried over Na$_2$SO$_4$, and concentrated. The crude residue was purified by a couple of silica gel chromatography (EtOAc/Hexanes=1/20, 1/10, then 1/7) to give 5a (43.3 mg, 58%, a liquid) with about 5% of dimer. Due to side products generated from dba of Pd$_2$dba$_3$(0), often, more than one column chromatography for purification were necessary. $^1$H NMR (500 MHz, CDCl$_3$) δ8.58-8.53 (m, 1H), 8.31-8.21 (m, 2H), 7.61-7.53 (m, 1H), 4.52-4.30 (m, 3H), 4.10 (dd, J=11.0, 7.2 Hz, 1H), 2.67 (dd, J=16.4, 6.1 Hz, 1H), 2.64-2.54 (m, 1H), 2.48-2.30 (m, 3H), 1.78 (m, 2H), 1.65-1.53 (m, 2H), 1.53-1.44 (m, 2H), 1.45-1.37 (m, 2H), 1.38-1.30 (m, 2H), 1.27 (m, 4H), 1.05 (d, J=6.8 Hz, 3H); $^{13}$C NMR (126 MHz, CDCl$_3$) δ210.17, 165.73, 165.71, 134.15, 134.05, 130.89, 130.50, 129.65, 128.80, 69.19, 65.21, 46.33, 42.68, 28.99, 28.32, 27.97, 27.74, 27.69, 27.05, 25.26, 23.32, 16.95; IR (neat) v 2927, 1721, 1376, 1302, 1139; HRMS (ESI) calculated for (C$_{22}$H$_{30}$O$_5$+H$^+$): 375.2166 found 375.2181.

Four portionwise addition of starting material: To a round-bottom flask were added PCy$_3$ (34 mg, 0.12 mmol), Pd$_2$dba$_3$(0) (55 mg, 0.06 mmol), and DMI (5 mL) in a glove box at room temperature. Then, CrCl$_3$ (47 mg, 0.3 mmol), Zn metal (640 mg, 10 mmol), NbCpCl$_4$ (18 mg, 0.06 mmol), and THF (3 mL) were added to give a homogeneous dark solution except Zn. To the mixture was added 4a (25.8 mg, 0.05 mmol) in THF (1 mL) and stirred vigorously at room temperature. After 7 h, to the mixture was added the second portion of 4a (25.8 mg, 0.05 mmol) in THF (0.3 mL) and stirred vigorously at room temperature overnight. Then addition of the third portion of 4a (25.8 mg, 0.05 mmol) in THF (0.3 mL), 7 h stirring, addition of the last portion 4a (25.8 mg, 0.05 mmol) in THF (0.3 mL), and overnight stirring were repeated to give 5a (41 mg, 55%, a liquid) after above procedure for work-up and purification.

Eight portionwise addition of starting material: To a round-bottom flask were added PCy$_3$ (17 mg, 0.06 mmol), Pd$_2$dba$_3$(0) (28 mg, 0.03 mmol), and DMI (2 mL) in a glove box at room temperature. Then, CrCl$_3$ (24 mg, 0.15 mmol), Zn metal (640 mg, 10 mmol), NbCpCl$_4$ (9 mg, 0.03 mmol), and THF (1 mL) were added to give a homogeneous dark solution except Zn. To the mixture was added 4a (12.9 mg, 0.025 mmol) in THF (0.15 mL) and stirred vigorously at room temperature. After 7 h, to the mixture was added the second portion of 4a (12.9 mg, 0.025 mmol) in THF (0.15 mL) and stirred vigorously at room temperature overnight. Then addition of the third to the eighth portion of 4a (12.9 mg, 0.025 mmol) in THF (0.15 mL) followed by more than 7 h stirring were repeated to give 5a (41 mg, 55%, a liquid) after above procedure for work-up and purification.

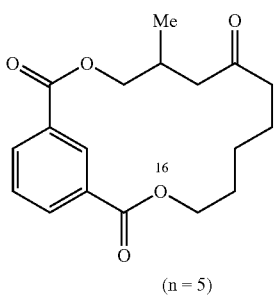

(n = 5)

5b (36.5 mg, 57%, a white foamy solid) was obtained from 4b (92 mg, 0.2 mmol) following procedure for 5a. Two portionwise addition, four portionwise addition, and eight portionwise addition provided 57% isolated yield. $^1$H NMR (500 MHz, CDCl$_3$) δ8.53-8.48 (m, 1H), 8.28-8.18 (m, 2H), 7.60-7.52 (m, 1H), 4.62 (dd, J=10.7, 4.3 Hz, 1H), 4.42-4.24 (m, 2H), 3.80 (t, J=10.5 Hz, 1H), 2.98 (dd, J=18.1, 5.8 Hz, 1H), 2.77-2.57 (m, 2H), 2.51-2.37 (m, 2H), 2.07-1.94 (m, 1H), 1.90-1.80 (m, 2H), 1.80-1.71 (m, 1H), 1.69-1.61 (m, 2H), 1.03 (d, J=7.0 Hz, 3H); $^{13}$C NMR (126 MHz, CDCl$_3$) δ209.54, 165.30, 164.96, 133.93, 133.84, 130.56, 130.44, 130.38, 128.93, 68.73, 65.91, 47.41, 42.74, 27.87, 27.24, 27.15, 24.51, 17.31; IR (neat) v 2930, 2855, 1720, 1303, 1233, 731; HRMS (ESI) calculated for (C$_{18}$H$_{22}$O$_5$+H$^+$): 319.1540 found 319.1555.

Synthesis Outlined in FIGS. 5A and 5B

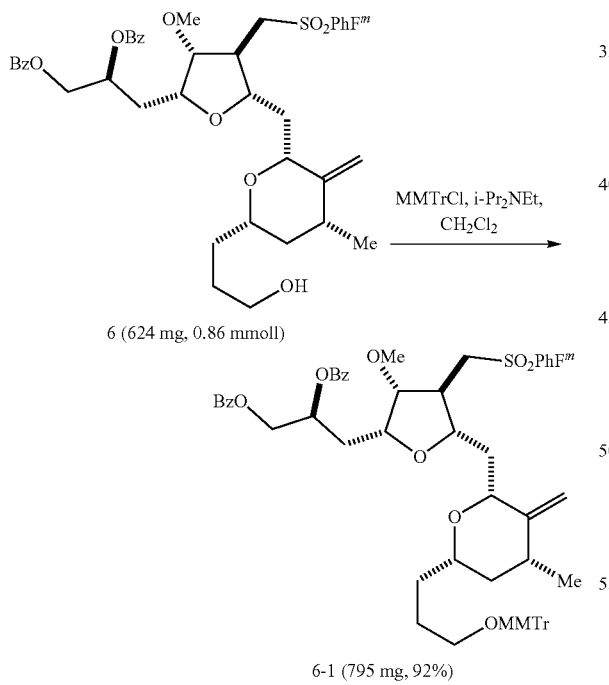

To 6 (624 mg, 0.85 mmol) (see, e.g., Liu et al., *Org. Lett.* 2012, 14, 2262) were added CH$_2$Cl$_2$ (9 mL), i-Pr$_2$NEt (0.5 mL, 2.6 mmol), and MMTrCl (393 mg, 1.28 mmol, 1.5 equiv) at room temperature and the mixture was stirred for 5 h. Then it was concentrated and subjected to a column chromatography (EtOAc/Hexanes=1/10 to 1/5) to provide 6-1 (795 mg, 93%, a foamy solid). [α]$_D^{20}$=+3.1° (c 1.0, CH$_2$Cl$_2$); $^1$H NMR (600 MHz, C$_6$D$_6$) δ8.22-8.16 (m, 2H), 8.16-8.11 (m, 2H), 7.64-7.60 (m, 4H), 7.59-7.56 (m, 1H), 7.52-7.48 (m, 1H), 7.46-7.42 (m, 2H), 7.18 (m, 4H), 7.08-7.04 (m, 3H), 7.04-6.98 (m, 3H), 6.98-6.94 (m, 2H), 6.77-6.73 (m, 2H), 6.72-6.68 (m, 1H), 6.66-6.60 (m, 1H), 5.95-5.86 (m, 1H), 4.82 (s, 1H), 4.70 (d, J=1.6 Hz, 1H), 4.61-4.53 (m, 2H), 3.89 (d, J=3.7 Hz, 1H), 3.87-3.78 (m, 3H), 3.38 (s, 3H), 3.37-3.32 (m, 1H), 3.30 (s, 3H), 3.20 (t, J=6.4 Hz, 2H), 2.90-2.83 (m, 2H), 2.57 (dd, J=14.7, 11.0 Hz, 1H), 2.45 (dt, J=15.0, 7.7 Hz, 1H), 2.38 (ddd, J=13.8, 9.4, 4.8 Hz, 1H), 2.25 (dt, J=14.5, 5.2 Hz, 1H), 2.12 (ddd, J=13.2, 8.9, 3.9 Hz, 1H), 1.99-1.91 (m, 1H), 1.78-1.70 (m, 1H), 1.62-1.52 (m, 1H), 1.52-1.46 (m, 2H), 1.41-1.35 (m, 1H), 0.93-0.88 (m, 1H), 0.90 (d, J=6.5 Hz, 3H); $^{13}$C NMR (126 MHz, C$_6$D$_6$) δ166.15, 166.10, 163.64, 161.63, 159.11, 150.98, 145.56, 145.54, 142.94, 136.40, 132.90, 132.87, 131.22, 131.16, 130.92, 130.80, 130.55, 130.06, 129.93, 128.90, 128.51, 128.05, 127.04, 123.87, 120.70, 120.53, 115.55, 115.36, 113.45, 104.79, 86.88, 86.58, 81.62, 78.41, 77.50, 75.78, 70.98, 66.11, 63.97, 58.02, 57.43, 54.71, 43.20, 42.69, 37.91, 35.71, 33.38, 30.97, 26.95, 18.02; IR (neat) v 2933, 1720, 1510, 1450, 1282, 1251, 1070, 711; HRMS (ESI) calculated for (C$_{60}$H$_{63}$FO$_{11}$S+Na$^+$): 1033.3967 found 1033.3928.

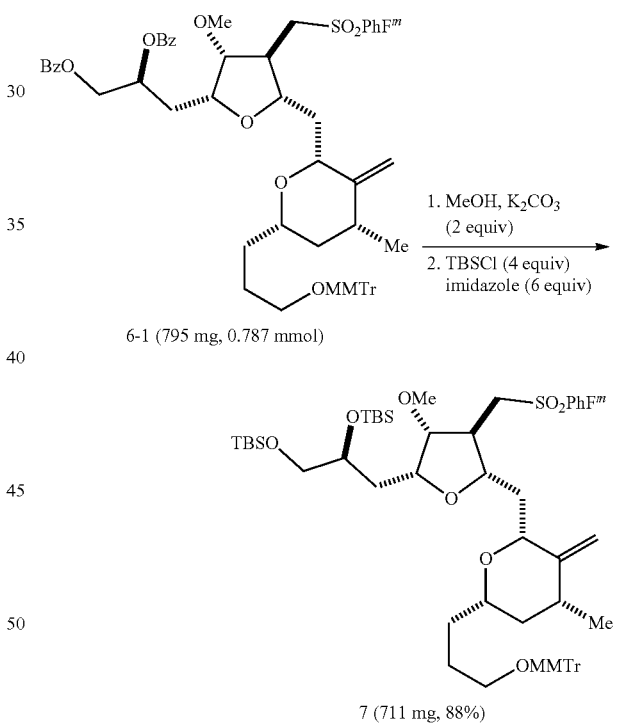

To 6-1 (795 mg, 0.79 mmol) were added K$_2$CO$_3$ (218 mg, 1.58 mmol), MeOH (10 mL), and CH$_2$Cl$_2$ (2 mL) at room temperature and the mixture was stirred at room temperature for 2 h. Then, to the concentrated crude in CH$_2$Cl$_2$ (2 mL) were added imidazole (322 mg, 4.74 mmol) and TBSCl (356 mg, 2.37 mmol). After stirring overnight, it was worked up with CH$_2$Cl$_2$ and saturated NaHCO$_3$, and dried over Na$_2$SO$_4$ (s). After a column chromatography (EtOAc/Hexanes=1/6), 7 (711 mg, 88%) was obtained as a foamy solid. [α]$_D^{20}$=+6.0° (c 1.0, CH$_2$Cl$_2$); $^1$H NMR (600 MHz, C$_6$D$_6$) δ7.66-7.63 (m, 1H), 7.63-7.60 (m, 4H), 7.58-7.54 (m, 1H), 7.45-7.42 (m, 2H), 7.21-7.17 (m, 4H), 7.10-7.05 (m, 2H), 6.79-6.74 (m, 2H), 6.72 (m, 1H), 6.65-6.60 (m, 1H), 4.85 (s, 1H), 4.70 (d, J=1.5 Hz, 1H), 4.16-4.11 (m, 1H), 4.09-4.02 (m, 2H), 3.92-3.88 (m, 1H), 3.85 (dd, J=9.6, 3.3 Hz, 1H), 3.80 (dd, J=10.3, 5.6 Hz, 1H), 3.73 (dd, J=10.3, 4.8 Hz, 1H), 3.47 (s, 3H), 3.41-3.34 (m, 1H), 3.32 (s, 3H), 3.19 (t, J=6.4 Hz, 2H), 3.04 (dd, J=14.0, 2.5 Hz, 1H), 3.00-2.95 (m, 1H), 2.82 (dd, J=14.0, 11.1 Hz, 1H), 2.49 (ddd, J=13.8, 9.7, 4.5 Hz, 1H), 2.33-2.27 (m, 2H), 2.18 (ddd, J=13.1, 9.2, 3.6 Hz, 1H), 2.00-1.93 (m, 1H), 1.81-1.71 (m, 1H), 1.61-1.52 (m, 1H), 1.51-1.46 (m, 2H), 1.41-1.36 (m, 1H), 1.04 (s, 9H), 0.99 (s, 9H), 0.93-0.88 (m, 1H), 0.90 (d, J=6.5 Hz, 3H), 0.23 (s, 3H), 0.22 (s, 3H), 0.11 (s, 3H), 0.10 (s, 3H); $^{13}$C NMR (126 MHz, C$_6$D$_6$) δ163.66, 161.66, 159.09, 151.02, 145.55, 145.52, 143.02, 142.97, 136.39, 131.30, 131.24, 130.77, 128.89, 128.04, 127.03, 123.84, 123.81, 120.76, 120.59, 115.51, 115.32, 113.44, 104.78, 86.74, 86.56, 81.40, 78.61, 77.54, 75.88, 72.12, 68.27, 63.91, 58.35, 57.49, 54.72, 43.30, 42.65, 38.06, 35.72, 34.11, 33.33, 27.01, 26.23, 26.20, 18.60, 18.46, 18.02, −3.92, −4.45, −5.12; IR (neat) v 2953, 2959, 1607, 1251, 1083, 834; HRMS (ESI) calculated for (C$_{58}$H$_{83}$FO$_9$SSi$_2$+Na$^+$): 1053.5173 found 1053.5137.

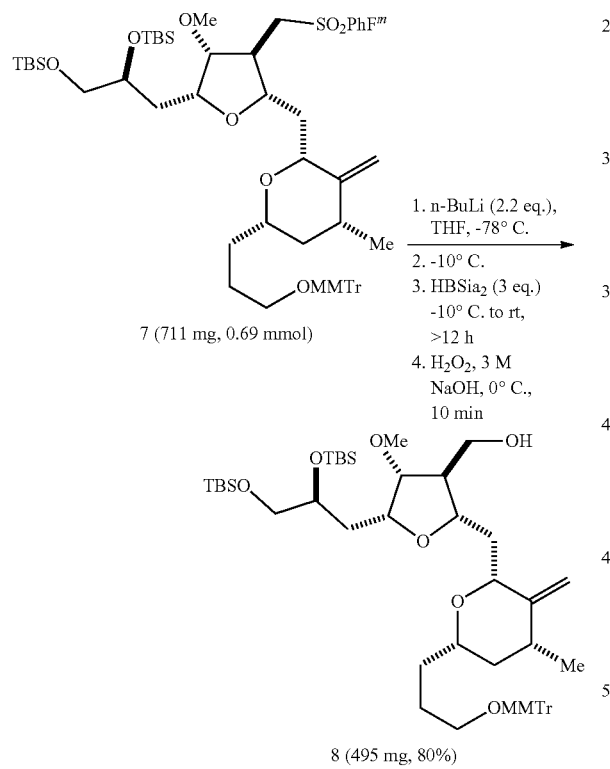

7 (711 mg, 0.69 mmol)

1. n-BuLi (2.2 eq.), THF, −78° C.
2. −10° C.
3. HBSia$_2$ (3 eq.) −10° C. to rt, >12 h
4. H$_2$O$_2$, 3 M NaOH, 0° C., 10 min 8 (495 mg, 80%)

Disiamylborane (0.825 M in THF) was prepared fresh by adding 2-methyl-2-butene (1.3 mL, 12.2 mmol) to a stirring solution of BH$_3$.THF (6 mL, 1 M in THF) at 0° C. The resulting solution was stirred at 0° C. for 2 h and at room temperature for 2 h under an argon atmosphere. To a stirred solution of sulfone 7 (711 mg, 0.69 mmol) in THF (3.3 mL) at −78° C. was added n-BuLi (1.3 mL, 1.2 M in hexane, 1.52 mmol, 2.2 equiv) dropwise. The resulting solution was stirred at −78° C. for 5 min and subsequently warmed to −10° C. for 10 min. Sia$_2$BH (2.5 mL, 0.825 M in THF, 2.1 mmol, 3 equiv) was added dropwise at −10° C., and the reaction was allowed to warm to room temperature, and stirred overnight. The reaction was then quenched by the sequential addition of H$_2$O (0.6 mL), 3 N NaOH (0.6 mL) and 30 wt. % H$_2$O$_2$ (0.8 mL) at 0° C. After stirring for 10 min, the mixture was extracted with EtOAc (3×10 mL). The combined organic layers were washed with saturated Na$_2$S$_2$O$_3$ and brine, dried over Na$_2$SO$_4$, filtered and concentrated. The crude residue was purified by a silica gel chromatography to give 8 (495 mg, 80%, a liquid). [α]$_D^{20}$=−2.8° (c 1.0, CH$_2$Cl$_2$); $^1$H NMR (600 MHz, C$_6$D$_6$) δ7.67-7.62 (m, 4H), 7.49-7.45 (m, 2H), 7.21-7.17 (m, 4H), 7.09-7.05 (m, 2H), 6.78-6.73 (m, 2H), 4.99 (s, 1H), 4.78 (s, 1H), 4.16-4.11 (m, 1H), 4.10-4.04 (m, 1H), 4.00 (dd, J=12.1, 6.6 Hz, 1H), 3.88 (dd, J=7.7, 4.5 Hz, 1H), 3.81 (dd, J=10.3, 5.6 Hz, 1H), 3.73 (dd, J=10.3, 4.5 Hz, 1H), 3.51-3.44 (m, 3H), 3.33-3.28 (m, 1H), 3.31 (s, 3H), 3.27-3.20 (m, 2H), 3.16 (s, 3H), 2.48-2.41 (m, 1H), 2.31-2.19 (m, 4H), 2.02-1.93 (m, 1H), 1.91-1.82 (m, 1H), 1.79-1.69 (m, 1H), 1.64-1.56 (m, 2H), 1.54-1.44 (m, 1H), 1.41-1.34 (m, 1H), 1.02 (s, 9H), 0.99 (s, 9H), 0.96-0.91 (m, 1H), 0.93 (d, J=6.4 Hz, 3H), 0.21 (s, 3H), 0.19 (s, 3H), 0.11 (s, 3H), 0.10 (s, 3H); $^{13}$C NMR (126 MHz, C$_6$D$_6$) δ159.07, 151.24, 145.63, 145.60, 136.50, 130.79, 128.92, 128.04, 127.01, 113.44, 104.78, 86.61, 85.98, 78.29, 78.15, 77.19, 76.08, 72.14, 68.30, 63.85, 63.61, 56.49, 54.71, 53.26, 42.90, 38.25, 35.91, 34.46, 33.07, 26.69, 26.23, 26.21, 18.62, 18.42, 18.08, −3.93, −4.45, −5.12, −5.14; IR (neat) v 2953, 2856, 1510, 1471, 1251, 1087, 834; HRMS (ESI) calculated for (C$_{52}$H$_{80}$O$_8$Si$_2$+Na$^+$): 911.5284 found 911.5282.

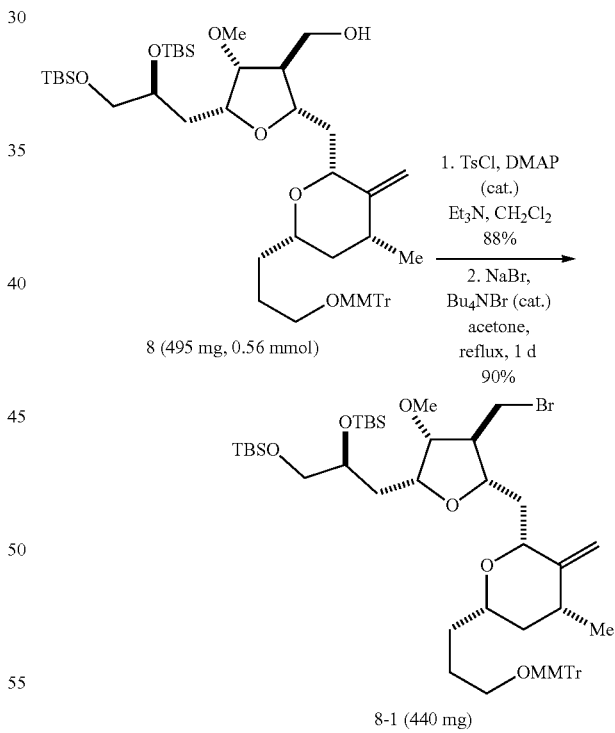

8 (495 mg, 0.56 mmol)

1. TsCl, DMAP (cat.) Et$_3$N, CH$_2$Cl$_2$ 88%
2. NaBr, Bu$_4$NBr (cat.) acetone, reflux, 1 d 90%

8-1 (440 mg)

To alcohol 8 (495 mg, 0.56 mmol) in CH$_2$Cl$_2$ (5 mL) and triethylamine (1 mL) were added DMAP (20 mg) and TsCl (160 mg, 0.84 mmol, 1.5 equiv) at room temperature. Then, the mixture was stirred for 6 h and quenched with saturated NaHCO$_3$, extracted with EtOAc, purified by a column chromatography (EtOAc/Hexanes=1/10 to 1/5) to yield the corresponding tosylate (503 mg, 88%).

To the tosylate (503 mg, 0.48 mmol) in acetone (10 mL) were added NaBr (500 mg) and n-Bu4NBr (50 mg). The mixture was stirred at 55° C. for 1 d, then cooled to room temperature and filtered (SiO$_2$, EtOAc). After a column chromatography (EtOAc/Hexanes=1/10) purification, bromide 8-1 (440 mg, 90%) was obtained. [α]$_D^{20}$=−7.0° (c 1.0, CH$_2$Cl$_2$); $^1$H NMR (500 MHz, C$_6$D$_6$) δ7.69-7.63 (m, 4H), 7.51-7.45 (m, 2H), 7.22-7.17 (m, 4H), 7.09-7.04 (m, 2H), 6.78-6.74 (m, 2H), 4.90 (s, 1H), 4.75 (d, J=1.4 Hz, 1H), 4.14-4.08 (m, 1H), 4.08-4.03 (m, 1H), 3.97-3.90 (m, 1H), 3.82-3.75 (m, 2H), 3.70 (dd, J=10.3, 4.8 Hz, 1H), 3.63 (dd, J=4.0, 1.3 Hz, 1H), 3.34-3.32 (m, 1H), 3.30 (s, 3H), 3.28-3.24 (m, 3H), 3.20 (s, 3H), 3.03 (dd, J=10.3, 9.0 Hz, 1H), 2.51-2.44 (m, 1H), 2.36 (ddd, J=13.1, 7.8, 5.0 Hz, 1H), 2.29-2.14 (m, 3H), 2.00-1.83 (m, 2H), 1.75-1.66 (m, 1H), 1.63-1.55 (m, 1H), 1.53-1.45 (m, 1H), 1.41-1.32 (m, 1H), 1.02 (s, 9H), 0.99 (s, 9H), 0.98-0.94 (m, 1H), 0.93 (d, J=6.4 Hz, 3H), 0.20 (s, 3H), 0.19 (s, 3H), 0.10 (s, 3H), 0.10 (s, 3H); $^{13}$C NMR (126 MHz, C$_6$D$_6$) δ159.08, 151.23, 145.65, 145.62, 136.54, 130.79, 128.94, 128.03, 127.00, 113.43, 104.57, 86.98, 86.57, 79.68, 78.15, 77.24, 75.79, 72.02, 68.26, 63.84, 56.61, 54.69, 52.87, 43.01, 37.71, 35.88, 34.28, 33.85, 33.23, 26.94, 26.21, 26.18, 18.60, 18.41, 18.06, −3.92, −4.48, −5.14, −5.15; IR (neat) ν 2953, 2856, 1510, 1463, 1251, 1087, 834; HRMS (ESI) calculated for (C$_{52}$H$_{79}$BrO$_7$Si$_2$+Na$^+$): 973.4440 found 973.4496.

3H), 0.20 (s, 3H), 0.19 (s, 3H), 0.11 (s, 3H), 0.10 (s, 3H); $^{13}$C NMR (126 MHz, C$_6$D$_6$) δ151.06, 104.70, 86.90, 79.66, 78.21, 77.33, 75.98, 71.99, 68.26, 62.71, 56.68, 52.87, 43.05, 37.65, 35.94, 34.31, 33.81, 32.85, 29.48, 26.20, 26.19, 18.61, 18.41, 18.03, −3.92, −4.47, −5.14; IR (neat) ν 2953, 2856, 1510, 1471, 1251, 1087, 834; HRMS (ESI) calculated for (C$_{32}$H$_{63}$BrO$_6$Si$_2$+H$^+$): 679.3419 found 679.3441.

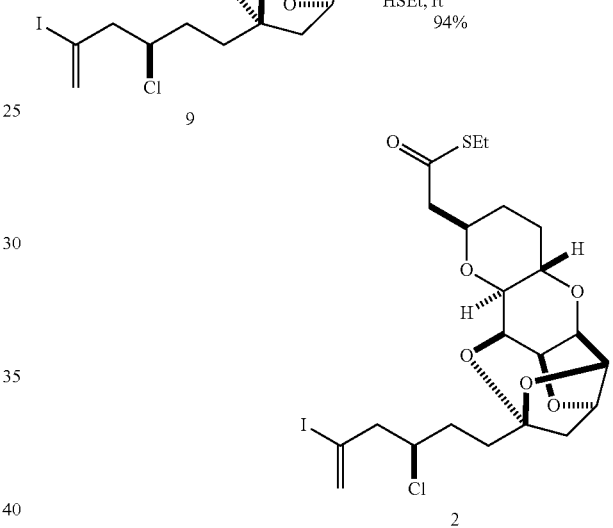

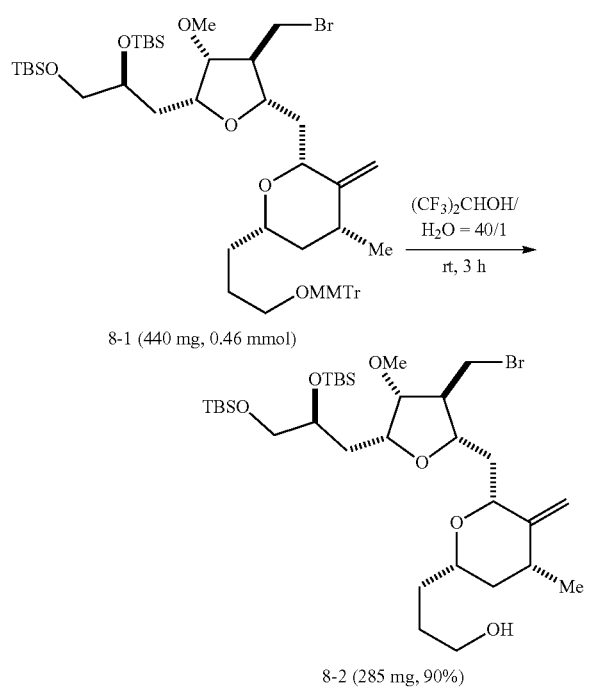

8-1 (440 mg, 0.46 mmol)

8-2 (285 mg, 90%)

To bromide 8-1 (440 mg, 0.46 mmol) was added (CF$_3$)$_2$CHOH/H$_2$O (40/1, 10 mL) and the solution was stirred at room temperature for 2 h. Then, it was diluted with PhH and concentrated. A column chromatography (EtOAc/Hexanes=1/5) provided alcohol 8-2 (285 mg, 90%). [α]$_D^{20}$=−19.0° (c 0.3, CH$_2$Cl$_2$); $^1$H NMR (500 MHz, C$_6$D$_6$) δ4.90 (s, 1H), 4.76 (d, J=1.7 Hz, 1H), 4.14-4.04 (m, 2H), 3.93 (dd, J=12.7, 6.1 Hz, 1H), 3.86-3.76 (m, 2H), 3.70 (dd, J=10.2, 4.8 Hz, 1H), 3.62 (dd, J=4.2, 1.7 Hz, 1H), 3.49-3.40 (m, 2H), 3.36-3.25 (m, 2H), 3.19 (s, 3H), 3.05 (dd, J=10.5, 8.7 Hz, 1H), 2.47-2.42 (m, 1H), 2.37-2.29 (m, 1H), 2.27-2.15 (m, 3H), 2.00-1.91 (m, 1H), 1.65-1.54 (m, 1H), 1.53-1.41 (m, 2H), 1.39-1.32 (m, 2H), 1.15 (t, J=5.4 Hz, 1H), 1.02 (s, 9H), 0.99 (s, 9H), 0.96-0.91 (m, 1H), 0.93 (d, J=6.5 Hz, To 9 (180 mg, 0.32 mmol) (see, e.g., Yan et al., J. Am. Chem. Soc. 2015, 137, 6219) were added Me$_3$SnOH (290 mg, 1.6 mmol, 5 equiv) and 1,2-dichloroethane (10 mL). The mixture was heated at 80~85° C. with vigorous stirring for 1 d. Upon completion of the reaction, it was cooled to room temperature and quenched with 0.1 N HCl. After stirring for 30 min, it was extracted with CH$_2$Cl$_2$ and dried over Na$_2$SO$_4$ (s). To the concentrate in CH$_2$Cl$_2$ were added EtSH, DMAP (cat.), and DCC (1.5 equiv) at room temperature. The mixture was stirred for 3 h, diluted with EtOAc, filtered (SiO$_2$, EtOAc), and purified by a column chromatography (EtOAc/Hexanes=1/3) to give 2 (179 mg, 94%, a white solid). [α]$_D^{20}$=−44.6° (c 1.0, CH$_2$Cl$_2$); $^1$H NMR (600 MHz, C$_6$D$_6$) δ5.85 (d, J=1.2 Hz, 1H), 5.70 (d, J=1.1 Hz, 1H), 4.40 (td, J=10.4, 4.4 Hz, 1H), 4.35 (dd, J=3.7, 1.8 Hz, 1H), 4.19-4.14 (m, 1H), 4.13 (t, J=4.5 Hz, 1H), 4.08 (t, J=4.7 Hz, 1H), 3.89 (dd, J=6.5, 4.7 Hz, 1H), 3.79-3.73 (m, 1H), 3.65 (dd, J=6.6, 4.0 Hz, 1H), 2.80 (dd, J=15.1, 7.2 Hz, 1H), 2.74-2.50 (m, 5H), 2.41 (dd, J=15.1, 5.4 Hz, 1H), 2.24-2.15 (m, 1H), 2.08-1.80 (m, 5H), 1.44-1.32 (m, 2H), 1.30-1.14 (m, 2H), 0.99 (t, J=7.4 Hz, 3H); $^{13}$C NMR (126 MHz, C$_6$D$_6$) δ195.78, 128.73, 109.68, 106.81, 82.38, 80.79, 78.53, 76.87, 74.80, 74.67, 74.13, 68.40, 61.67, 53.53, 50.16, 47.43, 36.26, 32.34, 30.84, 30.62, 23.46, 14.80; IR (neat) ν 2930, 2854, 1685, 1448, 1263, 1134, 1077; HRMS (ESI) calculated for $(C_{22}H_{30}ClIO_6S+H^+)$: 585.0569 found 585.0565.

$C_6D_6$) δ 5.25 (s, 1H), 4.98 (s, 1H), 4.92 (s, 1H), 4.77 (d, J=1.4 Hz, 1H), 4.46-4.36 (m, 2H), 4.34 (dd, J=3.8, 1.8 Hz,

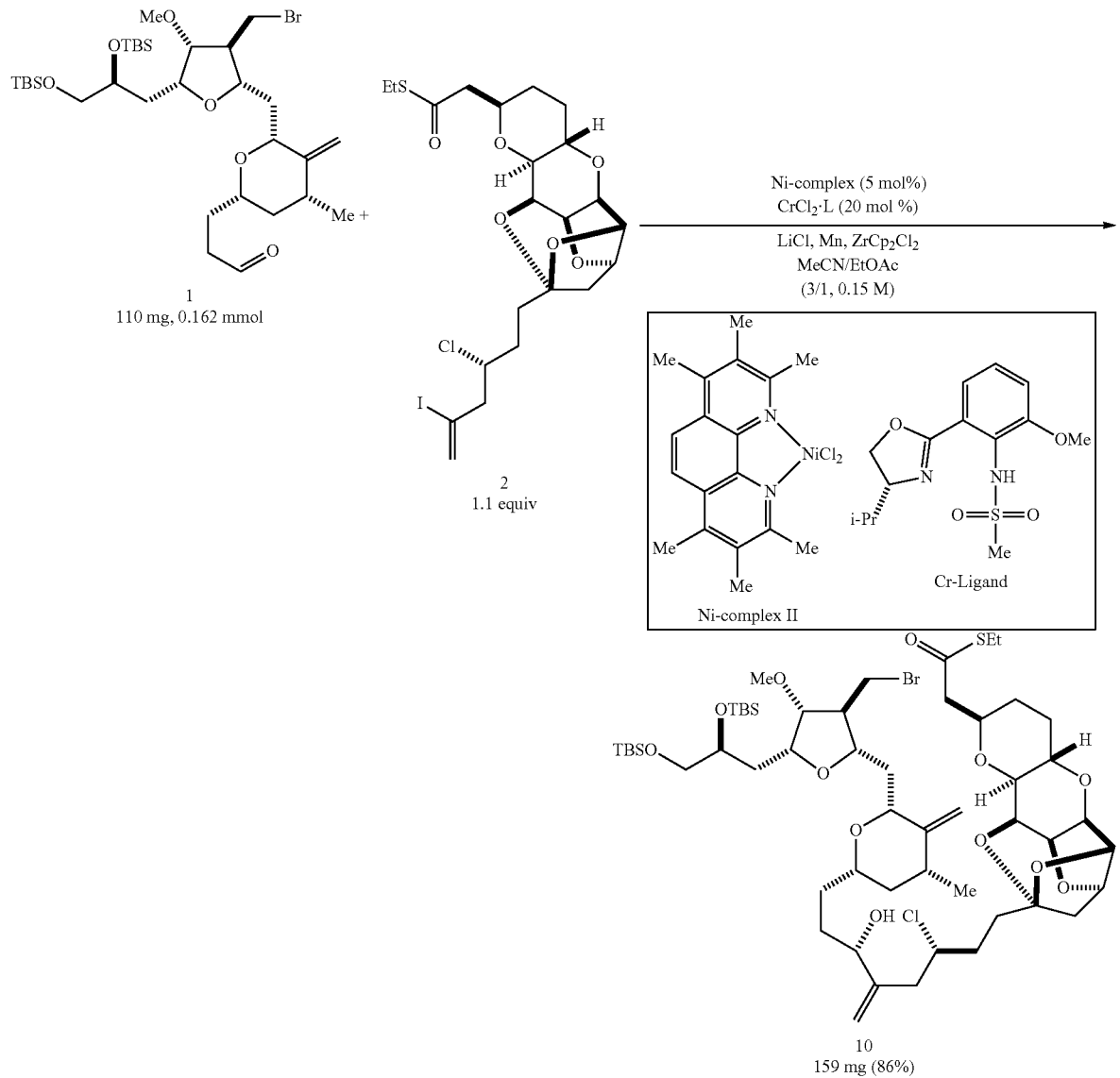

To a vial were added $CrCl_2$ (3.9 mg, 0.032 mmol, 20 mol %), sulfonamide ligand (12 mg, 0.038 mmol, 24 mol %), proton sponge (8.2 mg, 0.038 mmol, 24 mol %), and MeCN (0.8 ml, 0.04 M) and the mixture was stirred for 30 min to give a green solution. To another vial containing aldehyde 1 (110 mg, 0.16 mmol) and vinyl iodide 2 (103 mg, 0.176 mmol, 1.1 equiv) were added Mn (34 mg, 0.64 mmol, 4 equiv), $ZrCp_2Cl_4$ (70 mg, 0.24 mmol, 1.5 eq.), LiCl (13 mg, 0.32 mmol, 2 equiv), Ni-complex II ($Me_6Phen.NiCl_2$, 3.1 mg, 0.008 mmol, 5 mol %), and the solution of $CrCl_2$•ligand and EtOAc (0.25 ml). After it was stirred for 3 h, the mixture was diluted with EtOAc and quenched with potassium serinate (aq. 0.5 M) that was prepared from serine (10 g), $KHCO_3$ (10.5 g) and water (200 ml). Then, it was stirred for 30 min, extracted with EtOAc (×3), dried over $Na_2SO_4$ (s) and purified by a column chromatography (EtOAc/Hexanes=1/3) to give 10 (159 mg, 86%, a white foamy solid). $[α]_D^{20}$=−33.8° (c 1.0, $CH_2Cl_2$); $^1H$ NMR (500 MHz, $C_6D_6$) 1H), 4.18-4.12 (m, 2H), 4.12-4.05 (m, 3H), 4.00-3.92 (m, 1H), 3.90-3.84 (m, 2H), 3.82-3.71 (m, 3H), 3.72-3.67 (m, 1H), 3.67-3.61 (m, 2H), 3.42-3.32 (m, 2H), 3.22 (s, 3H), 3.17-3.09 (m, 1H), 2.89-2.77 (m, 2H), 2.75-2.63 (m, 2H), 2.59-2.43 (m, 4H), 2.43-2.32 (m, 3H), 2.30-2.17 (m, 3H), 2.16-1.89 (m, 7H), 1.87-1.75 (m, 1H), 1.73-1.66 (m, 1H), 1.49-1.38 (m, 3H), 1.30-1.21 (m, 2H), 1.05-1.02 (m, 1H), 1.03 (s, 9H), 1.02-0.99 (m, 12H), 0.94 (d, J=6.5 Hz, 3H), 0.21 (s, 3H), 0.20 (s, 3H), 0.12 (s, 3H), 0.11 (s, 3H); $^{13}C$ NMR (126 MHz, $C_6D_6$) δ195.99, 151.03, 148.40, 128.51, 113.68, 109.98, 104.77, 86.91, 82.38, 80.83, 79.66, 78.69, 78.24, 77.44, 76.91, 76.01, 75.39, 74.89, 74.82, 74.16, 72.02, 68.33, 68.27, 62.59, 56.68, 52.93, 50.22, 47.71, 43.01, 42.29, 37.71, 36.72, 35.94, 34.26, 33.95, 32.80, 32.49, 32.18, 30.86, 30.62, 26.22, 26.21, 23.47, 18.62, 18.42, 18.05, 14.82, −3.89, −4.45, −5.12; IR (neat) v 2953, 2928, 1686, 1472, 1251, 1078; HRMS (ESI) calculated for $(C_{54}H_{92}BrClO_{12}SSi_2+H^+)$: 1135.4793 found 1135.4821.

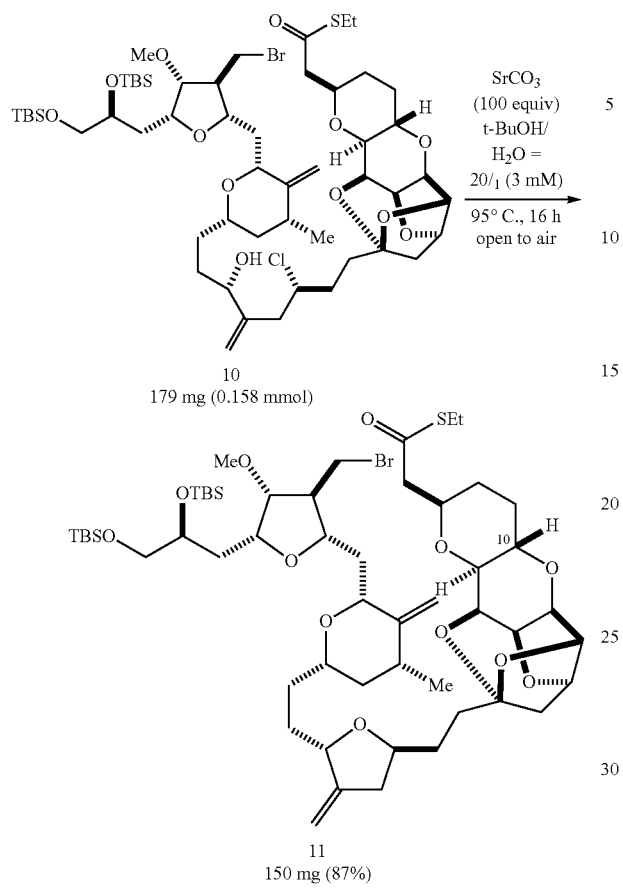

10
179 mg (0.158 mmol)

11
150 mg (87%)

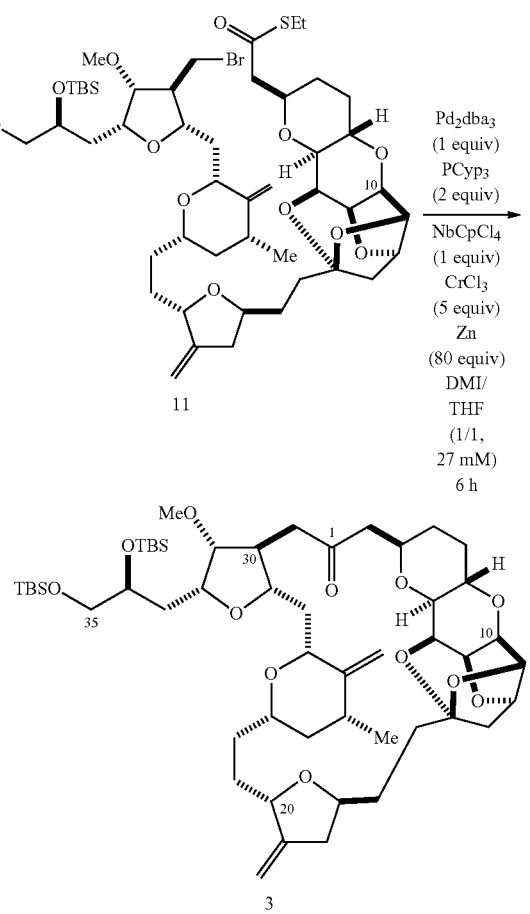

11

3

To 10 (179 mg, 0.158 mmol) in 100 ml round-bottom flask were added SrCO$_3$ (2.3 g, 15.8 mmol, 100 equiv) and t-BuOH/H$_2$O (20/1, 50 mL). It was set up with reflux condenser open to air and heated up to 93-95° C. with vigorous stirring. When the reaction was completed (16 h-20 h), it was cooled to room temperature, diluted with EtOAc, filtered (SiO$_2$, EtOAc) and purified by a column chromatography (EtOAc/Hexanes=1/4) to yield 11 (150 mg, 87%). $[\alpha]_D^{20}$=−43.8° (c 1.0, CH$_2$Cl$_2$); $^1$H NMR (500 MHz, C$_6$D$_6$) δ5.02-4.97 (m, 1H), 4.97-4.94 (m, 1H), 4.91 (s, 1H), 4.76 (d, J=1.5 Hz, 1H), 4.57-4.49 (m, 2H), 4.40 (dd, J=3.8, 1.8 Hz, 1H), 4.16 (t, J=4.5 Hz, 1H), 4.14-4.09 (m, 2H), 4.09-4.02 (m, 2H), 4.01-3.95 (m, 1H), 3.92-3.88 (m, 1H), 3.86-3.74 (m, 3H), 3.73-3.61 (m, 3H), 3.42-3.34 (m, 2H), 3.21 (s, 3H), 3.10 (dd, J=10.7, 9.4 Hz, 1H), 2.87 (dd, J=15.1, 7.3 Hz, 1H), 2.78-2.62 (m, 2H), 2.57-2.46 (m, 3H), 2.46-2.35 (m, 2H), 2.31-2.11 (m, 5H), 2.11-2.01 (m, 2H), 1.97 (d, J=13.1 Hz, 2H), 1.91-1.67 (m, 5H), 1.63-1.55 (m, 1H), 1.52-1.36 (m, 3H), 1.33-1.21 (m, 2H), 1.06-1.03 (m, 1H), 1.03 (s, 9H), 1.02-0.99 (m, 12H), 0.94 (d, J=6.4 Hz, 3H), 0.20 (s, 3H), 0.20 (s, 3H), 0.11 (s, 3H), 0.11 (s, 3H); $^{13}$C NMR (126 MHz, C$_6$D$_6$) δ195.91, 152.89, 151.35, 110.42, 104.60, 87.00, 82.29, 80.90, 79.73, 79.29, 78.59, 78.18, 77.39, 77.24, 76.95, 75.85, 74.85, 74.64, 74.26, 72.02, 68.39, 68.28, 56.65, 52.84, 50.18, 47.28, 43.14, 39.21, 37.76, 35.97, 35.82, 34.32, 33.90, 32.24, 32.02, 30.86, 30.61, 30.43, 26.22, 26.20, 23.42, 18.61, 18.42, 18.08, 14.83, −3.91, −4.47, −5.13; IR (neat) v 2957, 2928, 1690, 1472, 1259, 1088; HRMS (ESI) calculated for (C$_{54}$H$_{91}$BrO$_{12}$SSi$_2$+H$^+$): 1099.5026 found 1099.4998.

To a round-bottom flask were added PCyp$_3$ (22 mg, 0.091 mmol), Pd$_2$dba$_3$(0) (42 mg, 0.046 mmol), and DMI (0.9 mL) in a glove box at room temperature. Then, CrCl$_3$ (37 mg, 0.5 mmol), Zn metal (6.4 mg, 1 mmol), and NbCpCl$_4$ (15 mg, 0.046 mmol) were added to give a homogeneous dark solution except Zn. 11 (52 mg, 0.047 mmol) in a 10 mL round-bottom flask was charged with PhH and evaporated under vacuum (>7 times). To 11 in THF (0.7 mL) were added Zn (243 mg, 3.8 mmol) and above pre-mixture at room temperature. Then, it was stirred vigorously for 6 h. Et$_2$O and florisil were added. After stirring for 30 min, it was filtered (SiO$_2$, Et$_2$O). The filtrate was washed with water, dried over Na$_2$SO$_4$, concentrated, and purified by a silica gel chromatography (EtOAc/Hexanes=1/20, 1/10, then 1/7) to give macrocyclic ketone 3 (29 mg, 64%, a white solid). $[\alpha]_D^{20}$=−69.5° (c 1.0, CH$_2$Cl$_2$); $^1$H NMR (500 MHz, C$_6$D$_6$) δ5.05-4.98 (m, 2H), 4.80 (s, 1H), 4.64-4.58 (m, 2H), 4.47-4.37 (m, 1H), 4.27-4.22 (m, 2H), 4.22-4.17 (m, 1H), 4.17-4.12 (m, 2H), 4.12-4.05 (m, 2H), 4.05-3.98 (m, 1H), 3.88-3.79 (m, 2H), 3.74 (dd, J=10.3, 4.9 Hz, 1H), 3.72-3.65 (m, 2H), 3.62 (s, 3H), 3.60 (dd, J=6.5, 4.4 Hz, 1H), 3.52 (d, J=3.3 Hz, 1H), 2.94-2.86 (m, 1H), 2.81-2.69 (m, 2H), 2.69-2.63 (m, 2H), 2.61-2.52 (m, 2H), 2.46-2.31 (m, 4H), 2.26-2.12 (m, 3H), 2.06-1.88 (m, 5H), 1.76-1.57 (m, 3H), 1.51-1.34 (m, 4H), 1.33-1.24 (m, 2H), 1.23-1.13 (m, 1H), 1.04 (s, 9H), 0.99 (s, 9H), 0.98-0.95 (m, 1H), 0.82 (d, J=6.4 Hz, 3H), 0.22 (s, 3H), 0.20 (s, 3H), 0.10 (s, 3H), 0.10 (s, 3H); $^{13}$C NMR (126 MHz, C$_6$D$_6$) δ 205.56, 154.07, 151.68, 109.60, 104.43, 103.96, 88.02, 82.60, 81.09, 81.00, 78.02, 77.83, 76.74, 76.62, 75.23, 74.88, 73.96, 73.68, 73.45, 73.33, 72.30, 68.60, 68.51, 57.11, 48.73, 48.49, 48.40, 44.35, 43.83, 39.37, 39.14, 35.92, 35.38, 34.27, 32.29, 31.31, 30.79, 29.09, 26.24, 18.63, 18.49, 17.98, −3.83, −4.47, −5.14; IR (neat) v 2954, 2929, 1720, 1253, 1134, 1100, 1080; HRMS (ESI) calculated for ($C_{52}H_{86}O_{12}Si_2$+Na$^+$): 981.5552 found 981.5550 (see, e.g., Austad et al., *Synlett* 2013, 24, 333 and Kaburagi et al., *Tetrahedron Lett.* 2007, 48, 8967).

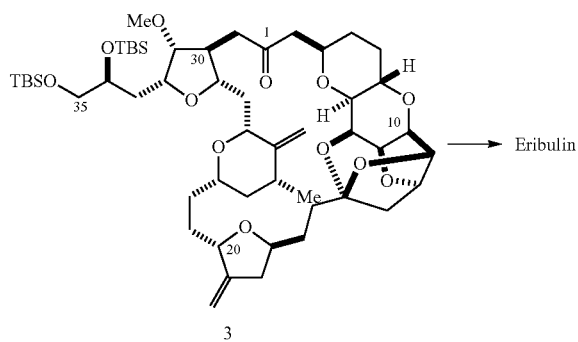

Synthesis of Ni-Complex II

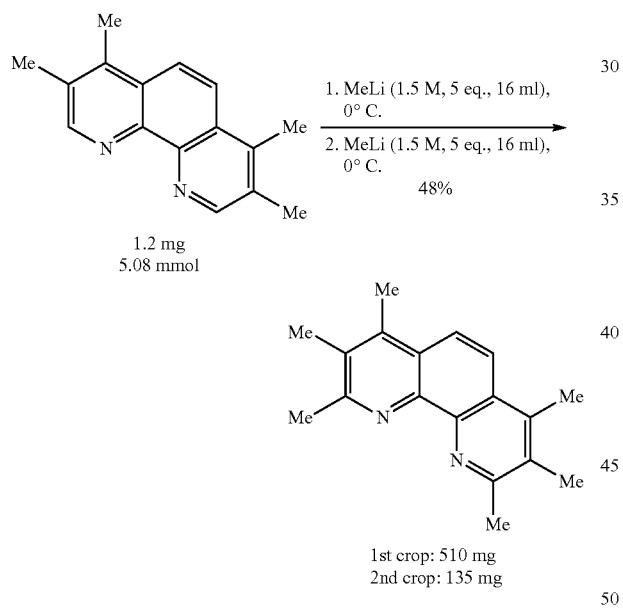

1st crop: 510 mg
2nd crop: 135 mg

MeLi (1.5 M in Et$_2$O, 5 eq., 25 mmol, 16 mL) was added dropwise at 0° C. to a stirred solution of 3,4,7,8-tetramethyl-1,10-phenanthroline(tmp) (1.2 g, 5.08 mmol) in anhydrous toluene (20 mL) (~2 h). The mixture was slowly warmed up to room temperature and stirred overnight at room temperature. Then, the mixture was cooled to 0° C. and quenched with ice and water (~10 mL). After extraction 3 times with CH$_2$Cl$_2$ (70 mL), the combined organic layer was dried over Na$_2$SO$_4$, concentrated to half volume, and MnO$_2$ (~8 g) was added to it. After stirring for 4 h, the mixture was filtered over celite and washed (CH$_2$Cl$_2$ then CH$_2$Cl$_2$/MeOH=9/1). After concentration and a short column purification (SiO$_2$, CH$_2$Cl$_2$ then CH$_2$Cl$_2$/MeOH=9/1) provided a yellow solid (~12 g) as a mixture of 2,3,4,7,8-pentamethyl-1,10-phenanthroline (major, >5/1) and 2,3,4,7,8,9-hexamethyl-1,10-phenanthroline.

The mixture was subjected to the above procedure again to give the desired product as a dark solid (~1 g) which was crystallized with EtOAc/CH$_2$Cl$_2$ (5 mL/15 mL) upon slow evaporation to 1/3 to yield a yellow solid (510 mg). Crystallization of the mother liquor furnished additional 130 mg. Also, it can be crystallized with EtOAc/CH$_2$Cl$_2$ (3/1) upon heating to dissolve and then cooling to room temperature (similar recovery was observed). $^1$H NMR (500 MHz, CDCl$_3$) δ7.94 (s, 2H), 2.89 (s, 6H), 2.68 (s, 6H), 2.46 (s, 6H); $^{13}$C NMR (126 MHz, CDCl$_3$) δ157.91, 143.18, 140.78, 129.24, 125.79, 121.25, 25.6, 15.89, 14.82; IR (neat) v 1485, 1437, 1380, 929, 908; HRMS (ESI) calculated for ($C_{18}H_{20}N_2$+H$^+$): 265.1699 found 265.1719.

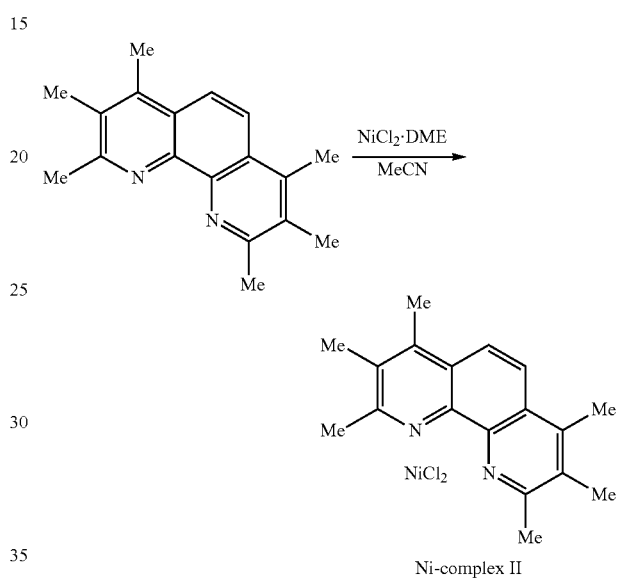

2,3,4,7,8,9-Hexametyl-1,10-phenanthroline (300 mg, 1.14 mmol) and NiCl$_2$•DME (236 mg, 1.08 mmol) were grounded finely and transferred to a vial. To the vial was added MeCN (10 mL) and it was stirred vigorously for 1 day. The color of solid changed from yellow to pink and then yellow again. The suspended solid was filtered, washed with EtOAc, dried, and grounded to give Ni-complex II as a yellow solid (390 mg, 92%).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (H-1):

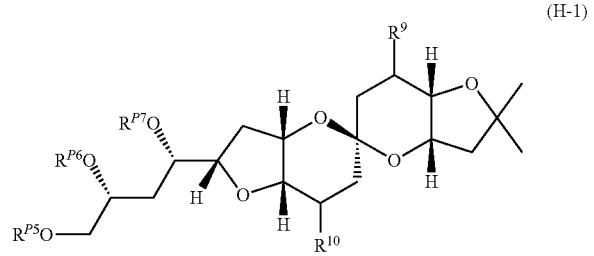

(H-1)

-continued

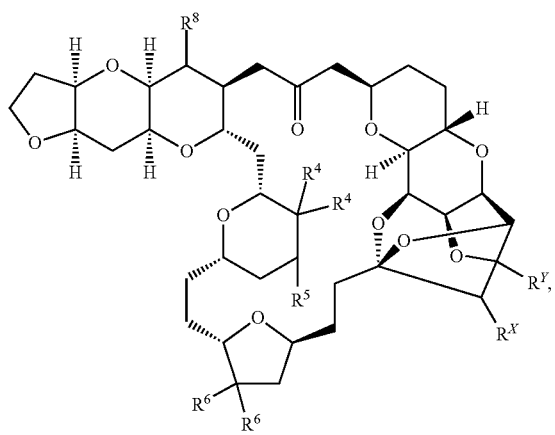

or a pharmaceutically acceptable salt thereof, wherein:

$R^{P5}$, $R^{P6}$, and $R^{P7}$ are independently hydrogen, optionally substituted alkyl, or an oxygen protecting group;

each instance of $R^4$ is independently hydrogen, halogen, or optionally substituted alkyl, or two $R^4$ groups are taken together to form:

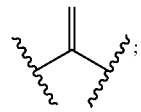

each instance of $R^6$ is independently hydrogen, halogen, or optionally substituted alkyl, or two $R^6$ groups are taken together to form:

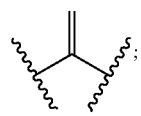 [SMILES: *C(*)=C]

$R^5$, $R^8$, $R^9$, and $R^{10}$ are independently hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with the intervening atoms to form optionally substituted heterocyclyl;

optionally wherein $R^{P5}$ and $R^{P6}$ are joined together with the intervening atoms to form optionally substituted heterocyclyl; or optionally wherein $R^{P6}$ and $R^{P7}$ are joined together with the intervening atoms to form optionally substituted heterocyclyl.

2. The compound of claim 1, wherein the compound is selected from the group consisting of:

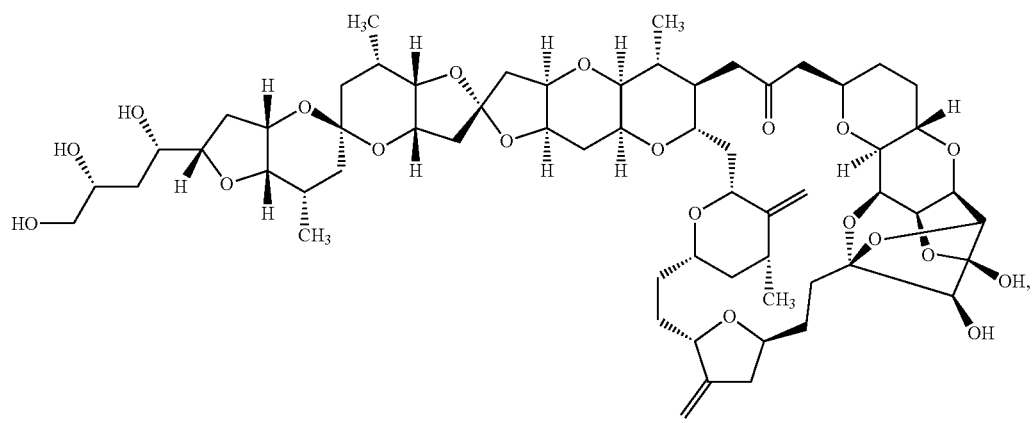
(keto-halichondrin A)
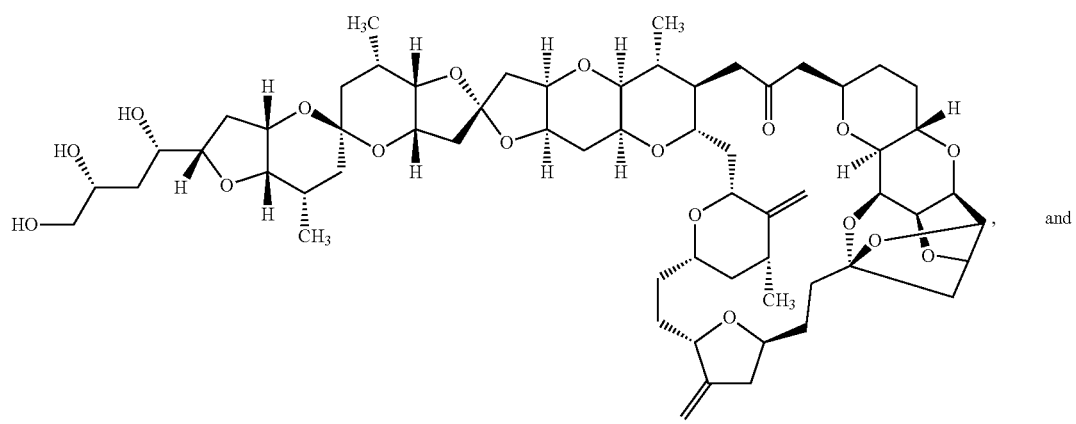
(keto-halichondrin B)
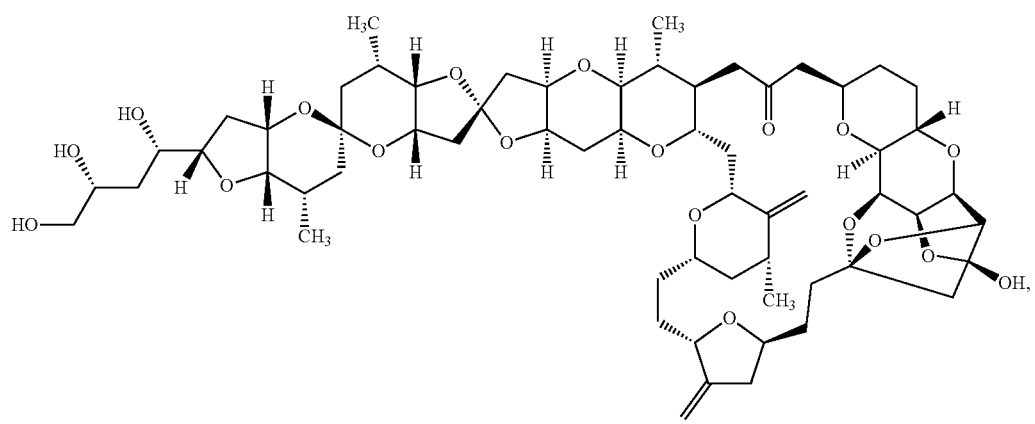
(keto-halichondrin C)
and pharmaceutically acceptable salts thereof.
3. A pharmaceutical composition comprising a compound of claim 1, or a pharmaceutically acceptable salt thereof, and optionally a pharmaceutically acceptable excipient.

4. A compound of Formula (NH-1):

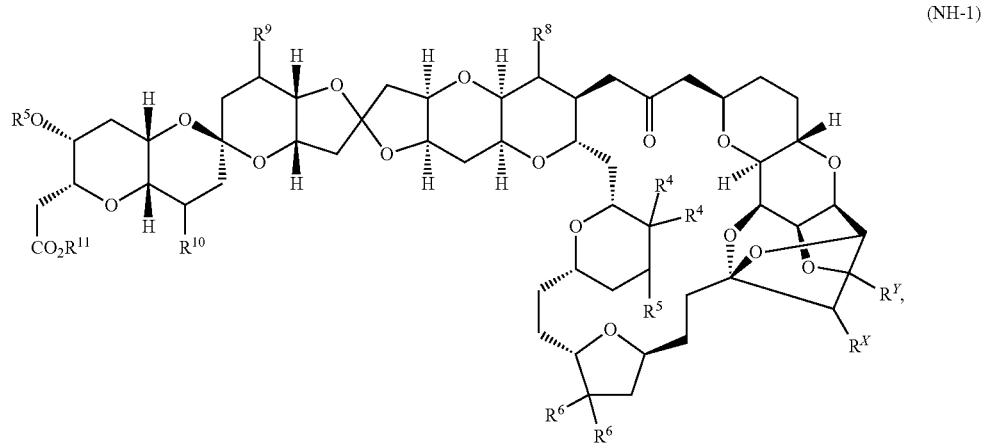

(NH-1)

or a pharmaceutically acceptable salt thereof, wherein:
$R^5$ and $R^{11}$ are each independently hydrogen, optionally substituted alkyl, or an oxygen protecting group;
each instance of $R^4$ is independently hydrogen, halogen, or optionally substituted alkyl, or two $R^4$ groups are taken together to form:

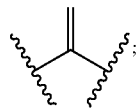 [SMILES: *C(*)=C];

each instance of $R^6$ is independently hydrogen, halogen, or optionally substituted alkyl, or two $R^6$ groups are taken together to form:

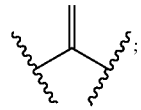 [SMILES: *C(*)=C];

$R^8$, $R^9$, and $R^{10}$ are independently hydrogen, halogen, or optionally substituted alkyl;

$R^X$ is hydrogen or —$OR^{Xa}$, wherein $R^{Xa}$ is hydrogen, optionally substituted alkyl, or an oxygen protecting group; and $R^Y$ is hydrogen or —$OR^{Ya}$, wherein $R^{Ya}$ is hydrogen, optionally substituted alkyl, or an oxygen protecting group;

optionally wherein $R^{Xa}$ and $R^{Ya}$ are joined together with the intervening atoms to form optionally substituted heterocyclyl.

5. The compound of claim 4, wherein the compound is selected from the group consisting of:

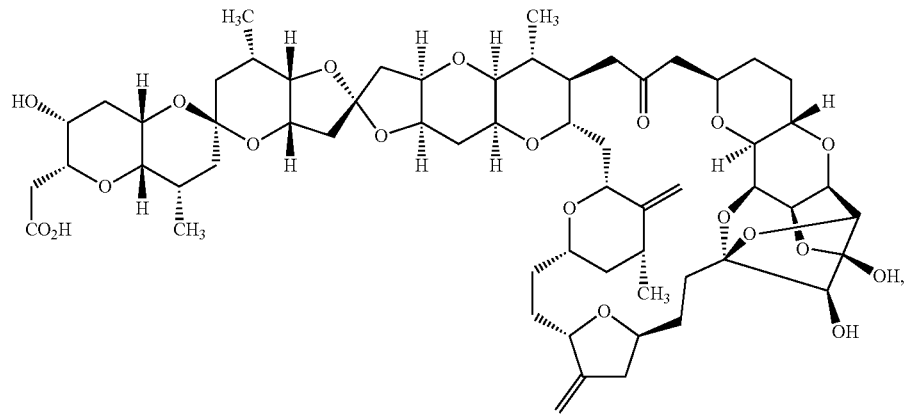

(keto-norhalichondrin A)

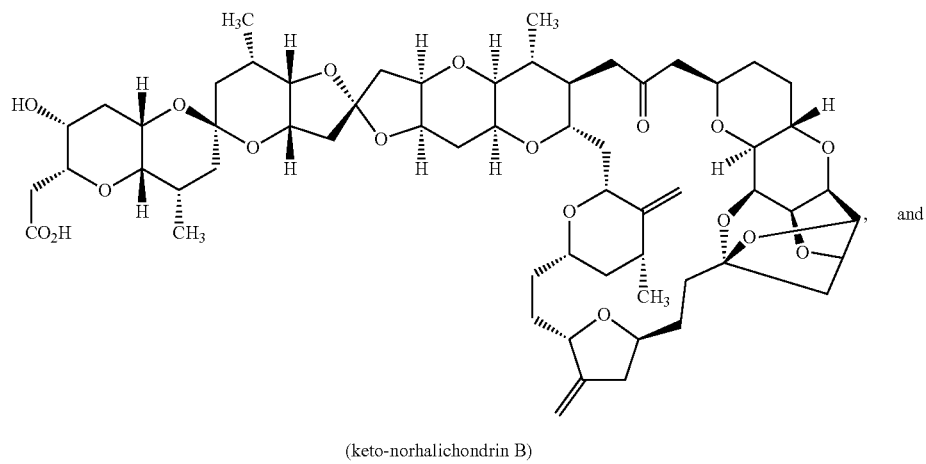

(keto-norhalichondrin B)

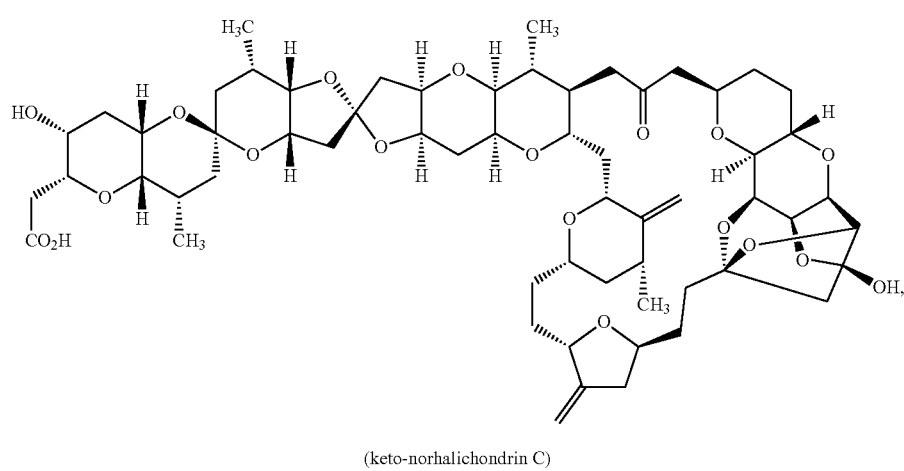

(keto-norhalichondrin C)

and pharmaceutically acceptable salts thereof.

6. A pharmaceutical composition comprising a compound of claim 4, or a pharmaceutically acceptable salt thereof, and optionally a pharmaceutically acceptable excipient.

7. The compound of claim 1, wherein $R^{P5}$, $R^{P6}$, and $R^{P7}$ are hydrogen.

8. The compound of claim 1, wherein two $R^4$ groups are taken together to form:

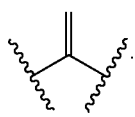

9. The compound of claim 1, wherein two $R^6$ groups are taken together to form:

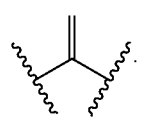

10. The compound of claim 1, wherein $R^5$ is unsubstituted $C_{1-6}$ alkyl.

11. The compound of claim 1, wherein $R^5$ is unsubstituted methyl.

12. The compound of claim 1, wherein $R^8$ is unsubstituted $C_{1-6}$ alkyl.

13. The compound of claim 1, wherein $R^8$ is unsubstituted methyl.

14. The compound of claim 1, wherein $R^9$ is unsubstituted $C_{1-6}$ alkyl.

15. The compound of claim 1, wherein $R^9$ is unsubstituted methyl.

16. The compound of claim 1, wherein $R^{10}$ is unsubstituted $C_{1-6}$ alkyl.

17. The compound of claim 1, wherein $R^{10}$ is unsubstituted methyl.

18. The compound of claim 1, wherein $R^X$ is hydrogen; and $R^Y$ is —OH.

19. The compound of claim 1, wherein $R^X$ and $R^Y$ are hydrogen.

20. The compound of claim 1, wherein $R^X$ and $R^Y$ are —OH.

21. The compound of claim 1, wherein:
$R^{P5}$, $R^{P6}$, and $R^{P7}$ are independently hydrogen or an oxygen protecting group;
each instance of $R^4$ is independently hydrogen or unsubstituted $C_{1-6}$ alkyl, or two $R^4$ groups are taken together to form:

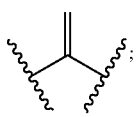 [SMILES: *C(*)=C]

each instance of $R^6$ is independently hydrogen or unsubstituted $C_{1-6}$ alkyl, or two $R^4$ groups are taken together to form:

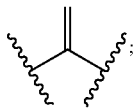 [SMILES: *C(*)=C]

$R^5$, $R^8$, $R^9$, and $R^{10}$ are independently hydrogen or unsubstituted $C_{1-6}$ alkyl;
$R^X$ is hydrogen or —OR$^{Xa}$, wherein $R^{Xa}$ is hydrogen or an oxygen protecting group; and
$R^Y$ is hydrogen or —OR$^{Ya}$, wherein $R^{Ya}$ is hydrogen or an oxygen protecting group.

22. The compound of claim 4, wherein $R^{11}$ is hydrogen.

23. The compound of claim 4, wherein two $R^4$ groups are taken together to form:

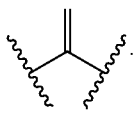

24. The compound of claim 4, wherein two $R^6$ groups are taken together to form:

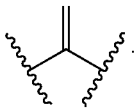

25. The compound of claim 4, wherein each $R^5$ is independently hydrogen or unsubstituted $C_{1-6}$ alkyl.

26. The compound of claim 4, wherein each $R^5$ is independently hydrogen or methyl.

27. The compound of claim 4, wherein $R^8$ is unsubstituted $C_{1-6}$ alkyl.

28. The compound of claim 4, wherein $R^8$ is unsubstituted methyl.

29. The compound of claim 4, wherein $R^9$ is unsubstituted $C_{1-6}$ alkyl.

30. The compound of claim 4, wherein $R^9$ is unsubstituted methyl.

31. The compound of claim 4, wherein $R^{10}$ is unsubstituted $C_{1-6}$ alkyl.

32. The compound of claim 4, wherein $R^{10}$ is unsubstituted methyl.

33. The compound of claim 4, wherein $R^X$ is hydrogen; and $R^Y$ is —OH.

34. The compound of claim 4, wherein $R^X$ and $R^Y$ are hydrogen.

35. The compound of claim 4, wherein $R^X$ and $R^Y$ are —OH.

36. The compound of claim 4, wherein:
$R^{11}$ hydrogen or an oxygen protecting group;
each instance of $R^4$ is independently hydrogen or unsubstituted $C_{1-6}$ alkyl, or two $R^4$ groups are taken together to form:

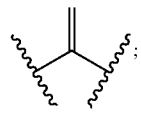

each instance of $R^6$ is independently hydrogen or unsubstituted $C_{1-6}$ alkyl, or two $R^4$ groups are taken together to form:

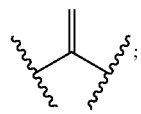 [SMILES: *C(*)=C]

$R^5$, $R^8$, $R^9$, and $R^{10}$ are independently hydrogen or unsubstituted $C_{1-6}$ alkyl;
$R^X$ is hydrogen or —OR$^{Xa}$, wherein $R^{Xa}$ is hydrogen or an oxygen protecting group; and
$R^Y$ is hydrogen or —OR$^{Ya}$, wherein $R^{Ya}$ is hydrogen or an oxygen protecting group.

37. The compound of claim 1, wherein the compound is the following:

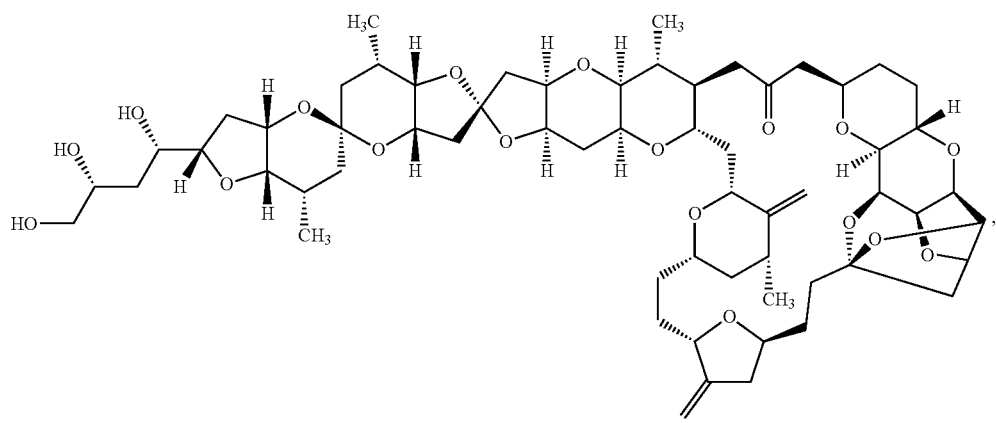
(keto-halichondrin B)
or a pharmaceutically acceptable salt thereof.
* * * * *